US011142551B2

(12) United States Patent
Uil et al.

(10) Patent No.: US 11,142,551 B2
(45) Date of Patent: Oct. 12, 2021

(54) ADENOVIRUS AND USES THEREOF

(71) Applicant: JANSSEN VACCINES & PREVENTION B.V., Leiden (NL)

(72) Inventors: Taco Gilles Uil, Amsterdam (NL); Soumitra Roy, Townsend, DE (US); Selina Khan, Leiden (NL); Jerôme H. H. V. Custers, Alphen aan den Rijn (NL)

(73) Assignee: Janssen Vaccines & Prevention B.V., Leiden (NL)

( * ) Notice: Subject to any disclaimer, the term of this patent is extended or adjusted under 35 U.S.C. 154(b) by 0 days.

(21) Appl. No.: 16/760,602

(22) PCT Filed: Oct. 30, 2018

(86) PCT No.: PCT/EP2018/079725
§ 371 (c)(1),
(2) Date: Apr. 30, 2020

(87) PCT Pub. No.: WO2019/086466
PCT Pub. Date: May 9, 2019

(65) Prior Publication Data

US 2021/0214398 A1 Jul. 15, 2021

(30) Foreign Application Priority Data

Oct. 31, 2017 (EP) .................................... 17199354

(51) Int. Cl.

| | |
|---|---|
| ***C12N 15/86*** | (2006.01) |
| ***C12N 7/00*** | (2006.01) |
| ***A61K 48/00*** | (2006.01) |
| ***A61K 39/00*** | (2006.01) |
| ***A61K 35/76*** | (2015.01) |
| ***C07K 14/005*** | (2006.01) |
| ***A61K 39/235*** | (2006.01) |
| ***A61P 31/20*** | (2006.01) |

(52) U.S. Cl.
CPC .......... *C07K 14/005* (2013.01); *A61K 39/235* (2013.01); *A61P 31/20* (2018.01); *C12N 7/00* (2013.01); *C12N 15/86* (2013.01); *A61K 2039/5256* (2013.01); *A61K 2039/53* (2013.01); *A61K 2039/575* (2013.01); *C12N 2750/00043* (2013.01); *C12N 2750/00052* (2013.01); *C12N 2750/14122* (2013.01)

(58) Field of Classification Search
CPC .......... C12N 15/86; C12N 2710/10343; C12N 7/00; C12N 2710/10322; C07K 14/005
See application file for complete search history.

(56) References Cited

U.S. PATENT DOCUMENTS

| | | |
|---|---|---|
| 5,559,099 A | 9/1996 | Wickham et al. |
| 5,837,511 A | 11/1998 | Falck-Pedersen et al. |
| 5,846,782 A | 12/1998 | Wickham et al. |
| 5,851,806 A | 12/1998 | Kovesdi et al. |
| 5,891,690 A | 4/1999 | Massie |
| 5,965,541 A | 10/1999 | Wickham et al. |
| 5,981,225 A | 11/1999 | Kochanek et al. |
| 5,994,106 A | 11/1999 | Kovesdi et al. |
| 5,994,128 A | 11/1999 | Fallaux et al. |
| 6,020,191 A | 2/2000 | Scaria et al. |
| 6,040,174 A | 3/2000 | Imler et al. |
| 6,113,913 A | 9/2000 | Brough et al. |

FOREIGN PATENT DOCUMENTS

| | | |
|---|---|---|
| EP | 2 350 268 | 8/2011 |
| EP | 2 536 829 | 12/2012 |
| WO | 98/39411 | 9/1989 |
| WO | 01/36615 | 5/2001 |
| WO | 2002/22080 | 3/2002 |
| WO | 2003/000283 | 1/2003 |
| WO | 2003/104467 | 12/2003 |
| WO | 2004/037189 | 5/2004 |
| WO | 2005/071093 | 8/2005 |
| WO | WO2005071093 | * 8/2005 |
| WO | 2006/040330 | 4/2006 |
| WO | 2007/104792 | 9/2007 |
| WO | 2009/073104 | 6/2009 |
| WO | 2010/086189 | 8/2010 |
| WO | 2001/02607 | 1/2011 |
| WO | 2011/130627 | 10/2011 |
| WO | 2013/016591 | 1/2013 |
| WO | 2013/052859 | 4/2013 |
| WO | 2013/173702 | 11/2013 |

OTHER PUBLICATIONS

Altschul et al., "Basic Local Alignment Search Tool," (1990) J. Mol. Biol. 215: 403-410.
Altschul et al., "Gapped BLAST and PSI-BLAST: a new generation of protein database search programs," (1997) Nucleic Acids Res. 25: 3389-3402.
Barnes E, et al., "Novel Adenovirus-Based Vaccines Induce Broad and Sustained T Cell Responses to HCV in Man," 2012 Science translational medicine 4: 115ra1.
Fallaux et al., "New Helper Cells and Matched Early Region 1-Deleted Adenovirus Vectors Prevent Generation of Replication-Competent Adenovirus," 1998, Hum Gene Ther 9: 1909-17.
Gao et al., "A Cell Line for High-Yield Production of E1-Deleted Adenovirus Vectors without the Emergence of Replication-Competent Virus," 2000, Hum Gene Ther 11: 213-19.
Havenga et al., "Novel replication-incompetent adenoviral B-group vectors: high vector stability and yield in PER.C6 cells," J. Gen. Virol. 87(8):2135-43 (2006).
Henikoff & Henikoff, Proc. Natl. Acad. Sci. USA 89:10915 (1989).
Karlin & Altschul, "Amino acid substitution matrices from protein blocks," Proc. Nat'l. Acad. Sci. USA, 90: 5873-5787 (1993).

(Continued)

*Primary Examiner* — Barry A Chestnut
(74) *Attorney, Agent, or Firm* — Ice Miller LLP

(57) ABSTRACT

Provided herein are adenoviral nucleic acid sequences and adenoviral vectors comprising said nucleic acid sequences. The provided adenoviral vectors can be used to induce a protective immune response in a subject.

15 Claims, 7 Drawing Sheets

Specification includes a Sequence Listing.

(56) References Cited

OTHER PUBLICATIONS

Kovesdi et al., "Adenoviral Producer Cells," 2010, Viruses 2: 1681-703.
Letvin et al., "Prospects for Vaccine Protection Against HIV-1 Infection and AIDS," Ann. Rev. Immunol. 20:73 (2002).
Maizel et al., "The Polypeptides of Adenovirus," Virology, 36(1):115-25 (1968).
Needleman & Wunsch, "A General Method Applicable to the Search for Similarities in the Amino Acid Sequence of Two Proteins," J. Mol. Biol. 48:443 (1970).
Pearson & Lipman, "Improved tools for biological sequence comparison," Proc. Nat'l. Acad. Sci. USA 85:2444 (1988).
Peruzzi D, et al., A novel Chimpanzee serotype-based adenoviral vector as delivery tool for cancer vaccines, 2009 Vaccine 27: 1293-300.
Quinn KM, et al., "Comparative Analysis of the Magnitude, Quality, Phenotype, and Protective Capacity of Simian Immunodeficiency Virus Gag-Specific CD8 T Cells following Human-, Simian-, and Chimpanzee-Derived Recombinant Adenoviral Vector Immunization," 2013, J Immunol 190: 2720-35.
Shiver et al., "Replication-incompetent adenoviral vacccine vector elicits effective anti-immunodeficiency-virus immunity," Nature 415:331 (2002).
Shiver and Emini, "Recent Advances in the Development of HIV-1 Vaccines Using Replication-Incompetent Adenovirus Vectors," Ann. Rev. Med. 55:355 (2004).
Smith & Waterman, "Comparison of Biosequences," Adv. Appl. Math. 2:482 (1981).
Sprangers et al., "Quantifying Adenovirus-Neutralizing Antibodies by Luciferase Transgene Detection: Addressing Preexisting Immunity to Vaccine and Gene Therapy Vectors," 2003, J.Clin. Microbiol. 41:5046-5052.
Susan J. Morris et al., "Simian adenoviruses as vaccine vectors," Future Virology, 11(9):649-659, 2016.
R.R. Bradley et al., "Adenovirus Serotype 5 Neutralizing Antibodies Target both Hexon and Fiber following Vaccination and Natural Infection," Journal of Virology, 86(1):625-629, 2011.
S.C. Jacobs, "Characterization and manipulation of the human adenovirus 4 genome," Journal of General Virology, 85(11):3361-3366, 2004.
Roberts Diane M. et al., "Hexon-chimaeric adenovirus serotype 5 vectors circumvent pre-existing anti-vector immunity," Nature, Macmillan Journals Ltd., London, 441(7090):239-243, 2006.
Julio Alonso-Padilla et al., "Development of Novel Adenoviral Vectors to Overcome Challenges Observed with HAdV-5-based Constructs," Molecular Therapy: The Journal of the American Society of Gene Therapy, 24(1):6-16, 2015.
Mohan Babu Appaiahgari et al., "Adenoviruses as gene/vaccine delivery vectors: promises and pitfalls," Expert Opinion on Biological Therapy, 15(3):337-351, 2014.
Abbink et al., "Comparative Seroprevalence and Immunogenicity of Six Rare Serotype Recombinant Adenovirus Vaccine Vectors from Subgroups B and D," Journal of Virology, 81(9):4654-4663, 2007.
Alba et al., "Vector Systems for Prenatal Gene Therapy: Principles of Adenovirus Design and Production," Methods in Molecular Biology, 891:55-84, 2012.
Bradley, et al., "Adenovirus Serotype 5-Specific Neutralizing Antibodies Target Multiple Hexon Hypervariable Regions," Journal of Virology, 86:1267-72, 2012.
Bruder et al., "Modification of Ad5 Hexon Hypervaribable Regions Circumvents Pre-Existing Ad5 Neutralizing Antibodies and Induces Protective Immune Responses," PLoS ONE, 7(4):e33920, 2012.
Gall et al., "Construction and Characterization of Hexon-Chimeric Adenoviruses: Specification of Adenovirus Serotype," Journal of Virology, 72(12):10260-10264, 1998.
Ma et al., "Synergistic suppression effect on tumor growth of hepatocellular carcinoma by combining oncolytic adenovirus carrying XAF1 with cisplatin," J Cancer Res Clin Oncol, 141:419-429, 2015.
Roy et al., "Circumvention of Immunity to the Adenovirus Major Coat Protein Hexon," Journal of Virology, 72(8):6875-6879, 1998.
Roy et al., "Use of chimeric adenoviral vectors to assess capsid neutralization determinants," Virology, 333:207-214, 2005.
Wu et al., "Construction and Characterization of Adenovirus Serotype 5 Packages by Serotype 3 Hexon," Journal of Virology, 76(24):12775-12782, 2002.
Youil et al., "Hexon Gene Switch Strategy for the Generation of Chimeric Recombinant Adenovirus," Human Gene Therapy, 13:311-320, 2002.
Yu et al., "Chimeric hexon HVRs protein reflects partial function of adenovirus," Biochemical and Biophysical Research Communication, 421:170-176, 2012.
Wevers et al, "Novel Adenoviruses in Wild Primates: a High Level of Genetic Diversity and Evidence of Zoonotic Transmissions," Journal of Virology, 85(20):10774-10784, 2011.
Ma et al., "Manipulating Adenovirus Hexon Hypervariable Loops Dictates Immune Neutralisation and Coagulation Factor X-dependent Cell Interaction In Vitro and In Vivo," PLoS Pathog, 11(2):e1004673, 2015.

* cited by examiner

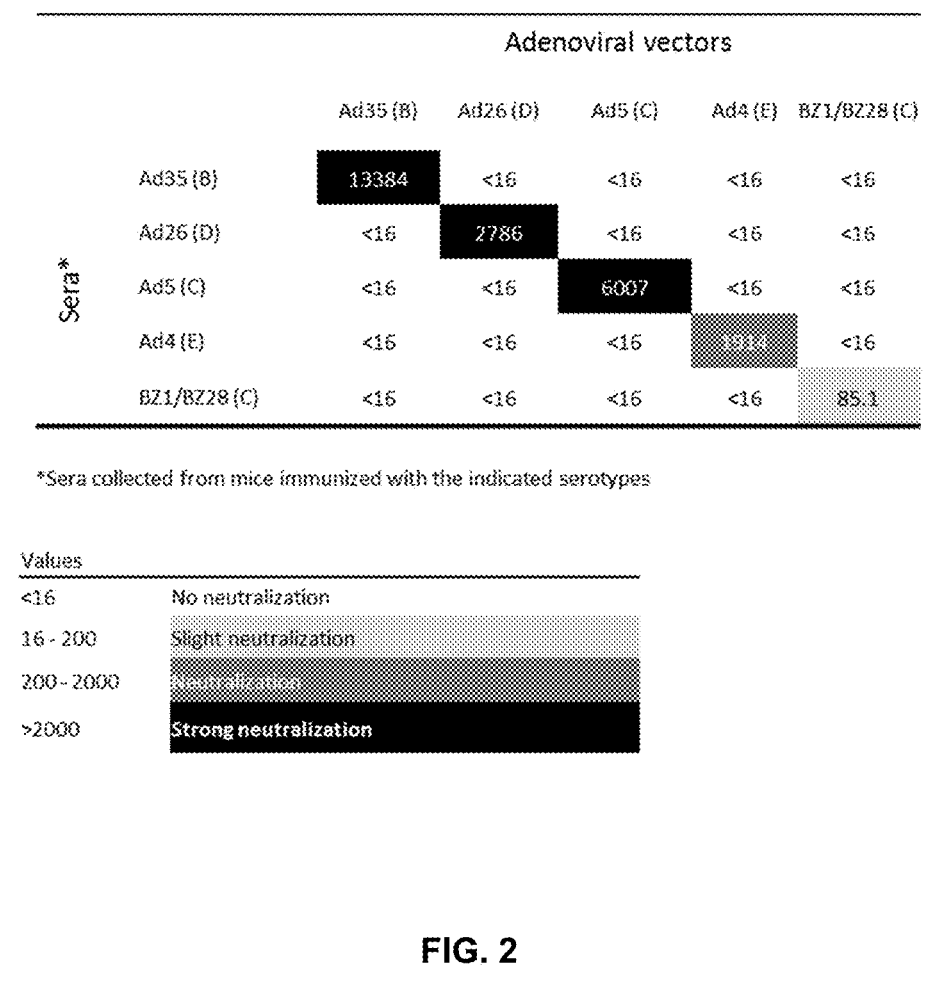

| | | Adenoviral vectors | | | | |
|---|---|---|---|---|---|---|
| | | Ad35 (B) | Ad26 (D) | Ad5 (C) | Ad4 (E) | BZ1/BZ28 (C) |
| Sera* | Ad35 (B) | 13384 | <16 | <16 | <16 | <16 |
| | Ad26 (D) | <16 | 2786 | <16 | <16 | <16 |
| | Ad5 (C) | <16 | <16 | 6007 | <16 | <16 |
| | Ad4 (E) | <16 | <16 | <16 | [illegible] | <16 |
| | BZ1/BZ28 (C) | <16 | <16 | <16 | <16 | 85.1 |

*Sera collected from mice immunized with the indicated serotypes

| Values | |
|---|---|
| <16 | No neutralization |
| 16 - 200 | Slight neutralization |
| 200 - 2000 | Neutralization |
| >2000 | Strong neutralization |

FIG. 2

ADENOVIRUS AND USES THEREOF

CROSS-REFERENCE TO RELATED APPLICATIONS

This application is a Section 371 of International Application No. PCT/EP2018/079725, filed Oct. 30, 2018, which was published in the English language on May 9, 2019 under International Publication No. WO 2019/086466 A1, and claims priority under 35 U.S.C. § 119(b) to European Application No. 17199354.6, filed Oct. 31, 2017, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "065768.11635SL," creation date of Apr. 29, 2020, and having a size of 445 KB. The sequence listing submitted via EFS-Web is part of the specification and is herein incorporated by reference in its entirety.

FIELD OF THE INVENTION

This invention relates to biotechnology. More particularly, to the field and use of adenoviral vectors, such as replication defective adenoviral vectors to deliver antigens and elicit an immune response in hosts.

BACKGROUND OF THE INVENTION

Recombinant adenoviral vectors are widely applied for gene therapy applications and vaccines. AdV-5 vector-based vaccines have been shown to elicit potent and protective immune responses in a variety of animal models (see, e.g., WO2001/02607; WO2002/22080; Shiver et al., Nature 415: 331 (2002); Letvin et al., Ann. Rev. Immunol. 20:73 (2002); Shiver and Emini, Ann. Rev. Med. 55:355 (2004)). However, the utility of recombinant AdV-5 vector-based vaccines will likely be limited by the high seroprevalence of AdV-5-specific neutralizing antibodies (NAbs) in human populations. The existence of anti-AdV-5 immunity has been shown to substantially suppress the immunogenicity of AdV-5-based vaccines in studies in mice, rhesus monkeys, and humans.

One promising strategy to circumvent the existence of pre-existing immunity in individuals previously infected or treated with the most common human adenovirus, e.g., AdV-5, involves the development of recombinant vectors from adenovirus serotypes that do not encounter such pre-existing immunities. One such strategy is based on the use of simian adenoviruses since these do not typically infect humans and exhibit low seroprevalence in human samples. Simian adenoviruses are applicable for human use since it was shown that these viruses could infect human cells in vitro (WO2003/000283; WO2004/037189).

Thus, there is a need in the field for alternative adenoviral vectors that are producible in large quantities, that do not encounter pre-existing immunities in the host, but that are still immunogenic and capable of inducing a strong immune response against the antigens encoded by the heterologous nucleic acids inserted in the vector.

BRIEF SUMMARY OF THE INVENTION

Novel ape adenoviruses have been isolated, which phylogenetically belong to the same group as human adenovirus species C. Adenoviral vectors containing novel nucleic acid sequences of the new ape adenovirus isolates have been developed to meet the unmet need. Provided are isolated nucleic acid sequences encoding hexon polypeptides of the novel ape adenovirus isolates. In certain embodiments, the hexon polypeptide comprises a hexon hypervariable regions-encompassing polypeptide having the amino acid sequence of SEQ ID NO:1. In certain embodiments, the hexon polypeptide comprises the amino acid sequence of a BZ1 hexon polypeptide (SEQ ID NO:2).

Also provided are isolated nucleic acid sequences encoding a fiber polypeptide of the novel ape adenovirus isolates. In certain embodiments, the fiber polypeptide comprises the amino acid sequence of a BZ28 fiber polypeptide (SEQ ID NO:3).

Embodiments of the invention also include isolated fiber and hexon polypeptides encoded by the nucleic acid sequences of the invention.

Further provided herein are isolated nucleic acids comprising a nucleic acid sequence encoding at least one of the hexon polypeptides disclosed herein, and a nucleic acid sequence encoding at least one of the fiber polypeptides disclosed herein. In certain embodiments, provided herein are vectors comprising the isolated nucleic acids described herein. In one embodiment, the vector is a viral vector. In another embodiment, the vector is an expression vector. In one preferred embodiment, the vector is an adenoviral vector. More preferably, the vector further comprises at least one transgene.

Also provided are recombinant cells comprising the vectors described herein.

Such cells can be used for recombinant protein production, recombinant protein expression, or the production of vectors or viral particles. Also provided are methods of producing a vector. The methods comprise (a) growing the recombinant cell disclosed herein under conditions for production of the vector; and (b) isolating the vector from the recombinant cell.

In certain embodiments, provided are immunogenic compositions comprising the vectors disclosed herein. Also provided are methods of inducing an immune response in a subject in need thereof, comprising administering to the subject the immunogenic compositions disclosed herein.

In certain embodiments, provided are adenoviral vectors comprising (a) at least one transgene; and (b) a nucleic acid sequence encoding a hexon polypeptide according to embodiments of the invention. The hexon polypeptide can, for example, comprise a hexon hypervariable regions-encompassing polypeptide having the amino acid sequence of SEQ ID NO:1. In certain embodiments, the hexon polypeptide comprises the amino acid sequence of a BZ1 hexon polypeptide (SEQ ID NO:2) or the amino acid sequence of a BZ28 hexon polypeptide (SEQ ID NO:5).

In certain embodiments, provided are adenoviral vectors comprising (a) at least one transgene; and (b) a nucleic acid sequence encoding a fiber polypeptide according to embodiments of the invention. In certain embodiments, the fiber polypeptide comprises an amino acid sequence selected from a BZ1 (SEQ ID NO:4) or a BZ28 fiber polypeptide (SEQ ID NO:3). Embodiments of the invention also include adenoviral vectors comprising (a) at least one transgene; (b) a nucleic acid sequence encoding a hexon polypeptide according to embodiments of the invention; and (c) a nucleic acid sequence encoding a fiber polypeptide according to embodiments of the invention.

In certain embodiments, the adenoviral vectors provided herein are replication-defective adenovirus vectors (rAd). In one embodiment, the adenoviral vectors can comprise an E1 deletion. In certain embodiments, the adenoviral vectors provided herein can further comprise an E3 deletion. The adenoviral vectors can be simian adenoviral vectors comprising adenoviral nucleic acid sequences from one or more simian adenoviruses (SAdV), such as chimpanzee adenoviruses (e.g., ChAd3); gorilla adenoviruses; or rhesus adenoviruses (e.g., rhAd51, rhAd52 or rhAd53). The adenoviral vectors can be human adenoviral vectors comprising adenoviral sequences from one or more human adenoviruses (e.g., hAdV-4, hAdV-5, hAdV-26, hAdV-35). Preferably, the adenoviral vector is a chimeric adenoviral vector comprising one or more human adenoviral nucleic acid sequences. The human adenoviral nucleic acid sequences can, for example, be from human adenovirus-4 (hAdV-4), human adenovirus-5 (hAdV-5), human adenovirus-26 (hAdV-26), or human adenovirus-35 (hAdV-35). The adenoviral vectors can, for example, comprise a human adenovirus-5 (hAdV-5) E4 orf6 and orf 6/7.

In certain embodiments, the transgene is located adjacent to an inverted terminal repeat (ITR). In certain embodiments, a transgene is located at or adjacent to the E1 deletion, at or adjacent to the E3 deletion, and/or adjacent to the right ITR (rITR).

In certain embodiments, the adenoviral vectors provided herein comprise the nucleic acid sequence of SEQ ID NO:9 or SEQ ID NO:10.

Also provided are immunogenic compositions or vaccines comprising the adenoviral vectors described herein and a pharmaceutically acceptable carrier. Further provided are methods for inducing an immune response in a subject in need thereof. The methods comprise administering to the subject the vaccines disclosed herein. Further provided are methods of producing a vaccine. The methods comprise combining an adenoviral vector disclosed herein with a pharmaceutically acceptable carrier.

BRIEF DESCRIPTION OF THE DRAWINGS

The foregoing summary, as well as the following detailed description of preferred embodiments of the present application, will be better understood when read in conjunction with the appended drawings. It should be understood, however, that the application is not limited to the precise embodiments shown in the drawings.

FIG. 1A shows the experimental set-up. FIG. 1B shows the cellular immune response induced by Ad26.FLuc and BZ1/BZ28.FLuc, against the vector-encoded insert (i.e. FLuc, firefly luciferase) 2 weeks after immunization, as determined by Interferon gamma (IFN-γ) ELISPOT analysis. FIG. 1C shows a graph of FLuc-specific IgG antibody titers induced in mice, 2 weeks after immunization with Ad26.FLuc, BZ1/BZ28.Fluc and an empty Ad26 vector.

FIG. 2 shows homologous and heterologous adenovirus neutralization titers induced in mice immunized with adenoviral vectors Ad35, Ad26, Ad5, Ad4, and BZ1/BZ28.

DETAILED DESCRIPTION OF THE INVENTION

Figure 1A:
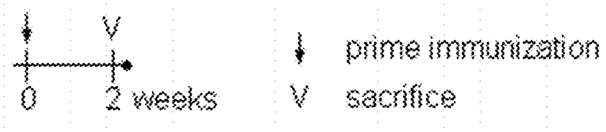
FIG. 1A-FIG. 1C show the cellular and humoral immune responses induced by BZ1/BZ28.FLuc.

This disclosure is based upon, at least in part, the isolation and identification of new ape adenovirus serotypes, allocated into human adenovirus species C, as well as construction and evaluation of vaccine vectors comprising the nucleic acids encoding variable regions of the ape hexon and fiber polypeptides. This disclosure is additionally based upon, at least in part, the creation of chimeric adenoviral vectors comprising a gorilla adenovirus backbone and a chimpanzee adenovirus hexon sequence. The adenoviral vectors are capable of eliciting an immune response and, furthermore, have low seroprevalence in humans. The adenoviral vectors can be formulated for vaccines and used to induce protective immunity against specific antigens of interest.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize or be able to ascertain using no more than routine experimentation, many equivalents to the specific embodiments of the invention described herein. Such equivalents are intended to be encompassed by the invention.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, the term "consists of," or variations such as "consist of" or "consisting of," as used throughout the specification and claims, indicate the inclusion of any recited integer or group of integers, but that no additional integer or group of integers can be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition. See M.P.E.P. § 2111.03.

As used herein, "subject" means any animal, preferably a mammal, most preferably a human, to whom will be or has been vaccinated by a method according to an embodiment of the invention. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

The words "right", "left", "lower" and "upper" designate directions in the drawings to which reference is made.

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

The terms "identical" or percent "identity," in the context of two or more nucleic acids or polypeptide sequences (e.g., hexon and fiber polypeptides and polynucleotides that encode them), refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990)*J Mol. Biol.* 215: 403-410 and Altschul et al. (1997) *Nucleic Acids Res.* 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased.

Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

As used herein, the term "protective immunity" or "protective immune response" means that the vaccinated subject is able to control an infection with the pathogenic agent against which the vaccination was done. The pathogenic agent can, for example, be an antigenic gene product or antigenic protein, or a fragment thereof. Usually, the subject having developed a "protective immune response" develops only mild to moderate clinical symptoms or no symptoms at all. Usually, a subject having a "protective immune response" or "protective immunity" against a certain agent will not die as a result of the infection with said agent.

The term "adjuvant" is defined as one or more substances that cause stimulation of the immune system. In this context, an adjuvant is used to enhance an immune response to the adenovirus vectors of the invention.

As used herein, the term "antigenic gene product or fragment thereof" or "antigenic protein" can include a bacterial, viral, parasitic, or fungal protein, or a fragment thereof. Preferably, an antigenic protein or antigenic gene product is capable of raising in a host a protective immune response, e.g., inducing an immune response against a disease or infection (e.g., a bacterial, viral, parasitic, or fungal disease or infection), and/or producing an immunity in (i.e., vaccinating) a subject against a disease or infection, that protects the subject against the disease or infection.

Adenoviral Vectors

Exposure to certain adenoviruses has resulted in immune responses against certain adenoviral serotypes, which can affect efficacy of adenoviral vectors. Because infections with human adenoviruses are common in humans, the prevalence of neutralizing antibodies against human adenoviruses in human populations is high. The presence of such neutralizing antibodies in individuals may be expected to reduce the efficacy of a gene transfer vector based on a human adenoviral backbone. One way to circumvent the reduction of efficacy is to replace the epitopes on the adenoviral capsid proteins that are the targets of neutralizing antibodies. The target sequences on the capsid proteins can be replaced with protein sequences from other adenoviruses which are of low prevalence, and therefore against which neutralizing antibodies are rare in human populations.

A "capsid protein" refers to a protein on the capsid of an adenovirus (e.g., BZ1, BZ28, HAdV-4) or a functional fragment or derivative thereof that is involved in determining the serotype and/or tropism of a particular adenovirus. Capsid proteins typically include the fiber, penton and/or hexon proteins. In certain embodiments, the capsid protein is an entire or full length capsid protein of the adenovirus. In other embodiments, the capsid protein is a fragment or a derivative of a full length capsid protein of the adenovirus.

In certain embodiments, the hexon, penton and fiber encoded by an adenoviral vector of the invention are of the same or different adenoviral background (i.e., a BZ1 hexon and BZ28 fiber, a BZ1 hexon and a BZ1 fiber, a BZ28 hexon and a BZ1 fiber, a BZ28 hexon and a BZ28 fiber, etc).

A "hexon polypeptide" refers to adenovirus hexon coat proteins, functional fragments, and derivatives thereof.

A "fiber polypeptide" refers to adenovirus fiber proteins, functional fragments, and derivatives thereof.

One target of neutralizing antibodies against adenoviruses is the major coat protein, the hexon protein. Replacing the hexon protein with the hexon protein from rare adenoviruses, more preferably replacing the variable sequences within the hexon protein that define serotype and that bind to neutralizing antibodies, such as those isolated from simians described herein, can allow for the construction of adenovirus vectors that would be less susceptible to neutralization by antibodies commonly found in humans.

A second target of neutralizing antibodies against adenoviruses is the fiber protein. Replacing the fiber protein with fiber sequences from rare adenoviruses that are of non-human origin, more preferably replacing the variable sequences within the fiber protein, such as those isolated from simians described herein, can also allow for the construction of adenovirus vectors that would be less susceptible to neutralization by antibodies commonly found in humans. A combination of the fiber replacement with hexon replacements described above can confer additional resistance to neutralization by antibodies commonly present in human populations.

This disclosure provides isolated nucleic acid sequences encoding hexon and/or fiber polypeptides derived from isolated simian adenovirus serotypes and adenoviral vectors comprising at least one of the isolated nucleic acid sequences.

An "adenoviral vector" refers to a recombinant vector derived from or containing at least a portion of an adenoviral genome.

In preferred embodiments, the isolated nucleic acid sequences encode hexon polypeptides comprising a hexon hypervariable regions-encompassing polypeptide having the amino acid sequence of SEQ ID NO:1. In certain embodiments, the hexon polypeptide comprises the amino acid sequence selected from a BZ1 hexon polypeptide (SEQ ID NO:2) or a BZ28 hexon polypeptide (SEQ ID NO:5).

In preferred embodiments, the isolated nucleic acid sequences encode fiber polypeptides. The fiber polypeptide can, for example, comprise the amino acid sequence selected from a BZ1 fiber polypeptide (SEQ ID NO:4) or a BZ28 fiber polypeptide (SEQ ID NO:3).

In preferred embodiments, provided is an isolated nucleic acid comprising a nucleic acid sequence encoding at least one of the hexon polypeptides disclosed herein and a nucleic acid sequence encoding at least one of the fiber polypeptides disclosed herein.

In preferred embodiments, provided are vectors, preferably adenoviral vectors, comprising at least one of an isolated nucleic acid sequence encoding a hexon polypeptide and/or an isolated nucleic acid sequence encoding a fiber polypeptide according to embodiments of the invention. The adenoviral vectors can, for example, comprise a BZ1 hexon polypeptide (SEQ ID NO:2) or a BZ28 hexon polypeptide (SEQ ID NO:5). The adenoviral vectors can, for example, comprise a BZ1 fiber polypeptide (SEQ ID NO:4) or a BZ28 fiber polypeptide (SEQ ID NO:3). In certain embodiments, the adenoviral vector comprises a nucleic acid encoding a hexon polypeptide, wherein the hexon polypeptide comprises an amino acid sequence selected from a BZ1 hexon polypeptide (SEQ ID NO:2) or a BZ28 hexon polypeptide (SEQ ID NO:5); and a nucleic acid encoding a fiber polypeptide, wherein the fiber polypeptide comprises an amino acid sequence selected from a BZ1 fiber polypeptide (SEQ ID NO:4) or a BZ28 fiber polypeptide (SEQ ID NO:3). The adenoviral vectors can, for example, comprise at least one transgene; and a nucleic acid sequence encoding a hexon polypeptide and/or a fiber polypeptide, wherein the hexon polypeptide comprises hexon hypervariable regions-encompassing polypeptides disclosed herein and the fiber polypeptide comprises fiber polypeptides described herein.

Typically, an adenoviral vector of the invention comprises the entire recombinant adenoviral genome on, e.g., a plasmid, cosmid, or baculovirus vector. The nucleic acid molecules of the invention can be in the form of RNA or in the form of DNA obtained by cloning or produced synthetically. The DNA can be double-stranded or single-stranded.

One of ordinary skill will recognize that elements derived from multiple serotypes can be combined in a single adenoviral vector, for example human or simian adenovirus. Thus, a chimeric adenovirus vector that combines desirable properties from different serotypes can be produced. Thus, in some embodiments, a chimeric adenovirus vector of the invention could combine the absence of pre-existing immunity of the simian hexon and/or fiber polypeptide sequences with the high level antigen delivery and presentation capacity of an existing adenoviral vectors, such as rAd4, rAd5, rAd26 or rAd35.

Advantages of adenoviral vectors for use as vaccines include ease of manipulation, good manufacturability at large scale, and an excellent safety record based on many years of experience in research, development, manufacturing and clinical trials with numerous adenoviral vectors that have been reported. Adenoviral vectors that are used as vaccines generally provide a good immune response to the transgene-encoded protein, including a cellular immune response. An adenoviral vector according to the invention can be based on any type of adenovirus, and in certain embodiments is a human adenovirus, which can be of any group or serotype.

In preferred embodiments, the recombinant adenovirus is based upon a human adenovirus from group A, B, C, D, E, F or G. In other preferred embodiments, the recombinant adenovirus is based upon a human adenovirus serotype 5, 11, 26, 34, 35, 48, 49, or 50. In other embodiments, it is a simian adenovirus, such as chimpanzee or gorilla adenovirus, which can be of any serotype. In certain embodiments, the recombinant adenovirus is based upon chimpanzee adenovirus type 1, 3, 7, 8, 21, 22, 23, 24, 25, 26, 27.1, 28.1, 29, 30, 31.1, 32, 33, 34, 35.1, 36, 37.2, 39, 40.1, 41.1, 42.1, 43, 44, 45, 46, 48, 49, 50, 67, or SA7P.

In a more preferred embodiment, the chimpanzee adenovirus vector of the second composition is ChAdV3. Recombinant chimpanzee adenovirus serotype 3 (ChAd3 or cAd3) is a subgroup C adenovirus with properties similar to those of human adenovirus serotype 5 (Ad5). ChAd3 has been shown to be safe and immunogenic in human studies evaluating candidate vaccines for hepatitis C virus (HCV) (Barnes E, et al. 2012 Science translational medicine 4: 115ra1). It was reported that ChAd3-based vaccines were capable of inducing an immune response comparable to a human Ad5 vectored vaccine. See, e.g., Peruzzi D, et al. 2009 Vaccine 27: 1293-300 and Quinn K M, et al. 2013 J Immunol 190: 2720-35; WO 2005/071093; WO2011/0130627, etc.

Adenoviral vectors, methods for construction thereof and methods for propagating thereof, are well known in the art and are described in, for example, U.S. Pat. Nos. 5,559,099, 5,837,511, 5,846,782, 5,851,806, 5,994,106, 5,994,128, 5,965,541, 5,981,225, 6,040,174, 6,020,191, and 6,113,913, and Thomas Shenk, "Adenoviridae and their Replication", M. S. Horwitz, "Adenoviruses", Chapters 67 and 68, respectively, in *Virology*, B. N. Fields et al., eds., 3d ed., Raven Press, Ltd., New York (1996), and other references mentioned herein. Typically, construction of adenoviral vectors involves the use of standard molecular biological techniques, such as those described in, for example, Sambrook et al., *Molecular Cloning, a Laboratory Manual,* 2d ed., Cold Spring Harbor Press, Cold Spring Harbor, N.Y. (1989), Watson et al., *Recombinant DNA,* 2d ed., *Scientific American Books* (1992), and Ausubel et al., *Current Protocols in Molecular Biology*, Wiley Interscience Publishers, NY (1995), and other references mentioned herein.

In certain embodiments, the adenoviral vector comprises an E1 deletion and/or an E3 deletion. An E1 or E3 deletion can, for example, include a complete deletion of the gene or a partial deletion, which renders the E1 or E3 gene product functionally defective. Thus, in certain embodiments, the adenovirus is replication deficient, e.g. because it contains a deletion in the E1 region of the genome. As known to the skilled person, in case of deletions of essential regions from the adenovirus genome, the functions encoded by these regions have to be provided in trans, preferably by the producer cell, i.e. when parts or whole of E1, E2 and/or E4 regions are deleted from the adenovirus, these have to be present in the producer cell, for instance integrated in the genome thereof, or in the form of so-called helper adenovirus or helper plasmids. The adenovirus may also have a deletion in the E3 region, which is dispensable for replication, and hence such a deletion does not have to be complemented. One or more of the E1, E2, E3 and E4 regions can also be inactivated by other means, such as by inserting a transgene of interest (usually linked to a promoter) into the regions to be inactivated.

A producer cell (sometimes also referred to in the art and herein as 'packaging cell' or 'complementing cell') that can be used can be any producer cell wherein a desired adenovirus can be propagated. For example, the propagation of recombinant adenovirus vectors is done in producer cells that complement deficiencies in the adenovirus. Such producer cells preferably have in their genome at least an adenovirus E1 sequence, and thereby are capable of complementing recombinant adenoviruses with a deletion in the E1 region. Any E1-complementing producer cell can be used, such as human retina cells immortalized by E1, e.g. 911 or PER.C6 cells (see U.S. Pat. No. 5,994,128), E1-transformed amniocytes (See EP patent 1230354), E1-transformed A549 cells (see e.g. WO 98/39411, U.S. Pat. No. 5,891,690), GH329:HeLa (Gao et al., 2000*, Hum Gene Ther* 11: 213-19), 293, and the like. In certain embodiments, the producer cells are for instance HEK293 cells, or PER.C6 cells, or 911 cells, or IT293SF cells, and the like. Production of adenoviral vectors in producer cells is reviewed in (Kovesdi et al., 2010*, Viruses* 2: 1681-703).

In certain embodiments, the adenoviral vector is a chimeric adenoviral vector comprising one or more human adenoviral nucleic acid sequences. The human adenoviral nucleic acids can, for example, be selected from human adenovirus-4 (Ad-4), human adenovirus-5 (Ad-5), human adenovirus-26 (Ad-26), or human adenovirus-35 (Ad-35). In certain embodiments, an E1-deficient adenoviral vector comprises the E4-orf6 coding sequence of an adenovirus of human Ad5. This allows propagation of such adenoviruses in well-known complementing cell lines that express the E1 genes of Ad5, such as for example 293 cells or PER.C6 cells (see, e.g. Fallaux et al., 1998, *Hum Gene Ther* 9: 1909-17, Havenga et al., 2006, *J Gen Virol* 87: 2135-43; WO 03/104467, incorporated in their entirety by reference herein).

In certain embodiments, the adenoviral vector comprises a transgene. A "transgene" refers to a heterologous nucleic acid, which is a nucleic acid that is not naturally present in the vector, and according to the present invention the transgene can encode an antigenic gene product or antigenic protein that elicits an immune response in the subject. The transgene can, for example, be introduced into the vector by standard molecular biology techniques. The transgene can, for example, be cloned into a deleted E1 or E3 region of an adenoviral vector, or in the region between the E4 region and the rITR. A transgene is generally operably linked to expression control sequences. In preferred embodiments, the transgene is inserted at a transgene insertion site.

If required, the hexon or fiber nucleic acid sequence according to embodiments of the invention, and/or the transgene can be codon-optimized to ensure proper expression in the treated host (e.g., human). Codon-optimization is a technology widely applied in the art.

The transgene can be under the control of (i.e., operably linked to) an adenovirus-derived promoter (e.g., the Major Late Promoter) or can be under the control of a heterologous promoter. Examples of suitable heterologous promoters include the CMV promoter and the RSV promoter. Preferably, the promoter is located upstream of the heterologous gene of interest within an expression cassette.

In preferred embodiments, the adenoviral vector comprises a nucleic acid sequence of SEQ ID NO:9 or SEQ ID NO:10.

Immunogenic Compositions

Immunogenic compositions are compositions comprising an immunologically effective amount of purified or partially purified human or simian (e.g., gorilla) adenoviral vectors for use in the invention. Said compositions can be formulated as a vaccine (also referred to as an "immunogenic composition") according to methods well known in the art. Such compositions can include adjuvants to enhance immune responses. The optimal ratios of each component in the formulation can be determined by techniques well known to those skilled in the art in view of the present disclosure.

The immunogenic compositions according to embodiments of the present invention can be made using methods known to those of skill in the art in view of the present disclosure. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

The immunogenic compositions useful in the invention can comprise adjuvants. Adjuvants suitable for co-administration in accordance with the invention should be ones that are potentially safe, well tolerated and effective in people including QS-21, Detox-PC, MPL-SE, MoGM-CSF, TiterMax-G, CRL-1005, GERBU, TERamide, PSC97B, Adjumer, PG-026, GSK-I, AS01, AS03, AS04, AS15, GcMAF, B-alethine, MPC-026, Adjuvax, CpG ODN, Betafectin, Alum, and MF59.

Other adjuvants that can be administered include lectins, growth factors, cytokines and lymphokines such as alpha-interferon, gamma interferon, platelet derived growth factor (PDGF), granulocyte-colony stimulating factor (gCSF), granulocyte macrophage colony stimulating factor (gMCSF), tumor necrosis factor (TNF), epidermal growth factor (EGF), IL-I, IL-2, IL-4, IL-6, IL-8, IL-10, and IL-12 or encoding nucleic acids therefore.

The compositions of the invention can comprise a pharmaceutically acceptable excipient, carrier, buffer, stabilizer or other materials well known to those skilled in the art. Such materials should be non-toxic and should not interfere with the efficacy of the active ingredient. The precise nature of the carrier or other material can depend on the route of administration, e.g., intramuscular, subcutaneous, oral, intravenous, cutaneous, intramucosal (e.g., gut), intranasal or intraperitoneal routes.

Method for Inducing Protective Immunity

Another general aspect of the invention relates to a method of inducing an immune response in a subject in need thereof. The methods can, for example, comprise administering to the subject a vaccine comprising an adenoviral vector described herein and a pharmaceutically acceptable carrier. Also provided herein are methods of producing a vaccine. The methods comprise combining an adenoviral vector described herein with a pharmaceutically acceptable carrier.

Any of the immunogenic compositions according to embodiments of the invention, including but not limited to those described herein, can be used in methods of the invention as a vaccine.

Administration of the immunogenic compositions/vaccines comprising the vectors is typically intramuscular or subcutaneous. However other modes of administration such as intravenous, cutaneous, intradermal or nasal can be envisaged as well. Intramuscular administration of the immunogenic compositions can be achieved by using a needle to inject a suspension of the adenovirus vector. An alternative is the use of a needleless injection device to administer the composition (using, e.g., Biojector™) or a freeze-dried powder containing the vaccine.

For intravenous, cutaneous or subcutaneous injection, or injection at the site of affliction, the vector will be in the form of a parenterally acceptable aqueous solution which is pyrogen-free and has suitable pH, isotonicity and stability. Those of skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required. A slow-release formulation can also be employed.

Typically, administration will have a prophylactic aim to generate an immune response against an antigen of interest (e.g., a bacterial, viral, parasitic, and/or fungal pathogen) before infection or development of symptoms. Diseases and disorders that can be treated or prevented in accordance with the invention include those in which an immune response can play a protective or therapeutic role. In other embodiments, the adenovirus vectors can be administered for post-exposure prophylactics.

The immunogenic compositions containing the human or simian (e.g., gorilla) adenovirus vectors are administered to a subject, giving rise to an immune response to the antigen of interest in the subject. An amount of a composition sufficient to induce a detectable immune response is defined to be an "immunologically effective dose" or an "effective amount" of the composition. The immunogenic compositions of the invention can induce a humoral as well as a cell-mediated immune response. In a typical embodiment the immune response is a protective immune response.

The actual amount administered, and rate and time-course of administration, will depend on the nature and severity of what is being treated. Prescription of treatment, e.g., decisions on dosage etc., is within the responsibility of general practitioners and other medical doctors, or in a veterinary context a veterinarian, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. ed., 1980.

Following production of adenovirus vectors and optional formulation of such particles into compositions, the vectors can be administered to an individual, particularly human or other primate. Administration can be to humans, or another mammal, e.g., mouse, rat, hamster, guinea pig, rabbit, sheep, goat, pig, horse, cow, donkey, monkey, dog or cat. Delivery to a non-human mammal need not be for a therapeutic purpose, but can be for use in an experimental context, for instance in investigation of mechanisms of immune responses to the adenovirus vectors.

In one exemplary regimen, the adenoviral vector is administered (e.g., intramuscularly) in a volume ranging between about 100 μl to about 10 ml containing concentrations of about $10^4$ to $10^{12}$ virus particles/ml. Preferably, the adenoviral vector is administered in a volume ranging between 0.1 and 2.0 ml. For example, the adenoviral vector can be administered with 100 μl, 500 μl, 1 ml, 2 ml. More preferably the adenoviral vector is administered in a volume of 0.5 ml. Optionally, the adenoviral vector can be administered in a concentration of about $10^7$ vp/ml, $10^8$ vp/ml, $10^9$ vp/ml, $10^{10}$ vp/ml, $5\times10^{10}$ vp/ml, $10^{11}$ vp/ml, or $10^{12}$ vp/ml. Typically, the adenoviral vector is administered in an amount of about $10^9$ to about $10^{12}$ viral particles (vp) to a human subject during one administration, more typically in an amount of about $10^{10}$ to about $10^{12}$ vp.

The initial vaccination can be followed by a boost or a kick from a vaccine/composition comprising the same adenoviral vector encoding an antigen of interest or a vaccine/composition comprising a different adenoviral vector encoding the same antigen of interest.

The composition can, if desired, be presented in a kit, pack or dispenser, which can contain one or more unit dosage forms containing the active ingredient. The kit, for example, can comprise metal or plastic foil, such as a blister pack. The kit, pack, or dispenser can be accompanied by instructions for administration.

The compositions of the invention can be administered alone or in combination with other treatments, either simultaneously or sequentially dependent upon the condition to be treated.

EMBODIMENTS

The invention provides also the following non-limiting embodiments.

Embodiment 1 is an isolated nucleic acid sequence encoding a hexon polypeptide comprising a hexon hypervariable regions-encompassing polypeptide having the amino acid sequence of SEQ ID NO:1.

Embodiment 2 is the isolated nucleic acid sequence of embodiment 1, wherein the hexon polypeptide comprises the amino acid sequence of a BZ1 hexon polypeptide (SEQ ID NO:2).

Embodiment 3 is an isolated nucleic acid sequence of embodiment 1 or 2, further comprising a nucleic acid sequence encoding a fiber polypeptide.

Embodiment 4 is the isolated nucleic acid sequence of embodiment 3, wherein the fiber polypeptide comprises an amino acid sequence selected from a BZ1 fiber polypeptide (SEQ ID NO:4) or a BZ28 fiber polypeptide (SEQ ID NO:3).

Embodiment 5 is an isolated nucleic acid sequence encoding a fiber polypeptide comprising the amino acid sequence of a BZ28 fiber polypeptide (SEQ ID NO:3).

Embodiment 6 is a vector comprising the nucleic acid of any of embodiments 1-5.

Embodiment 7 is the vector of embodiment 6, being an adenoviral vector, and further comprising at least one transgene.

Embodiment 8 is a recombinant cell comprising the vector of embodiment 6 or 7.

Embodiment 9 is a method of producing a vector, comprising; (a) growing the recombinant cell of embodiment 8 under conditions for production of the vector; and (b) isolating the vector from the recombinant cell.

Embodiment 10 is an immunogenic composition comprising the vector of embodiment 7.

Embodiment 11 is a method of inducing an immune response in a subject in need thereof, comprising administering to the subject the immunogenic composition of embodiment 10.

Embodiment 12 is an adenoviral vector comprising (a) at least one transgene; and (b) a nucleic acid sequence encoding a hexon polypeptide comprising a hexon hypervariable regions-encompassing polypeptide having the amino acid sequence of SEQ ID NO:1.

Embodiment 13 is the adenoviral vector of embodiment 12, wherein the hexon polypeptide comprises the amino acid sequence of a BZ1 hexon polypeptide (SEQ ID NO:2).

Embodiment 14 is the adenoviral vector of embodiment 12 or 13 further comprising a nucleic acid sequence encoding a fiber polypeptide.

Embodiment 15 is the adenoviral vector of embodiment 14, wherein the fiber polypeptide comprises an amino acid sequence selected from a BZ1 fiber polypeptide (SEQ ID NO:4) or a BZ28 fiber polypeptide (SEQ ID NO:3).

Embodiment 16 is an adenoviral vector comprising (a) at least one transgene; and (b) a nucleic acid sequence encoding a fiber polypeptide comprising the amino acid sequence of a BZ28 fiber polypeptide (SEQ ID NO:3).

Embodiment 17 is an adenoviral vector comprising (a) at least one transgene; (b) a nucleic acid sequence encoding a hexon polypeptide comprising an amino acid sequence selected from a BZ1 hexon polypeptide (SEQ ID NO:2) or a BZ28 hexon polypeptide (SEQ ID NO:5); and (c) a nucleic acid sequence encoding a fiber polypeptide comprising an amino acid sequence selected from a BZ1 fiber polypeptide (SEQ ID NO:4) or a BZ28 fiber polypeptide (SEQ ID NO:3).

Embodiment 18 is the adenoviral vector of any one of embodiments 12-17, wherein the adenoviral vector further comprises an E1 deletion.

Embodiment 19 is the adenoviral vector of any one of embodiments 12-18, wherein the adenoviral vector further comprises an E3 deletion.

Embodiment 20 is the adenoviral vector of any one of embodiments 12-19, wherein the adenoviral vector is a chimeric adenoviral vector comprising one or more human adenoviral nucleic acid sequences.

Embodiment 21 is the adenoviral vector of embodiment 20, wherein the human adenoviral nucleic acid sequences are from human adenovirus-4, human adenovirus-5, human adenovirus-26, or human adenovirus-35.

Embodiment 22 is the adenoviral vector of embodiment 21, wherein the adenoviral vector comprises a human adenovirus-5 (HAdv-5) E4 orf6.

Embodiment 23 is the adenoviral vector of any one or embodiments 12-22, wherein the transgene is located adjacent to an inverted terminal repeat (ITR).

Embodiment 24 is the adenoviral vector of embodiment 23, wherein a transgene is located at or adjacent to the E1 deletion, at or adjacent to the E3 deletion, and/or adjacent to the ITR.

Embodiment 25 is the adenoviral vector of any one of embodiments 12-24, wherein the adenoviral vector comprises a nucleic acid sequence selected from SEQ ID NO:9 or SEQ ID NO:10.

Embodiment 26 is a vaccine comprising an adenoviral vector according to any of embodiments 12-25 and a pharmaceutically acceptable carrier.

Embodiment 27 is a method for inducing an immune response in a subject in need thereof, the method comprising administering to the subject the vaccine of embodiment 26.

Embodiment 28 is a method of producing a vaccine, comprising combining an adenoviral vector according to any of embodiments 12-25 with a pharmaceutically acceptable carrier.

Embodiment 29 is an isolated hexon polypeptide comprising a hexon hypervariable regions-encompassing polypeptide having the amino acid sequence of SEQ ID NO:1.

Embodiment 30 is the isolated hexon polypeptide of embodiment 29, wherein the hexon polypeptide comprises the amino acid sequence of a BZ1 hexon polypeptide (SEQ ID NO:2).

Embodiment 31 is an isolated fiber polypeptide, wherein the fiber polypeptide comprises the amino acid sequence of a BZ28 fiber polypeptide (SEQ ID NO:3).

EXAMPLES

Example 1: Generation of E1- and E3-Deleted Vectors Based on the Backbone of Novel Adenovirus Isolate BZ1 and Comprising the Fiber Sequence of Novel Adenovirus Isolate BZ28

A new gorilla adenovirus isolate, BZ1 (also designated JAd4-WT), was identified and its genome fully sequenced. A new chimpanzee isolate, BZ28 (also designated JAd5-WT), was also identified and its fiber gene and a portion of its hexon gene sequenced. The new adenovirus isolates BZ1 and BZ28 were both found to phylogenetically belong to the human adenovirus species C (HAdV-C). The full genome nucleotide sequence of BZ1 was determined to be SEQ ID NO:6. The fiber and (partial) hexon nucleotide sequences of BZ28 were determined to be SEQ ID NO:3 and SEQ ID NO:5, respectively.

Figure 4:
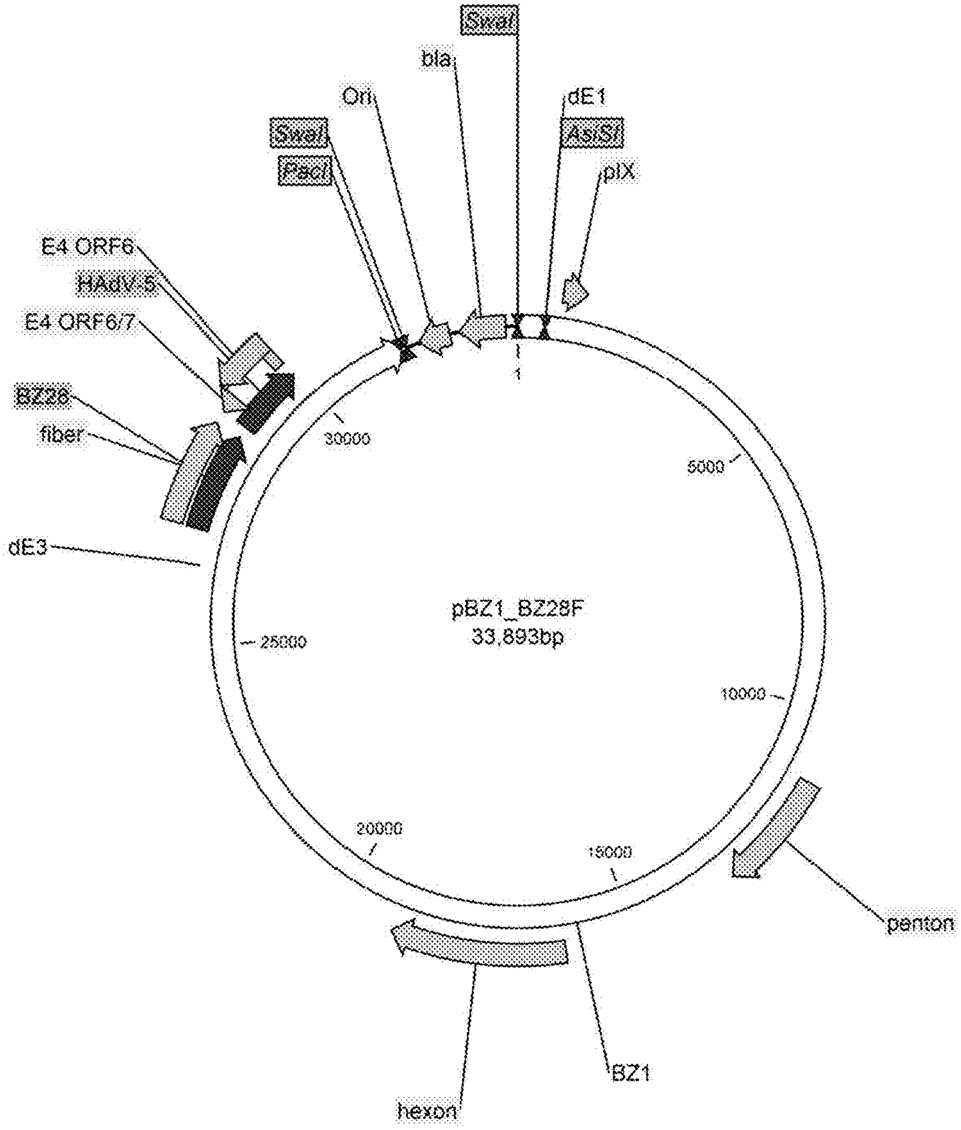
FIG. 4 shows a schematic of the plasmid pBZ1_BZ28F.
Figure 5:
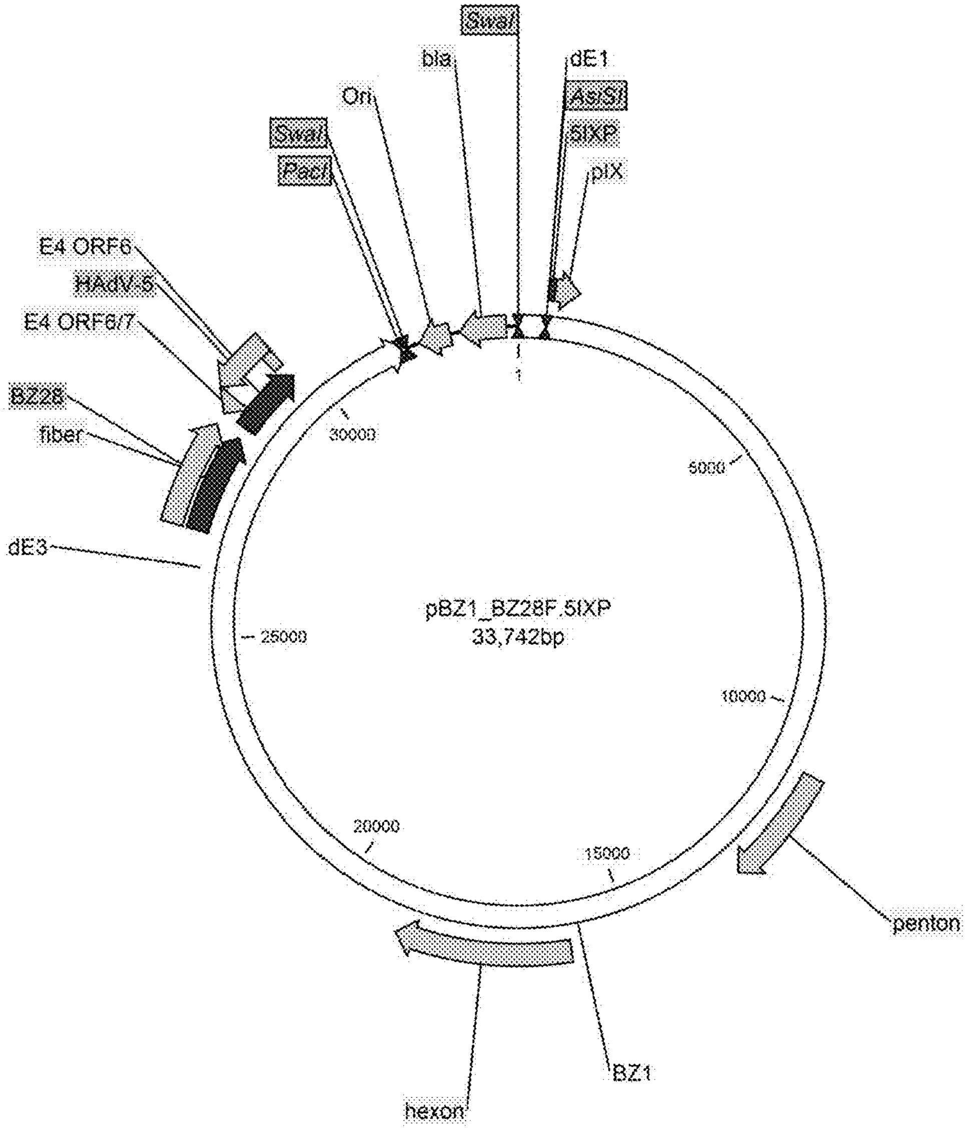
FIG. 5 shows a schematic of the plasmid pBZ1_BZ28F.5IXP.

Description of the Single Plasmid System Used for the Generation of BZ1/BZ28-Based Ad Vectors pBZ1_BZ28F (SEQ ID NO:9; FIG. 4) and pBZ1_BZ28F.5IXP (SEQ ID NO:10; FIG. 5) are plasmids that each carry a full-length, E1- and E3-deleted, BZ1 isolate-based adenoviral vector genome wherein the fiber-encoding sequence is replaced by that of the BZ28 isolate. The BZ1/BZ28-based Ad vector genome sequences contained within these plasmids are set forth in SEQ ID NO:11 and SEQ ID NO:12, respectively. Within each of these plasmids, the adenoviral vector genome is flanked by two SwaI restriction enzyme sites (i.e. one SwaI site is located at either end of the vector genome). These SwaI sites are meant to facilitate excision of the Ad vector genome from the plasmid backbone prior to viral rescue by transfection of suitable E1-complementing cells (such as HEK293, 911, and PER.C6 cells). The Ad vector genomes comprised by these plasmids further carry certain restriction enzyme sites introduced in the location of the E1 deletion and adjacent to the right inverted terminal repeat (RITR). These restriction enzyme sites were selected to be unique in the context of the complete Ad genome plasmids. They represent "transgene insertion sites" that allow for the facile construction, by standard molecular cloning techniques, of Ad vectors carrying one or more transgene expression cassettes inserted at any of said respective locations or any combinations thereof. Ad vector designs and plasmid constructions are described in more detail in the sections below.

BZ1/BZ28-Based Ad Vector Genome Design

The BZ1/BZ28 and BZ1/BZ28.5IXP Ad vector genomes (i.e. SEQ ID NO:11 and SEQ ID NO:12, respectively) were each designed to comprise an E1 deletion, an E3 deletion, different transgene insertion sites, and a replacement of the native E4 open reading frame (orf) 6 and orf6/7 with that of human adenovirus-5 (HAdV-5). The E1 region of each adenovirus was deleted and replaced with a transgene insertion site comprising an AsiSI restriction enzyme site sequence. Another transgene insertion site was created by insertion of a PacI restriction enzyme site sequence adjacent to the inverted terminal repeat (ITR) of each adenovirus. The Ad vector genomes further comprised a replacement of the (BZ1) E4 orf6 and orf6/7 coding sequences by the corresponding sequences of human adenovirus-5 (HAdV-5). The HAdV-5 replacement sequence, set forth in SEQ ID NO:7, consists of nucleotides 32914-34077 of GenBank sequence AC_000008.

Two types of E1 region deletions were designed and constructed. The BZ1/BZ28-based Ad vector genome comprised by pBZ1_BZ28F carries an E1 region deletion corresponding to removal of nucleotides 491 to 3324 of SEQ ID NO:6. By contrast, the BZ1/BZ28-based Ad vector genome comprised by pBZ1_BZ28F.5IXP carries a larger E1 region-comprising sequence deletion that removes all the E1 coding sequences of BZ1 (i.e. nucleotides 491 to 3484 of SEQ ID NO:6). Furthermore, this latter Ad vector genome was additionally designed to carry a replacement of the non-coding sequence stretch between E1B 55K and pIX coding sequences by that of HAdV-5 (i.e. sequences corresponding to 3485 to 3574 of SEQ ID NO:6 were replaced by nucleotides 3510 to 3608 of GenBank AC_000008 (i.e. by SEQ ID NO:8)).

Construction of Single Plasmids Comprising BZ1/BZ28-Based Ad Vector Genomes pBZ1_BZ28F (SEQ ID NO:9) was constructed by several steps of gene synthesis (performed by GenScript) and standard molecular cloning procedures. First, several successive gene synthesis and subcloning steps were performed that together resulted in the replacement of the 2.3-kbp EcoRI-NdeI fragment of pBR322 (GenBank accession number—J01749.1) by an 8.1-kbp synthesized nucleotide sequence comprising a SwaI restriction sites-flanked sequence that comprises left- and right-end parts of the designed BZ1/BZ28 Ad vector genome wherein said left-end part encompasses the aforementioned E1 deletion and said right-end part encompasses the aforementioned E3 deletion, BZ28 fiber replacement, HAdV-5 E4 orf6 and orf6/7 replacement, and PacI restriction site insertion adjacent to the rITR (within the right-end part). The nucleotide sequence of the resulting plasmid, BZ1/BZ28 intermediate plasmid 1, is set forth in SEQ ID NO:13. Second, the 12.3-kbp NheI-AscI restriction fragment of the BZ1 viral genome (SEQ ID NO:6) was ligated into NheI- and AscI-digested BZ1/BZ28 intermediate plasmid 1, leading to BZ1/BZ28 intermediate plasmid 2. Third, the 11.8-kbp NdeI-HpaI restriction fragment of the BZ1 viral genome was ligated into NdeI- and HpaI-digested BZ1/BZ28 intermediate plasmid 2, leading to BZ1/BZ28 intermediate plasmid 3. Fourth, the 3.3-kbp NdeI-NdeI restriction fragment of the BZ1 viral genome was ligated into NdeI-digested BZ1/BZ28 intermediate plasmid 3, leading to the final plasmid pBZ1_BZ28F (SEQ ID NO:9).

pBZ1_BZ28F.5IXP (SEQ ID NO:10) was constructed by standard gene synthesis and molecular cloning procedures as follows. First, a 2927 bp DNA fragment (SEQ ID NO:14) consisting of a modified BZ1/BZ28 vector genome fragment comprising certain pIX promoter sequences of HAdV-5 (i.e. those set forth in SEQ ID NO:8) was synthesized and ligated, as a AsiSI-SalI restriction fragment, into AsiSI- and SalI-digested BZ1/BZ28 intermediate plasmid 2, leading to BZ1/BZ28.5IXP intermediate plasmid 1. Second, the 15.2-kbp SalI-SalI restriction fragment of the BZ1 viral gnome (SEQ ID NO:6) was ligated into SalI-digested BZ1/BZ28.5IXP intermediate plasmid 1, leading to BZ1/BZ28.5IXP intermediate plasmid 2. Third, the 10.0-kbp ClaI-SpeI restriction fragment of the BZ1 viral genome was ligated into ClaI- and SpeI-digested BZ1.BZ28.5IXP intermediate plasmid 2, leading to the final plasmid pBZ1_BZ28F.5IXP (SEQ ID NO:10).

pBZ1_BZ28F.Fluc (SEQ ID NO:15) and pBZ1_BZ28F.RSVF-2A-GLuc (SEQ ID NO:16) are pBZ1_BZ28F-derived plasmids that each harbor a BZ1/BZ28-based Ad vector genome equipped with a transgene expression cassette inserted at the location of the E1 deletion. The Ad vector genome sequences carried within these plasmids are set forth in SEQ ID NO:17 and SEQ ID NO:18, respectively. pBZ1_BZ28F.Fluc carries a transgene expression cassette for firefly luciferase (FLuc). This cassette is driven by the cytomegalovirus major immediate early promoter (i.e. the “CMV promoter”) and contains an SV40-derived polyadenylation signal. pBZ1_BZ28F.RSVF-2A-GLuc carries a transgene expression cassette for “RSV-$F_{A2}$-2A-GLuc” (RSVF-2A-GLuc), which is a chimeric protein composed of the respiratory syncytial virus strain A2 fusion glycoprotein, a foot-and-mouth-disease virus 2A peptide, and Gaussia luciferase (GLuc). Like the Fluc cassette, this cassette is driven a CMV promoter and carries an SV40 polyadenlyation signal. In addition, this cassette contains within its 5'untranslated region a sequence comprising intron 2 of the human Apolipoprotein A1 gene. The Fluc and RSVF-2A-GLuc expression cassettes were each constructed by several standard gene synthesis and molecular cloning steps after which they were ligated into the unique AsiSI restriction enzyme site of pBZ1_BZ28F, generating pBZ1_BZ28F.Fluc and pBZ1_BZ28F.RSVF-2A-GLuc, respectively.

Generation and Production of BZ1/BZ28-Based Adenoviral Vectors

Adenoviral vectors BZ1/BZ28.Fluc (also designated JAd4C5NVT003) and BZ1/BZ28.RSVF-2A-Gluc (also designated JAd4C5NVT001), which respectively comprise adenoviral vector genome sequences SEQ ID NO:17 and SEQ ID NO:18), were generated by transfection of the corresponding Ad vector genome plasmids (i.e. pBZ1_BZ28F.Fluc and pBZ1_BZ28F.RSVF-2A-GLuc) into E1-complementing PER.C6 cells. Prior to transfection into PER.C6 cells, which were grown as adherent cell cultures in Dulbecco's modified Eagle's medium (DMEM) supplemented with 10% fetal bovine serum (FBS) and 10 mM $MgCl_2$, the Ad vector genome plasmids were digested with SwaI to release the respective adenoviral vector genomes from the plasmid. The transfections were performed according to standard procedures using Lipofectamine transfection reagent (Invitrogen; Carlsbad, Calif.). After harvesting of the viral rescue transfections, the viruses were further amplified by several successive infection rounds on PER.C6 cell cultures. The viruses were purified from crude viral harvests using a two-step cesium chloride (CsCl) density gradient ultracentrifugation procedure as described before (Havenga et al., “Novel replication-incompetent adenoviral B-group vectors: high vector stability and yield in PER.C6 cells,” J. Gen. Virol. 87(8):2135-43 (2006)). Viral particle (VP) titers were measured by a spectrophotometry-based procedure described previously (Maizel et al., “The polypeptides of adenovirus: I. Evidence for multiple protein components in the virion and a comparison of types 2, 7A, and 12,” Virology, 36(1):115-25 (1968)).

Example 2: Cellular and Humoral Immune Responses Induced by BZ1/BZ28.FLuc

Cellular and humoral immunogenicity of novel adenoviral vector BZ1/BZ28 was evaluated using firefly luciferase (FLuc) as a vector-encoded (model) vaccine antigen. Balb/C mice were immunized intramuscularly with Ad26.FLuc (positive control) or BZ1/BZ28.FLuc (both at $10^9$ and $10^{10}$ viral particles per mouse), or with a negative control vector not encoding a transgene (Ad26 empty, $10^{10}$ viral particles per mouse). Mice were sacrificed after two weeks and blood samples and splenocytes were collected (FIG. 1A).

Figure 1B:
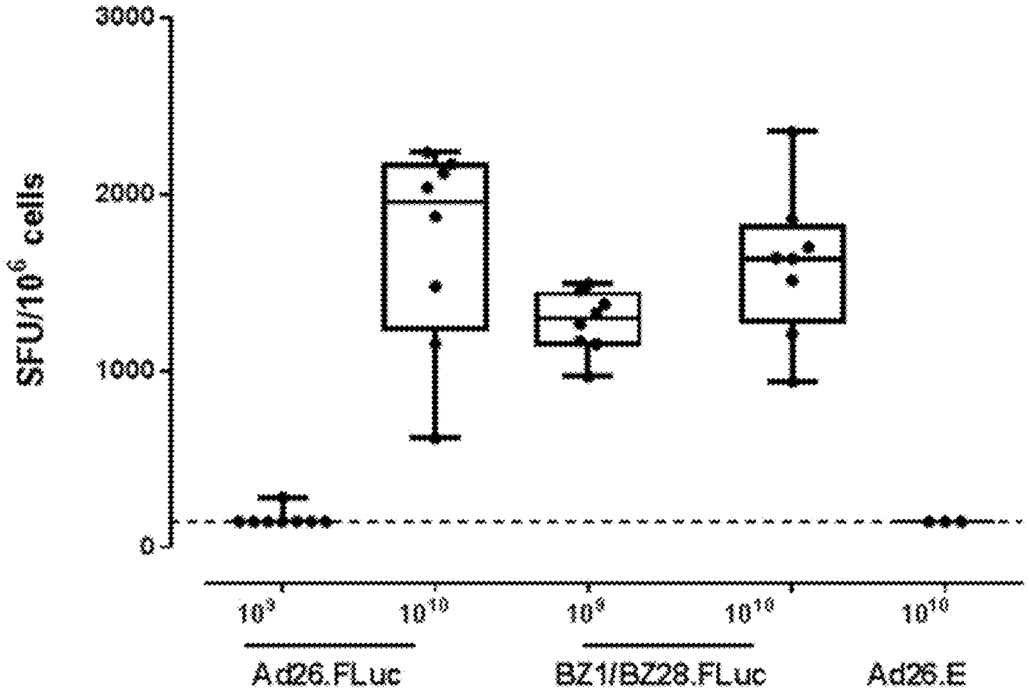

Induction of cellular immunity against the vector-encoded antigen was evaluated by an FLuc-specific ELISPOT assay. To this end, the isolated splenocytes were stimulated overnight with 15mer overlapping peptides spanning the FLuc protein and cellular immune responses were determined by ex-vivo ELISPOT assay measuring the relative number of IFN-γ-secreting cells (FIG. 1B). The results show that at the higher-dose immunization ($10^{10}$), the cellular immune responses induced by BZ1/BZ28 were about as high as the response seen for Ad26.FLuc. By contrast, at the lower-dose immunization ($10^9$), BZ1/BZ28.FLuc gave a much stronger response than Ad26.FLuc.

Figure 1C:
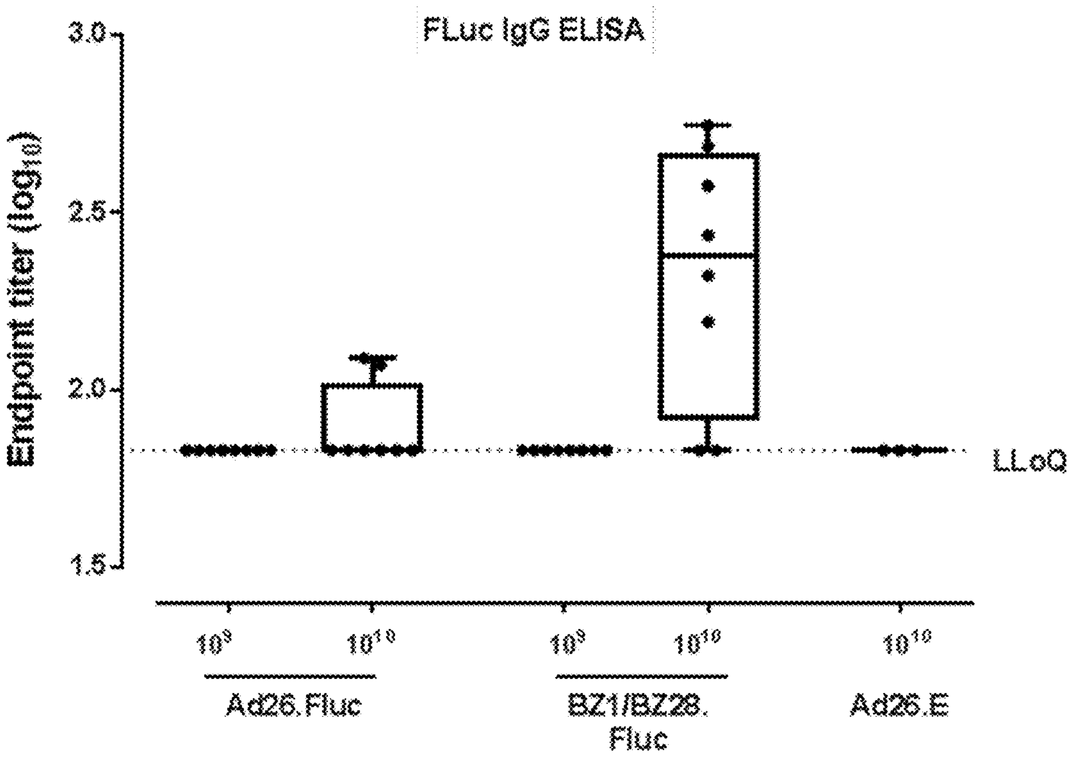

The ability of BZ1/BZ28 to induce humoral immunity against its encoded antigen was assessed by measuring antibodies raised against FLuc. Sera from the immunized mice (collected at 2 weeks) were tested in an FLuc-specific IgG antibody ELISA. FIG. 1C shows that at $10^{10}$ vp per mouse the BZ1/BZ28 vector expressing firefly luciferase, elicited higher endpoint titers than the Ad26.FLuc benchmark. As expected, no Fluc-specific antibody titers were detected in sera from mice immunized with empty vectors not encoding Firefly luciferase.

Altogether, the data show that the BZ1/BZ28 vector can induce potent cellular and humoral immune responses against a vector-encoded antigen, higher in magnitude than those induced by the benchmark vector based on HAdV-26. These immune responses clearly indicate potent immunogenicity of the BZ1/BZ28 vector in mice.

Example 3: Evaluation of Serological Cross-Neutralization Among Novel and Existing Adenoviral Vectors For their potential utility as new adenoviral vaccine vectors, the novel BZ1/BZ28 adenoviral vectors created herein would preferably be serologically distinct from existing adenoviral vectors currently already in development as vaccine vectors, such as vectors based on human adenovirus serotypes HAdV-5 and HAdV-35. Therefore, cross-neutralization tests were performed among the novel BZ1/BZ28 adenoviral vectors and several existing vectors based on HAdV-4, HAdV-5, HAdV-26 and HAdV-35. To this end, mice antisera, each raised against one of these adenoviral vectors, were tested against each of the different vectors in an adenovirus neutralization assay. The mice antisera used for this assay were collected from Balb/C mice, two or eight weeks after their immunization with $10^{10}$ vector particles per mouse. The adenovirus neutralization assay was carried out as described previously (Spangers et al 2003. J. Clin. Microbiol. 41:5046-5052). Briefly, starting from a 1:16 dilution, the sera were 2-fold serially diluted, then pre-mixed with the adenoviral vectors expressing firefly luciferase (FLuc), and subsequently incubated overnight with A549 cells (at multiplicity of infection of 500 virus particles per cell). Luciferase activity levels in infected cell lysates measured 24 hours post-infection represented vector infection efficiencies. Neutralization titers against a given vector were defined as the highest serum dilution capable of giving a 90% reduction of vector infection efficiency. The neutralization titers were arbitrarily divided into the following categories: <16 (no neutralization), 16 to 200, 200 to 2,000, and >2,000.

The results show no cross-neutralization among the vectors tested (FIG. 2).BZ1/BZ28 displayed a homologous neutralization antibody response but no cross-neutralization with the human adenoviral vectors included in the tested panel, i.e. Ad26, Ad35, Ad5 and Ad4. Therefore, the new adenoviral vector BZ1/BZ28 could potentially be used in combination with one or more of these or other distinct adenoviral vectors in sequential immunizations, for example in the context of a heterologous prime-boost vaccination regimen or, alternatively or additionally, in the context of a series of two or more consecutive vaccination regimens against different diseases or antigens.

Example 4: Human Seroprevalence of Novel Adenoviral Vectors

Figure 3:
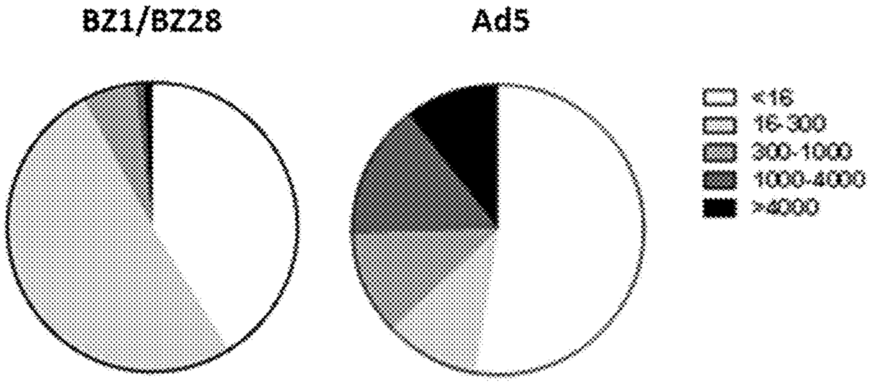
FIG. 3 shows the seroprevalence of Ad26 and BZ1/BZ28 in 200 human cohort serum samples from adults, age 18 to 55 years, living in the United States (US) and the European Union (EU). Neutralization titers measured in these sera against each vector were divided into four categories (<16 (no-neutralization), 16 to 300, 300 to 1,000, 1000 to 4000 and >4000), represented in the charts as indicated.

Important for their potential use as efficacious vaccine vectors is that the novel adenoviral vectors described herein are not hampered by high levels of pre-existing anti-vector humoral immunity in vaccine target populations. Therefore, the BZ1/BZ28 vector was evaluated for its seroprevalence within 200 human cohort serum samples from adults, ages 18 to 55 years, living in the United States (US) and the European Union (EU). The vector was tested for neutralization by the human serum samples by performing a standard adenovirus neutralization assay as described previously (Sprangers et al 2003. J. Clin. Microbiol. 41:5046-5052). Briefly, starting from a 1:16 dilution, the sera were 2-fold serially diluted, then pre-mixed with the adenoviral vectors expressing firefly luciferase (FLuc), and subsequently incubated overnight with A549 cells (at a multiplicity of infection of 500 virus particles per cell). Luciferase activity levels in infected cell lysates, measured 24 hours post-infection, represented vector infection efficiencies. Neutralization titers against a given vector were defined as the highest serum dilution capable of giving a 90% reduction of vector infection efficiency. The neutralization titers were arbitrarily divided into the following categories: <16 (no neutralization), 16 to 300, 300 to 1000, 1000 to 4000 and >4000. The results indicate that the seroprevalence of BZ1/BZ28 in the human subjects studied is similar to that of Ad5 (FIG. 3). However, compared to Ad5, the positive neutralization titers that were seen against the novel BZ1/BZ28 vector were generally quite low. For example, of all sera tested, more than 25% showed Ad5 neutralization titers of >1000 while only about 3% had BZ1/BZ28 neutralization titers of that level.

Altogether, the above data indicate that pre-existing humoral anti-vector immunity against BZ1/BZ28 vectors in terms of the pre-existing vector neutralization titer levels may be considered relatively low in the evaluated vaccine target populations, suggesting that these vectors have potential as efficacious vaccine vectors in these populations.

Example 5: Adenoviral Vector Productivity in Suspension PER.C6 Cells

Adenovirus vectors to be used in clinical trials and beyond need to be readily producible to high titers in a scalable, serum-free adenovirus production platform. Suspension-adapted PER.C6® cells, also referred to herein as suspension PER.C6 cells or sPER.C6, represent such a platform as they have been shown to support large-scale manufacturing of adenoviral vectors in bioreactors, achieving large quantities of high-titer, clinical grade vector preparations, e.g. of E1-deleted vectors based on HAdV-26 or HAdV-35 (EP 2536829 B1, EP 2350268 B1).

As an initial assessment as to whether the novel vectors described herein would fit sPER.C6 cell-based production processes, small-scale vector productivity experiments were performed on sPER.C6 cells cultured in shaker flasks. These productivity experiments were carried out using the Fluc-encoding version of the novel Ad vector BZ1/BZ28 described in Example 1. Taken along as a benchmark control was the HAdV-26-based vector Ad26.Fluc. Suspension PER.C6 cell cultures, seeded into shaker flasks at a density of 1×106 cells/ml in a total volume of 10 ml of PERMEXCIS® medium (available from Lonza) supplemented with 4 mM L-Glutamine (Lonza), were infected with the different vectors at different virus particle (VP)-to-cell ratios and then incubated for 4 days. The different VP-to-cell ratios used for infection were 70, 150 and 900. Samples of the infected cell cultures were taken every day and VP titers were determined in these samples by a quantitative PCR (qPCR)-based protocol that employs primers and probe that are specific for the CMV promoter (which is present in all the vectors tested). This protocol entails a DNAse treatment of the test samples prior to the qPCR to remove any free vector DNA (i.e. vector genomes that are not packaged into viral particles).

Figure 6:
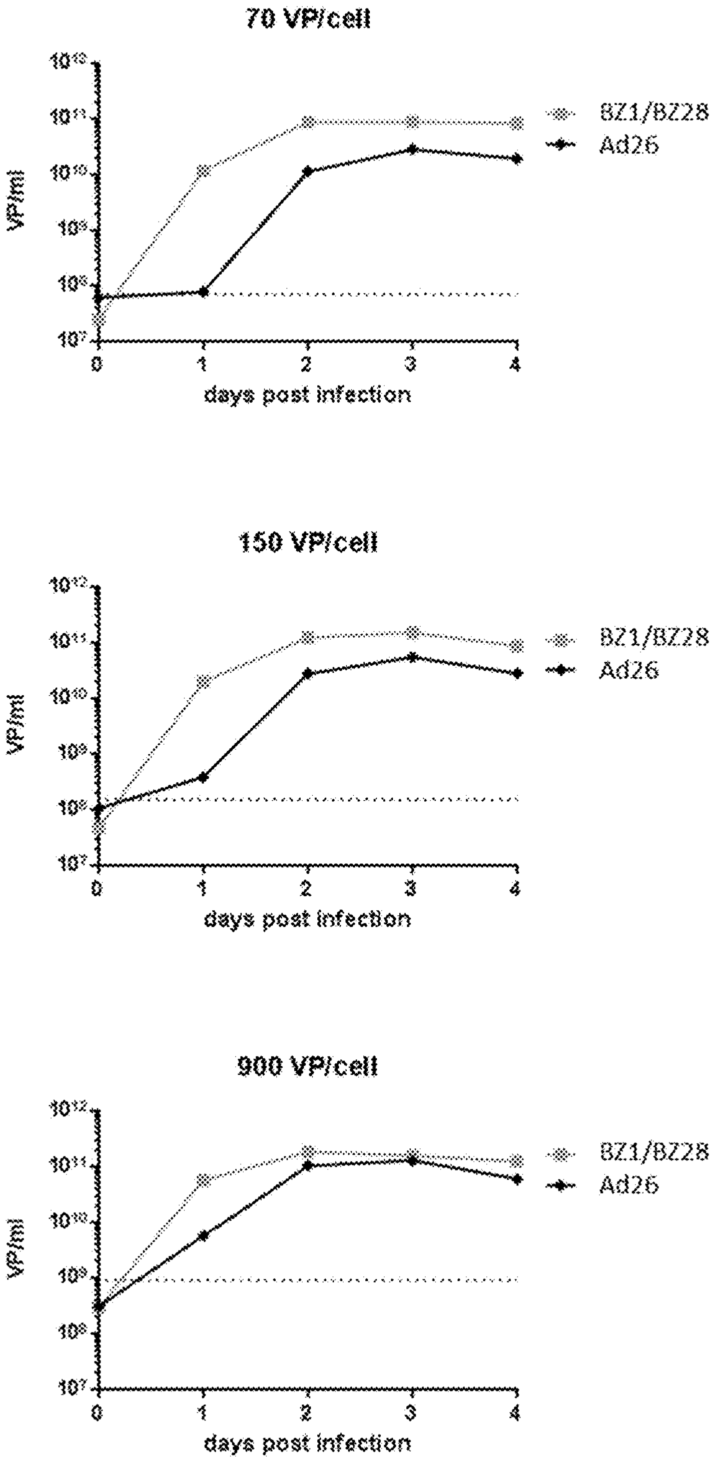
FIG. 6 shows productivity of novel vector BZ1/BZ28.Fluc in production cell line sPER.C6.

The productivity results obtained for the novel vector BZ1/BZ28.Fluc are shown in FIG. 6. BZ1/BZ28.Fluc displayed higher VP titers than the benchmark control vector Ad26.Fluc at all VP-to-cell infection ratios and harvest time points tested. These results demonstrate good productivity of the novel BZ1/BZ28 vector on a sPER.C6-based, serum-free suspension cell culture model.

Collectively, the studies of humoral and cellular immune responses induced by the novel recombinant BZ1/BZ28-based adenoviral vectors of the invention, as presented above, clearly indicate potent immunogenicity of these vectors in mice. In addition, the vectors demonstrated to induce no cross-neutralizing antibody responses against certain existing adenoviral vaccine vector candidates (e.g. Ad26, Ad35, and Ad5) or vice versa. Furthermore, when comparing to Ad5, the new vectors showed relatively low pre-existing vector neutralization titer levels in humans. Finally, the new vectors can be readily produced at high yields. The combination of low seroprevalence, potent immunogenicity and producibility suggests that the novel adenoviral vectors of the invention can be useful as novel vaccine vector candidates against a variety of pathogens and may additionally have utility in gene therapy and/or diagnostics.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

It is claimed:

1. An isolated nucleic acid sequence encoding a hexon polypeptide comprising a hexon hypervariable regions-encompassing polypeptide having the amino acid sequence of SEQ ID NO:1.

2. The isolated nucleic acid sequence of claim 1, wherein the hexon polypeptide comprises the amino acid sequence of SEQ ID NO:2.

3. The isolated nucleic acid sequence of claim 1, further comprising a nucleic acid sequence encoding a fiber polypeptide.

4. The isolated nucleic acid sequence of claim 3, wherein the fiber polypeptide comprises the amino acid sequence of SEQ ID NO:3.

5. An isolated nucleic acid sequence encoding a fiber polypeptide comprising the amino acid sequence of SEQ ID NO:3.

6. A vector comprising the nucleic acid of claim 1.

7. The vector of claim 6, being an adenoviral vector, and further comprising a transgene.

8. The adenoviral vector of claim 7, wherein the adenoviral vector further comprises at least one of an E1 deletion and an E3 deletion.

9. The adenoviral vector of claim 7, wherein the adenoviral vector is a chimeric adenoviral vector comprising one or more human adenoviral nucleic acid sequences, preferably the human adenoviral nucleic acid sequences are from at least one of human adenovirus-4, human adenovirus-5, human adenovirus-26, or human adenovirus-35.

10. The adenoviral vector of claim 7, wherein the adenoviral vector comprises a nucleic acid sequence selected from the group consisting of SEQ ID NO:9 and SEQ ID NO:10.

11. A recombinant cell comprising the vector of claim 6.

12. A method of producing a vector, comprising;

(a) growing the recombinant cell of claim 11 under conditions for production of the vector; and (b) isolating the vector from the recombinant cell.

13. An immunogenic composition comprising the adenoviral vector of claim 7.

14. A method of inducing an immune response in a subject in need thereof, comprising administering to the subject the immunogenic composition of claim 13.

15. A method of producing a vaccine, comprising combining an adenoviral vector according to claim 7 with a pharmaceutically acceptable carrier.

* * * * *

SEQUENCE LISTING

<160> NUMBER OF SEQ ID NOS: 19

<210> SEQ ID NO 1
<211> LENGTH: 321
<212> TYPE: PRT
<213> ORGANISM: Artificial Sequence
<220> FEATURE:
<223> OTHER INFORMATION: BZ1 hexon HVRs

<400> SEQUENCE: 1

Glu Thr Gln Asn Glu Val Gln Ala Asn Glu Glu Gln Leu Ala Glu Glu
1 5 10 15

Glu Asp Glu Glu Met Ala Gln Glu Asp Gln Gln Pro Thr Lys Lys Thr
20 25 30

His Val Tyr Ala Gln Ala Pro Leu Ser Gly Glu Gln Ile Thr Lys Asp
35 40 45

Gly Leu Gln Ile Gly Ala Glu Val Thr Gly Glu Thr Ser Lys Pro Ile
50 55 60

Phe Ala Asp Lys Thr Phe Gln Pro Glu Pro Gln Ile Gly Glu Ser Gln
65 70 75 80

Trp Asn Glu Ala Asp Ala Thr Val Ala Gly Gly Arg Val Leu Lys Lys
85 90 95

Thr Thr Pro Met Lys Pro Cys Tyr Gly Ser Tyr Ala Arg Pro Thr Asn
100 105 110

Ala Asn Gly Gly Gln Gly Ile Leu Glu Ala Asn Ala Lys Gly Glu Leu
115 120 125

Glu Ser Lys Val Glu Met Gln Phe Phe Ser Asn Thr Thr Thr Leu Asn
130 135 140

Val Arg Asp Gly Glu Asn Gly Leu Lys Pro Lys Val Val Leu Tyr Ser
145 150 155 160

Glu Asp Val Asn Leu Glu Ser Pro Asp Thr His Leu Ser Tyr Lys Pro
165 170 175

Lys Lys Asp Asp Val Asn Ala Lys Ile Met Leu Gly Gln Gln Ala Met
180 185 190

Pro Asn Arg Pro Asn Leu Ile Gly Phe Arg Asp Asn Phe Ile Gly Leu
195 200 205

Met Tyr Tyr Asn Ser Thr Gly Asn Met Gly Val Leu Ala Gly Gln Ala
210 215 220

Ser Gln Leu Asn Ala Val Val Asp Leu Gln Asp Arg Asn Thr Glu Leu
225 230 235 240

Ser Tyr Gln Leu Met Leu Asp Ser Ile Gly Asp Arg Thr Arg Tyr Phe
245 250 255

Ser Met Trp Asn Gln Ala Val Asp Ser Tyr Asp Pro Asp Val Arg Ile
260 265 270

Ile Glu Asn His Gly Val Glu Asp Glu Leu Pro Asn Tyr Cys Phe Pro
275 280 285

Leu Gly Gly Ile Gly Ile Thr Asp Thr Tyr Gln Ala Ile Lys Ala Ala
290 295 300

Asn Gly Gly Asp Ala Thr Thr Trp Ser Ala Asp Asn Thr Phe Ala Asp
305 310 315 320

Arg

<210> SEQ ID NO 2
<211> LENGTH: 961
<212> TYPE: PRT
<213> ORGANISM: Artificial Sequence -continued
<220> FEATURE:
<223> OTHER INFORMATION: BZ1 hexon

<400> SEQUENCE: 2

```
Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Asn Met Ser Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ser Leu Ala Pro Lys Gly
        115                 120                 125

Ala Pro Asn Ser Cys Glu Trp Glu Glu Glu Thr Gln Asn Glu Val Gln
    130                 135                 140

Ala Asn Glu Glu Gln Leu Ala Glu Glu Glu Asp Glu Glu Met Ala Gln
145                 150                 155                 160

Glu Asp Gln Gln Pro Thr Lys Lys Thr His Val Tyr Ala Gln Ala Pro
                165                 170                 175

Leu Ser Gly Glu Gln Ile Thr Lys Asp Gly Leu Gln Ile Gly Ala Glu
            180                 185                 190

Val Thr Gly Glu Thr Ser Lys Pro Ile Phe Ala Asp Lys Thr Phe Gln
        195                 200                 205

Pro Glu Pro Gln Ile Gly Glu Ser Gln Trp Asn Glu Ala Asp Ala Thr
    210                 215                 220

Val Ala Gly Gly Arg Val Leu Lys Lys Thr Thr Pro Met Lys Pro Cys
225                 230                 235                 240

Tyr Gly Ser Tyr Ala Arg Pro Thr Asn Ala Asn Gly Gly Gln Gly Ile
                245                 250                 255

Leu Glu Ala Asn Ala Lys Gly Glu Leu Glu Ser Lys Val Glu Met Gln
            260                 265                 270

Phe Phe Ser Asn Thr Thr Thr Leu Asn Val Arg Asp Gly Glu Asn Gly
        275                 280                 285

Leu Lys Pro Lys Val Val Leu Tyr Ser Glu Asp Val Asn Leu Glu Ser
    290                 295                 300

Pro Asp Thr His Leu Ser Tyr Lys Pro Lys Lys Asp Asp Val Asn Ala
305                 310                 315                 320

Lys Ile Met Leu Gly Gln Gln Ala Met Pro Asn Arg Pro Asn Leu Ile
                325                 330                 335

Gly Phe Arg Asp Asn Phe Ile Gly Leu Met Tyr Tyr Asn Ser Thr Gly
            340                 345                 350

Asn Met Gly Val Leu Ala Gly Gln Ala Ser Gln Leu Asn Ala Val Val
        355                 360                 365

Asp Leu Gln Asp Arg Asn Thr Glu Leu Ser Tyr Gln Leu Met Leu Asp
    370                 375                 380

Ser Ile Gly Asp Arg Thr Arg Tyr Phe Ser Met Trp Asn Gln Ala Val
385                 390                 395                 400
```

-continued

```
Asp Ser Tyr Asp Pro Asp Val Arg Ile Ile Glu Asn His Gly Val Glu
                405                 410                 415

Asp Glu Leu Pro Asn Tyr Cys Phe Pro Leu Gly Gly Ile Gly Ile Thr
            420                 425                 430

Asp Thr Tyr Gln Ala Ile Lys Ala Ala Asn Gly Gly Asp Ala Thr Thr
        435                 440                 445

Trp Ser Ala Asp Asn Thr Phe Ala Asp Arg Asn Glu Ile Gly Val Gly
    450                 455                 460

Asn Asn Phe Ala Met Glu Ile Asn Ile Gln Ala Asn Leu Trp Arg Asn
465                 470                 475                 480

Phe Leu Tyr Ala Asn Val Gly Leu Tyr Leu Pro Asp Lys Leu Lys Tyr
                485                 490                 495

Asn Pro Thr Asn Val Asp Ile Ser Asp Asn Pro Asn Thr Tyr Asp Tyr
            500                 505                 510

Met Asn Lys Arg Val Val Ala Pro Gly Leu Val Asp Cys Phe Val Asn
        515                 520                 525

Val Gly Ala Arg Trp Ser Leu Asp Tyr Met Asp Asn Val Asn Pro Phe
    530                 535                 540

Asn His His Arg Asn Ala Gly Leu Arg Tyr Arg Ser Met Ile Leu Gly
545                 550                 555                 560

Asn Gly Arg Tyr Val Pro Phe His Ile Gln Val Pro Gln Lys Phe Phe
                565                 570                 575

Ala Ile Lys Asn Leu Leu Leu Leu Pro Gly Ser Tyr Thr Tyr Glu Trp
            580                 585                 590

Asn Phe Arg Lys Asp Val Asn Met Val Leu Gln Ser Ser Leu Gly Asn
        595                 600                 605

Asp Leu Arg Val Asp Gly Ala Ser Ile Lys Phe Asp Ser Ile Thr Leu
    610                 615                 620

Tyr Ala Thr Phe Phe Pro Met Ala His Asn Thr Ala Ser Thr Leu Glu
625                 630                 635                 640

Ala Met Leu Arg Asn Asp Thr Asn Asp Gln Ser Phe Asn Asp Tyr Leu
                645                 650                 655

Ser Gly Ala Asn Met Leu Tyr Pro Ile Pro Ala Lys Ala Thr Asn Val
            660                 665                 670

Pro Ile Ser Ile Pro Ser Arg Asn Trp Ala Ala Phe Arg Gly Trp Ala
        675                 680                 685

Phe Thr Arg Leu Lys Thr Lys Glu Thr Pro Ser Leu Gly Ser Gly Phe
    690                 695                 700

Asp Pro Tyr Phe Val Tyr Ser Gly Ser Ile Pro Tyr Leu Asp Gly Thr
705                 710                 715                 720

Phe Tyr Leu Asn His Thr Phe Lys Lys Ile Ser Ile Met Tyr Asp Ser
                725                 730                 735

Ser Val Ser Trp Pro Gly Asn Asp Arg Leu Leu Thr Pro Asn Glu Phe
            740                 745                 750

Glu Val Lys Arg Ala Val Asp Gly Glu Gly Tyr Asn Val Ala Gln Cys
        755                 760                 765

Asn Met Thr Lys Asp Trp Phe Leu Val Gln Met Leu Ala Asn Tyr Asn
    770                 775                 780

Ile Gly Tyr Gln Gly Phe Tyr Ile Pro Glu Ser Tyr Lys Asp Arg Met
785                 790                 795                 800

Tyr Ser Phe Phe Arg Asn Phe Gln Pro Met Ser Arg Gln Val Val Asp
                805                 810                 815
```

```
Glu Thr Asn Tyr Lys Asp Tyr Gln Ala Ile Gly Ile Thr His Gln His
            820                 825                 830

Asn Asn Ser Gly Phe Val Gly Tyr Leu Ala Pro Thr Met Arg Glu Gly
        835                 840                 845

Gln Ala Tyr Pro Ala Asn Phe Pro Tyr Pro Leu Ile Gly Lys Thr Ala
    850                 855                 860

Val Asp Ser Val Thr Gln Lys Lys Phe Leu Cys Asp Arg Thr Leu Trp
865                 870                 875                 880

Arg Ile Pro Phe Ser Ser Asn Phe Met Ser Met Gly Ala Leu Thr Asp
                885                 890                 895

Leu Gly Gln Asn Leu Leu Tyr Ala Asn Ser Ala His Ala Leu Asp Met
            900                 905                 910

Thr Phe Glu Val Asp Pro Met Asp Glu Pro Thr Leu Leu Tyr Ile Val
        915                 920                 925

Phe Glu Val Phe Asp Val Val Arg Val His Gln Pro His Arg Gly Val
    930                 935                 940

Ile Glu Thr Val Tyr Leu Arg Thr Pro Phe Ser Ala Gly Asn Ala Thr
945                 950                 955                 960

Thr


<210> SEQ ID NO 3
<211> LENGTH: 543
<212> TYPE: PRT
<213> ORGANISM: Artificial Sequence
<220> FEATURE:
<223> OTHER INFORMATION: BZ28 fiber

<400> SEQUENCE: 3

Met Lys Arg Thr Lys Thr Ser Asp Glu Ser Phe Asn Pro Val Tyr Pro
1               5                   10                  15

Tyr Asp Thr Glu Asn Gly Pro Pro Ser Val Pro Phe Leu Thr Pro Pro
            20                  25                  30

Phe Val Ser Pro Asp Gly Phe Gln Glu Ser Pro Pro Gly Val Leu Ser
        35                  40                  45

Leu Asn Leu Ala Glu Pro Leu Val Thr Ser His Gly Met Leu Ala Leu
    50                  55                  60

Lys Met Gly Ser Gly Leu Ser Leu Asp Asp Ala Gly Asn Leu Thr Ser
65                  70                  75                  80

Gln Asp Val Thr Thr Thr Thr Pro Pro Leu Lys Lys Thr Lys Thr Asn
                85                  90                  95

Leu Ser Leu Glu Thr Ser Ala Pro Leu Thr Val Ser Thr Ser Gly Ala
            100                 105                 110

Leu Thr Leu Ala Ala Ala Val Pro Leu Ala Val Ala Gly Thr Ser Leu
        115                 120                 125

Thr Met Gln Ser Glu Ala Pro Leu Thr Val Gln Asp Ala Lys Leu Thr
    130                 135                 140

Leu Ala Thr Lys Gly Pro Leu Thr Val Ser Glu Gly Lys Leu Ala Leu
145                 150                 155                 160

Gln Thr Ser Ala Pro Leu Thr Ala Ala Asp Ser Ser Ala Leu Thr Val
                165                 170                 175

Ser Ala Thr Pro Pro Ile Ser Val Ser Ser Gly Ser Leu Gly Leu Asp
            180                 185                 190

Met Glu Asp Pro Met Tyr Thr His Asp Gly Lys Leu Gly Ile Arg Ile
        195                 200                 205

Gly Gly Pro Leu Arg Val Val Asp Ser Leu His Thr Leu Thr Val Val
```

-continued

```
    210                 215                 220

Thr Gly Asn Gly Ile Ala Val Asp Asn Asn Ala Leu Gln Thr Arg Val
225                 230                 235                 240

Thr Gly Ala Leu Gly Tyr Asp Thr Ser Gly Asn Leu Gln Leu Arg Ala
                245                 250                 255

Ala Gly Gly Met Arg Ile Asp Ala Asn Gly Gln Leu Ile Leu Asp Val
            260                 265                 270

Ala Tyr Pro Phe Asp Ala Gln Asn Asn Leu Ser Leu Arg Leu Gly Gln
        275                 280                 285

Gly Pro Leu Tyr Val Asn Thr Asp His Asn Leu Asp Leu Asn Cys Asn
    290                 295                 300

Arg Gly Leu Thr Thr Thr Thr Thr Asn Asn Thr Lys Lys Leu Glu Thr
305                 310                 315                 320

Lys Ile Gly Ser Gly Leu Asp Tyr Asp Thr Asn Gly Ala Val Ile Ile
                325                 330                 335

Lys Leu Gly Thr Gly Val Ser Phe Asp Ser Thr Gly Ala Leu Thr Val
            340                 345                 350

Gly Asn Thr Gly Asp Asp Lys Leu Thr Leu Trp Thr Thr Pro Asp Pro
        355                 360                 365

Ser Pro Asn Cys Arg Ile His Ala Asp Lys Asp Cys Lys Phe Thr Leu
    370                 375                 380

Val Leu Thr Lys Cys Gly Ser Gln Ile Leu Ala Ser Val Ala Ala Leu
385                 390                 395                 400

Ala Val Ser Gly Asn Leu Ala Ser Ile Thr Gly Thr Val Ala Ser Val
                405                 410                 415

Thr Ile Phe Leu Arg Phe Asp Gln Asn Gly Val Leu Met Glu Asn Ser
            420                 425                 430

Ser Leu Asp Lys Gln Tyr Trp Asn Phe Arg Asn Gly Asn Ser Thr Asn
        435                 440                 445

Ala Thr Pro Tyr Thr Asn Ala Val Gly Phe Met Pro Asn Leu Ala Ala
    450                 455                 460

Tyr Pro Lys Thr Gln Ser Gln Thr Ala Lys Asn Asn Ile Val Ser Gln
465                 470                 475                 480

Val Tyr Leu Asn Gly Asp Lys Ser Lys Pro Met Thr Leu Thr Ile Thr
                485                 490                 495

Leu Asn Gly Thr Asn Glu Ser Ser Glu Thr Ser Gln Val Ser His Tyr
            500                 505                 510

Ser Met Ser Phe Thr Trp Ala Trp Glu Ser Gly Gln Tyr Ala Thr Glu
        515                 520                 525

Thr Phe Ala Thr Asn Ser Phe Thr Phe Ser Tyr Ile Ala Glu Gln
    530                 535                 540


<210> SEQ ID NO 4
<211> LENGTH: 580
<212> TYPE: PRT
<213> ORGANISM: Artificial Sequence
<220> FEATURE:
<223> OTHER INFORMATION: BZ1 fiber

<400> SEQUENCE: 4

Met Lys Arg Ala Arg Ser Ser Asp Glu Thr Phe Asn Pro Val Tyr Pro
1               5                   10                  15

Tyr Asp Thr Glu Ile Ala Pro Thr Ser Val Pro Phe Leu Thr Pro Pro
            20                  25                  30

Phe Val Ser Ser Ala Gly Met Gln Glu Asn Pro Ala Gly Val Leu Ser
```

-continued

```
        35                  40                  45

Leu His Leu Ser Glu Pro Leu Thr Thr His Asn Gly Ala Leu Thr Leu
    50                  55                  60

Lys Met Gly Gly Gly Leu Thr Leu Asp Lys Glu Gly Asn Leu Thr Ser
65                  70                  75                  80

Gln Asn Ile Thr Ser Val Asp Pro Pro Leu Lys Lys Ser Lys Asn Asn
                85                  90                  95

Ile Ser Leu Gln Thr Ala Ala Pro Leu Ala Val Ser Ser Gly Ala Leu
            100                 105                 110

Thr Leu Phe Ala Thr Pro Pro Leu Ala Val Ser Gly Asp Asn Leu Thr
        115                 120                 125

Val Gln Ser Gln Ala Pro Phe Thr Leu Glu Asp Ser Lys Leu Thr Leu
    130                 135                 140

Ala Thr Lys Gly Pro Leu Thr Val Ser Glu Gly Lys Leu Val Leu Glu
145                 150                 155                 160

Thr Glu Ala Pro Leu His Ala Ser Asp Ser Ser Ser Leu Gly Leu Ser
                165                 170                 175

Val Thr Ala Pro Leu Ser Ile Asn Asn Asp Ser Leu Gly Leu Asp Met
            180                 185                 190

Gln Ala Pro Ile Ser Ser Arg Asp Gly Lys Leu Ala Leu Thr Val Ala
        195                 200                 205

Ala Pro Leu Thr Val Ala Glu Gly Ile Asn Ala Leu Ala Val Ala Thr
    210                 215                 220

Gly Asn Gly Ile Gly Leu Asn Glu Thr Asn Thr His Leu Gln Ala Lys
225                 230                 235                 240

Leu Val Ala Pro Leu Gly Phe Asp Thr Asn Gly Asn Ile Lys Leu Ser
                245                 250                 255

Val Ala Gly Gly Met Arg Leu Asn Asn Asn Thr Leu Ile Leu Asp Val
            260                 265                 270

Asn Tyr Pro Phe Glu Ala Gln Gly Gln Leu Ser Leu Arg Val Gly Ser
        275                 280                 285

Gly Pro Leu Tyr Val Asp Ser Ser Ser His Asn Leu Thr Ile Arg Cys
    290                 295                 300

Leu Arg Gly Leu Tyr Val Thr Ser Ser Asn Asn Gln Asn Gly Leu Glu
305                 310                 315                 320

Ala Asn Ile Lys Leu Thr Lys Gly Leu Val Tyr Asp Gly Asn Ala Ile
                325                 330                 335

Ala Val Asn Val Gly Lys Gly Leu Glu Tyr Ser Pro Thr Gly Thr Thr
            340                 345                 350

Glu Lys Pro Ile Gln Thr Lys Ile Gly Leu Gly Met Glu Tyr Asp Thr
        355                 360                 365

Glu Gly Ala Met Met Thr Lys Leu Gly Ser Gly Leu Ser Phe Asp Asn
    370                 375                 380

Ser Gly Ala Ile Val Val Gly Asn Lys Asn Asp Asp Arg Leu Thr Leu
385                 390                 395                 400

Trp Thr Thr Pro Asp Pro Ser Pro Asn Cys Gln Ile Tyr Ser Glu Lys
                405                 410                 415

Asp Ala Lys Leu Thr Leu Val Leu Thr Lys Cys Gly Ser Gln Val Val
            420                 425                 430

Gly Thr Val Ser Ile Ala Ala Leu Lys Gly Ser Leu Val Pro Ile Thr
        435                 440                 445

Ser Ala Ile Ser Val Val Gln Val Tyr Leu Arg Phe Asp Glu Asn Gly
    450                 455                 460
```

-continued

```
Val Leu Met Ser Asn Ser Ser Leu Asn Gly Glu Tyr Trp Asn Phe Arg
465                 470                 475                 480

Asn Gly Asp Ser Thr Asn Gly Thr Pro Tyr Thr Asn Ala Val Gly Phe
                485                 490                 495

Met Pro Asn Leu Leu Ala Tyr Pro Lys Gly Gln Thr Thr Thr Ala Lys
            500                 505                 510

Ser Asn Ile Val Ser Gln Val Tyr Met Asn Gly Asp Asp Thr Lys Pro
        515                 520                 525

Met Thr Phe Thr Ile Asn Phe Asn Gly Leu Ser Glu Thr Gly Asp Thr
    530                 535                 540

Pro Val Ser Lys Tyr Ser Met Thr Phe Ser Trp Arg Trp Pro Asn Gly
545                 550                 555                 560

Ser Tyr Ile Gly His Asn Phe Val Thr Asn Ser Phe Thr Phe Ser Tyr
                565                 570                 575

Ile Ala Gln Glu
            580


<210> SEQ ID NO 5
<211> LENGTH: 579
<212> TYPE: PRT
<213> ORGANISM: Artificial Sequence
<220> FEATURE:
<223> OTHER INFORMATION: BZ28 partial hexon

<400> SEQUENCE: 5

Lys Phe Arg Asn Pro Thr Val Ala Pro Thr His Asp Val Thr Thr Asp
1               5                   10                  15

Arg Ser Gln Arg Leu Thr Leu Arg Phe Ile Pro Val Asp Arg Glu Asp
            20                  25                  30

Thr Ala Tyr Ser Tyr Lys Ala Arg Phe Thr Leu Ala Val Gly Asp Asn
        35                  40                  45

Arg Val Leu Asp Met Ala Ser Thr Tyr Phe Asp Ile Arg Gly Val Leu
    50                  55                  60

Asp Arg Gly Pro Thr Phe Lys Pro Tyr Ser Gly Thr Ala Tyr Asn Ser
65                  70                  75                  80

Leu Ala Pro Lys Gly Ala Pro Asn Ser Cys Glu Trp Glu Gln Glu Glu
                85                  90                  95

Thr Gln Ala Val Glu Glu Ala Ala Glu Glu Glu Glu Glu Asp Ala Asp
            100                 105                 110

Gly Gln Ala Glu Glu Glu Gln Ala Ala Thr Lys Lys Thr His Val Tyr
        115                 120                 125

Ala Gln Ala Pro Leu Ser Gly Glu Lys Ile Ser Lys Asp Gly Leu Gln
    130                 135                 140

Ile Gly Thr Asp Ala Thr Ala Thr Glu Gln Lys Pro Ile Tyr Ala Asp
145                 150                 155                 160

Pro Thr Phe Gln Pro Glu Pro Gln Ile Gly Glu Ser Gln Trp Asn Glu
                165                 170                 175

Ala Asp Ala Thr Val Ala Gly Gly Arg Val Leu Lys Lys Ser Thr Pro
            180                 185                 190

Met Lys Pro Cys Tyr Gly Ser Tyr Ala Arg Pro Thr Asn Ala Asn Gly
        195                 200                 205

Gly Gln Gly Val Leu Thr Ala Asn Ala Gln Gly Gln Leu Glu Ser Gln
    210                 215                 220

Val Glu Met Gln Phe Phe Ser Thr Ser Glu Asn Ala Arg Asn Glu Ala
225                 230                 235                 240
```

-continued

```
Asn Asn Ile Gln Pro Lys Leu Val Leu Tyr Ser Glu Asp Val His Met
                245                 250                 255

Glu Thr Pro Asp Thr His Leu Ser Tyr Lys Pro Ala Lys Ser Asp Asp
            260                 265                 270

Asn Ser Lys Ile Met Leu Gly Gln Gln Ser Met Pro Asn Arg Pro Asn
        275                 280                 285

Tyr Ile Gly Phe Arg Asp Asn Phe Ile Gly Leu Met Tyr Tyr Asn Ser
    290                 295                 300

Thr Gly Asn Met Gly Val Leu Ala Gly Gln Ala Ser Gln Leu Asn Ala
305                 310                 315                 320

Val Val Asp Leu Gln Asp Arg Asn Thr Glu Leu Ser Tyr Gln Leu Leu
                325                 330                 335

Leu Asp Ser Met Gly Asp Arg Thr Arg Tyr Phe Ser Met Trp Asn Gln
            340                 345                 350

Ala Val Asp Ser Tyr Asp Pro Asp Val Arg Ile Ile Glu Asn His Gly
        355                 360                 365

Thr Glu Asp Glu Leu Pro Asn Tyr Cys Phe Pro Leu Gly Gly Ile Gly
    370                 375                 380

Val Thr Asp Thr Tyr Gln Ala Val Lys Thr Asn Asn Gly Asn Asn Gly
385                 390                 395                 400

Gly Gln Val Thr Trp Thr Lys Asp Glu Thr Phe Ala Asp Arg Asn Glu
                405                 410                 415

Ile Gly Val Gly Asn Asn Phe Ala Met Glu Ile Asn Leu Ser Ala Asn
            420                 425                 430

Leu Trp Arg Asn Phe Leu Tyr Ser Asn Val Ala Leu Tyr Leu Pro Asp
        435                 440                 445

Lys Leu Lys Tyr Asn Pro Ser Asn Val Asp Ile Ser Asp Asn Pro Asn
    450                 455                 460

Thr Tyr Asp Tyr Met Asn Lys Arg Val Val Ala Pro Gly Leu Val Asp
465                 470                 475                 480

Cys Tyr Ile Asn Leu Gly Ala Arg Trp Ser Leu Asp Tyr Met Asp Asn
                485                 490                 495

Val Asn Pro Phe Asn His His Arg Asn Ala Gly Leu Arg Tyr Arg Ser
            500                 505                 510

Met Leu Leu Gly Asn Gly Arg Tyr Val Pro Phe His Ile Gln Val Pro
        515                 520                 525

Gln Lys Phe Phe Ala Ile Lys Asn Leu Leu Leu Leu Pro Gly Ser Tyr
    530                 535                 540

Thr Tyr Glu Trp Asn Phe Arg Lys Asp Val Asn Met Val Leu Gln Ser
545                 550                 555                 560

Ser Leu Gly Asn Asp Leu Arg Val Asp Gly Ala Ser Ile Lys Phe Glu
                565                 570                 575

Ser Ile Cys
```

<210> SEQ ID NO 6
<211> LENGTH: 37204
<212> TYPE: DNA
<213> ORGANISM: Artificial Sequence
<220> FEATURE:
<223> OTHER INFORMATION: BZ1 genome

<400> SEQUENCE: 6

```
catcatcaat aatatacctt attttggatt gtggccaata tgataatgag gtgggcgggg      60

cgaggcgggg cgggtgacgt aggacgtgcg agtagggttg ggaggtgtgg cggaagtgtg     120
```

-continued

```
gcatttgtaa gtgggaggag cttacatgca agcttccgtc gcggaaaatg tgacgttttt    180
tatgagcgcc gcctacctcc ggaagtgcca attttcgcgc gctttttacc ggatatcgta    240
gtaattttgg gcgggaccat gtaagatttg gccattttcg cgcgaaaagt gaaacgggga    300
agtgaaaact gaataatagg gcgttagtca tagcgcgtaa tatttaccga gggccgaggg    360
actttgaccg attacgtgga ggactcgccc aggtgttttt tacgtgaatt tccgcgttcc    420
gggtcaaagt ctccgttttt attgtcaccg tcatttgacg cggagggtat ttaaacccgc    480
tgcgctccta aagaggccac tcttgagtgc cagcgagaag agttttctcc tccgctctgt    540
ttcggcgatc gaaaaatgag acatttagcc tgcactccgg gtcttctgtc cggccgggcg    600
gcgtccgagc ttttggacgc tttgctcaat gaggtcctga gcgatgattt tccgtctact    660
acccacttta gcccacctac tcttcacgaa ctgtacgatc tggatgtact ggtggatgtg    720
aacgatccta acgaggaggc ggtttctacg tttttcccg agtctgcgct tttggccgcc    780
caggagggat ttgacctaca cactccgccg ctgcctattt tagagtctcc gctgccggag    840
cccagtggta taccttatat gcctgaactg cttcccgaag tggtagacct gacctgccac    900
gagccgggct ttccgcccag cgacgatgag ggtgagcctt ttgttttaga ttatgctgag    960
atacccgggc tcggttgcag gtcttgtgca tatcatcaaa gggttaccgg agaccccgag   1020
gttaagtgtt cgctgtgcta tatgaggctg acctcttcct ttatctacag taagtttttt   1080
gtgtaggtgg gctttttggg taggtgggtt ttgtggcagg acaggtgtaa atgttgcttg   1140
tgtttttttg tacctgcagg tccggtgtcc gagccagacc cggagcccga ccgcgatccc   1200
gagccggatc ccgagcctcc tcgcagggca aggaaattac cttctattct gtgcaagcct   1260
aagacacctg taaggaccag cgaggcagac agcactgact ctggcacttc tacctctcct   1320
cctgaaattc acccagtggt tcctttgggt atacataaac ctgttgctat tagagtttgc   1380
gggcgacgcc ctgcagtaga gtgcattgag gacttgctta acgatcccga gggacctttg   1440
gacttgagca ttaaacgccc taggcaataa accccaccta agtaataaac cccacctaag   1500
taataaactt taccgccctt ggttattaag atgacgccca atgtttgctt ttgaatgact   1560
tcatgtgtat aataaaagtg agtgtggtca taggtctctt gtttgtctgg gcggggctta   1620
agggtatata agtttctcgg ggctaaactt ggttacactt gaccccaatg gaggcgtggg   1680
ggtgcttgga ggagtttgcg gacgtgcgcc gtttgctgga cgagagctct agcaatacct   1740
atagtatttg gaggtatctg tggggctcta ctcaggccaa gttggtttgc agaattaagc   1800
aggattacaa gtgcgatttt gaagagcttt ttagttcctg tggtgagctt ttgcaatcct   1860
tgaatctggg ccaccaggct atcttccagg aaaaggttct ctcgactttg gatttttcca   1920
ctcccgggcg caccgccgct tgtgtggctt ttgtgtcttt tgtgcaagat aaatggagcg   1980
gggagaccca cctgagtcac ggctacgtgc tggatttcat ggcgatggct ctttggaggg   2040
cttacaacaa atggaagatt cagaaggaac tgtacggttc cgccctacgt cgtccacttc   2100
tgcagcggca ggggctgatg tttcccgacc atcgccagca tcagaatctg gaagacgagt   2160
cggaggagcg agcggagaag atcagcttga gagccggcct ggaccctcct caggaggaat   2220
gaatctcccg caggtggttg agctgtttcc cgaactgaga cgggtcctga ctatcaggga   2280
ggatggtcag tttgtgaaga agctgaagag ggatcggggt gagggagatg atgaggcggc   2340
tagcaattta gcttttagtc tgataacccg ccaccgaccg gaatgtatta cctatcagca   2400
gattaaggag agttgtgcca acgagctgga tcttttgggt cagaagtata gcatagaaca   2460
```

-continued

```
gcttaccact tactggcttc agcccgggga tgattgggaa gaggcgatca gggtgtatgc   2520
aaaggtggcc ctgcggcccg attgcaagta taagattact aagttggtta atattagaaa   2580
ctgctgctat atttctggaa acggggccga agtggagata gatactgagg acagggtggc   2640
tattaggtgt tgcatgataa acatgtggcc cgggatactg ggatggatg gggtgatatt   2700
tatgaatgtg aggttcacgg gccccaactt taatggtacg gtgtttatgg gcaacaccaa   2760
cttgctcctg catggtgcga gtttctatgg gtttaacaac acctgtatag aggcctggac   2820
cgatgtaaag gttcgaggtt gttcctttta tagctgttgg aaggcggtgg tgtgtcgccc   2880
taaaagcagg ggttctgtga agaaatgctt gtttgaaagg tgtaccctag gtatcctttc   2940
tgagggcaac tccagggtgc gccataatgt ggcttcgaac tgcggttgct ttatgcaagt   3000
gaagggggtg agcgttatca agcataactc ggtctgtgga aactgcgagg atcgcgcctc   3060
tcagatgctg acctgctttg atggcaactg tcacctgttg aagaccattc atataagcag   3120
tcaccccaga aaggcctggc ccgtgtttga gcataacatt ctgacccgct gttccttgca   3180
tctgggggtc aggaggggta tgttcctgcc ttaccagtgt aacttcagtc acactaaaat   3240
cctgttggaa cccgagtgca tgaccaaggt cagcctgaat ggtgtgtttg atgtgagtct   3300
gaagatttgg aaggtgctga ggtatgatga gaccaggacc aggtgccgac cctgcgagtg   3360
cggcggcaag cacatgagaa atcagcctgt gatgttggat gtgaccgagg agcttaggcc   3420
tgaccatctg gtgctggcct gcaccagggc cgagtttggg tctagcgatg aggataccga   3480
ttgaggtggg taaggtgggc gtggctagca gggtgggcgt gtataaattg gggtctaag   3540
gggtctctct gtttgtcttg caacagccgc cgccatgagc gacaccggca acagctttga   3600
tggaagcatc tttagcccct atctgacagt gcgcatgcct cactgggccg gagtgcgtca   3660
gaatgtgatg ggttccaacg tggatggacg tcccgttctg ccttcaaatt cgtctacgat   3720
ggcctacgcg accgtgggag gaactccgct ggacgccgcg acctccgccg ccgcctccgc   3780
cgccgccgcg accgcgcgca gcatggctac ggacctttac agctctttgg tggcgagcag   3840
cgcggcctct cgcgcgtctg ctcgggatga aaaactgact gctctgctgc ttaaactgga   3900
agacttgacc cgggagctgg gtcaactgac ccagcaggtc tccagcttgc gtgagagcag   3960
ccttgcctcc ccctaatggc ccataatata aataaaagcc agtctgtttg gattaagcaa   4020
gtgtatgttc tttatttaac tctccgcgcg cggtaagccc gggaccagcg gtctcggtcg   4080
tttagggtgc ggtggattct ttccaacacg tggtacaggt ggctctggat gtttagatac   4140
atgggcatga gtccatccct ggggtggagg tagcaccact gcagagcttc gtgctcgggg   4200
gtggtgttgt atatgatcca gtcgtagcag gagcgctggg cgtggtgctg aaaaatgtcc   4260
ttaagcaaga ggcttatagc taggggggagg cccttggtgt aagtgtttac aaatctgctt   4320
agctgggagg ggtgcatccg gggggatatg atgtgcatct tggactggat ttttaggttg   4380
gctatgttcc cacccagatc ccttctggga ttcatgttgt gcaggaccac cagcacggta   4440
tatccagtgc acttgggaaa tttatcgtgg agcttagacg ggaatgcatg gaagaacttg   4500
gagacgccct tgtggcctcc cagattttcc atacattcgt ccatgatgat ggcaatgggc   4560
ccgtgggaag ctgcctgagc aaaaacgttt ctggcatcgc tcacatcgta gttatgttcc   4620
agggtgaggt catcatagga catctttaca aatcgggggc ggagggtccc ggactggggg   4680
atgatggtac cctcgggccc cggggcgtag ttcccctcac agatctgcat ctcccaggct   4740
ttcatttcag agggagggat catatccacc tgcggggcga tgaaaaagac agtttctggc   4800
gcaggggaga ttaactggga tgagagcagg tttctgagca gctgtgactt tccacagccg   4860
```

```
gtgggcccat atatcacgcc tatcaccggc tgcagctggt agttaagaga gctgcagctg   4920
ccgtcctccc ggagcagggg ggccacctcg ttgagcatat ccctgacgtg gatgttctcc   4980
ctgaccagtt ccgccagaag gcgctcgccg cccagcgaaa gcagctcttg caaggaagca   5040
aaatttttca gcggtttcag gccatcggcc gtgggcatgt ttttcagcgt ctgggtcagc   5100
agctccagcc tgtcccagag ctcggtgatg tgctctacgg catctcgatc cagcagatct   5160
cctcgtttcg cgggttgggg cggctttcgc tgtagggcac cagccgatgg gcgtccagcg   5220
gggccagagt catgtccttc catgggcgca gagtcctcgt cagggtggtc tgggtcacgg   5280
tgaaggggtg cgctccgggt tgggcactgg ccagggtgcg cttgaggctg gttctgctgg   5340
tgctgaatcg ctgccgctct tcgccctgcg cgtcggccag gtagcatttg accatggtct   5400
cgtagtcgag accctcggcg gcgtgcccct tggcgcggag ctttcccttg gaggtggcgc   5460
cgcacgaggg gcactgcagg ctcttcaggg cgtagagctt gggagcgaga aacacggact   5520
ctggggagta ggcgtccgcg ccgcaggccg cgcagaccgt ctcgcattcc accagccaag   5580
tgagttccgg gcggtcaggg tcaaaaacca ggttgccccc atgctttttg atgcgtttct   5640
tacctcggct ctccatgagg cggtgtccct tctcggtgac gaagaggctg tccgtgtccc   5700
cgtagaccga cttcaggggc ctgtcttcca gcggagtgcc tctgtcctcc tcgtagagaa   5760
actctgacca ctctgagacg aaggcccgtg tccaggccag gacgaaggag gccacgtggg   5820
aggggtagcg gtcgttgtcc actagcgggt ccaccttctc cagggtgtgc agacacatgt   5880
ccccctcctc cgcgtccaga aaagtgattg gcttataggt gtaggacacg tgaccggggg   5940
ttcccgacgg gggggtataa aagggggtgg gcgccctttc atcttcactc tcttccgcat   6000
cgctgtctgc gagagccagc tgctggggta agtattccct ttcaaaggcg ggcatgacct   6060
cagcgctcag gttgtcagtt tctaaaaatg aggaggattt gatgttcacc tgtccggaag   6120
tgataccttt gagggtacct gggtccatct ggtcagaaaa cactattttt ttgttgtcaa   6180
gcttggtggc gaacgacccg tagagggcgt tggagagcag cttggcaatg gagcgcaggg   6240
tctggttttt gtcgcggtcg gctcgctcct tggccgcgat gttgagttgc acgtattcgc   6300
gggccacgca cttccactcg ggaagacgg tggtgcgctc gtctgggatc aggcgcaccc   6360
tccagccgcg gttgtgcagg gtgaccatgt cgacgctggt ggcgacctca ccgcgcagac   6420
gctcgttggt ccagcagagg cggccgcctt tgcgcgagca gaaggggggt agggggtcca   6480
gctggtcctc gtttgggggg tccgcgtcga tggtaaagac cccggggagc aggcgcgggt   6540
caaagtagtc gatcttgcaa gcttgcatgt ccagagcccg ctgccattcg cgggcggcga   6600
gcgcgcgctc gtaggggttg aggggcgggc cccagggcat ggggtgggtg agcgcggagg   6660
cgtacatgcc gcagatgtca tacacgtaca ggggttccct gaggataccg aggtaggtgg   6720
ggtagcagcg ccccccgcgg atgctggcgc gcacgtagtc atagagctcg tgggaggggg   6780
ccagcatgtt gagcccaagg ttggtgcgct gggggcgctc ggcgcggaag acgatctgtc   6840
tgaagatggc atgggagttg gaggagatgg tgggtcgctg gaagacgttg aagcttgctt   6900
cttgcaagcc cacggagtcc ctgacgaagg aggcgtagga ctcgcgcagc ttgtgcacca   6960
gctcggcggt gacctggacg tcgagcgcgc agtagtcgag ggtctcgcgg atgatgtcat   7020
acttatcctc cccttcttt ttccacagct cgcggttgag gacgaactct tcgcggtctt   7080
tccagtactc ttggagggga aacccgtccg tgtccgaacg gtaagagcct agcatgtaga   7140
actggttgac ggcctggtag gggcagcagc ccttctccac gggcagcgcg taggcctgcg   7200
```

-continued

```
ccgccttgcg gagggaggtg tgggtaaggg cgaaagtgtc cctgaccatg actttgaggt   7260
attgatgtct gaagtctgtg tcatcgcagc cgccctgttc ccacagggtg tagtccgtgc   7320
gctttttgga gcgcgggttg ggcagggaga aggtgaggtc attgaagagg atcttccccg   7380
ctcgaggcat gaagtttctg gtgatgcgaa agggccctgg gaccgaggag cggttgttga   7440
tgacctgggc ggccaggacg atctcgtcaa agccgtttat gttgtggccc acgatgtaga   7500
gctccaggaa gcggggctgg cccttgatgg aggggagctt tttaagttcc tcgtaggtaa   7560
gctcctcggg cgattccagg ccgtgctcct ccagggccca gtcttgcaag tgagggttgg   7620
ccgccaggaa ggatcgccag aggtcgcggg ccatgagggt ctgcaggcgg tcgcggaagg   7680
ttctgaactg ccgccctacg gccatctttt cgggggtgat gcagtagaag gtgagggggt   7740
ctttctccca ggggtcccat ctgagctctt gggcgaggtc gcgcgcggcg gcgaccagag   7800
cctcgtcgcc ccccagtttc atgaccagca tgaagggcac gagctgcttg ccaaaggctc   7860
ccatccaagt gtaggtctct acatcgtagg tgacaaagag gcgctccgtg cgaggatgag   7920
agccgatcgg gaagaactgg atctcccgcc accagttgga ggattggctg ttgatgtggt   7980
gaaagtagaa gtcccgtctg cgggccgagc actcgtgctg gcttttgtaa aagcgaccgc   8040
agtactggca gcgctgcacg ggttgtatat cttgcacgag gtgaacctgg cgacctctga   8100
cgaggaagcg cagcgggaat ctaagtcccc cgcctggggt cccgtgtggc tggtggtctt   8160
ctactttggt tgtctggccg ccagcatctg tctcctggag ggcgatggtg gagcagacca   8220
ccacgccgcg agagccgcag gtccagatct cggcgctcgg cgggcggagt ttgatgacga   8280
catcgcgcac attggagctg tccatggtct ccagctcccg cggcggcagg tcagccggga   8340
gttcctggag gttcacctcg cagagacggg tcaaggcgcg gacagtgttg agatggtatc   8400
tgatttcaag ggcgtgttgg aggcggagt cgatggcttg cagaaggccg cagccccggg   8460
gggccacgat ggttccccgc ggggcgcgag gggaggcgga agctgggggt gtgttcagaa   8520
gcggtgacgc gggcgggccc ccggaggtag ggggggttcc ggccccacag gcatgggcgg   8580
caggggcacg tcttcgccgc gcgcgggcag gggctggtgc tggctccgga gagcgcttgc   8640
gtgcgcgacg acgcgacggt tggtgtcctg tatctggcgc ctctgagtga agaccacggg   8700
tcccgtgacc ttgaacctga aagagagttc gacagaatca atctcggcat cgttgacagc   8760
ggcctggcgc aggatctcct gcacgtcgcc cgagttgtcc tggtaggcga tctctgccat   8820
gaactgctcg atctcttcct cctggagatc tcctcgtccg gcgcgctcca cggtggccgc   8880
caggtcgttg gagatgcgac ccatgagctg cgagaaggcg ttgaggccgc cctcgttcca   8940
gacccggctg tagaccacgc ccccctcggc gtcgcgggcg cgcatgacca cctgggccag   9000
gttgagctcc acgtgtcgcg tgaagacggc gtagttgcgc aggcgctgga aaaggtagtt   9060
cagggtggtg gcggtgtgtt cggcgacgaa gaagtacatg acccagcgcc gcaacgtgga   9120
ttcattgatg tcccccaagg cctccaggcg ctccatggcc tcgtagaagt ccacggcgaa   9180
gttgaaaaac tgggagttgc gagcggacac ggtcaactcc tcctccagaa gacggatgag   9240
ctcggcgaca gtgtcgcgca cctcgcgctc gaaggccacg gggggcgctt cttcctcttc   9300
cacctcttct tccatgattg cttcttcttc ctcagccggg acgggagggg gcggcggcgg   9360
gggaggggcg cggcggcggc ggcggcgcac cggcaggcgg tcgatgaagc gctcgatcat   9420
ctccccccgc atgcggcgca tggtctcggt gacggcgcgg ccgttctccc gggggcgcag   9480
ctcaaagacg ccgcctctca tctcgccgcg gggcgggcgg ccgtgaggta gcgagacggc   9540
gctgactatg catcttaaca attgctgtgt aggtacgccg ccaagggacc tgattgagtc   9600
```

-continued

```
cagatccacc ggatccgaaa acctttggag gaaagcgtct atccagtcgc agtcgcaagg   9660
taggctgagc accgtggcgg gcgggggcgg gtcgggagag ttcctggcgg agatgctgct   9720
gatgatgtaa ttaaagtagg cggtcttgag aaggcggatg gtggacagga gcaccatgtc   9780
tttgggtccg gcctgttgga tgcggaggcg gtcggccatg ccccaggcct cgttctgaca   9840
ccggcgcagg tctttgtagt agtcttgcat gagtctttcc accggcacct cttctccttc   9900
ctcttctcca tctcgccggt ggtttctcgc gccgcccatg cgcgtgaccc caaagcccct   9960
gagcggctgc agcagggcca ggtcggcgac cacgcgctcg gccaagatgg cctgctgtac  10020
ctgagtgagg gtcctctcga agtcatccat gtccacgaag cggtggtagg cgcccgtgtt  10080
gatggtgtag gtgcagttgg ccatgacgga ccagttgacg gtctggtgtc ccggctgcga  10140
gagctccgtg taccgcaggc gcgagaaggc gcgggaatcg aacacgtagt cgttgcaagt  10200
ccgcaccaga tactggtagc ccaccaggaa gtgcggcgga ggttggcgat agaggggcca  10260
gcgctgggtg gcgggggcgc cgggcgccag gtcttccagc atgaggcggt ggtatccgta  10320
gatgtacctg gacatccagg tgatgccggc ggcggtggtg gtggcgcgcg cgtagtcgcg  10380
gacccggttc cagatgtttc gcaggggcga gaagtgttcc atggtcggca cgctctggcc  10440
ggtgaggcgc gcgcagtcgt tgacgctcta tacacacaca aaaacgaaag cgtttacagg  10500
gctttcgttc tgtagcctgg aggaaagtaa atgggttggg ttgcggtgtg ccccggttcg  10560
agaccaagct gagctcggcc ggctgaagcc gcagctaacg tggtattggc agtcccgtct  10620
cgacccaggc cctgtatcct ccaggatacg gtcgagagcc cttttgcttt cttggccaag  10680
cgcccgtggc gcgatctggg atagatggtc gcgatgagag gacaaaagcg gctcgcttcc  10740
gtagtctgga gaaacaatcg ccagggttgc gttgcggcgt accccggttc gagcccctat  10800
ggcggcttgg atcggccgga accgcggcta acgtgggctg tggcagcccc gtcctcagga  10860
ccccgccagc cgacttctcc agttacggga gcgagcccct tttgtttttt attttttaga  10920
tgcatcccgt gctgcggcag atgcgcccct cgccccggcc cgatcagcag cagcaacagc  10980
aggcatgcag accccccctct cctctacccg ccccggtcac cacggccgcg gcggccgtgt  11040
ccggcgcggg gggcgcgctg gagtcagatg agccaccgcg gcggcgacct aggcagtatc  11100
tggacttgga agagggcgag ggactggcgc ggctgggggc gagctctcca gagcgccacc  11160
cgcgggtgca gttgaaaagg gacgcgcgcg aggcgtacct gccgcggcag aacctgtttc  11220
gcgaccgcgg gggcgaggag cccgaggaga tgcgagactg caggttccaa gcggggcgcg  11280
agctgcgccg cgggttggac agacagcgcc tgctgcgcga ggaggacttt gagcccgaca  11340
cgcagacggg catcagcccc gcgcgcgcgc acgtggccgc ggccgacctg gtgaccgcct  11400
acgagcagac ggtgaaccag gagcgcaact tccaaaaaag cttcaacaac cacgtgcgca  11460
cgctggtggc gcgcgaggag gtgaccctgg gtctcatgca tctgtgggac ctggtggagg  11520
cgatcgtgca gaaccccagc agcaagcccc tgaccgcgca gctgttcctg gtggtgcagc  11580
acagcaggga caacgaggcc ttcagggagg cgctgctgaa catcaccgag ccggaggggc  11640
gctggctcct ggacctgata aacatcctgc agagcatagt ggtgcaggag cgcagcctga  11700
gcctggccga gaaggtggcg gccattaact attctatgct gagcttgggc aagttctacg  11760
cccgcaagat ctacaagacc ccctacgtgc ccatagacaa ggaggtgaag atagacagct  11820
tctacatgcg catggcgcta aaggtgctga ccctgagcga cgacctggga gtgtaccgca  11880
acgagcgcat ccacaaggcc gtgagcgcca gccggcggcg cgagctgagc gaccgcgagc  11940
```

-continued tgatgcacag tctgcagcgc gcgctcaccg gcgcgggcga gggcgacagg gaggtcgagt 12000
cctacttcga catgggggct gacctgcact ggcagccgag ccgccgcgcc ctggaggcgg 12060
cgggggcgta tggcggcccc ctggcggccg atgacgagga agaggaggac tatgagctag 12120
aggagggcga gtacctggag gactgacctg gctggtggtg ttttggtata gatgcaagat 12180
ccgaacgtgg cggacccggc ggtccgggcg gcgctgcaga gccagccgtc cggcattaac 12240
tcctctgacg actgggccgc ggccatgggt cgcatcatgg ccctgaccgc gcgcaacccc 12300
gaggccttca ggcagcagcc tcaggctaac cggctggcgg ccatcttgga agcggtagtg 12360
cccgcgcgct ccaaccccac ccacgagaag gtgctggcca tagtcaacgc gctggcggag 12420
agcagggcca tccgggcgga cgaggccgga ctggtgtacg atgcgctgct gcagcgggtg 12480
gcgcggtaca acagcggcaa cgtgcagacc aacctggacc gcctggtgac ggacgtgcgc 12540
gaggccgtgg cgcagcgcga gcgcttgcat caggacggta acctgggctc gctggtggcg 12600
ctaaacgcct tcctcagcac ccagccggcc aacgtaccgc gggggcagga ggactacacc 12660
aacttcttga gcgcgctgcg gctgatggtg accgaggtcc ctcagagcga ggtgtaccag 12720
tcggggcccg actacttctt ccagaccagc agacagggct tgcaaaccgt gaacctgagc 12780
caggctttca agaacctgcg ggggctgtgg ggagtgaaag cgcccaccgg cgaccgagct 12840
acggtgtcca gcctgctaac ccccaactcg cgcctgctgc tgctgctgat cgcgcccttc 12900
acggacagcg ggagcgtctc gcgggagacc tatctgggcc acctgctgac gctgtaccgc 12960
gaggccatcg ggcaggcgca ggtggacgag cacaccttcc aagagatcac cagcgtgagc 13020
cacgcgctgg ggcaggagga cacgggcagc ctgcaggcga ccctgaacta cctgctgacc 13080
aacaggcggc agaagattcc cacgctgcac agcctgaccc aggaggagga gcgcatcttg 13140
cgctacgtgc agcagagcgt gagcctgaac ctgatgcgcg acggcgtgac gcccagcgtg 13200
gcgctggaca tgaccgcgcg caacatggaa ccgggcatgt acgcttccca gcggccgttc 13260
atcaaccgcc tgatggacta cttgcatcgg gcggcggccg tgaaccccga gtacttcacc 13320
aatgccattc tgaatcccca ctggatgccc cctccgggtt tctacaacgg agacttcgag 13380
gtgcctgagg tcaatgatgg gttcctctgg gatgacatgg atgacagtgt gttctccccc 13440
aacccgctgc gcgccgcgtc tctgcgattg aaggagggct ctgacaggga aggaccgagg 13500
agtctggcct cctccctggc tctgggggcg gtgggcgcca cgggcgcggc ggcgcggggc 13560
agcagcccct tccccagcct ggcagactct ctgaatagcg ggcgggtgag caggccccgc 13620
ttgctaggcg aggaggagta tctgaacaac tccctgctgc agcccgtgag ggacaaaaac 13680
gctcagcgac agcagtttcc caacaacggg atagagagcc tggtggacaa gatgtccaga 13740
tggaagacat atgcgcagga gtacaaggag tgggaggacc gccagccgcg gcccctgccg 13800 cccccctagac agcgctggca gcggcgcgcg tccaaccgcc gctggagaca gggacccgag 13860
gacgatgatg actctgcaga tgacagcagc gtgttggacc tgggcgggag cgggaacccc 13920
ttttcgcacc tgcgcccacg cctgggcaag atgttttaaa agagaaaaat aaaactcacc 13980
aaggccatgg cgacgagcgt tggtttttttg ttcccttcct tagtatgcgg cgcgcggcga 14040
tgttcgagga ggggcctccc ccctcttacg agagcgcgat gggaatttct cctgcggcgc 14100
ccctgcagcc tccctacgtg cctcctcggt acctgcaacc tacagggggg agaaatagca 14160
tctgttactc tgagctgcag cccctgtacg ataccaccag actgtacctg gtggacaaca 14220
agtccgcgga cgtggcctcc ctgaactacc agaacgacca cagcgatttt ttgaccacgg 14280
tgatccaaaa caacgacttc accccaaccg aggccagtac ccagaccata aacctggaca 14340
acaggtcgaa ctggggcggc gacctgaaga ccatcctgca caccaacatg cccaacgtga 14400
acgagttcat gtttaccaac tcttttaagg cgcgggttat ggtggcgcgc gagcaggggg 14460
aggcgaagta cgagtgggtg gacttcacgc tgcccgaggg caactactca gagaccatga 14520
ctattgacct gatgaacaat gcgatcgtgg aacactacct gaaagtgggc aggcagaacg 14580
gggtgaagga gagcgatatc ggggtcaagt ttgacaccag aaactttcgt ctgggctggg 14640
accccgtgac cgggctggtc atgccggggg tctacaccaa cgaggccttt catcccgata 14700
tagtgctcct gcccggctgt ggggtggact ttacccagag ccggctgagc aacctgctgg 14760
gcgttcgcaa gcggcaacct ttccaggagg gtttcaagat cacctatgag gatctggagg 14820
ggggcaacat tcccgcgctc cttgatctgg acgcctacga ggagagcttg aaacccgagg 14880
agagcgctgg cgacagcggc gagagtggcg aggagcaagc cggcggcggt ggcagcgcgt 14940
cggtagaaaa cgaaagtact cccgcagtgg cggcagacgc tgcggaggtc gagccagagg 15000
ccatgcagca ggacgcagag gagggcgcac aggagggcgc gcaggaggac atgaacgatg 15060
gggagatcag gggagacact ttcgccaccc ggggcgaaga aaaagaggca gaggcggtgg 15120
cggcgacggt ggaagccgaa accgaggcag aggcagagcc caagaccgaa gttatggaag 15180
acatgaatga tggagaacgt aggggtgaca cgtttgccac ccggggcgaa gagaaggcgg 15240
cggaggcaga agccgcggct gaggaggcgg ctgcggctgc ggccgaggct gaggctgcgg 15300
ctgaggctaa ggtcgaagcc gatgttgcgg ttgaggctca ggctgaggag gaggaggcgg 15360
cgactgaagc agttaaggaa aaggcccagg cagagcagga agagaaaaaa cctgtcattc 15420
aacctctaaa agaagatagc aaaaagcgca gttacaacgt catcgagggc agcaccttta 15480
cccagtaccg cagctggtac ctggcgtaca actacggcga cccggtcaag ggggtgcgct 15540
cgtggaccct gctctgcacg ccggacgtca cctgcggctc cgagcagatg tattggtcgc 15600
tgccaaacat gatgcaagac ccggtgacct tccgctccac gcggcaggtt agcaacttcc 15660
cggtggtggg cgccgaactg ctgcccgtgc actccaagag tttttacaac gagcaggccg 15720
tctactccca gctgatccgc caggccacct ctctgaccca cgtgttcaat cgctttcccg 15780
agaaccagat tttggcgcgc ccgccggccc ccaccatcac caccgtcagt gaaaacgttc 15840
ctgccctcac agatcacggg acgctaccgc tgcgcaacag catctcagga gtccagcgag 15900
tgaccattac tgacgccaga cgccggacct gcccctacgt ttacaaggcc ttgggcatag 15960
tctcgccgcg cgtcctctcc agtcgcactt tttaaaatac atctaccctc acgcttcaaa 16020
atcatgtccg tactcatctc acccagcaac aacaccggct gggggctgcg cgcgcccagc 16080
aagatgtttg gaggggcgag gaaacgctcc gagcagcacc cagtgcgcgt gcgcggccac 16140
taccgcgcgc cctggggagc gcacaagcgc gggcgcgcag ggcgcaccac tgtggacgac 16200
gccattgact ccgtagtgga gcaggcgcgc cactacacac ccggcgcgcc gtccgccccc 16260
gccgtgtcca ccgtggacga ggcgatcgag agcgtggtac agggcgcgcg gcactatgcc 16320
aaccttaaaa atcgacgccg tcgcgtggct cgccgccatc gccggagacc ccgggccacc 16380
gccgccgcgc gccttgctaa ggctctgctc aggcgcgcca ggcgaactgg ccgccgggcc 16440
gccatgaggg ccgcacggcg ggctgccgcc agcgcggccg ccgcggcccc acgggcacga 16500
aggcgcgcgg ccgctgccgc cgccgccgcc atttccagct tggcctcgac gcggcgcggt 16560
aacatatact gggtgcgcga ctcggtaacc ggcacgcggg tacccgtgcg ctttcgcccc 16620
ccgcggaatt agcacaagac aacatacaca ctgagtctcc tgctgttgtg tatcccagcg 16680

-continued

```
gcgaccgtca gcagcggcga catgtccaag cgcaaaatta aagaagagat gctccaggtc  16740
atcgcgccgg agatctatgg gcccccgaag aaggaggagg atgattacaa gccccgcaag  16800
ctaaagcggg tcaaaaagaa aaagaaagat gatgacgttg acgaggcggt ggagtttgtc  16860
cgccgcatgg cgcccaggcg ccccgtgcag tggaagggtc ggcgcgtgca gcgagtcctg  16920
cgccccggca ccgcggtggt ctttacgccc ggcgagcgtt ccacgcgcac tttcaagcgg  16980
gtgtacgatg aggtgtacgg cgacgaggat ctgttggagc aggccaacca tcgctttggg  17040
gagtttgcat atgggaaacg gccccgcgag agcctaaaag aggacctgct ggcgctaccg  17100
ctggacgagg gcaatcccac cccgagtctg aagccggtaa ccctgcaaca ggtgctgcct  17160
ttgagcgcgc ccagcgagca gaagcgaggg ttgaagcgcg agggcgggga cctggcaccc  17220
accgtgcagt tgatggtgcc caagcggcag aagctggagg acgtgctgga gaaaatgaaa  17280
gtagagcccg ggatccagcc cgaaatcaag gtccgcccca tcaagcaggt ggcgcccggc  17340
gtgggagtcc agaccgtgga cgttaggatt cccacggagg agatggaaac ccaaaccgcc  17400
actccctctt cggcggctag cgccaccacc ggctccgctt cggtagaggt gcagacggac  17460
ccctggctag ccgccgccgc cccggccgcc ccccgttcgc gcgggcgcaa gagaaattat  17520
ccagcggcca gcgcgctcat gccccagtac gcactgcatc catccatcgc gcccaccccc  17580
ggctaccgcg ggtactcgta ccgcccgcgc agatcagccg gcacccgcgg ccgccgccgc  17640
cgtgcgacca caaccagccg ccgccgtcgc cgccgccgcc agccagtgct gacccccgtg  17700
tctgtaagga aggtggctcg ctcggggagc acgctggtgg tgcccagagc gcgctaccac  17760
cccagcattg tttaaagccg gtctctgtat ggttcttgca gatatggccc tcacttgtcg  17820
cctccgcttc ccggtgccgg gataccgagg aagaactcac cgccgcagag gcatggcggg  17880
cagtggtctc cgcggcggcc gtcgccatcg ccggcgcgca aagagcaggc gcatgcgcgg  17940
cggtgtgctg cccttcctaa tcccgctaat cgccgcggcg atcggtgccg tgcccgggat  18000
cgcctccgtg gccctgcagg cgtcccagaa acattgactc ttgcaacctt gcaagcttgc  18060
attttttgga ggaaaaaata aaaagtctag actctcacgc tcgcttggtc ctgtgactat  18120
tttgtagaaa aaagatggaa gacatcaact ttgcgtcgct ggccccgcgt cacggctcgc  18180
gcccgttcat gggagactgg acagatatcg gcaccagcaa tatgagcggt ggcgccttca  18240
gctggggcag tctgtggagt ggccttaaaa attttggttc caccattaag aactatggca  18300
acaaagcgtg gaacagcagc acgggtcaga tgctgagaga caagttgaaa gagcagaact  18360
tccaggagaa ggtggcacag ggcctggcct ctggcatcag cggggtggtg gacatagcta  18420
accaggccgt gcagaaaaag ataaacagtc atctggaccc ccgccctcag gtggaggaaa  18480
cgcctccagc catggagacg gtgtctcccg agggcaaagg cgaaaagcgc ccgcggcccg  18540
acagggaaga gaccctggtg tcacacaccg aggagccgcc ctcttacgag gaggcagtca  18600
aggccggcct gcccaccact cgccccatag ctcccatggc caccggtgtg gtgggtcaca  18660
ggcaacacac ccccgcgaca ctagatctgc ccccgccgtc cgagccgact cgccagccaa  18720
aggcggtgac ggtgcccgct ccctccactt ccgccgccaa cagagtgcct ctgcgccgcg  18780
ctgcgagcgg cccccgggcc tcgcgagtca gcggcaactg gcagagcaca ctgaacagca  18840
tcgtgggcct gggagtgagg agtgtgaagc gccgccgttg ctactgaatg agcaagctag  18900
ctaacgtgtt gtatgtgtgt atgcgtccta tgtcgccgcc agaggagctg ttgagccgcc  18960
ggcgccgtct gcactccagc gaatttcaag atggcgaccc catcgatgat gcctcagtgg  19020
tcgtacatgc acatctcggg ccaggacgct tcggagtacc tgagccccgg gctggtgcag  19080
```

-continued

```
ttcgcccgcg ccacagacac ctacttcaac atgagtaaca agttcaggaa ccccactgtg  19140
gcgcccaccc acgatgtgac cacggaccgg tcgcagcgcc tgacgctgcg gttcatcccc  19200
gtggatcggg aggacaccgc ttactcttac aaggcgcggt tcacgctggc cgtgggcgac  19260
aaccgcgtgc tggacatggc ctccacttac tttgacatcc ggggggtgct ggacaggggc  19320
cccactttca agccctactc gggcactgcc tacaactccc tggcccccaa gggcgctccc  19380
aattcttgcg agtgggagga ggaaacacaa aatgaggtac aagccaatga agaacaacta  19440
gcagaagaag aggatgaaga aatggctcaa gaggatcagc agcctactaa aaaaacccat  19500
gtatatgctc aggcacctct ttctggcgaa cagattacca aagatggctt gcaaatagga  19560
gctgaagtta caggagaaac atcaaagccc atttttgcag acaagacatt ccaaccagaa  19620
cctcagatag gagagtctca atggaatgag gccgatgcta cagtagcagg aggtagggtt  19680
ttgaaaaaga ctacccctat gaaaccttgc tatggatcct atgccagacc taccaatgcc  19740
aatggagggc aggggatact tgaggcaaat gctaaagggg aactcgaatc taaagttgag  19800
atgcagtttt tctctaacac cacaactctt aatgtaagag acggtgaaaa tggccttaaa  19860
ccaaaagtag tgctgtatag cgaagatgtc aacctggaat cccctgacac tcatctgtct  19920
tacaagccca aaaaagatga tgttaatgcc aaaatcatgt tgggtcagca agccatgccc  19980
aacagaccca acctcattgg atttagagat aatttcattg ggctcatgta ttacaacagc  20040
actggaaaca tgggagtgct ggcgggtcag gcctctcagt tgaatgctgt ggtggacttg  20100
caggatagaa acacggaact gtcatatcag cttatgcttg attccattgg agatagaacc  20160
agatactttt ccatgtggaa ccaggcagtg gatagctatg acccagatgt tagaatcatt  20220
gaaaaccatg ggtggagga tgagctgccc aactactgtt ttcccttggg cggtatagga  20280
attacagata cataccaggc cataaaagca gccaatggtg gagatgctac tacgtggtct  20340
gctgataaca catttgcaga ccgcaacgaa ataggggtgg gaaacaactt cgccatggag  20400
atcaacatcc aggccaacct ctggagaaac ttcctctatg cgaacgtggg actctacctg  20460
ccagacaagc tcaagtacaa ccccaccaac gtggacatct ctgacaaccc caacacctat  20520
gactacatga acaagcgggt ggtggccccc ggcctggtgg actgctttgt caatgtggga  20580
gccaggtggt ccctggacta catggacaac gtcaacccct tcaaccacca ccgcaatgcg  20640
ggtctgcgct accgctccat gatcctgggc aacgggcgct atgtgccctt ccacatccag  20700
gtaccccaga agttctttgc catcaagaac ctcctgctcc tgcccggctc ctacacctac  20760
gagtggaact tcaggaagga tgtaaacatg gtcctacaga gctctctggg caatgacctt  20820
agggtagatg gggccagcat caagtttgac agcatcaccc tctatgctac atttttcccc  20880
atggcccaca acaccgcctc cacgcttgag gccatgctga gaaacgacac caacgaccag  20940
tccttcaatg actacctctc tggggccaac atgctctacc caatcccagc caaggccacc  21000
aacgtgccca tctccatccc ctctcgcaac tgggccgcct ttagaggctg ggcctttacc  21060
cgccttaaga ccaaggagac cccctccctg ggctcgggtt ttgatcccta ctttgtttac  21120
tcgggatcca tcccctacct ggatggcacc ttctacctca accacacttt caagaagata  21180
tccatcatgt atgactcctc cgtcagctgg ccgggcaacg accgcttgct caccccccaat  21240
gagttcgagg tcaagcgcgc cgtggacggc gagggctaca acgtggccca gtgcaacatg  21300
accaaggact ggttcctggt gcagatgctg gccaactaca acataggcta ccagggcttc  21360
tacatcccag agagctacaa ggacaggatg tattccttct tcagaaattt ccaacccatg  21420
```

-continued

```
agccgacagg tggtggacga gaccaattac aaggactatc aggccattgg catcacccac  21480
cagcacaaca actcgggttt cgtgggctac ctggcgccca ccatgcgcga gggacaggcc  21540
taccccgcca acttccccta ccccctgata ggcaagaccg cggtcgacag cgtcacccag  21600
aaaaagttcc tctgcgaccg caccctctgg cgcatcccct tctctagcaa ctttatgtcc  21660
atgggtgcgc tcacggacct gggccaaaac ctgctttatg ccaactctgc ccatgcgctg  21720
gacatgactt ttgaggtgga ccccatggac gagcccaccc ttctctatat tgtgtttgaa  21780
gtgttcgacg tggtcagagt gcaccagccg caccgcggtg tcatcgagac cgtgtacctg  21840
cgtacgccct tctcagccgg caacgccacc acctaaggag acagcgccgc cgcctgcatg  21900
actggttcca ccgagcaaga gctcagggcc atcgccagag acctgggatg cggaccctat  21960
tttttgggca cctatgacaa acgcttcccg ggttttatct cccgagacaa gctcgcctgc  22020
gccatcgtca acacggccgc gcgcgagacc gggggcgtgc actggctggc ctttggctgg  22080
gacccgcgct ctaaaacttg ctacctcttt gacccctttg gcttctccga tcagcgcctc  22140
aggcagattt atgagtttga gtacgagggg ctgttgcgcc gcagcgcgct tgcctcctcg  22200
cccgaccgct gcatcaccct tgagaagtcc accgagaccg tgcaggggcc ccactcggcc  22260
gcctgcggtc tcttctgttg catgtttttg cacgcctttg tgcactggcc tcagagtccc  22320
atggatcgca accccaccat gaacttgcta aagggagtgc ccaacgccat gctccagagc  22380
ccccaggtcc tgcccaccct gcgccgcaac caggaacagc tctaccgctt cctggagcgc  22440
cactccccct acttccgcag ccacagcgcg cgcatccggg gggccacctc tttttgccac  22500
ttgcaagaaa acatgcaaga cggaaaatga tgtacagcat gcttttaata aatgtaaaga  22560
ctgtgcactt tatttataca cgggctcttt ctggttattt attcaacacc gccgtcgcca  22620
tctagaaatc gaaagggttc tgccgcgcgt cgccgtgcgc cacgggcaga gacacgttgc  22680
gatactggaa gcggctcgcc cacttgaact cgggcaccac catgcggggc agtggttcct  22740
cggggaaatt ctcgctccac agggtgcggg tcagctgcag cgcgctcagg aggtcgggag  22800
ccgagatctt gaagtcgcag ttggggccgg aaccctgcgc gcgcgagttg cggtacacgg  22860
ggttgcagca ctggaacacc agcagggccg gattattcac gctggccagc aggctctcgt  22920
cgctaatcat gtcgctgtcc agatcctccg cgttgctcag ggcgaatggg gtcatcttgc  22980
agacctgcct gcccaggaaa ggcgggagcc caggcttgcc gttacagtcg cagcgcaggg  23040
gcattagcag gtgcccacgg cccgactgcg cctgcgggta caacgcgcgc atgaaggctt  23100
cgatctgcct aaaagccacc tgggtcttgg ctccctccga aaagaacatc ccacaggact  23160
tgctggagaa ctggttcgcg ggacagctgg catcgtgcag gcagcagcgc gcgtcagtgt  23220
tggcgatctg caccacgttg cgaccccacc ggtttttcac tatcttggcc ttggaagcct  23280
gctcctttag cgcgcgctgg ccgttctcgc tggtcacatc catctctatc acctgttcct  23340
tgttgatcat gtttgtcccg tgcagacact ttaggtcgcc ctccgtctgg gtgcagcggt  23400
gctcccacag cgcgcaaccg gtgggctccc aatttttgtg ggtcaccccc gcgtaggcct  23460
gcaggtaggc ctgcaggaag cgccccatca tggtcataaa ggtcttctgg ctcgtaaagg  23520
tcagctgcag gccgcgatgc tcttcgttca gccaggtctt gcagatggcg gccagcgcct  23580
cggtctgctc gggcagcatc ttaaaatttg tcttcaggtc gttatccacg tggtacttgt  23640
ccatcatggc acgcgccgcc tccatgccct tctcccaggc ggacaccatg ggcaggctta  23700
gggggtttat cacttccagc ggcgaggaca ccgtactttc gatttcttct tcctccccct  23760
cttcccggcg cgcgcccccg ctgttgcgcg ctcttaccgc ctgcaccaag ggtcgtctt  23820
```

-continued

```
caggcaagcg ccgcaccgag cgcttgccgc ccttgacctg cttgatcagt accggcgggt  23880
tgctgaagcc caccatggtc agcgccgcct gctcttcttc gtcttcgctg tctaccacta  23940
tttctgggga ggggcttctc cgctctgcgg caaaggcggc ggatcgcttc ttttttttct  24000
tgggagccgc cgcgatggag tccgccacgg cgaccgaggt cgagggcgtg ggctgggggg  24060
tgcgcggcac cagggcctcg tcgccctcgg actcttcctc tgactccagg cggcggcgga  24120
gtcgcttctt tgggggcgcg cgcgttagcg gcggcggaga cggggacggg gacggggacg  24180
ggacgccctc cacagggggc ggtcttcgcg cagacccgcg gccgcgctcg gggtcttct  24240
cgcgctggtc ttggtcccga ctggccattg tatcctcctc ctcctaggca gagagacata  24300
aggagtctat catgcaagtc gagaaggagg agagcttaac cacccccctct gagaccgccg  24360
tcgccgtcgc ccccgctacc gccgacgcgc ccgccacacc gagcgacacc cccgcggacc  24420
cccccgccga cgcacccctg ttcgaggaag cggccgtgga gcaggacccg ggctttgtct  24480
cggcagagga ggatttgcaa gaggaggagg ataaggagga gaagccctca gtgccaaaag  24540
atcataaaga gcaagacgag cacgacgcag acgcacacca gggtgaagtc gggcgggggg  24600
acggagggca tggcggcgcc gactacctag acgaaggaaa cgacgtgctc ttgaagcacc  24660
tgcatcgtca gtgcgccatt gtctgcgacg ctctgcagga gcgcagcgag gtgcccctca  24720
gcgtggcgga ggtcagccgc gcctacgagc tcagcctctt ttccccccgg gtgccccccc  24780
gccgccgcga aaacggcaca tgcgagccca acccgcgcct caacttctac cccgcctttg  24840
tggtgcccga ggtcctggcc acctatcaca tcttctttca aaattgcaag atccccatct  24900
cgtgccgcgc caaccgtagc cgcgccgata agatgctggc cctgcgccag ggcgaccaca  24960
tacctgatat cgccgctttg gaagatgtgc caaagatctt cgagggtctg ggtcgcaacg  25020
agaagcgggc agcaaactct ctgcaacagg aaaacagcga aaatgagagt cacactggag  25080
cgctggtgga gctggagggc gacaacgccc gcctggcggt gctcaagcgc agcatcgagg  25140
tcacccactt tgcctacccc gcgctcaacc tgccccccaa agtcatgaac gcggtcatgg  25200
acgggctaat catgcgccgc ggccggcccc ttgctccaga tgcaaacttg catgaggaga  25260
ccgaggacgg tcagcccgtg gtcagcgacg agcagctgac gcgctggctg gaaaccgcgg  25320
accccgccga actggaggag cggcgcaaga tgatgatggc cgcggtgctg gtcaccgtag  25380
agctggagtg tctgcagcgc ttcttcggcg accccgagat gcagagaaag gtcgaggaga  25440
ccctacacta caccttccgc cagggctacg tgcgccaggc ttgcaagatc tccaacgtgg  25500
agctcagcaa cctggtgtcc tacctgggca tcttgcatga aaaccgcctt gggcagagcg  25560
tgctacactc caccctgcgc ggggaggcgc gccgcgacta cgtgcgcgac tgcgtttacc  25620
tcttcctctg ctacacctgg cagacggcca tgggggtctg gcagcagtgc ctggaggagc  25680
gcaacctcaa ggagctggag aagctcctgc agcgcgcgct caaagacctc tggacgggct  25740
acaacgagcg ctcggtggcc gccgcgctgg ccgacctcat cttccccgag cgcctgctca  25800
aaactctcca gcaggggctg cccgacttca ccagccaaag catgttgcaa aattttagga  25860
actttatcct ggagcgttct ggcatcctac ccgccacctg ctgcgccctg cccagcgact  25920
ttgtcccccct cgtgtaccgc gagtgccccc cgccgctgtg ggccactgc tacctgttcc  25980
aactggccaa ctacctgtcc taccacgcgg acctcatgga agactccagc ggcgaggggc  26040
tcatggagtg ccactgccgc tgcaacctct gcacgcccca ccgctccctg gtctgcaaca  26100
cccaactgct cagcgagagt cagattatcg gtaccttcga gctacagggt ccgtcctcct  26160
```

-continued

```
cagacgagaa gtccgcggct ccggggctaa aactcactcc ggggctgtgg acttccgcct  26220
acctgcgcaa atttgtacct gaagactacc acgcccacga gatcaggttt tacgaggacc  26280
aatcccgccc gcccaaggcg gagctgaccg cctgcgtcat cacccagggc gagatcctag  26340
gccaattgca agccatccaa aaagcccgcc aagagttttt gctgagaaag ggtcgggggg  26400
tgtatctgga cccccagtcg ggtgaggagc tcaacccggt tcccccgctg ccgccgccgc  26460
gggaccttgc ttcccaggat aagcatcgcc atggctccca gaaagaagca gcagcggccg  26520
ccactgccgc caccccacac gctggaggaa gaggaggaat actgggacag tcaggcagag  26580
gaggtttcgg acgaggagga gccggagacg gagatggaag agtgggagga ggacagctta  26640
gacgaggagg cttccgaagc cgaagaggca ggcgcaacac cgtcaccctc ggccgcagcc  26700
ccctcgcagg cgcccccgaa gtccgctccc agcatcagca gcaacagcag cgctataacc  26760
tccgctcctc caccgccgcg acccacggcc gaccgcagac ccaaccgtag atgggacacc  26820
accggaaccg gggccggtaa gtcctccggg aaaggcaagc aagcgcagcg ccaaggctac  26880
cgctcgtggc gcgctcacaa gaacgccata gtcgcttgct tgcaagactg cggggggaac  26940
atctccttcg cccgccgctt cctgctcttc caccacggtg tggccttccc ccgtaacgtc  27000
ctgcattact accgtcatct ctacagcccc tactgcggcg gcagtgagcc agaggcggcc  27060
ggcggcagcg gcgcccgttt cggtgcctag gaagacccag ggcaagactt cagccaagaa  27120
actcgcggcg gccgcggcga acgcggtcgc gggggccctg cgcctgacgg tgaacgaacc  27180
cctgtcgacc cgcgaactga ggaaccgaat cttccccact ctctatgcca tcttccagca  27240
gagcagaggg caggatcagg aactgaaagt aaaaaacagg tctctgcgct ccctcacccg  27300
cagctgtctg tatcacaaga gcgaagacca gcttcggcgc acgctggagg acgctgaggc  27360
actcttcagc aaatactgcg cgctcactct taaggactag ctccgcgccc ttctcgaatt  27420
taggcgggaa cgcctacgtc atcgcagcgc cgccgtcatg agcaaggaca ttcccacgcc  27480
atacatgtgg agctatcagc cgcagatggg actcgcggcg ggcgcctccc aggattactc  27540
cacccgcatg aactggctca gtgccggccc acacatgatc tcacaggtta atgacatccg  27600
cacccatcga aaccaaatat tggtggagca ggcggcaatt accaccacgc cccgcaataa  27660
tcccaacccc agggagtggc ccgcgtccct ggtgtatcag gaaattcccg gccccaccac  27720
cgtactactt ccgcgtgatt cccaggccga agtccaaatg actaactcag ggcacagct   27780
cgcgggcggc tgtcgtcaca gggtgcggcc tcctcgccag ggtataactc acctgaagat  27840
ccgaggcaga ggtattcagc tcaacgacga gtcggtgagc tcctcgctcg gtctcagacc  27900
tgacgggacc ttccagatag ccggagccgg ccgatcttcc ttcacgcccc gccaggcgta  27960
cctgactctg cagagctcgt cctcggcgcc gcgctcgggc ggcatcggga ctctccagtt  28020
cgtgcaggag tttgtgccct cggtctactt caacccctt  tcgggctctc ccggtcgcta  28080
cccggaccag ttcatcccga actttgacgc cgcgagggac tcggtggacg gctacgactg  28140
aatgtcgggt ggacccggtg cagagcaact tcgcctgaag caccttgacc actgccgccg  28200
ccctcagtgc tttgcccgct gtcagaccgg tgagttccag tacttttccc tgcccgactc  28260
gcacccggac ggcccggcgc acggggtgcg ctttttcatc ccgagtcagg tccgctctac  28320
cctaatcagg gagttcaccg cccgtcccct actggcggag ttggaaaagg ggccttctat  28380
cctaaccatt gcctgcatct gctctaaccc tggattacac caagatcttt gctgtcattt  28440
gtgtgctgag tataataaag gctgagatca gaatctactc gggctcctgt cgccatcctg  28500
tcaacgccac cgtccaagcc cggcccgatc agcccgaggt gaacctcacc tgcggtctgc  28560
```

-continued

```
accggcgcct gaggaaatac ctagcttggt actacaacag cactcccttt gtggtttaca  28620
acagctttga ccaggacggg gtctcactga gggataacct ctcgaacctg agctactcca  28680
tcaggaagaa caacaccctc gagctacttc ctccttacct gcccgggact taccagtgtg  28740
tcaccggtcc ctgcacccac acccacctgt tgatcgtaaa cgactctctt ccgagaacag  28800
acctcaataa ctcctctccg cagttcccca gaacaggagg tgagctcagg aaaccccggg  28860
taaagaaggg tggacaagag ttaacacttg tggggtttct ggtgtatgtg acgctggtgg  28920
tggctctttt gattaaggct tttccttcca tgtctgaact atccctcttc ttttatgaac  28980
aactcgacta gtgctaacgg gaccctaccc aacgaatcgg gattgaatat cggtaaccag  29040
gttgcagttt cacttttgat taccttcata gtcctcttcc tgctagtgct gtcgcttctg  29100
tgcctgcgga tcgggggctg ctgcatccac gtttatatct ggtgctggct gtttagaagg  29160
ttcggagacc accgcaggta gaataaacat gctactgctc gccttcctta tcctggcgct  29220
ggccgcccaa tgccaagcct tttccgaggc tgactttgta gagccccagt gcaacgttac  29280
ttttagagcc tatgcacagc gttgtcatac tataatcaaa tgtgccaccg aacacaatgg  29340
ataccttatt cagtataaag ataaatcaca caaagtggca cttgttgaca tctgggaacc  29400
cgaagaccct ctggaataca atgttaccgt tttccagggt gacctcttca gaacttacaa  29460
ttacactttc ccatttgacc agatgtgtga ctttgtcatg tacatggaaa agcagcacaa  29520
gctgtggcct ccaactcccc agggctgtgt ggaaaatcca ggctctttct gtatgatctc  29580
tctctgtgta actgtgctgg cactaatact cacgcttctg tatctcagat ttaaatcaag  29640
gcaaagcttt attgatgaaa agaaaatgcc ttaatcgctt tcacgcttga ttgctaacac  29700
cgggttttta tccgcagaat gattggaatc accctactaa tcacctccct ccttgcgatt  29760
gcccatgggt tggaacgaat cgaagtccct gtgggggcca atgttaccct ggtggggcct  29820
gtcggcaatg ctacattaat gtgggaaaaa tatactaaaa atcaatgggt ctcttactgc  29880
actaacaaaa acagccacaa gcccagagcc atctgcgatg ggcaaaattt aaccttgatt  29940
gatgttcaat tgctggatgc gggctactat tatgggcagc tgggtacaat gattaattac  30000
tggagacccc acagagatta catgcttcac gtagtaaagg gtcccattaa cagcccaacc  30060
accacctcta ccacccccac taccaccact actcccacca ccagcactgc cgcccagcct  30120
cctcatagca gaacaaccac ttttatcaat tccaagtccc actcccccca cattgccggc  30180
gggccctccg cctcagactc cgagactacc gagatctgct tctgcaaatg ctctgacgcc  30240
attgcccagg atttggaaga tcacaaggaa gatgagcatg actacgcaga tgcatgccag  30300
gcatcagagt cagaagcgct gccggtggcc ctaaaacagt atgcagaccc ccacaccacc  30360
cccgaccttc ctccaccttc ccagaagcca agtttcctgg gggaaaatga aactctgcct  30420
ctctccatac tagctctgac atctgttgct attttggccg ctctgctggt gcttctatgc  30480
tctatatgct acctgatctg ctgcagaaag aaaaaatctc acggccatgc tcaccagccc  30540
ctcatgcact tcccttaccc tccagagctg ggcgaccaca aactttaagt ctgcagtagc  30600
tatctgccca tcccttgtca gtcgacagcg atgagcccca ctaatctaac agcctctgga  30660
cttacaacat tgtctcttaa tgagaccacc gctcctcaag acctgtacga tggtgtctcc  30720
gcgctggtta accagtggga tcacctgggc atatggtggc tcctcatagg agcagtgacc  30780
ctgtgcctaa tcctggtctg gatcatctgc tgcatcaaaa gcagaagacc caggcggcgg  30840
cccatctaca ggcccttcgt catcacacct gaagatgatg atgatgacac cacctccagg  30900
```

ctgcagagcc taaagcggct actcttctct tttacagcat ggtaaattga atcatgcccc 30960
gcattttcat ctacttgctt ctccttccac tttttctggg ctcctctaca ttggccgctg 31020
tgtcccacat cgaggtagac tgcctcacgc ccttcacagt ctacctgctt ttcggctttg 31080
tcatctgcac ctttgtctgc agcgttatca ctgtagtgat ctgcttcata cagtgcatcg 31140
actacatctg tgtgcgggtg gcctacttta gacaccaccc ccagtatcgc aacagggaca 31200
tagcggctct cctaagactt gtttaaatca tggccaaatt acctgtgatt ggtcttctga 31260
ttatctgctg cgtcctagcc gcgattggga ctcaacctaa taccaccacc agcgctccca 31320
gaaagagaca tgtatcctgc agcttcaagc gtccctggaa tataccccaa tgctttactg 31380
atgaacctga aatctctttg gcttggtact tcagcgtcac cgcccttctc atcttctgca 31440
gtacggttat tgctcttgcc atctaccctt cccttaacct gggctggaat gctgtcaact 31500
ctatggaata tcccaccttc ccagaaccag acctgccaga cctggttgtt ctaaacgcgt 31560
ttcctcctcc tccagttcaa aatcagtttc gccctccgtc ccctacgccc actgaggtca 31620
gctactttaa tctaacaggc ggagatgact gaaaacctag acctagaaat ggacggtctc 31680
tgcagcgagc aacgcatact agagaggcgc cggcaaaaag cagagctcga gcgtcttaaa 31740
caagagctcc aagacgccgt ggccatacac cagtgcaaaa aagggctctt ctgtctggta 31800
aaacaggcca cgctcaccta tgaaaaaaca ggtgacaccc accgcctagg atacaagctg 31860
cccacacagc gccaaaagtt tgcccttatg ataggtgaac aacccatcac cgtgacccag 31920
cactccgtgg agacagaagg ctgcattcat gctccctgca ggggcgctga ctgcctctac 31980
accttgatca aaaccctttg cggtctcaga gaccttatcc ctttcaattg atcataactg 32040
taatcaataa aaaatcactt acttgaaatc tgatagcaag cctctgtcca atttttttcag 32100
caacacttcc ttcccctctt cccaactctg gtactctagg cgcctcctag ctgcaaactt 32160
cctccacagt ctgaagggaa tgtcagattc ctcctcctcc tgtccctccg cacccacgat 32220
cttcatgttg ttgcagatga aacgcgcaag atcgtctgac gagaccttca accccgtgta 32280
cccctacgat accgagatcg ctccgacttc tgtccctttc cttacccctc cctttgtgtc 32340
atccgcagga atgcaagaaa atccagctgg ggtgctgtcc ctgcacctgt cagagcccct 32400
taccacccac aatggggccc taactctaaa aatgggggggc ggcctaaccc tggacaagga 32460
agggaatctc acttcccaaa acatcaccag tgtcgatccc cctctcaaaa aaagcaaaaa 32520
caacatcagc cttcagaccg ccgcacccct cgccgtcagc tccggggccc taacccttt 32580
tgccactccc cccctagcgg tcagtggcga caaccttact gtgcagtctc aggcccccttt 32640
cactttggaa gactcaaaac taactctggc caccaaagga cccctaactg tgtccgaagg 32700
caaacttgtc ctagaaacag aggctcccct gcatgcaagt gacagcagta gcctgggcct 32760
tagcgtcacg gccccactta gcattaacaa tgacagccta ggactagaca tgcaagcgcc 32820
catcagctct cgagatggaa aactggctct aacagtggcg gcccccctaa ctgtggccga 32880
gggtatcaat gctttggcag tagccacagg taatggtatt ggactaaatg aaaccaacac 32940
acacctgcag gcaaaactgg tcgcgcccct aggctttgat accaacggca acattaagct 33000
aagcgtcgca ggaggcatga ggctaaacaa taacacactg atactagatg taaactaccc 33060
atttgaggct caaggccaac tgagcctaag agtgggctcg ggcccactat atgtagattc 33120
tagtagtcat aacctaacca ttagatgcct taggggattg tatgtaacat cttctaacaa 33180
ccaaaacggt ctagaggcca acattaaact aacaaaaggc cttgtgtatg acggaaatgc 33240
catagcagtt aatgttggca aagggctgga atacagccct actggcacaa cagaaaaacc 33300

-continued

```
tatacagact aaaataggtc taggcatgga gtatgacact gagggagcca tgatgacaaa  33360
actaggctct ggactaagct ttgacaattc aggagccatt gtggtgggaa acaaaaatga  33420
tgacaggctt actttgtgga ccacaccgga cccatcgccc aactgtcaga tttactctga  33480
aaaagatgct aaactaacct tggtactgac taaatgtggc agtcaggttg taggcacagt  33540
atctatcgcc gctcttaaag gtagccttgt gccaatcact agtgcaatca gtgtggttca  33600
ggtataccta aggtttgatg aaaatggggt actgatgagt aactcttcac ttaatggcga  33660
atactggaat tttagaaacg gagactcaac taatggcaca ccatatacaa acgcagtggg  33720
ttttatgcct aatctactgg cctatcctaa aggtcaaact acaactgcaa aaagtaacat  33780
tgtcagccag gtttacatga atggggacga tactaaaccc atgacattta caatcaactt  33840
caatggcctt agtgaaacag gggatacccc tgtcagtaaa tattccatga cattctcatg  33900
gaggtggcca aatggaagct acatagggca caattttgta acaaactcct ttactttctc  33960
ctacatcgcc caagaataaa gaaagcacag agatgcttgt tttgatttc aaaattgtgt  34020
gcttttattt attttcaagc ttacagtatt tccagtagtc attcgaatag agcttaatga  34080
aactgcatga gaacccttcc acatagctta aattatcacc agtgcaaatg gagaaaaatc  34140
aacatacctt tttatccaga tatcatagaa ctctagtggt cagttttccc ccaccctccc  34200
aactcacaga atacacagtc ctttcccccc ggctggcttt aaacaacact atctcattgg  34260
taacagacat attcttaggt gtaataatcc acacggtctc ttggcgggcc aaacgctggt  34320
cagtgatgtt aataaactcc ccaggcagct ctttcaagtt cacgtcgctg tccaactgct  34380
gaagcgctcg cggctccgac tgcgcctcta gcggaggcaa cggcaacacc cgatccttga  34440
tctataaagg agtagagtca taatccccca taagaatagg gcggtgatgc tgcaacaagg  34500
cgcgcagcaa ctcctgccgc cgcctctccg tacgacagga atgcaacggg gtggtggtct  34560
cctccgcgat aatccgcacc gctcgcagca tcagcgtcct cgtcctccgg gcacagcagc  34620
gcattctgat ctcactgaga tcggcgcagt aagtgcagca caacaccaag atgttattta  34680
agatcccaca gtgcaaagca ctgtacccaa agctcatggc gggaaggaca gcccccacgt  34740
gaccatcata ccagatcctc aggtaaatca aatgacgacc tctcatgaac acgctggaca  34800
tgtacatcac ctccttgggc atgtgctgat tcaccacctc tcgataccac aggcatcgct  34860
gattaattaa agacccctcg agcaccatcc tgaaccagga agccagcacc tgaccccccg  34920
ccaggcactg cagggacccc ggtgaatcgc agtggcagtg aagactccag cgctcgtagc  34980
cgtgaaccat agagctggtc attatatcca cattggcaca acacagacac actttcatac  35040
actttttcat gattagcagc tcctctctag tcaggaccat atcccaagga atcacccact  35100
cttgaatcaa ggtaaatccc acacagcagg gcaggcctct cacataactc acgttatgca  35160
tagtaagcgt gtcgcaatct ggaaataccg gatgatcttc catcaccgaa gcccgggtct  35220
ccgtctcaaa gggaggtaaa cggtccctcg tgtagggaca gtggcgggat aatcgagatc  35280
gtgttgaacg tagaatcatg ccaaagggaa cagcggacgt actcatattt cctccagcag  35340
aaccaagtgc gcgcgtggca gctatccttg cgtcttctgt ctcgccgcct gccccgctcg  35400
gtgtagtagt tgtaatacag ccactccctc agaccgtcaa ggcgctccct ggcgtccgga  35460
tctataacaa caccatcctg cagcgccgcc ctgatgacat ccaccaccgt agagtatgcc  35520
aagcccagcc aggaaatgca ctcactttga cagcgagaga taggaggagc gggaagagat  35580
ggaagaacca tgatagtaaa agaactttta ttccaatcga tcctctacaa tgtcaaagtg  35640
```

-continued

```
tagatctatc agatggcact ggtctcctcc gctgagtcga tcaaaaataa cagctaaacc  35700
acaaacaaca cgattggtca aatgctgcac aagggcttgc agcataaaat cgcctcgaaa  35760
gtccaccgca agcataacat caaagccacc gcccctatca tgatctatga taaaaacccc  35820
acagctatcc accagaccca tatagttttc atctctccat cgtgaaaaaa tatttacaag  35880
ctcctccttt aaatcacctc caaccaattc aaaaagttga gccagaccgc cctccacctt  35940
cattttcagc atgcgcatca tgattgcaaa aattcaggct cctcagacac ctgtataaga  36000
ttgagaagcg gaacgttaac atcaatgttt cgctcgcgaa gatcgcgcct cagtgcaagc  36060
atgatataat cccacaggtc ggagcggatc agcgaggaca tctccccgcc aggaaccaac  36120
tcaacggagc ctatgctgat tataatacgc atattcgggg ctatgctaac cagcacggcc  36180
cccaaatagg cgtactgcat aggcggcgac aaaaagtgaa cagtttgggt taaaaaatca  36240
ggcaaacact cgcgcaaaaa agcaagaaca tcataaccat gctcatgcaa atagatgcaa  36300
gtaagctcag gaacgaccac agaaaaatgc acaatttttc tctcaaacat gactgcgagc  36360
cctgcaaaaa ataaaaaaga aacattacac aagagtagcc tgtcttacaa tgggatagac  36420
tactctaacc aacataagac gggccacgac atcgcccgcg tggccataaa aaaaattatc  36480
cgtgtgatta aaaagaagca cagatagctg gccagtcata tccggagtca tcacgtgcga  36540
acccgtgtag acccccgggt tggacacatc ggccaaagaa agaaagcggc caatgtatcc  36600
cggaggaatg ataacactaa gacgaagata caacagaata accccatggg ggggaataac  36660
aaagttagta ggtgaataaa aacgataaac acccgaaact ccctcctgcg taggcaaaat  36720
agcgccctcc ccttccaaaa caacatacag cgcttccaca gcagccatga caaaagactc  36780
aaaacactca aaagactcag tcttaccagg aaaataaaag cactctcaca gcaccagcac  36840
taatcagagt gtgaagaggg ccaagtgccg aacgagtata tataggaatt aaaaatgacg  36900
taaatgtgta aaggtcaaaa aacgcccaga aaaatacaca gaccaacgcc cgaaacgaaa  36960
acccgcgaaa aaatacccag aagttcctca acaaccgcca cttccgcttt cccacgatac  37020
gtcacttcct cgaaaatagc aaactacatt tcccacatgt acaaaaccga aaccactccc  37080
cttgtcaccg cccacaactt acatcattac aaacgtcaaa gcctacgtca gccgccccgc  37140
ctcgccccgc ccacctcatt atcatattgg ccacaatcca aaataaggta tattattgat  37200
gatg                                                                37204
```

<210> SEQ ID NO 7
<211> LENGTH: 1164
<212> TYPE: DNA
<213> ORGANISM: Artificial Sequence
<220> FEATURE:
<223> OTHER INFORMATION: HAdV-5 E4 orf 6/7

<400> SEQUENCE: 7

```
tcacagaacc ctagtattca acctgccacc tccctcccaa cacacagagt acacagtcct    60
ttctccccgg ctggccttaa aaagcatcat atcatgggta acagacatat tcttaggtgt   120
tatattccac acggtttcct gtcgagccaa acgctcatca gtgatattaa taaactcccc   180
gggcagctca cttaagttca tgtcgctgtc cagctgctga gccacaggct gctgtccaac   240
ttgcggttgc ttaacgggcg gcgaaggaga agtccacgcc tacatggggg tagagtcata   300
atcgtgcatc aggatagggc ggtggtgctg cagcagcgcg cgaataaact gctgccgccg   360
ccgctccgtc ctgcaggaat acaacatggc agtggtctcc tcagcgatga ttcgcaccgc   420
ccgcagcata aggcgccttg tcctccgggc acagcagcgc accctgatct cacttaaatc   480
```

agcacagtaa ctgcagcaca gcaccacaat attgttcaaa atcccacagt gcaaggcgct 540
gtatccaaag ctcatggcgg ggaccacaga acccacgtgg ccatcatacc acaagcgcag 600
gtagattaag tggcgacccc tcataaacac gctggacata aacattacct cttttggcat 660
gttgtaattc accacctccc ggtaccatat aaacctctga ttaaacatgg cgccatccac 720
caccatccta aaccagctgg ccaaaacctg cccgccggct atacactgca gggaaccggg 780
actggaacaa tgacagtgga gagcccagga ctcgtaacca tggatcatca tgctcgtcat 840
gatatcaatg ttggcacaac acaggcacac gtgcatacac ttcctcagga ttacaagctc 900
ctcccgcgtt agaaccatat cccagggaac aacccattcc tgaatcagcg taaatcccac 960
actgcaggga agacctcgca cgtaactcac gttgtgcatt gtcaaagtgt tacattcggg 1020
cagcagcgga tgatcctcca gtatggtagc gcgggtttct gtctcaaaag gaggtagacg 1080
atccctactg tacggagtgc gccgagacaa ccgagatcgt gttggtcgta gtgtcatgcc 1140
aaatggaacg ccggacgtag tcat 1164

<210> SEQ ID NO 8
<211> LENGTH: 99
<212> TYPE: DNA
<213> ORGANISM: Artificial Sequence
<220> FEATURE:
<223> OTHER INFORMATION: HAdV-5 protein IX promoter

<400> SEQUENCE: 8
ggtactgaaa tgtgtgggcg tggcttaagg gtgggaaaga atatataagg tgggggtctt 60
atgtagtttt gtatctgttt tgcagcagcc gccgccgcc 99

<210> SEQ ID NO 9
<211> LENGTH: 33893
<212> TYPE: DNA
<213> ORGANISM: Artificial Sequence
<220> FEATURE:
<223> OTHER INFORMATION: pBZ1_BZ28F

<400> SEQUENCE: 9
catcatcaat aatatacctt attttggatt gtggccaata tgataatgag gtgggcgggg 60
cgaggcgggg cgggtgacgt aggacgtgcg agtagggttg ggaggtgtgg cggaagtgtg 120
gcatttgtaa gtgggaggag cttacatgca agcttccgtc gcggaaaatg tgacgttttt 180
tatgagcgcc gcctacctcc ggaagtgcca attttcgcgc gctttttacc ggatatcgta 240
gtaattttgg gcgggaccat gtaagatttg gccattttcg cgcgaaaagt gaaacgggga 300
agtgaaaact gaataatagg gcgttagtca tagcgcgtaa tatttaccga gggccgaggg 360
actttgaccg attacgtgga ggactcgccc aggtgttttt tacgtgaatt tccgcgttcc 420
gggtcaaagt ctccgttttt attgtcaccg tcatttgacg cggagggtat ttaaacccgc 480
tgcgctccta gcgatcgctg atgagaccag gaccaggtgc cgaccctgcg agtgcggcgg 540
caagcacatg agaaatcagc ctgtgatgtt ggatgtgacc gaggagctta ggcctgacca 600
tctggtgctg gcctgcacca gggccgagtt tgggtctagc gatgaggata ccgattgagg 660
tgggtaaggt gggcgtggct agcagggtgg gcgtgtataa attgggggtc taaggggtct 720
ctctgtttgt cttgcaacag ccgccgccat gagcgacacc ggcaacagct ttgatggaag 780
catctttagc ccctatctga cagtgcgcat gcctcactgg gccggagtgc gtcagaatgt 840
gatgggttcc aacgtggatg gacgtcccgt tctgccttca aattcgtcta cgatggccta 900

-continued

```
cgcgaccgtg ggaggaactc cgctggacgc cgcgacctcc gccgccgcct ccgccgccgc    960
cgcgaccgcg cgcagcatgg ctacggacct ttacagctct ttggtggcga gcagcgcggc   1020
ctctcgcgcg tctgctcggg atgaaaaact gactgctctg ctgcttaaac tggaagactt   1080
gacccgggag ctgggtcaac tgacccagca ggtctccagc ttgcgtgaga gcagccttgc   1140
ctccccctaa tggcccataa tataaataaa agccagtctg tttggattaa gcaagtgtat   1200
gttctttatt taactctccg cgcgcggtaa gcccgggacc agcggtctcg gtcgtttagg   1260
gtgcggtgga ttctttccaa cacgtggtac aggtggctct ggatgtttag atacatgggc   1320
atgagtccat ccctggggtg gaggtagcac cactgcagag cttcgtgctc gggggtggtg   1380
ttgtatatga tccagtcgta gcaggagcgc tgggcgtggt gctgaaaaat gtccttaagc   1440
aagaggctta tagctagggg gaggcccttg gtgtaagtgt ttacaaatct gcttagctgg   1500
gaggggtgca tccgggggga tatgatgtgc atcttggact ggatttttag gttggctatg   1560
ttcccaccca gatcccttct gggattcatg ttgtgcagga ccaccagcac ggtatatcca   1620
gtgcacttgg gaaatttatc gtggagctta gacgggaatg catggaagaa cttggagacg   1680
cccttgtggc ctcccagatt ttccatacat tcgtccatga tgatggcaat gggcccgtgg   1740
gaagctgcct gagcaaaaac gtttctggca tcgctcacat cgtagttatg ttccagggtg   1800
aggtcatcat aggacatctt tacaaatcgg gggcggaggg tcccggactg gggatgatg    1860
gtaccctcgg gccccggggc gtagttcccc tcacagatct gcatctccca ggctttcatt   1920
tcagagggag ggatcatatc cacctgcggg gcgatgaaaa agacagtttc tggcgcaggg   1980
gagattaact gggatgagag caggtttctg agcagctgtg actttccaca gccggtgggc   2040
ccatatatca cgcctatcac cggctgcagc tggtagttaa gagagctgca gctgccgtcc   2100
tcccggagca ggggggccac ctcgttgagc atatccctga cgtggatgtt ctccctgacc   2160
agttccgcca gaaggcgctc gccgcccagc gaaagcagct cttgcaagga agcaaaattt   2220
ttcagcggtt tcaggccatc ggccgtgggc atgtttttca gcgtctgggt cagcagctcc   2280
agcctgtccc agagctcggt gatgtgctct acggcatctc gatccagcag atctcctcgt   2340
ttcgcgggtt ggggcggctt tcgctgtagg gcaccagccg atgggcgtcc agcggggcca   2400
gagtcatgtc cttccatggg cgcagagtcc tcgtcagggt ggtctgggtc acggtgaagg   2460
ggtgcgctcc gggttgggca ctggccaggg tgcgcttgag gctggttctg ctggtgctga   2520
atcgctgccg ctcttcgccc tgcgcgtcgg ccaggtagca tttgaccatg gtctcgtagt   2580
cgagaccctc ggcggcgtgc cccttggcgc ggagctttcc cttggaggtg gcgccgcacg   2640
aggggcactg caggctcttc agggcgtaga gcttgggagc gagaaacacg gactctgggg   2700
agtaggcgtc cgcgccgcag gccgcgcaga ccgtctcgca ttccaccagc caagtgagtt   2760
ccgggcggtc agggtcaaaa accaggttgc ccccatgctt tttgatgcgt ttcttacctc   2820
ggctctccat gaggcggtgt cccttctcgg tgacgaagag gctgtccgtg tccccgtaga   2880
ccgacttcag ggcctgtct  tccagcggag tgcctctgtc ctcctcgtag agaaactctg   2940
accactctga gacgaaggcc cgtgtccagg ccaggacgaa ggaggccacg tgggaggggt   3000
agcggtcgtt gtccactagc gggtccacct tctccagggt gtgcagacac atgtccccct   3060
cctccgcgtc cagaaaagtg attggcttat aggtgtagga cacgtgaccg ggggttcccg   3120
acggggggt  ataaaagggg gtgggcgccc tttcatcttc actctcttcc gcatcgctgt   3180
ctgcgagagc cagctgctgg ggtaagtatt ccctttcaaa ggcgggcatg acctcagcgc   3240
tcaggttgtc agtttctaaa aatgaggagg atttgatgtt cacctgtccg gaagtgatac   3300
```

-continued

```
ctttgagggt acctgggtcc atctggtcag aaaacactat ttttttgttg tcaagcttgg   3360
tggcgaacga cccgtagagg gcgttggaga gcagcttggc aatggagcgc agggtctggt   3420
ttttgtcgcg gtcggctcgc tccttggccg cgatgttgag ttgcacgtat tcgcgggcca   3480
cgcacttcca ctcggggaag acggtggtgc gctcgtctgg gatcaggcgc accctccagc   3540
cgcggttgtg cagggtgacc atgtcgacgc tggtggcgac ctcaccgcgc agacgctcgt   3600
tggtccagca gaggcggccg cctttgcgcg agcagaaggg gggtaggggg tccagctggt   3660
cctcgtttgg ggggtccgcg tcgatggtaa agaccccggg gagcaggcgc gggtcaaagt   3720
agtcgatctt gcaagcttgc atgtccagag cccgctgcca ttcgcgggcg gcgagcgcgc   3780
gctcgtaggg gttgaggggc gggccccagg gcatggggtg ggtgagcgcg gaggcgtaca   3840
tgccgcagat gtcatacacg tacaggggtt ccctgaggat accgaggtag gtggggtagc   3900
agcgcccccc gcggatgctg gcgcgcacgt agtcatagag ctcgtgggag ggggccagca   3960
tgttgagccc aaggttggtg cgctgggggc gctcggcgcg gaagacgatc tgtctgaaga   4020
tggcatggga gttggaggag atggtgggtc gctggaagac gttgaagctt gcttcttgca   4080
agcccacgga gtccctgacg aaggaggcgt aggactcgcg cagcttgtgc accagctcgg   4140
cggtgacctg gacgtcgagc gcgcagtagt cgagggtctc gcggatgatg tcatacttat   4200
cctccccctt ctttttccac agctcgcggt tgaggacgaa ctcttcgcgg tctttccagt   4260
actcttggag ggaaacccg  tccgtgtccg aacggtaaga gcctagcatg tagaactggt   4320
tgacggcctg gtaggggcag cagcccttct ccacgggcag cgcgtaggcc tgcgccgcct   4380
tgcggaggga ggtgtgggta agggcgaaag tgtccctgac catgactttg aggtattgat   4440
gtctgaagtc tgtgtcatcg cagccgccct gttcccacag ggtgtagtcc gtgcgctttt   4500
tggagcgcgg gttgggcagg gagaaggtga ggtcattgaa gaggatcttc cccgctcgag   4560
gcatgaagtt tctggtgatg cgaaagggcc ctgggaccga ggagcggttg ttgatgacct   4620
gggcggccag gacgatctcg tcaaagccgt ttatgttgtg gcccacgatg tagagctcca   4680
ggaagcgggg ctggcccttg atggagggga gctttttaag ttcctcgtag gtaagctcct   4740
cgggcgattc caggccgtgc tcctccaggg cccagtcttg caagtgaggg ttggccgcca   4800
ggaaggatcg ccagaggtcg cgggccatga gggtctgcag gcggtcgcgg aaggttctga   4860
actgccgccc tacggccatc ttttcggggg tgatgcagta gaaggtgagg gggtctttct   4920
cccaggggtc ccatctgagc tcttgggcga ggtcgcgcgc ggcggcgacc agagcctcgt   4980
cgccccccag tttcatgacc agcatgaagg gcacgagctg cttgccaaag gctcccatcc   5040
aagtgtaggt ctctacatcg taggtgacaa agaggcgctc cgtgcgagga tgagagccga   5100
tcgggaagaa ctggatctcc cgccaccagt tggaggattg gctgttgatg tggtgaaagt   5160
agaagtcccg tctgcgggcc gagcactcgt gctggctttt gtaaaagcga ccgcagtact   5220
ggcagcgctg cacgggttgt atatcttgca cgaggtgaac ctggcgacct ctgacgagga   5280
agcgcagcgg gaatctaagt cccccgcctg gggtcccgtg tggctggtgg tcttctactt   5340
tggttgtctg gccgccagca tctgtctcct ggagggcgat ggtggagcag accaccacgc   5400
cgcgagagcc gcaggtccag atctcggcgc tcggcgggcg gagtttgatg acgacatcgc   5460
gcacattgga gctgtccatg gtctccagct cccgcggcgg caggtcagcc gggagttcct   5520
ggaggttcac ctcgcagaga cgggtcaagg cgcggacagt gttgagatgg tatctgattt   5580
caaggggcgt gttggaggcg gagtcgatgg cttgcagaag gccgcagccc cgggggggca   5640
```

-continued

```
cgatggttcc ccgcggggcg cgaggggagg cggaagctgg gggtgtgttc agaagcggtg   5700
acgcgggcgg gcccccggag gtaggggggg ttccggcccc acaggcatgg gcggcagggg   5760
cacgtcttcg ccgcgcgcgg gcaggggctg gtgctggctc cggagagcgc ttgcgtgcgc   5820
gacgacgcga cggttggtgt cctgtatctg gcgcctctga gtgaagacca cgggtcccgt   5880
gaccttgaac ctgaaagaga gttcgacaga atcaatctcg gcatcgttga cagcggcctg   5940
gcgcaggatc tcctgcacgt cgcccgagtt gtcctggtag gcgatctctg ccatgaactg   6000
ctcgatctct tcctcctgga gatctcctcg tccggcgcgc tccacggtgg ccgccaggtc   6060
gttggagatg cgacccatga gctgcgagaa ggcgttgagg ccgccctcgt tccagacccg   6120
gctgtagacc acgcccccct cggcgtcgcg ggcgcgcatg accacctggg ccaggttgag   6180
ctccacgtgt cgcgtgaaga cggcgtagtt gcgcaggcgc tggaaaaggt agttcagggt   6240
ggtggcggtg tgttcggcga cgaagaagta catgacccag cgccgcaacg tggattcatt   6300
gatgtccccc aaggcctcca ggcgctccat ggcctcgtag aagtccacgg cgaagttgaa   6360
aaactgggag ttgcgagcgg acacggtcaa ctcctcctcc agaagacgga tgagctcggc   6420
gacagtgtcg cgcacctcgc gctcgaaggc cacgggggggc gcttcttcct cttccacctc   6480
ttcttccatg attgcttctt cttcctcagc cgggacggga gggggcggcg gcgggggagg   6540
ggcgcggcgg cggcggcggc gcaccggcag gcggtcgatg aagcgctcga tcatctcccc   6600
ccgcatgcgg cgcatggtct cggtgacggc gcggccgttc tcccgggggc gcagctcaaa   6660
gacgccgcct ctcatctcgc cgcggggcgg gcggccgtga ggtagcgaga cggcgctgac   6720
tatgcatctt aacaattgct gtgtaggtac gccgccaagg gacctgattg agtccagatc   6780
caccggatcc gaaaaccttt ggaggaaagc gtctatccag tcgcagtcgc aaggtaggct   6840
gagcaccgtg gcgggcgggg gcgggtcggg agagttcctg gcggagatgc tgctgatgat   6900
gtaattaaag taggcggtct tgagaaggcg gatggtggac aggagcacca tgtctttggg   6960
tccggcctgt tggatgcgga ggcggtcggc catgccccag gcctcgttct gacaccggcg   7020
caggtctttg tagtagtctt gcatgagtct ttccaccggc acctcttctc cttcctcttc   7080
tccatctcgc cggtggtttc tcgcgccgcc catgcgcgtg accccaaagc ccctgagcgg   7140
ctgcagcagg gccaggtcgg cgaccacgcg ctcggccaag atggcctgct gtacctgagt   7200
gagggtcctc tcgaagtcat ccatgtccac gaagcggtgg taggcgcccg tgttgatggt   7260
gtaggtgcag ttggccatga cggaccagtt gacggtctgg tgtcccggct gcgagagctc   7320
cgtgtaccgc aggcgcgaga aggcgcggga atcgaacacg tagtcgttgc aagtccgcac   7380
cagatactgg tagcccacca ggaagtgcgg cggaggttgg cgatagaggg gccagcgctg   7440
ggtggcgggg gcgccgggcg ccaggtcttc cagcatgagg cggtggtatc cgtagatgta   7500
cctggacatc caggtgatgc cggcggcggt ggtggtggcg cgcgcgtagt cgcggacccg   7560
gttccagatg tttcgcaggg gcgagaagtg ttccatggtc ggcacgctct ggccggtgag   7620
gcgcgcgcag tcgttgacgc tctatacaca cacaaaaacg aaagcgttta cagggctttc   7680
gttctgtagc ctggaggaaa gtaaatgggt tgggttgcgg tgtgccccgg ttcgagacca   7740
agctgagctc ggccggctga agccgcagct aacgtggtat tggcagtccc gtctcgaccc   7800
aggccctgta tcctccagga tacggtcgag agcccttttg ctttcttggc caagcgcccg   7860
tggcgcgatc tgggatagat ggtcgcgatg agaggacaaa agcggctcgc ttccgtagtc   7920
tggagaaaca atcgccaggg ttgcgttgcg gcgtaccccg gttcgagccc ctatggcggc   7980
ttggatcggc cggaaccgcg gctaacgtgg gctgtggcag ccccgtcctc aggaccccgc   8040
```

-continued

```
cagccgactt ctccagttac gggagcgagc ccccttttgtt ttttattttt tagatgcatc   8100
ccgtgctgcg gcagatgcgc ccctcgcccc ggcccgatca gcagcagcaa cagcaggcat   8160
gcagaccccc ctctcctcta cccgccccgg tcaccacggc cgcggcggcc gtgtccggcg   8220
cggggggcgc gctggagtca gatgagccac cgcggcggcg acctaggcag tatctggact   8280
tggaagaggg cgagggactg gcgcggctgg gggcgagctc tccagagcgc cacccgcggg   8340
tgcagttgaa aagggacgcg cgcgaggcgt acctgccgcg gcagaacctg tttcgcgacc   8400
gcgggggcga ggagcccgag gagatgcgag actgcaggtt ccaagcgggg cgcgagctgc   8460
gccgcgggtt ggacagacag cgcctgctgc gcgaggagga ctttgagccc gacacgcaga   8520
cgggcatcag ccccgcgcgc gcgcacgtgg ccgcggccga cctggtgacc gcctacgagc   8580
agacggtgaa ccaggagcgc aacttccaaa aaagcttcaa caaccacgtg cgcacgctgg   8640
tggcgcgcga ggaggtgacc ctgggtctca tgcatctgtg ggacctggtg gaggcgatcg   8700
tgcagaaccc cagcagcaag cccctgaccg cgcagctgtt cctggtggtg cagcacagca   8760
gggacaacga ggccttcagg gaggcgctgc tgaacatcac cgagccggag gggcgctggc   8820
tcctggacct gataaacatc ctgcagagca tagtggtgca ggagcgcagc ctgagcctgg   8880
ccgagaaggt ggcggccatt aactattcta tgctgagctt gggcaagttc tacgcccgca   8940
agatctacaa gacccccctac gtgcccatag acaaggaggt gaagatagac agcttctaca   9000
tgcgcatggc gctaaaggtg ctgaccctga gcgacgacct gggagtgtac cgcaacgagc   9060
gcatccacaa ggccgtgagc gccagccggc ggcgcgagct gagcgaccgc gagctgatgc   9120
acagtctgca gcgcgcgctc accggcgcgg gcgagggcga cagggaggtc gagtcctact   9180
tcgacatggg ggctgacctg cactggcagc cgagccgccg cgccctggag gcggcggggg   9240
cgtatggcgg cccccctggcg gccgatgacg aggaagagga ggactatgag ctagaggagg   9300
gcgagtacct ggaggactga cctggctggt ggtgttttgg tatagatgca agatccgaac   9360
gtggcggacc cggcggtccg ggcggcgctg cagagccagc cgtccggcat taactcctct   9420
gacgactggg ccgcggccat gggtcgcatc atggccctga ccgcgcgcaa ccccgaggcc   9480
ttcaggcagc agcctcaggc taaccggctg gcggccatct tggaagcggt agtgcccgcg   9540
cgctccaacc ccacccacga gaaggtgctg gccatagtca acgcgctggc ggagagcagg   9600
gccatccggg cggacgaggc cggactggtg tacgatgcgc tgctgcagcg ggtggcgcgg   9660
tacaacagcg gcaacgtgca gaccaacctg gaccgcctgg tgacggacgt gcgcgaggcc   9720
gtggcgcagc gcgagcgctt gcatcaggac ggtaacctgg gctcgctggt ggcgctaaac   9780
gccttcctca gcacccagcc ggccaacgta ccgcgggggc aggaggacta caccaacttc   9840
ttgagcgcgc tgcggctgat ggtgaccgag gtccctcaga gcgaggtgta ccagtcgggg   9900
cccgactact tcttccagac cagcagacag ggcttgcaaa ccgtgaacct gagccaggct   9960
ttcaagaacc tgcgggggct gtggggagtg aaagcgccca ccggcgaccg agctacggtg  10020
tccagcctgc taacccccaa ctcgcgcctg ctgctgctgc tgatcgcgcc cttcacggac  10080
agcgggagcg tctcgcggga gacctatctg ggccacctgc tgacgctgta ccgcgaggcc  10140
atcgggcagg cgcaggtgga cgagcacacc ttccaagaga tcaccagcgt gagccacgcg  10200
ctggggcagg aggacacggg cagcctgcag gcgaccctga actacctgct gaccaacagg  10260
cggcagaaga ttcccacgct gcacagcctg acccaggagg aggagcgcat cttgcgctac  10320
gtgcagcaga gcgtgagcct gaacctgatg cgcgacggcg tgacgcccag cgtggcgctg  10380
```

-continued

```
gacatgaccg cgcgcaacat ggaaccgggc atgtacgctt cccagcggcc gttcatcaac  10440
cgcctgatgg actacttgca tcgggcggcg gccgtgaacc ccgagtactt caccaatgcc  10500
attctgaatc cccactggat gcccccctccg ggtttctaca acggagactt cgaggtgcct  10560
gaggtcaatg atgggttcct ctgggatgac atggatgaca gtgtgttctc ccccaacccg  10620
ctgcgcgccg cgtctctgcg attgaaggag ggctctgaca gggaaggacc gaggagtctg  10680
gcctcctccc tggctctggg ggcggtgggc gccacgggcg cggcggcgcg gggcagcagc  10740
cccttcccca gcctggcaga ctctctgaat agcgggcggg tgagcaggcc ccgcttgcta  10800
ggcgaggagg agtatctgaa caactccctg ctgcagcccg tgagggacaa aaacgctcag  10860
cgacagcagt ttcccaacaa cgggatagag agcctggtgg acaagatgtc cagatggaag  10920
acatatgcgc aggagtacaa ggagtgggag gaccgccagc cgcggcccct gccgcccct  10980
agacagcgct ggcagcggcg cgcgtccaac cgccgctgga gacagggacc cgaggacgat  11040
gatgactctg cagatgacag cagcgtgttg gacctgggcg ggagcgggaa ccccttttcg  11100
cacctgcgcc cacgcctggg caagatgttt taaaagagaa aaataaaact caccaaggcc  11160
atggcgacga gcgttggttt tttgttccct tccttagtat gcggcgcgcg gcgatgttcg  11220
aggaggggcc tcccccctct tacgagagcg cgatgggaat ttctcctgcg gcgcccctgc  11280
agcctcccta cgtgcctcct cggtacctgc aacctacagg ggggagaaat agcatctgtt  11340
actctgagct gcagcccctg tacgatacca ccagactgta cctggtggac aacaagtccg  11400
cggacgtggc ctccctgaac taccagaacg accacagcga ttttttgacc acggtgatcc  11460
aaaacaacga cttcacccca accgaggcca gtacccagac cataaacctg gacaacaggt  11520
cgaactgggg cggcgacctg aagaccatcc tgcacaccaa catgcccaac gtgaacgagt  11580
tcatgtttac caactctttt aaggcgcggg ttatggtggc gcgcgagcag ggggaggcga  11640
agtacgagtg ggtggacttc acgctgcccg agggcaacta ctcagagacc atgactattg  11700
acctgatgaa caatgcgatc gtggaacact acctgaaagt gggcaggcag aacggggtga  11760
aggagagcga tatcggggtc aagtttgaca ccagaaactt tcgtctgggc tgggaccccg  11820
tgaccgggct ggtcatgccg gggtctaca ccaacgaggc ctttcatccc gatatagtgc  11880
tcctgcccgg ctgtggggtg gactttaccc agagccggct gagcaacctg ctgggcgttc  11940
gcaagcggca acctttccag gagggtttca agatcaccta tgaggatctg gagggggca  12000
acattcccgc gctccttgat ctggacgcct acgaggagag cttgaaaccc gaggagagcg  12060
ctggcgacag cggcgagagt ggcgaggagc aagccggcgg cggtggcagc gcgtcggtag  12120
aaaacgaaag tactcccgca gtggcggcag acgctgcgga ggtcgagcca gaggccatgc  12180
agcaggacgc agaggagggc gcacaggagg gcgcgcagga ggacatgaac gatggggaga  12240
tcaggggaga cactttcgcc acccggggcg aagaaaaaga ggcagaggcg gtggcggcga  12300
cggtggaagc cgaaaccgag gcagaggcag agcccaagac cgaagttatg gaagacatga  12360
atgatggaga acgtaggggt gacacgtttg ccacccgggg cgaagagaag gcggcggagg  12420
cagaagccgc ggctgaggag gcggctgcgg ctgcggccga ggctgaggct gcggctgagg  12480
ctaaggtcga agccgatgtt gcggttgagg ctcaggctga ggaggaggag gcggcgactg  12540
aagcagttaa ggaaaaggcc caggcagagc aggaagagaa aaaacctgtc attcaacctc  12600
taaaagaaga tagcaaaaag cgcagttaca acgtcatcga gggcagcacc tttacccagt  12660
accgcagctg gtacctggcg tacaactacg gcgacccggt caagggggtg cgctcgtgga  12720
ccctgctctg cacgccggac gtcacctgcg gctccgagca gatgtattgg tcgctgccaa  12780
```

```
acatgatgca agacccggtg accttccgct ccacgcggca ggttagcaac ttcccggtgg  12840
tgggcgccga actgctgccc gtgcactcca agagtttttta caacgagcag gccgtctact  12900
cccagctgat ccgccaggcc acctctctga cccacgtgtt caatcgcttt cccgagaacc  12960
agattttggc gcgcccgccg gcccccacca tcaccaccgt cagtgaaaac gttcctgccc  13020
tcacagatca cgggacgcta ccgctgcgca acagcatctc aggagtccag cgagtgacca  13080
ttactgacgc cagacgccgg acctgcccct acgtttacaa ggccttgggc atagtctcgc  13140
cgcgcgtcct ctccagtcgc actttttaaa atacatctac cctcacgctt caaaatcatg  13200
tccgtactca tctcacccag caacaacacc ggctgggggc tgcgcgcgcc cagcaagatg  13260
tttggagggg cgaggaaacg ctccgagcag cacccagtgc gcgtgcgcgg ccactaccgc  13320
gcgccctggg gagcgcacaa gcgcgggcgc gcagggcgca ccactgtgga cgacgccatt  13380
gactccgtag tggagcaggc gcgccactac acacccggcg cgccgtccgc ccccgccgtg  13440
tccaccgtgg acgaggcgat cgagagcgtg gtacagggcg cgcggcacta tgccaacctt  13500
aaaaatcgac gccgtcgcgt ggctcgccgc catcgccgga gaccccgggc caccgccgcc  13560
gcgcgccttg ctaaggctct gctcaggcgc gccaggcgaa ctggccgccg ggccgccatg  13620
agggccgcac ggcgggctgc cgccagcgcg gccgccgcgg ccccacgggc acgaaggcgc  13680
gcggccgctg ccgccgccgc cgccatttcc agcttggcct cgacgcggcg cggtaacata  13740
tactgggtgc gcgactcggt aaccggcacg cgggtacccg tgcgctttcg ccccccgcgg  13800
aattagcaca agacaacata cacactgagt ctcctgctgt tgtgtatccc agcggcgacc  13860
gtcagcagcg gcgacatgtc caagcgcaaa attaaagaag agatgctcca ggtcatcgcg  13920
ccggagatct atgggccccc gaagaaggag gaggatgatt acaagccccg caagctaaag  13980
cgggtcaaaa agaaaaagaa agatgatgac gttgacgagg cggtggagtt tgtccgccgc  14040
atggcgccca ggcgccccgt gcagtggaag ggtcggcgcg tgcagcgagt cctgcgcccc  14100
ggcaccgcgg tggtctttac gcccggcgag cgttccacgc gcactttcaa gcgggtgtac  14160
gatgaggtgt acggcgacga ggatctgttg gagcaggcca accatcgctt tggggagttt  14220
gcatatggga aacggccccg cgagagccta aaagaggacc tgctggcgct accgctggac  14280
gagggcaatc ccaccccgag tctgaagccg gtaaccctgc aacaggtgct gcctttgagc  14340
gcgcccagcg agcagaagcg agggttgaag cgcgagggcg gggacctggc acccaccgtg  14400
cagttgatgg tgcccaagcg gcagaagctg gaggacgtgc tggagaaaat gaaagtagag  14460
cccgggatcc agcccgaaat caaggtccgc cccatcaagc aggtggcgcc cggcgtggga  14520
gtccagaccg tggacgttag gattcccacg gaggagatgg aaacccaaac cgccactccc  14580
tcttcggcgg ctagcgccac caccggctcc gcttcggtag aggtgcagac ggacccctgg  14640
ctagccgccg ccgccccggc cgccccccgt tcgcgcgggc gcaagagaaa ttatccagcg  14700
gccagcgcgc tcatgcccca gtacgcactg catccatcca tcgcgcccac ccccggctac  14760
cgcgggtact cgtaccgccc gcgcagatca gccggcaccc gcggccgccg ccgccgtgcg  14820
accacaacca gccgccgccg tcgccgccgc cgccagccag tgctgacccc cgtgtctgta  14880
aggaaggtgg ctcgctcggg gagcacgctg gtggtgccca gagcgcgcta ccaccccagc  14940
attgtttaaa gccggtctct gtatggttct tgcagatatg gccctcactt gtcgcctccg  15000
cttcccggtg ccgggatacc gaggaagaac tcaccgccgc agaggcatgg cgggcagtgg  15060
tctccgcggc ggccgtcgcc atcgccggcg cgcaaagagc aggcgcatgc gcggcggtgt  15120
```

-continued

```
gctgcccttc ctaatcccgc taatcgccgc ggcgatcggt gccgtgcccg ggatcgcctc  15180
cgtggccctg caggcgtccc agaaacattg actcttgcaa ccttgcaagc ttgcattttt  15240
tggaggaaaa aataaaaagt ctagactctc acgctcgctt ggtcctgtga ctattttgta  15300
gaaaaaagat ggaagacatc aactttgcgt cgctggcccc gcgtcacggc tcgcgcccgt  15360
tcatgggaga ctggacagat atcggcacca gcaatatgag cggtggcgcc ttcagctggg  15420
gcagtctgtg gagtggcctt aaaaattttg gttccaccat taagaactat ggcaacaaag  15480
cgtggaacag cagcacgggt cagatgctga gagacaagtt gaaagagcag aacttccagg  15540
agaaggtggc acagggcctg gcctctggca tcagcggggt ggtggacata gctaaccagg  15600
ccgtgcagaa aaagataaac agtcatctgg acccccgccc tcaggtggag gaaacgcctc  15660
cagccatgga gacggtgtct cccgagggca aaggcgaaaa gcgcccgcgg cccgacaggg  15720
aagagaccct ggtgtcacac accgaggagc cgccctctta cgaggaggca gtcaaggccg  15780
gcctgcccac cactcgcccc atagctccca tggccaccgg tgtggtgggt cacaggcaac  15840
acacccccgc gacactagat ctgcccccgc cgtccgagcc gactcgccag ccaaaggcgg  15900
tgacggtgcc cgctccctcc acttccgccg ccaacagagt gcctctgcgc cgcgctgcga  15960
gcggcccccg ggcctcgcga gtcagcggca actggcagag cacactgaac agcatcgtgg  16020
gcctgggagt gaggagtgtg aagcgccgcc gttgctactg aatgagcaag ctagctaacg  16080
tgttgtatgt gtgtatgcgt cctatgtcgc cgccagagga gctgttgagc cgccggcgcc  16140
gtctgcactc cagcgaattt caagatggcg accccatcga tgatgcctca gtggtcgtac  16200
atgcacatct cgggccagga cgcttcggag tacctgagcc ccgggctggt gcagttcgcc  16260
cgcgccacag acacctactt caacatgagt aacaagttca ggaaccccac tgtggcgccc  16320
acccacgatg tgaccacgga ccggtcgcag cgcctgacgc tgcggttcat ccccgtggat  16380
cgggaggaca ccgcttactc ttacaaggcg cggttcacgc tggccgtggg cgacaaccgc  16440
gtgctggaca tggcctccac ttactttgac atccgggggg tgctggacag gggccccact  16500
ttcaagccct actcgggcac tgcctacaac tccctggccc ccaagggcgc tcccaattct  16560
tgcgagtggg aggaggaaac acaaaatgag gtacaagcca atgaagaaca actagcagaa  16620
gaagaggatg aagaaatggc tcaagaggat cagcagccta ctaaaaaaac ccatgtatat  16680
gctcaggcac ctctttctgg cgaacagatt accaaagatg gcttgcaaat aggagctgaa  16740
gttacaggag aaacatcaaa gcccattttt gcagacaaga cattccaacc agaacctcag  16800
ataggagagt ctcaatggaa tgaggccgat gctacagtag caggaggtag ggttttgaaa  16860
aagactaccc ctatgaaacc ttgctatgga tcctatgcca gacctaccaa tgccaatgga  16920
gggcagggga tacttgaggc aaatgctaaa ggggaactcg aatctaaagt tgagatgcag  16980
tttttctcta acaccacaac tcttaatgta agagacggtg aaaatggcct taaaccaaaa  17040
gtagtgctgt atagcgaaga tgtcaacctg gaatcccctg acactcatct gtcttacaag  17100
cccaaaaaag atgatgttaa tgccaaaatc atgttgggtc agcaagccat gcccaacaga  17160
cccaacctca ttggatttag agataatttc attgggctca tgtattacaa cagcactgga  17220
aacatgggag tgctggcggg tcaggcctct cagttgaatg ctgtggtgga cttgcaggat  17280
agaaacacgg aactgtcata tcagcttatg cttgattcca ttggagatag aaccagatac  17340
ttttccatgt ggaaccaggc agtggatagc tatgacccag atgttagaat cattgaaaac  17400
catggggtgg aggatgagct gcccaactac tgttttccct tgggcggtat aggaattaca  17460
gatacatacc aggccataaa agcagccaat ggtggagatg ctactacgtg gtctgctgat  17520
```

-continued

```
aacacatttg cagaccgcaa cgaaataggg gtgggaaaca acttcgccat ggagatcaac  17580
atccaggcca acctctggag aaacttcctc tatgcgaacg tgggactcta cctgccagac  17640
aagctcaagt acaaccccac caacgtggac atctctgaca accccaacac ctatgactac  17700
atgaacaagc gggtggtggc ccccggcctg gtggactgct ttgtcaatgt gggagccagg  17760
tggtccctgg actacatgga caacgtcaac cccttcaacc accaccgcaa tgcgggtctg  17820
cgctaccgct ccatgatcct gggcaacggg cgctatgtgc ccttccacat ccaggtaccc  17880
cagaagttct ttgccatcaa gaacctcctg ctcctgcccg gctcctacac ctacgagtgg  17940
aacttcagga aggatgtaaa catggtccta cagagctctc tgggcaatga ccttagggta  18000
gatggggcca gcatcaagtt tgacagcatc accctctatg ctacattttt ccccatggcc  18060
cacaacaccg cctccacgct tgaggccatg ctgagaaacg acaccaacga ccagtccttc  18120
aatgactacc tctctggggc caacatgctc tacccaatcc cagccaaggc caccaacgtg  18180
cccatctcca tcccctctcg caactgggcc gcctttagag gctgggcctt tacccgcctt  18240
aagaccaagg agacccccctc cctgggctcg ggttttgatc cctactttgt ttactcggga  18300
tccatcccct acctggatgg caccttctac ctcaaccaca ctttcaagaa gatatccatc  18360
atgtatgact cctccgtcag ctggccgggc aacgaccgct tgctcacccc caatgagttc  18420
gaggtcaagc gcgccgtgga cggcgagggc tacaacgtgg cccagtgcaa catgaccaag  18480
gactggttcc tggtgcagat gctggccaac tacaacatag gctaccaggg cttctacatc  18540
ccagagagct acaaggacag gatgtattcc ttcttcagaa atttccaacc catgagccga  18600
caggtggtgg acgagaccaa ttacaaggac tatcaggcca ttggcatcac ccaccagcac  18660
aacaactcgg gtttcgtggg ctacctggcg cccaccatgc gcgagggaca ggcctacccc  18720
gccaacttcc cctacccccct gataggcaag accgcggtcg acagcgtcac ccagaaaaag  18780
ttcctctgcg accgcaccct ctggcgcatc cccttctcta gcaactttat gtccatgggt  18840
gcgctcacgg acctgggcca aaacctgctt tatgccaact ctgcccatgc gctggacatg  18900
acttttgagg tggaccccat ggacgagccc acccttctct atattgtgtt tgaagtgttc  18960
gacgtggtca gagtgcacca gccgcaccgc ggtgtcatcg agaccgtgta cctgcgtacg  19020
cccttctcag ccggcaacgc caccacctaa ggagacagcg ccgccgcctg catgactggt  19080
tccaccgagc aagagctcag ggccatcgcc agagacctgg gatgcggacc ctatttttg  19140
ggcacctatg acaaacgctt cccgggtttt atctcccgag acaagctcgc ctgcgccatc  19200
gtcaacacgg ccgcgcgcga gaccgggggc gtgcactggc tggcctttgg ctgggacccg  19260
cgctctaaaa cttgctacct ctttgacccc tttggcttct ccgatcagcg cctcaggcag  19320
atttatgagt ttgagtacga ggggctgttg cgccgcagcg cgcttgcctc ctcgcccgac  19380
cgctgcatca cccttgagaa gtccaccgag accgtgcagg ggccccactc ggccgcctgc  19440
ggtctcttct gttgcatgtt tttgcacgcc tttgtgcact ggcctcagag tcccatggat  19500
cgcaacccca ccatgaactt gctaaaggga gtgcccaacg ccatgctcca gagcccccag  19560
gtcctgccca ccctgcgccg caaccaggaa cagctctacc gcttcctgga gcgccactcc  19620
ccctacttcc gcagccacag cgcgcgcatc cgggggggcca cctctttttg ccacttgcaa  19680
gaaaacatgc aagacggaaa atgatgtaca gcatgctttt aataaatgta aagactgtgc  19740
actttattta tacacgggct ctttctggtt atttattcaa caccgccgtc gccatctaga  19800
aatcgaaagg gttctgccgc gcgtcgccgt gcgccacggg cagagacacg ttgcgatact  19860
```

-continued

```
ggaagcggct cgcccacttg aactcgggca ccaccatgcg gggcagtggt tcctcgggga  19920
aattctcgct ccacagggtg cgggtcagct gcagcgcgct caggaggtcg ggagccgaga  19980
tcttgaagtc gcagttgggg ccggaaccct gcgcgcgcga gttgcggtac acggggttgc  20040
agcactggaa caccagcagg gccggattat tcacgctggc cagcaggctc tcgtcgctaa  20100
tcatgtcgct gtccagatcc tccgcgttgc tcagggcgaa tggggtcatc ttgcagacct  20160
gcctgcccag gaaaggcggg agcccaggct tgccgttaca gtcgcagcgc aggggcatta  20220
gcaggtgccc acggcccgac tgcgcctgcg ggtacaacgc gcgcatgaag gcttcgatct  20280
gcctaaaagc cacctgggtc ttggctccct ccgaaaagaa catcccacag gacttgctgg  20340
agaactggtt cgcgggacag ctggcatcgt gcaggcagca gcgcgcgtca gtgttggcga  20400
tctgcaccac gttgcgaccc caccggtttt tcactatctt ggccttggaa gcctgctcct  20460
ttagcgcgcg ctggccgttc tcgctggtca catccatctc tatcacctgt tccttgttga  20520
tcatgtttgt cccgtgcaga cactttaggt cgccctccgt ctgggtgcag cggtgctccc  20580
acagcgcgca accggtgggc tcccaatttt tgtgggtcac ccccgcgtag gcctgcaggt  20640
aggcctgcag gaagcgcccc atcatggtca taaaggtctt ctggctcgta aaggtcagct  20700
gcaggccgcg atgctcttcg ttcagccagg tcttgcagat ggcggccagc gcctcggtct  20760
gctcgggcag catcttaaaa tttgtcttca ggtcgttatc cacgtggtac ttgtccatca  20820
tggcacgcgc cgcctccatg cccttctccc aggcggacac catgggcagg cttagggggt  20880
ttatcacttc cagcggcgag gacaccgtac tttcgatttc ttcttcctcc ccctcttccc  20940
ggcgcgcgcc cccgctgttg cgcgctctta ccgcctgcac caaggggtcg tcttcaggca  21000
agcgccgcac cgagcgcttg ccgcccttga cctgcttgat cagtaccggc gggttgctga  21060
agcccaccat ggtcagcgcc gcctgctctt cttcgtcttc gctgtctacc actatttctg  21120
gggaggggct tctccgctct gcggcaaagg cggcggatcg cttctttttt ttcttgggag  21180
ccgccgcgat ggagtccgcc acggcgaccg aggtcgaggg cgtggggctg ggggtgcgcg  21240
gcaccagggc ctcgtcgccc tcggactctt cctctgactc caggcggcgg cggagtcgct  21300
tctttggggg cgcgcgcgtt agcggcggcg gagacgggga cggggacggg gacgggacgc  21360
cctccacagg gggcggtctt cgcgcagacc cgcggccgcg ctcgggggtc ttctcgcgct  21420
ggtcttggtc ccgactggcc attgtatcct cctcctccta ggcagagaga cataaggagt  21480
ctatcatgca agtcgagaag gaggagagct taaccacccc ctctgagacc gccgtcgccg  21540
tcgcccccgc taccgccgac gcgcccgcca caccgagcga cacccccgcg gacccccccg  21600
ccgacgcacc cctgttcgag gaagcggccg tggagcagga cccgggcttt gtctcggcag  21660
aggaggattt gcaagaggag gaggataagg aggagaagcc ctcagtgcca aaagatcata  21720
aagagcaaga cgagcacgac gcagacgcac accagggtga agtcgggcgg ggggacggag  21780
ggcatggcgg cgccgactac ctagacgaag gaaacgacgt gctcttgaag cacctgcatc  21840
gtcagtgcgc cattgtctgc gacgctctgc aggagcgcag cgaggtgccc ctcagcgtgg  21900
cggaggtcag ccgcgcctac gagctcagcc tcttttcccc ccgggtgccc ccccgccgcc  21960
gcgaaaacgg cacatgcgag cccaacccgc gcctcaactt ctaccccgcc tttgtggtgc  22020
ccgaggtcct ggccacctat cacatcttct ttcaaaattg caagatcccc atctcgtgcc  22080
gcgccaaccg tagccgcgcc gataagatgc tggccctgcg ccagggcgac cacatacctg  22140
atatcgccgc tttggaagat gtgccaaaga tcttcgaggg tctgggtcgc aacgagaagc  22200
gggcagcaaa ctctctgcaa caggaaaaca gcgaaaatga gagtcacact ggagcgctgg  22260
```

-continued

```
tggagctgga gggcgacaac gcccgcctgg cggtgctcaa gcgcagcatc gaggtcaccc  22320
actttgccta ccccgcgctc aacctgcccc ccaaagtcat gaacgcggtc atggacgggc  22380
taatcatgcg ccgcggccgg ccccttgctc cagatgcaaa cttgcatgag gagaccgagg  22440
acggtcagcc cgtggtcagc gacgagcagc tgacgcgctg gctggaaacc gcggaccccg  22500
ccgaactgga ggagcggcgc aagatgatga tggccgcggt gctggtcacc gtagagctgg  22560
agtgtctgca gcgcttcttc ggcgaccccg agatgcagag aaaggtcgag gagaccctac  22620
actacacctt ccgccagggc tacgtgcgcc aggcttgcaa gatctccaac gtggagctca  22680
gcaacctggt gtcctacctg ggcatcttgc atgaaaaccg ccttgggcag agcgtgctac  22740
actccaccct gcgcggggag gcgcgccgcg actacgtgcg cgactgcgtt tacctcttcc  22800
tctgctacac ctggcagacg gccatggggg tctggcagca gtgcctggag gagcgcaacc  22860
tcaaggagct ggagaagctc ctgcagcgcg cgctcaaaga cctctggacg ggctacaacg  22920
agcgctcggt ggccgccgcg ctggccgacc tcatcttccc cgagcgcctg ctcaaaactc  22980
tccagcaggg gctgcccgac ttcaccagcc aaagcatgtt gcaaaatttt aggaacttta  23040
tcctggagcg ttctggcatc ctacccgcca cctgctgcgc cctgcccagc gactttgtcc  23100
ccctcgtgta ccgcgagtgc cccccgccgc tgtggggcca ctgctacctg ttccaactgg  23160
ccaactacct gtcctaccac gcggacctca tggaagactc cagcggcgag gggctcatgg  23220
agtgccactg ccgctgcaac ctctgcacgc ccccaccgctc cctggtctgc aacacccaac  23280
tgctcagcga gagtcagatt atcggtacct tcgagctaca gggtccgtcc tcctcagacg  23340
agaagtccgc ggctccgggg ctaaaactca ctccggggct gtggacttcc gcctacctgc  23400
gcaaatttgt acctgaagac taccacgccc acgagatcag gttttacgag gaccaatccc  23460
gcccgcccaa ggcggagctg accgcctgcg tcatcaccca gggcgagatc ctaggccaat  23520
tgcaagccat ccaaaaagcc cgccaagagt tttgctgag aaagggtcgg ggggtgtatc  23580
tggaccccca gtcgggtgag gagctcaacc cggttccccc gctgccgccg ccgcgggacc  23640
ttgcttccca ggataagcat cgccatggct cccagaaaga agcagcagcg gccgccactg  23700
ccgccacccc acacgctgga ggaagaggag gaatactggg acagtcaggc agaggaggtt  23760
tcggacgagg aggagccgga gacggagatg gaagagtggg aggaggacag cttagacgag  23820
gaggcttccg aagccgaaga ggcaggcgca acaccgtcac cctcggccgc agccccctcg  23880
caggcgcccc cgaagtccgc tcccagcatc agcagcaaca gcagcgctat aacctccgct  23940
cctccaccgc cgcgacccac ggccgaccgc agacccaacc gtagatggga caccaccgga  24000
accggggccg gtaagtcctc cgggaaaggc aagcaagcgc agcgccaagg ctaccgctcg  24060
tggcgcgctc acaagaacgc catagtcgct tgcttgcaag actgcggggg gaacatctcc  24120
ttcgcccgcc gcttcctgct cttccaccac ggtgtggcct tcccccgtaa cgtcctgcat  24180
tactaccgtc atctctacag cccctactgc ggcggcagtg agccagaggc ggccggcggc  24240
agcggcgccc gtttcggtgc ctaggaagac ccagggcaag acttcagcca agaaactcgc  24300
ggcggccgcg gcgaacgcgg tcgcgggggc cctgcgcctg acggtgaacg aacccctgtc  24360
gacccgcgaa ctgaggaacc gaatcttccc cactctctat gccatcttcc agcagagcag  24420
agggcaggat caggaactga aagtaaaaaa caggtctctg cgctccctca cccgcagctg  24480
tctgtatcac aagagcgaag accagcttcg gcgcacgctg gaggacgctg aggcactctt  24540
cagcaaatac tgcgcgctca ctcttaagga ctagctccgc gcccttctcg aatttaggcg  24600
```

-continued ggaacgccta cgtcatcgca gcgccgccgt catgagcaag gacattccca cgccatacat 24660
gtggagctat cagccgcaga tgggactcgc ggcgggcgcc tcccaggatt actccacccg 24720
catgaactgg ctcagtgccg gcccacacat gatctcacag gttaatgaca tccgcaccca 24780
tcgaaaccaa atattggtgg agcaggcggc aattaccacc acgccccgca ataatcccaa 24840
ccccagggag tggcccgcgt ccctggtgta tcaggaaatt cccggcccca ccaccgtact 24900
acttccgcgt gattcccagg ccgaagtcca aatgactaac tcaggggcac agctcgcggg 24960
cggctgtcgt cacagggtgc ggcctcctcg ccagggtata actcacctga agatccgagg 25020
cagaggtatt cagctcaacg acgagtcggt gagctcctcg ctcggtctca gacctgacgg 25080
gaccttccag atagccggag ccggccgatc ttccttcacg ccccgccagg cgtacctgac 25140
tctgcagagc tcgtcctcgg cgccgcgctc gggcggcatc gggactctcc agttcgtgca 25200
ggagtttgtg ccctcggtct acttcaaccc cttctcgggc tctcccggtc gctacccgga 25260
ccagttcatc ccgaactttg acgccgcgag ggactcggtg gacggctacg actgaatgtc 25320
gggtggaccc ggtgcagagc aacttcgcct gaagcacctt gaccactgcc gccgccctca 25380
gtgctttgcc cgctgtcaga ccggtgagtt ccagtacttt tccctgcccg actcgcaccc 25440
ggacggcccg gcgcacgggg tgcgcttttt catcccgagt caggtccgct ctaccctaat 25500
cagggagttc accgcccgtc ccctactggc ggagttggaa aaggggcctt ctatcctaac 25560
cattgcctgc atctgctcta accctggatt acaccaagat ctttgctgtc atttgtgtgc 25620
tgagtataat aaaggctgag atcagaatct actcgggctc ctgtcgccat cctgtcaacg 25680
ccaccgtcca agcccggccc gatcagcccg aggtgaacct cacctgcggt ctgcaccggc 25740
gcctgaggaa atacctagct tggtactaca acagcactcc ctttgtggtt tacaacagct 25800
ttgaccagga cggggtctca ctgagggata acctctcgaa cctgagctac tccatcagga 25860
agaacaacac cctcgagcta cttcctcctt acctgcccgg gacttaccag tgtgtcaccg 25920
gtccctgcac ccacacccac ctgttgatcg taaacgactc tcttccgaga acagacctca 25980
ataactcctc tccgcagttc cccagaacag gaggtgagct caggaaaccc cgggtaaaga 26040
agggtggaca agagttaaca cttgtggggt ttctggtgta tgtgacgctg gtggtggctc 26100
ttttgattaa ggcttttcct tccatgtctg aactatccct cttcttttat gaacaactcg 26160
actagtgcta acgggaccct acccaacgaa tcgggattga atatcggtaa ccaggttgca 26220
gtttcacttt tgattacctt catagtcctc ttcctgctag tgctgtcgct tctgtgcctg 26280
cggatcgggg gctgctgcat ccacgtttat atctggtgct ggctgtttag aaggttcgga 26340
gaccaccgca ggtagaataa acaaacctag acctagaaat ggacggtctc tgcagcgagc 26400
aacgcatact agagaggcgc cggcaaaaag cagagctcga gcgtcttaaa caagagctcc 26460
aagacgccgt ggccatacac cagtgcaaaa aagggctctt ctgtctggta aaacaggcca 26520
cgctcaccta tgaaaaaaca ggtgacaccc accgcctagg atacaagctg cccacacagc 26580
gccaaaagtt tgcccttatg ataggtgaac aacccatcac cgtgacccag cactccgtgg 26640
agacagaagg ctgcattcat gctccctgca ggggcgctga ctgcctctac accttgatca 26700
aaaccctttg cggtctcaga gaccttatcc ctttcaattg atcataactg taatcaataa 26760
aaaatcactt acttgaaatc tgatagcaag cctctgtcca attttttcag caacacttcc 26820
ttcccctctt cccaactctg gtactctagg cgcctcctag ctgcaaactt cctccacagt 26880
ctgaagggaa tgtcagattc ctcctcctcc tgtccctccg cacccacgat cttcatgttg 26940
ttgcagatga agcgcaccaa aacgtctgac gagagcttca accccgtgta cccctatgac 27000

-continued

```
acggaaaacg gtcctccctc cgtccctttc ctcacccctc ccttcgtgtc tcccgatgga  27060
ttccaagaga gcccccccgg ggtcctgtct ctgaacctgg ccgagcccct ggtcacttcc  27120
cacggcatgc tcgccctgaa aatgggaagt ggcctctccc tggacgacgc cggcaacctc  27180
acctctcaag atgtcaccac cactacccct cccctgaaaa aaaccaagac caacctcagc  27240
ctagaaacct cagcccccct gactgtgagc acctcaggcg ccctcaccct agcagccgcc  27300
gttcccctgg cggtggccgg cacctccctc accatgcaat cagaggcccc cctgacagtc  27360
caagatgcaa aactcaccct ggccaccaag ggcccccctga ccgtgtctga aggcaaactg  27420
gccttgcaga cctcggcccc gctgacggcc gctgacagca gcgccctcac cgttagcgcc  27480
acaccaccca tcagtgtaag cagtggaagt ttgggcttag acatggaaga ccccatgtat  27540
actcatgatg gaaaactggg aataagaatt ggaggcccac tgagagtagt agacagcctg  27600
cacacactga ctgtagttac cggaaatgga atagctgtag ataacaatgc cctccaaact  27660
agagttacgg gcgccctggg ttatgacaca tcaggaaacc tacaactgag agccgcgggg  27720
ggtatgcgaa ttgatgcaaa tggccaactt atccttgatg tggcataccc atttgatgct  27780
caaaacaatc tcagccttag acttggtcag ggacccctgt atgtaaacac agaccacaac  27840
ctagatttga attgcaacag aggtctgacc acaactacca ccaacaacac aaaaaaactt  27900
gaaactaaaa ttggctcagg cttagactat gataccaatg gtgctgtcat tattaaactt  27960
ggtactggtg taagctttga cagcacaggc gccctaactg tgggaaacac tggcgatgat  28020
aaactgactc tgtggacaac cccagaccca tctccaaatt gcagaattca cgcagacaaa  28080
gactgcaagt ttactctagt cctaactaag tgtggaagtc aaatcctggc ttctgtcgcc  28140
gccctagcgg tgtcaggaaa tctggcttca ataacaggca ccgttgccag cgttaccatc  28200
tttctcagat ttgatcagaa tggagtgctt atggaaaact cctccctaga caagcagtac  28260
tggaacttca gaaatggtaa ctcaaccaat gccacccccct acaccaatgc agttgggttc  28320
atgccaaacc tcgcagcata ccccaagaca cagagccaga ctgctaaaaa caacattgta  28380
agtcaggttt acttgaatgg ggacaaatcc aaacccatga cccttaccat taccctcaat  28440
ggaactaatg aatccagtga aactagccag gtgagtcact actccatgtc atttacatgg  28500
gcttgggaga gtgggcaata tgccaccgaa acctttgcca ccaattcctt taccttctct  28560
tacattgctg aacaataaag aaagcacaga gatgcttgtt tttgatttca aaattgtgtg  28620
cttttattta ttttcaagct tacagtattt ccagtagtca ttcgaataga gcttaatgaa  28680
actgcatgag aacccttcca catagcttaa attatcacca gtgcaaatgg agaaaaatca  28740
acatacctttt ttatccagat atcacagaac cctagtattc aacctgccac ctccctccca  28800
acacacagag tacacagtcc tttctccccg gctggcctta aaaagcatca tatcatgggt  28860
aacagacata ttcttaggtg ttatattcca cacggtttcc tgtcgagcca aacgctcatc  28920
agtgatatta ataaactccc cgggcagctc acttaagttc atgtcgctgt ccagctgctg  28980
agccacaggc tgctgtccaa cttgcggttg cttaacgggc ggcgaaggag aagtccacgc  29040
ctacatgggg gtagagtcat aatcgtgcat caggataggg cggtggtgct gcagcagcgc  29100
gcgaataaac tgctgccgcc gccgctccgt cctgcaggaa tacaacatgg cagtggtctc  29160
ctcagcgatg attcgcaccg cccgcagcat aaggcgcctt gtcctccggg cacagcagcg  29220
caccctgatc tcacttaaat cagcacagta actgcagcac agcaccacaa tattgttcaa  29280
aatcccacag tgcaaggcgc tgtatccaaa gctcatggcg ggaccacag aacccacgtg  29340
```

-continued gccatcatac cacaagcgca ggtagattaa gtggcgaccc ctcataaaca cgctggacat 29400
aaacattacc tcttttggca tgttgtaatt caccacctcc cggtaccata taaacctctg 29460
attaaacatg gcgccatcca ccaccatcct aaaccagctg gccaaaacct gcccgccggc 29520
tatacactgc agggaaccgg gactggaaca atgacagtgg agagcccagg actcgtaacc 29580
atggatcatc atgctcgtca tgatatcaat gttggcacaa cacaggcaca cgtgcataca 29640
cttcctcagg attacaagct cctcccgcgt tagaaccata tcccagggaa caacccattc 29700
ctgaatcagc gtaaatccca cactgcaggg aagacctcgc acgtaactca cgttgtgcat 29760
tgtcaaagtg ttacattcgg gcagcagcgg atgatcctcc agtatggtag cgcgggtttc 29820
tgtctcaaaa ggaggtagac gatccctact gtacggagtg cgccgagaca accgagatcg 29880
tgttggtcgt agtgtcatgc caaatggaac gccggacgta gtcatatttc ctccagcaga 29940
accaagtgcg cgcgtggcag ctatccttgc gtcttctgtc tcgccgcctg ccccgctcgg 30000
tgtagtagtt gtaatacagc cactccctca gaccgtcaag gcgctccctg gcgtccggat 30060
ctataacaac accatcctgc agcgccgccc tgatgacatc caccaccgta gagtatgcca 30120
agcccagcca ggaaatgcac tcactttgac agcgagagat aggaggagcg ggaagagatg 30180
gaagaaccat gatagtaaaa gaacttttat tccaatcgat cctctacaat gtcaaagtgt 30240
agatctatca gatggcactg gtctcctccg ctgagtcgat caaaaataac agctaaacca 30300
caaacaacac gattggtcaa atgctgcaca agggcttgca gcataaaatc gcctcgaaag 30360
tccaccgcaa gcataacatc aaagccaccg cccctatcat gatctatgat aaaaacccca 30420
cagctatcca ccagacccat atagttttca tctctccatc gtgaaaaaat atttacaagc 30480
tcctccttta aatcacctcc aaccaattca aaaagttgag ccagaccgcc ctccaccttc 30540
attttcagca tgcgcatcat gattgcaaaa attcaggctc ctcagacacc tgtataagat 30600
tgagaagcgg aacattaaca tcaatgtttc gctcgcgaag atcgcgcctc agtgcaagca 30660
tgatataatc ccacaggtcg gagcggatca gcgaggacat ctccccgcca ggaaccaact 30720
caacggagcc tatgctgatt ataatacgca tattcggggc tatgctaacc agcacggccc 30780
ccaaataggc gtactgcata ggcggcgaca aaaagtgaac agtttgggtt aaaaaatcag 30840
gcaaacactc gcgcaaaaaa gcaagaacat cataaccatg ctcatgcaaa tagatgcaag 30900
taagctcagg aacgaccaca gaaaaatgca caatttttct ctcaaacatg actgcgagcc 30960
ctgcaaaaaa taaaaaagaa acattacaca agagtagcct gtcttacaat gggatagact 31020
actctaacca acataagacg ggccacgaca tcgcccgcgt ggccataaaa aaaattatcc 31080
gtgtgattaa aaagaagcac agatagctgg ccagtcatat ccggagtcat cacgtgcgaa 31140
cccgtgtaga cccccgggtt ggacacatcg gccaaagaaa gaaagcggcc aatgtatccc 31200
ggaggaatga taacactaag acgaagatac aacagaataa ccccatgggg gggaataaca 31260
aagttagtag gtgaataaaa acgataaaca cccgaaactc cctcctgcgt aggcaaaata 31320
gcgccctccc cttccaaaac aacatacagc gcttccacag cagccatgac aaaagactca 31380
aaacactcaa aagactcagt cttaccagga aaataaaagc actctcacag caccagcact 31440
aatcagagtg tgaagagggc caagtgccga acgagtatat ataggaatta aaaatgacgt 31500
aaatgtgtaa aggtcaaaaa acgcccagaa aaatacacag accaacgccc gaaacgaaaa 31560
cccgcgaaaa aatacccaga agttcctcaa caaccgccac ttccgctttc ccacgatacg 31620
tcacttcctc gaaaatagca aactacattt cccacatgta caaaaccgaa accactcccc 31680
ttgtcaccgc ccacaactta catcttaatt aacaaacgtc aaagcctacg tcagccgccc 31740

```
cgcctcgccc cgcccacctc attatcatat tggccacaat ccaaaataag gtatattatt  31800

gatgatgatt taaatattat gcggtgtgaa ataccgcaca gatgcgtaag gagaaaatac  31860

cgcatcaggc gctcttccgc ttcctcgctc actgactcgc tgcgctcggt cgttcggctg  31920

cggcgagcgg tatcagctca ctcaaaggcg gtaatacggt tatccacaga atcaggggat  31980

aacgcaggaa agaacatgtg agcaaaaggc cagcaaaagg ccaggaaccg taaaaaggcc  32040

gcgttgctgg cgtttttcca taggctccgc ccccctgacg agcatcacaa aaatcgacgc  32100

tcaagtcaga ggtggcgaaa cccgacagga ctataaagat accaggcgtt tccccctgga  32160

agctccctcg tgcgctctcc tgttccgacc ctgccgctta ccggatacct gtccgccttt  32220

ctcccttcgg gaagcgtggc gctttctcat agctcacgct gtaggtatct cagttcggtg  32280

taggtcgttc gctccaagct gggctgtgtg cacgaacccc ccgttcagcc cgaccgctgc  32340

gccttatccg gtaactatcg tcttgagtcc aacccggtaa gacacgactt atcgccactg  32400

gcagcagcca ctggtaacag gattagcaga gcgaggtatg taggcggtgc tacagagttc  32460

ttgaagtggt ggcctaacta cggctacact agaaggacag tatttggtat ctgcgctctg  32520

ctgaagccag ttaccttcgg aaaaagagtt ggtagctctt gatccggcaa acaaaccacc  32580

gctggtagcg gtggtttttt tgtttgcaag cagcagatta cgcgcagaaa aaaaggatct  32640

caagaagatc ctttgatctt ttctacgggg tctgacgctc agtggaacga aaactcacgt  32700

taagggattt tggtcatgag attatcaaaa aggatcttca cctagatcct tttaaattaa  32760

aaatgaagtt ttaaatcaat ctaaagtata tatgagtaaa cttggtctga cagttaccaa  32820

tgcttaatca gtgaggcacc tatctcagcg atctgtctat ttcgttcatc catagttgcc  32880

tgactccccg tcgtgtagat aactacgata cgggagggct taccatctgg ccccagtgct  32940

gcaatgatac cgcgagaccc acgctcaccg gctccagatt tatcagcaat aaaccagcca  33000

gccggaaggg ccgagcgcag aagtggtcct gcaactttat ccgcctccat ccagtctatt  33060

aattgttgcc gggaagctag agtaagtagt tcgccagtta atagtttgcg caacgttgtt  33120

gccattgctg caggcatcgt ggtgtcacgc tcgtcgtttg gtatggcttc attcagctcc  33180

ggttcccaac gatcaaggcg agttacatga tcccccatgt tgtgcaaaaa agcggttagc  33240

tccttcggtc ctccgatcgt tgtcagaagt aagttggccg cagtgttatc actcatggtt  33300

atggcagcac tgcataattc tcttactgtc atgccatccg taagatgctt ttctgtgact  33360

ggtgagtact caaccaagtc attctgagaa tagtgtatgc ggcgaccgag ttgctcttgc  33420

ccggcgtcaa cacgggataa taccgcgcca catagcagaa ctttaaaagt gctcatcatt  33480

ggaaaacgtt cttcggggcg aaaactctca aggatcttac cgctgttgag atccagttcg  33540

atgtaaccca ctcgtgcacc caactgatct tcagcatctt ttactttcac cagcgtttct  33600

gggtgagcaa aaacaggaag gcaaaatgcc gcaaaaaagg gaataagggc gacacggaaa  33660

tgttgaatac tcatactctt cctttttcaa tattattgaa gcatttatca gggttattgt  33720

ctcatgagcg gatacatatt tgaatgtatt tagaaaaata aacaaatagg ggttccgcgc  33780

acatttcccc gaaaagtgcc acctgacgtc taagaaacca ttattatcat gacattaacc  33840

tataaaaata ggcgtatcac gaggcccttt cgtcttcaag aattgattta aat         33893
```

<210> SEQ ID NO 10
<211> LENGTH: 33742
<212> TYPE: DNA
<213> ORGANISM: Artificial Sequence
<220> FEATURE:

-continued

<223> OTHER INFORMATION: pBZ1_BZ28F.5IXP

<400> SEQUENCE: 10

```
catcatcaat aatatacctt attttggatt gtggccaata tgataatgag gtgggcgggg     60
cgaggcgggg cgggtgacgt aggacgtgcg agtagggttg ggaggtgtgg cggaagtgtg    120
gcatttgtaa gtgggaggag cttacatgca agcttccgtc gcggaaaatg tgacgttttt    180
tatgagcgcc gcctacctcc ggaagtgcca attttcgcgc gctttttacc ggatatcgta    240
gtaattttgg gcgggaccat gtaagatttg gccattttcg cgcgaaaagt gaaacgggga    300
agtgaaaact gaataatagg gcgttagtca tagcgcgtaa tatttaccga gggccgaggg    360
actttgaccg attacgtgga ggactcgccc aggtgttttt tacgtgaatt tccgcgttcc    420
gggtcaaagt ctccgttttt attgtcaccg tcatttgacg cggagggtat ttaaacccgc    480
tgcgctccta gcgatcgcgg tactgaaatg tgtgggcgtg gcttaagggt gggaaagaat    540
atataaggtg gggtcttat gtagttttgt atctgttttg cagcagccgc cgccgccatg    600
agcgacaccg gcaacagctt tgatggaagc atctttagcc cctatctgac agtgcgcatg    660
cctcactggg ccggagtgcg tcagaatgtg atgggttcca acgtggatgg acgtcccgtt    720
ctgccttcaa attcgtctac gatggcctac gcgaccgtgg gaggaactcc gctggacgcc    780
gcgacctccg ccgccgcctc cgccgccgcc gcgaccgcgc gcagcatggc tacggacctt    840
tacagctctt tggtggcgag cagcgcggcc tctcgcgcgt ctgctcggga tgaaaaactg    900
actgctctgc tgcttaaact ggaagacttg acccgggagc tgggtcaact gacccagcag    960
gtctccagct tgcgtgagag cagccttgcc tccccctaat ggcccataat ataaataaaa   1020
gccagtctgt ttggattaag caagtgtatg ttctttattt aactctccgc gcgcggtaag   1080
cccgggacca gcggtctcgg tcgtttaggg tgcggtggat tctttccaac acgtggtaca   1140
ggtggctctg gatgtttaga tacatgggca tgagtccatc cctggggtgg aggtagcacc   1200
actgcagagc ttcgtgctcg gggtggtgt tgtatatgat ccagtcgtag caggagcgct   1260
gggcgtggtg ctgaaaaatg tccttaagca agaggcttat agctaggggg aggcccttgg   1320
tgtaagtgtt tacaaatctg cttagctggg aggggtgcat ccgggggat atgatgtgca   1380
tcttggactg gatttttagg ttggctatgt tcccacccag atcccttctg ggattcatgt   1440
tgtgcaggac caccagcacg gtatatccag tgcacttggg aaatttatcg tggagcttag   1500
acgggaatgc atggaagaac ttggagacgc ccttgtggcc tcccagattt tccatacatt   1560
cgtccatgat gatggcaatg ggcccgtggg aagctgcctg agcaaaaacg tttctggcat   1620
cgctcacatc gtagttatgt tccagggtga ggtcatcata ggacatcttt acaaatcggg   1680
ggcggagggt cccggactgg gggatgatgg taccctcggg ccccggggcg tagttcccct   1740
cacagatctg catctcccag gctttcattt cagagggagg gatcatatcc acctgcgggg   1800
cgatgaaaaa gacagtttct ggcgcagggg agattaactg ggatgagagc aggtttctga   1860
gcagctgtga ctttccacag ccggtgggcc catatatcac gcctatcacc ggctgcagct   1920
ggtagttaag agagctgcag ctgccgtcct cccggagcag gggggccacc tcgttgagca   1980
tatccctgac gtggatgttc tccctgacca gttccgccag aaggcgctcg ccgcccagcg   2040
aaagcagctc ttgcaaggaa gcaaaatttt tcagcggttt caggccatcg gccgtgggca   2100
tgtttttcag cgtctgggtc agcagctcca gcctgtccca gagctcggtg atgtgctcta   2160
cggcatctcg atccagcaga tctcctcgtt tcgcgggttg ggcggcttt cgctgtaggg   2220
caccagccga tggcgtcca gcggggccag agtcatgtcc ttccatgggc gcagagtcct    2280
```

-continued

```
cgtcagggtg gtctgggtca cggtgaaggg gtgcgctccg ggttgggcac tggccagggt   2340
gcgcttgagg ctggttctgc tggtgctgaa tcgctgccgc tcttcgccct gcgcgtcggc   2400
caggtagcat ttgaccatgg tctcgtagtc gagaccctcg gcggcgtgcc ccttggcgcg   2460
gagctttccc ttggaggtgg cgccgcacga ggggcactgc aggctcttca gggcgtagag   2520
cttgggagcg agaaacacgg actctgggga gtaggcgtcc gcgccgcagg ccgcgcagac   2580
cgtctcgcat tccaccagcc aagtgagttc cgggcggtca gggtcaaaaa ccaggttgcc   2640
cccatgcttt ttgatgcgtt tcttacctcg gctctccatg aggcggtgtc ccttctcggt   2700
gacgaagagg ctgtccgtgt ccccgtagac cgacttcagg ggcctgtctt ccagcggagt   2760
gcctctgtcc tcctcgtaga gaaactctga ccactctgag acgaaggccc gtgtccaggc   2820
caggacgaag gaggccacgt gggaggggta gcggtcgttg tccactagcg ggtccacctt   2880
ctccagggtg tgcagacaca tgtccccctc ctccgcgtcc agaaaagtga ttggcttata   2940
ggtgtaggac acgtgaccgg gggttcccga cggggggggta taaaaggggg tgggcgccct   3000
ttcatcttca ctctcttccg catcgctgtc tgcgagagcc agctgctggg gtaagtattc   3060
cctttcaaag gcgggcatga cctcagcgct caggttgtca gtttctaaaa atgaggagga   3120
tttgatgttc acctgtccgg aagtgatacc tttgagggta cctgggtcca tctggtcaga   3180
aaacactatt tttttgttgt caagcttggt ggcgaacgac ccgtagaggg cgttggagag   3240
cagcttggca atggagcgca gggtctggtt tttgtcgcgg tcggctcgct ccttggccgc   3300
gatgttgagt tgcacgtatt cgcgggccac gcacttccac tcggggaaga cggtggtgcg   3360
ctcgtctggg atcaggcgca ccctccagcc gcggttgtgc agggtgacca tgtcgacgct   3420
ggtggcgacc tcaccgcgca gacgctcgtt ggtccagcag aggcggccgc ctttgcgcga   3480
gcagaagggg ggtagggggt ccagctggtc ctcgtttggg gggtccgcgt cgatggtaaa   3540
gaccccgggg agcaggcgcg ggtcaaagta gtcgatcttg caagcttgca tgtccagagc   3600
ccgctgccat tcgcgggcgg cgagcgcgcg ctcgtagggg ttgaggggcg ggccccaggg   3660
catggggtgg gtgagcgcgg aggcgtacat gccgcagatg tcatacacgt acaggggttc   3720
cctgaggata ccgaggtagg tggggtagca gcgccccccg cggatgctgg cgcgcacgta   3780
gtcatagagc tcgtgggagg gggccagcat gttgagccca aggttggtgc gctgggggcg   3840
ctcggcgcgg aagacgatct gtctgaagat ggcatgggag ttggaggaga tggtgggtcg   3900
ctggaagacg ttgaagcttg cttcttgcaa gcccacggag tccctgacga aggaggcgta   3960
ggactcgcgc agcttgtgca ccagctcggc ggtgacctgg acgtcgagcg cgcagtagtc   4020
gagggtctcg cggatgatgt catacttatc ctcccccttc tttttccaca gctcgcggtt   4080
gaggacgaac tcttcgcggt ctttccagta ctcttggagg ggaaacccgt ccgtgtccga   4140
acggtaagag cctagcatgt agaactggtt gacggcctgg taggggcagc agcccttctc   4200
cacgggcagc gcgtaggcct gcgccgcctt gcggagggag gtgtgggtaa gggcgaaagt   4260
gtccctgacc atgactttga ggtattgatg tctgaagtct gtgtcatcgc agccgccctg   4320
ttcccacagg gtgtagtccg tgcgcttttt ggagcgcggg ttgggcaggg agaaggtgag   4380
gtcattgaag aggatcttcc ccgctcgagg catgaagttt ctggtgatgc gaaagggccc   4440
tgggaccgag gagcggttgt tgatgacctg ggcggccagg acgatctcgt caaagccgtt   4500
tatgttgtgg cccacgatgt agagctccag gaagcggggc tggcccttga tggaggggag   4560
ctttttaagt tcctcgtagg taagctcctc gggcgattcc aggccgtgct cctccagggc   4620
```

-continued

```
ccagtcttgc aagtgagggt tggccgccag gaaggatcgc cagaggtcgc gggccatgag   4680
ggtctgcagg cggtcgcgga aggttctgaa ctgccgccct acggccatct tttcgggggt   4740
gatgcagtag aaggtgaggg ggtctttctc ccaggggtcc catctgagct cttgggcgag   4800
gtcgcgcgcg gcggcgacca gagcctcgtc gccccccagt ttcatgacca gcatgaaggg   4860
cacgagctgc ttgccaaagg ctcccatcca agtgtaggtc tctacatcgt aggtgacaaa   4920
gaggcgctcc gtgcgaggat gagagccgat cgggaagaac tggatctccc gccaccagtt   4980
ggaggattgg ctgttgatgt ggtgaaagta gaagtcccgt ctgcgggccg agcactcgtg   5040
ctggcttttg taaaagcgac cgcagtactg gcagcgctgc acgggttgta tatcttgcac   5100
gaggtgaacc tggcgacctc tgacgaggaa gcgcagcggg aatctaagtc ccccgcctgg   5160
ggtcccgtgt ggctggtggt cttctacttt ggttgtctgg ccgccagcat ctgtctcctg   5220
gagggcgatg gtggagcaga ccaccacgcc gcgagagccg caggtccaga tctcggcgct   5280
cggcgggcgg agtttgatga cgacatcgcg cacattggag ctgtccatgg tctccagctc   5340
ccgcggcggc aggtcagccg ggagttcctg gaggttcacc tcgcagagac gggtcaaggc   5400
gcggacagtg ttgagatggt atctgatttc aaggggcgtg ttggaggcgg agtcgatggc   5460
ttgcagaagg ccgcagcccc ggggggccac gatggttccc cgcggggcgc gaggggaggc   5520
ggaagctggg ggtgtgttca gaagcggtga cgcgggcggg cccccggagg tagggggggt   5580
tccggcccca caggcatggg cggcaggggc acgtcttcgc cgcgcgcggg caggggctgg   5640
tgctggctcc ggagagcgct tgcgtgcgcg acgacgcgac ggttggtgtc ctgtatctgg   5700
cgcctctgag tgaagaccac gggtcccgtg accttgaacc tgaaagagag ttcgacagaa   5760
tcaatctcgg catcgttgac agcggcctgg cgcaggatct cctgcacgtc gcccgagttg   5820
tcctggtagg cgatctctgc catgaactgc tcgatctctt cctcctggag atctcctcgt   5880
ccggcgcgct ccacggtggc cgccaggtcg ttggagatgc gacccatgag ctgcgagaag   5940
gcgttgaggc cgccctcgtt ccagacccgg ctgtagacca cgcccccctc ggcgtcgcgg   6000
gcgcgcatga ccacctgggc caggttgagc tccacgtgtc gcgtgaagac ggcgtagttg   6060
cgcaggcgct ggaaaaggta gttcagggtg gtggcggtgt gttcggcgac gaagaagtac   6120
atgacccagc gccgcaacgt ggattcattg atgtccccca aggcctccag gcgctccatg   6180
gcctcgtaga agtccacggc gaagttgaaa aactgggagt tgcgagcgga cacggtcaac   6240
tcctcctcca gaagacggat gagctcggcg acagtgtcgc gcacctcgcg ctcgaaggcc   6300
acgggggcg  cttcttcctc ttccacctct tcttccatga ttgcttcttc ttcctcagcc   6360
gggacgggag ggggcggcgg cgggggaggg gcgcggcggc ggcggcggcg caccggcagg   6420
cggtcgatga agcgctcgat catctccccc cgcatgcggc gcatggtctc ggtgacggcg   6480
cggccgttct cccgggggcg cagctcaaag acgccgcctc tcatctcgcc gcggggcggg   6540
cggccgtgag gtagcgagac ggcgctgact atgcatctta acaattgctg tgtaggtacg   6600
ccgccaaggg acctgattga gtccagatcc accggatccg aaaacctttg gaggaaagcg   6660
tctatccagt cgcagtcgca aggtaggctg agcaccgtgg cgggcggggg cgggtcggga   6720
gagttcctgg cggagatgct gctgatgatg taattaaagt aggcggtctt gagaaggcgg   6780
atggtggaca ggagcaccat gtctttgggt ccggcctgtt ggatgcggag gcggtcggcc   6840
atgccccagg cctcgttctg acaccggcgc aggtctttgt agtagtcttg catgagtctt   6900
tccaccggca cctcttctcc ttcctcttct ccatctcgcc ggtggtttct cgcgccgccc   6960
atgcgcgtga ccccaaagcc cctgagcggc tgcagcaggg ccaggtcggc gaccacgcgc   7020
```

-continued

```
tcggccaaga tggcctgctg tacctgagtg agggtcctct cgaagtcatc catgtccacg   7080
aagcggtggt aggcgcccgt gttgatggtg taggtgcagt tggccatgac ggaccagttg   7140
acggtctggt gtcccggctg cgagagctcc gtgtaccgca ggcgcgagaa ggcgcgggaa   7200
tcgaacacgt agtcgttgca agtccgcacc agatactggt agcccaccag gaagtgcggc   7260
ggaggttggc gatagagggg ccagcgctgg gtggcggggg cgccgggcgc caggtcttcc   7320
agcatgaggc ggtggtatcc gtagatgtac ctggacatcc aggtgatgcc ggcggcggtg   7380
gtggtggcgc gcgcgtagtc gcggacccgg ttccagatgt ttcgcagggg cgagaagtgt   7440
tccatggtcg gcacgctctg gccggtgagg cgcgcgcagt cgttgacgct ctatacacac   7500
acaaaaacga aagcgtttac agggctttcg ttctgtagcc tggaggaaag taaatgggtt   7560
gggttgcggt gtgccccggt tcgagaccaa gctgagctcg gccggctgaa gccgcagcta   7620
acgtggtatt ggcagtcccg tctcgaccca ggccctgtat cctccaggat acggtcgaga   7680
gcccttttgc tttcttggcc aagcgcccgt ggcgcgatct gggatagatg gtcgcgatga   7740
gaggacaaaa gcggctcgct tccgtagtct ggagaaacaa tcgccagggt tgcgttgcgg   7800
cgtaccccgg ttcgagcccc tatggcggct tggatcggcc ggaaccgcgg ctaacgtggg   7860
ctgtggcagc cccgtcctca ggaccccgcc agccgacttc tccagttacg ggagcgagcc   7920
ccttttgttt tttatttttt agatgcatcc cgtgctgcgg cagatgcgcc cctcgccccg   7980
gcccgatcag cagcagcaac agcaggcatg cagacccccc tctcctctac ccgccccggt   8040
caccacggcc gcggcggccg tgtccggcgc ggggggcgcg ctggagtcag atgagccacc   8100
gcggcggcga cctaggcagt atctggactt ggaagagggc gagggactgg cgcggctggg   8160
ggcgagctct ccagagcgcc acccgcgggt gcagttgaaa agggacgcgc gcgaggcgta   8220
cctgccgcgg cagaacctgt ttcgcgaccg cgggggcgag gagcccgagg agatgcgaga   8280
ctgcaggttc caagcggggc gcgagctgcg ccgcgggttg gacagacagc gcctgctgcg   8340
cgaggaggac tttgagcccg acacgcagac gggcatcagc cccgcgcgcg cgcacgtggc   8400
cgcggccgac ctggtgaccg cctacgagca gacggtgaac caggagcgca acttccaaaa   8460
aagcttcaac aaccacgtgc gcacgctggt ggcgcgcgag gaggtgaccc tgggtctcat   8520
gcatctgtgg gacctggtgg aggcgatcgt gcagaacccc agcagcaagc ccctgaccgc   8580
gcagctgttc ctggtggtgc agcacagcag ggacaacgag gccttcaggg aggcgctgct   8640
gaacatcacc gagccggagg ggcgctggct cctggacctg ataaacatcc tgcagagcat   8700
agtggtgcag gagcgcagcc tgagcctggc cgagaaggtg gcggccatta actattctat   8760
gctgagcttg ggcaagttct acgcccgcaa gatctacaag acccccctacg tgcccataga   8820
caaggaggtg aagatagaca gcttctacat gcgcatggcg ctaaaggtgc tgaccctgag   8880
cgacgacctg ggagtgtacc gcaacgagcg catccacaag gccgtgagcg ccagccggcg   8940
gcgcgagctg agcgaccgcg agctgatgca cagtctgcag cgcgcgctca ccggcgcggg   9000
cgagggcgac agggaggtcg agtcctactt cgacatgggg gctgacctgc actggcagcc   9060
gagccgccgc gccctggagg cggcgggggc gtatggcggc cccctggcgg ccgatgacga   9120
ggaagaggag gactatgagc tagaggaggg cgagtacctg gaggactgac ctggctggtg   9180
gtgttttggt atagatgcaa gatccgaacg tggcggaccc ggcggtccgg gcggcgctgc   9240
agagccagcc gtccggcatt aactcctctg acgactgggc cgcggccatg ggtcgcatca   9300
tggccctgac cgcgcgcaac cccgaggcct tcaggcagca gcctcaggct aaccggctgg   9360
```

-continued

```
cggccatctt ggaagcggta gtgcccgcgc gctccaaccc cacccacgag aaggtgctgg   9420
ccatagtcaa cgcgctggcg gagagcaggg ccatccgggc ggacgaggcc ggactggtgt   9480
acgatgcgct gctgcagcgg gtggcgcggt acaacagcgg caacgtgcag accaacctgg   9540
accgcctggt gacggacgtg cgcgaggccg tggcgcagcg cgagcgcttg catcaggacg   9600
gtaacctggg ctcgctggtg gcgctaaacg ccttcctcag cacccagccg gccaacgtac   9660
cgcgggggca ggaggactac accaacttct tgagcgcgct gcggctgatg gtgaccgagg   9720
tccctcagag cgaggtgtac cagtcggggc ccgactactt cttccagacc agcagacagg   9780
gcttgcaaac cgtgaacctg agccaggctt tcaagaacct gcgggggctg tggggagtga   9840
aagcgcccac cggcgaccga gctacggtgt ccagcctgct aacccccaac tcgcgcctgc   9900
tgctgctgct gatcgcgccc ttcacggaca gcgggagcgt ctcgcgggag acctatctgg   9960
gccacctgct gacgctgtac cgcgaggcca tcgggcaggc gcaggtggac gagcacacct  10020
tccaagagat caccagcgtg agccacgcgc tggggcagga ggacacgggc agcctgcagg  10080
cgaccctgaa ctacctgctg accaacaggc ggcagaagat tcccacgctg cacagcctga  10140
cccaggagga ggagcgcatc ttgcgctacg tgcagcagag cgtgagcctg aacctgatgc  10200
gcgacggcgt gacgcccagc gtggcgctgg acatgaccgc gcgcaacatg gaaccgggca  10260
tgtacgcttc ccagcggccg ttcatcaacc gcctgatgga ctacttgcat cgggcggcgg  10320
ccgtgaaccc cgagtacttc accaatgcca ttctgaatcc ccactggatg ccccctccgg  10380
gtttctacaa cggagacttc gaggtgcctg aggtcaatga tgggttcctc tgggatgaca  10440
tggatgacag tgtgttctcc cccaacccgc tgcgcgccgc gtctctgcga ttgaaggagg  10500
gctctgacag ggaaggaccg aggagtctgg cctcctccct ggctctgggg gcggtgggcg  10560
ccacgggcgc ggcggcgcgg ggcagcagcc ccttccccag cctggcagac tctctgaata  10620
gcgggcgggt gagcaggccc cgcttgctag gcgaggagga gtatctgaac aactccctgc  10680
tgcagcccgt gagggacaaa aacgctcagc gacagcagtt tcccaacaac gggatagaga  10740
gcctggtgga caagatgtcc agatggaaga catatgcgca ggagtacaag gagtgggagg  10800
accgccagcc gcggcccctg ccgcccccta gacagcgctg gcagcggcgc gcgtccaacc  10860
gccgctggag acagggaccc gaggacgatg atgactctgc agatgacagc agcgtgttgg  10920
acctgggcgg gagcgggaac cccttttcgc acctgcgccc acgcctgggc aagatgtttt  10980
aaaagagaaa aataaaactc accaaggcca tggcgacgag cgttggtttt ttgttccctt  11040
ccttagtatg cggcgcgcgg cgatgttcga ggaggggcct ccccccctctt acgagagcgc  11100
gatgggaatt tctcctgcgg cgcccctgca gcctccctac gtgcctcctc ggtacctgca  11160
acctacaggg gggagaaata gcatctgtta ctctgagctg cagcccctgt acgataccac  11220
cagactgtac ctggtggaca acaagtccgc ggacgtggcc tccctgaact accagaacga  11280
ccacagcgat tttttgacca cggtgatcca aaacaacgac ttcaccccaa ccgaggccag  11340
tacccagacc ataaacctgg acaacaggtc gaactggggc ggcgacctga agaccatcct  11400
gcacaccaac atgcccaacg tgaacgagtt catgtttacc aactctttta aggcgcgggt  11460
tatggtggcg cgcgagcagg gggaggcgaa gtacgagtgg gtggacttca cgctgcccga  11520
gggcaactac tcagagacca tgactattga cctgatgaac aatgcgatcg tggaacacta  11580
cctgaaagtg ggcaggcaga acggggtgaa ggagagcgat atcggggtca agtttgacac  11640
cagaaacttt cgtctgggct gggaccccgt gaccgggctg gtcatgccgg gggtctacac  11700
caacgaggcc tttcatcccg atatagtgct cctgcccggc tgtggggtgg actttaccca  11760
```

gagccggctg agcaacctgc tgggcgttcg caagcggcaa cctttccagg agggtttcaa 11820
gatcacctat gaggatctgg aggggggcaa cattcccgcg ctccttgatc tggacgccta 11880
cgaggagagc ttgaaacccg aggagagcgc tggcgacagc ggcgagagtg gcgaggagca 11940
agccggcggc ggtggcagcg cgtcggtaga aaacgaaagt actcccgcag tggcggcaga 12000
cgctgcggag gtcgagccag aggccatgca gcaggacgca gaggagggcg cacaggaggg 12060
cgcgcaggag gacatgaacg atggggagat caggggagac actttcgcca cccggggcga 12120
agaaaaagag gcagaggcgg tggcggcgac ggtggaagcc gaaaccgagg cagaggcaga 12180
gcccaagacc gaagttatgg aagacatgaa tgatggagaa cgtaggggtg acacgtttgc 12240
cacccggggc gaagagaagg cggcggaggc agaagccgcg gctgaggagg cggctgcggc 12300
tgcggccgag gctgaggctg cggctgaggc taaggtcgaa gccgatgttg cggttgaggc 12360
tcaggctgag gaggaggagg cggcgactga agcagttaag gaaaaggccc aggcagagca 12420
ggaagagaaa aaacctgtca ttcaacctct aaaagaagat agcaaaaagc gcagttacaa 12480
cgtcatcgag ggcagcacct ttacccagta ccgcagctgg tacctggcgt acaactacgg 12540
cgacccggtc aagggggtgc gctcgtggac cctgctctgc acgccggacg tcacctgcgg 12600
ctccgagcag atgtattggt cgctgccaaa catgatgcaa gacccggtga ccttccgctc 12660
cacgcggcag gttagcaact tcccggtggt gggcgccgaa ctgctgcccg tgcactccaa 12720
gagtttttac aacgagcagg ccgtctactc ccagctgatc cgccaggcca cctctctgac 12780
ccacgtgttc aatcgctttc ccgagaacca gattttggcg cgcccgccgg cccccaccat 12840
caccaccgtc agtgaaaacg ttcctgccct cacagatcac gggacgctac cgctgcgcaa 12900
cagcatctca ggagtccagc gagtgaccat tactgacgcc agacgccgga cctgccccta 12960
cgtttacaag gccttgggca tagtctcgcc gcgcgtcctc tccagtcgca ctttttaaaa 13020
tacatctacc ctcacgcttc aaaatcatgt ccgtactcat ctcacccagc aacaacaccg 13080
gctgggggct gcgcgcgccc agcaagatgt ttggaggggc gaggaaacgc tccgagcagc 13140
acccagtgcg cgtgcgcggc cactaccgcg cgccctgggg agcgcacaag cgcgggcgcg 13200
cagggcgcac cactgtggac gacgccattg actccgtagt ggagcaggcg cgccactaca 13260
cacccggcgc gccgtccgcc cccgccgtgt ccaccgtgga cgaggcgatc gagagcgtgg 13320
tacagggcgc gcggcactat gccaacctta aaaatcgacg ccgtcgcgtg gctcgccgcc 13380
atcgccggag accccgggcc accgccgccg cgcgccttgc taaggctctg ctcaggcgcg 13440
ccaggcgaac tggccgccgg gccgccatga gggccgcacg gcgggctgcc gccagcgcgg 13500
ccgccgcggc cccacgggca cgaaggcgcg cggccgctgc cgccgccgcc gccatttcca 13560
gcttggcctc gacgcggcgc ggtaacatat actgggtgcg cgactcggta accggcacgc 13620
gggtacccgt gcgctttcgc cccccgcgga attagcacaa gacaacatac acactgagtc 13680
tcctgctgtt gtgtatccca gcggcgaccg tcagcagcgg cgacatgtcc aagcgcaaaa 13740
ttaaagaaga gatgctccag gtcatcgcgc cggagatcta tgggccccccg aagaaggagg 13800 aggatgatta caagccccgc aagctaaagc gggtcaaaaa gaaaaagaaa gatgatgacg 13860
ttgacgaggc ggtggagttt gtccgccgca tggcgcccag gcgccccgtg cagtggaagg 13920
gtcggcgcgt gcagcgagtc ctgcgccccg gcaccgcggt ggtctttacg cccggcgagc 13980
gttccacgcg cactttcaag cgggtgtacg atgaggtgta cggcgacgag gatctgttgg 14040
agcaggccaa ccatcgcttt ggggagtttg catatgggaa acggccccgc gagagcctaa 14100
aagaggacct gctggcgcta ccgctggacg agggcaatcc caccccgagt ctgaagccgg 14160
taaccctgca acaggtgctg cctttgagcg cgcccagcga gcagaagcga gggttgaagc 14220
gcgagggcgg ggacctggca cccaccgtgc agttgatggt gcccaagcgg cagaagctgg 14280
aggacgtgct ggagaaaatg aaagtagagc ccgggatcca gcccgaaatc aaggtccgcc 14340
ccatcaagca ggtggcgccc ggcgtgggag tccagaccgt ggacgttagg attcccacgg 14400
aggagatgga aacccaaacc gccactccct cttcggcggc tagcgccacc accggctccg 14460
cttcggtaga ggtgcagacg gacccctggc tagccgccgc cgccccggcc gcccccgtt 14520 cgcgcgggcg caagagaaat tatccagcgg ccagcgcgct catgccccag tacgcactgc 14580
atccatccat cgcgcccacc cccggctacc gcgggtactc gtaccgcccg cgcagatcag 14640
ccggcacccg cggccgccgc cgccgtgcga ccacaaccag ccgccgccgt cgccgccgcc 14700
gccagccagt gctgaccccc gtgtctgtaa ggaaggtggc tcgctcgggg agcacgctgg 14760
tggtgcccag agcgcgctac caccccagca ttgtttaaag ccggtctctg tatggttctt 14820
gcagatatgg ccctcacttg tcgcctccgc ttcccggtgc cgggataccg aggaagaact 14880
caccgccgca gaggcatggc gggcagtggt ctccgcggcg gccgtcgcca tcgccggcgc 14940
gcaaagagca ggcgcatgcg cggcggtgtg ctgcccttcc taatcccgct aatcgccgcg 15000
gcgatcggtg ccgtgcccgg gatcgcctcc gtggccctgc aggcgtccca gaaacattga 15060
ctcttgcaac cttgcaagct tgcatttttt ggaggaaaaa ataaaaagtc tagactctca 15120
cgctcgcttg gtcctgtgac tattttgtag aaaaaagatg gaagacatca actttgcgtc 15180
gctggccccg cgtcacggct cgcgcccgtt catgggagac tggacagata tcggcaccag 15240
caatatgagc ggtggcgcct tcagctgggg cagtctgtgg agtggcctta aaaattttgg 15300
ttccaccatt aagaactatg gcaacaaagc gtggaacagc agcacgggtc agatgctgag 15360
agacaagttg aaagagcaga acttccagga gaaggtggca cagggcctgg cctctggcat 15420
cagcggggtg gtggacatag ctaaccaggc cgtgcagaaa aagataaaca gtcatctgga 15480
cccccgccct caggtggagg aaacgcctcc agccatggag acggtgtctc ccgagggcaa 15540
aggcgaaaag cgcccgcggc ccgacaggga agagaccctg gtgtcacaca ccgaggagcc 15600
gccctcttac gaggaggcag tcaaggccgg cctgcccacc actcgcccca tagctcccat 15660
ggccaccggt gtggtgggtc acaggcaaca cacccccgcg acactagatc tgcccccgcc 15720
gtccgagccg actcgccagc caaaggcggt gacggtgccc gctccctcca cttccgccgc 15780
caacagagtg cctctgcgcc gcgctgcgag cggcccccgg gcctcgcgag tcagcggcaa 15840
ctggcagagc acactgaaca gcatcgtggg cctgggagtg aggagtgtga agcgccgccg 15900
ttgctactga atgagcaagc tagctaacgt gttgtatgtg tgtatgcgtc ctatgtcgcc 15960
gccagaggag ctgttgagcc gccggcgccg tctgcactcc agcgaatttc aagatggcga 16020
ccccatcgat gatgcctcag tggtcgtaca tgcacatctc gggccaggac gcttcggagt 16080
acctgagccc cgggctggtg cagttcgccc gcgccacaga cacctacttc aacatgagta 16140
acaagttcag gaaccccact gtggcgccca cccacgatgt gaccacggac cggtcgcagc 16200
gcctgacgct gcggttcatc cccgtggatc gggaggacac cgcttactct tacaaggcgc 16260
ggttcacgct ggccgtgggc gacaaccgcg tgctggacat ggcctccact tactttgaca 16320
tccgggggtt gctggacagg ggccccactt tcaagcccta ctcgggcact gcctacaact 16380
ccctggcccc caagggcgct cccaattctt gcgagtggga ggaggaaaca caaaatgagg 16440
tacaagccaa tgaagaacaa ctagcagaag aagaggatga agaaatggct caagaggatc 16500

-continued

```
agcagcctac taaaaaaacc catgtatatg ctcaggcacc tctttctggc gaacagatta  16560
ccaaagatgg cttgcaaata ggagctgaag ttacaggaga aacatcaaag cccatttttg  16620
cagacaagac attccaacca gaacctcaga taggagagtc tcaatggaat gaggccgatg  16680
ctacagtagc aggaggtagg gttttgaaaa agactacccc tatgaaacct tgctatggat  16740
cctatgccag acctaccaat gccaatggag ggcaggggat acttgaggca aatgctaaag  16800
gggaactcga atctaaagtt gagatgcagt tttctctaa caccacaact cttaatgtaa  16860
gagacggtga aaatggcctt aaaccaaaag tagtgctgta tagcgaagat gtcaacctgg  16920
aatcccctga cactcatctg tcttacaagc ccaaaaaaga tgatgttaat gccaaaatca  16980
tgttgggtca gcaagccatg cccaacagac ccaacctcat tggatttaga gataatttca  17040
ttgggctcat gtattacaac agcactggaa acatgggagt gctggcgggt caggcctctc  17100
agttgaatgc tgtggtggac ttgcaggata gaaacacgga actgtcatat cagcttatgc  17160
ttgattccat tggagataga accagatact tttccatgtg gaaccaggca gtggatagct  17220
atgacccaga tgttagaatc attgaaaacc atggggtgga ggatgagctg cccaactact  17280
gttttccctt gggcggtata ggaattacag atacatacca ggccataaaa gcagccaatg  17340
gtggagatgc tactacgtgg tctgctgata acacatttgc agaccgcaac gaaatagggg  17400
tgggaaacaa cttcgccatg gagatcaaca tccaggccaa cctctggaga aacttcctct  17460
atgcgaacgt gggactctac ctgccagaca agctcaagta caaccccacc aacgtggaca  17520
tctctgacaa ccccaacacc tatgactaca tgaacaagcg ggtggtggcc cccggcctgg  17580
tggactgctt tgtcaatgtg ggagccaggt ggtccctgga ctacatggac aacgtcaacc  17640
ccttcaacca ccaccgcaat gcgggtctgc gctaccgctc catgatcctg ggcaacgggc  17700
gctatgtgcc cttccacatc caggtacccc agaagttctt tgccatcaag aacctcctgc  17760
tcctgcccgg ctcctacacc tacgagtgga acttcaggaa ggatgtaaac atggtcctac  17820
agagctctct gggcaatgac cttagggtag atggggccag catcaagttt gacagcatca  17880
ccctctatgc tacatttttc cccatggccc acaacaccgc ctccacgctt gaggccatgc  17940
tgagaaacga caccaacgac cagtccttca atgactacct ctctggggcc aacatgctct  18000
acccaatccc agccaaggcc accaacgtgc ccatctccat cccctctcgc aactgggccg  18060
cctttagagg ctgggccttt acccgcctta agaccaagga gaccccctcc ctgggctcgg  18120
gttttgatcc ctactttgtt tactcgggat ccatccccta cctggatggc accttctacc  18180
tcaaccacac tttcaagaag atatccatca tgtatgactc ctccgtcagc tggccgggca  18240
acgaccgctt gctcaccccc aatgagttcg aggtcaagcg cgccgtggac ggcgagggct  18300
acaacgtggc ccagtgcaac atgaccaagg actggttcct ggtgcagatg ctggccaact  18360
acaacatagg ctaccagggc ttctacatcc cagagagcta caaggacagg atgtattcct  18420
tcttcagaaa tttccaaccc atgagccgac aggtggtgga cgagaccaat tacaaggact  18480
atcaggccat tggcatcacc caccagcaca acaactcggg tttcgtgggc tacctggcgc  18540
ccaccatgcg cgagggacag gcctaccccg ccaacttccc ctaccccctg ataggcaaga  18600
ccgcggtcga cagcgtcacc cagaaaaagt tcctctgcga ccgcaccctc tggcgcatcc  18660
ccttctctag caactttatg tccatgggtg cgctcacgga cctgggccaa aacctgcttt  18720
atgccaactc tgcccatgcg ctggacatga cttttgaggt ggaccccatg gacgagccca  18780
cccttctcta tattgtgttt gaagtgttcg acgtggtcag agtgcaccag ccgcaccgcg  18840
```

-continued gtgtcatcga gaccgtgtac ctgcgtacgc ccttctcagc cggcaacgcc accacctaag 18900
gagacagcgc cgccgcctgc atgactggtt ccaccgagca agagctcagg gccatcgcca 18960
gagacctggg atgcggaccc tattttttgg gcacctatga caaacgcttc ccgggtttta 19020
tctcccgaga caagctcgcc tgcgccatcg tcaacacggc cgcgcgcgag accgggggcg 19080
tgcactggct ggcctttggc tgggacccgc gctctaaaac ttgctacctc tttgacccct 19140
ttggcttctc cgatcagcgc ctcaggcaga tttatgagtt tgagtacgag gggctgttgc 19200
gccgcagcgc gcttgcctcc tcgcccgacc gctgcatcac ccttgagaag tccaccgaga 19260
ccgtgcaggg gccccactcg gccgcctgcg gtctcttctg ttgcatgttt ttgcacgcct 19320
ttgtgcactg gcctcagagt cccatggatc gcaaccccac catgaacttg ctaaagggag 19380
tgcccaacgc catgctccag agcccccagg tcctgcccac cctgcgccgc aaccaggaac 19440
agctctaccg cttcctggag cgccactccc cctacttccg cagccacagc gcgcgcatcc 19500
ggggggccac ctctttttgc cacttgcaag aaaacatgca agacggaaaa tgatgtacag 19560
catgctttta ataaatgtaa agactgtgca ctttatttat acacgggctc tttctggtta 19620
tttattcaac accgccgtcg ccatctagaa atcgaaaggg ttctgccgcg cgtcgccgtg 19680
cgccacgggc agagacacgt tgcgatactg gaagcggctc gcccacttga actcgggcac 19740
caccatgcgg ggcagtggtt cctcggggaa attctcgctc cacagggtgc gggtcagctg 19800
cagcgcgctc aggaggtcgg gagccgagat cttgaagtcg cagttggggc cggaaccctg 19860
cgcgcgcgag ttgcggtaca cggggttgca gcactggaac accagcaggg ccggattatt 19920
cacgctggcc agcaggctct cgtcgctaat catgtcgctg tccagatcct ccgcgttgct 19980
cagggcgaat ggggtcatct tgcagacctg cctgcccagg aaaggcggga gcccaggctt 20040
gccgttacag tcgcagcgca ggggcattag caggtgccca cggcccgact gcgcctgcgg 20100
gtacaacgcg cgcatgaagg cttcgatctg cctaaaagcc acctgggtct tggctccctc 20160
cgaaaagaac atcccacagg acttgctgga gaactggttc gcgggacagc tggcatcgtg 20220
caggcagcag cgcgcgtcag tgttggcgat ctgcaccacg ttgcgacccc accggttttt 20280
cactatcttg gccttggaag cctgctcctt tagcgcgcgc tggccgttct cgctggtcac 20340
atccatctct atcacctgtt ccttgttgat catgtttgtc ccgtgcagac actttaggtc 20400
gccctccgtc tgggtgcagc ggtgctccca cagcgcgcaa ccggtgggct cccaattttt 20460
gtgggtcacc cccgcgtagg cctgcaggta ggcctgcagg aagcgcccca tcatggtcat 20520
aaaggtcttc tggctcgtaa aggtcagctg caggccgcga tgctcttcgt tcagccaggt 20580
cttgcagatg gcggccagcg cctcggtctg ctcgggcagc atcttaaaat ttgtcttcag 20640
gtcgttatcc acgtggtact tgtccatcat ggcacgcgcc gcctccatgc ccttctccca 20700
ggcggacacc atgggcaggc ttagggggtt tatcacttcc agcggcgagg acaccgtact 20760
ttcgatttct tcttcctccc cctcttcccg gcgcgcgccc ccgctgttgc gcgctcttac 20820
cgcctgcacc aaggggtcgt cttcaggcaa gcgccgcacc gagcgcttgc cgcccttgac 20880
ctgcttgatc agtaccggcg ggttgctgaa gcccaccatg gtcagcgccg cctgctcttc 20940
ttcgtcttcg ctgtctacca ctatttctgg ggaggggctt ctccgctctg cggcaaaggc 21000
ggcggatcgc ttcttttttt tcttgggagc cgccgcgatg gagtccgcca cggcgaccga 21060
ggtcgagggc gtggggctgg gggtgcgcgg caccagggcc tcgtcgccct cggactcttc 21120
ctctgactcc aggcggcggc ggagtcgctt ctttgggggc gcgcgcgtta gcggcggcgg 21180
agacggggac ggggacgggg acgggacgcc ctccacaggg ggcggtcttc gcgcagaccc 21240

-continued

```
gcggccgcgc tcgggggtct tctcgcgctg gtcttggtcc cgactggcca ttgtatcctc  21300
ctcctcctag gcagagagac ataaggagtc tatcatgcaa gtcgagaagg aggagagctt  21360
aaccaccccc tctgagaccg ccgtcgccgt cgcccccgct accgccgacg cgcccgccac  21420
accgagcgac acccccgcgg acccccccgc cgacgcaccc ctgttcgagg aagcggccgt  21480
ggagcaggac ccgggctttg tctcggcaga ggaggatttg caagaggagg aggataagga  21540
ggagaagccc tcagtgccaa aagatcataa agagcaagac gagcacgacg cagacgcaca  21600
ccagggtgaa gtcgggcggg gggacggagg gcatggcggc gccgactacc tagacgaagg  21660
aaacgacgtg ctcttgaagc acctgcatcg tcagtgcgcc attgtctgcg acgctctgca  21720
ggagcgcagc gaggtgcccc tcagcgtggc ggaggtcagc cgcgcctacg agctcagcct  21780
cttttccccc cgggtgcccc cccgccgccg cgaaaacggc acatgcgagc ccaacccgcg  21840
cctcaacttc taccccgcct ttgtggtgcc cgaggtcctg gccacctatc acatcttctt  21900
tcaaaattgc aagatcccca tctcgtgccg cgccaaccgt agccgcgccg ataagatgct  21960
ggccctgcgc cagggcgacc acatacctga tatcgccgct ttggaagatg tgccaaagat  22020
cttcgagggt ctgggtcgca acgagaagcg ggcagcaaac tctctgcaac aggaaaacag  22080
cgaaaatgag agtcacactg gagcgctggt ggagctggag ggcgacaacg cccgcctggc  22140
ggtgctcaag cgcagcatcg aggtcaccca ctttgcctac cccgcgctca acctgccccc  22200
caaagtcatg aacgcggtca tggacgggct aatcatgcgc cgcggccggc cccttgctcc  22260
agatgcaaac ttgcatgagg agaccgagga cggtcagccc gtggtcagcg acgagcagct  22320
gacgcgctgg ctggaaaccg cggaccccgc cgaactggag gagcggcgca agatgatgat  22380
ggccgcggtg ctggtcaccg tagagctgga gtgtctgcag cgcttcttcg gcgaccccga  22440
gatgcagaga aaggtcgagg agaccctaca ctacaccttc cgccagggct acgtgcgcca  22500
ggcttgcaag atctccaacg tggagctcag caacctggtg tcctacctgg gcatcttgca  22560
tgaaaaccgc cttgggcaga gcgtgctaca ctccaccctg cgcggggagg cgcgccgcga  22620
ctacgtgcgc gactgcgttt acctcttcct ctgctacacc tggcagacgg ccatgggggt  22680
ctggcagcag tgcctggagg agcgcaacct caaggagctg gagaagctcc tgcagcgcgc  22740
gctcaaagac ctctggacgg gctacaacga gcgctcggtg gccgccgcgc tggccgacct  22800
catcttcccc gagcgcctgc tcaaaactct ccagcagggg ctgcccgact tcaccagcca  22860
aagcatgttg caaaatttta ggaactttat cctggagcgt tctggcatcc tacccgccac  22920
ctgctgcgcc ctgcccagcg actttgtccc cctcgtgtac cgcgagtgcc ccccgccgct  22980
gtggggccac tgctacctgt tccaactggc caactacctg tcctaccacg cggacctcat  23040
ggaagactcc agcggcgagg ggctcatgga gtgccactgc cgctgcaacc tctgcacgcc  23100
ccaccgctcc ctggtctgca acacccaact gctcagcgag agtcagatta tcggtacctt  23160
cgagctacag ggtccgtcct cctcagacga gaagtccgcg gctccggggc taaaactcac  23220
tccggggctg tggacttccg cctacctgcg caaatttgta cctgaagact accacgccca  23280
cgagatcagg ttttacgagg accaatcccg cccgcccaag gcggagctga ccgcctgcgt  23340
catcacccag ggcgagatcc taggccaatt gcaagccatc caaaaagccc gccaagagtt  23400
tttgctgaga aagggtcggg gggtgtatct ggacccccag tcgggtgagg agctcaaccc  23460
ggttcccccg ctgccgccgc cgcgggacct tgcttcccag gataagcatc gccatggctc  23520
ccagaaagaa gcagcagcgg ccgccactgc cgccacccca cacgctggag gaagaggagg  23580
```

-continued

```
aatactggga cagtcaggca gaggaggttt cggacgagga ggagccggag acggagatgg  23640
aagagtggga ggaggacagc ttagacgagg aggcttccga agccgaagag gcaggcgcaa  23700
caccgtcacc ctcggccgca gccccctcgc aggcgccccc gaagtccgct cccagcatca  23760
gcagcaacag cagcgctata acctccgctc ctccaccgcc gcgacccacg gccgaccgca  23820
gacccaaccg tagatgggac accaccggaa ccggggccgg taagtcctcc gggaaaggca  23880
agcaagcgca gcgccaaggc taccgctcgt ggcgcgctca caagaacgcc atagtcgctt  23940
gcttgcaaga ctgcgggggg aacatctcct tcgcccgccg cttcctgctc ttccaccacg  24000
gtgtggcctt cccccgtaac gtcctgcatt actaccgtca tctctacagc ccctactgcg  24060
gcggcagtga gccagaggcg gccggcggca gcggcgcccg tttcggtgcc taggaagacc  24120
cagggcaaga cttcagccaa gaaactcgcg gcggccgcgg cgaacgcggt cgcgggggcc  24180
ctgcgcctga cggtgaacga acccctgtcg acccgcgaac tgaggaaccg aatcttcccc  24240
actctctatg ccatcttcca gcagagcaga gggcaggatc aggaactgaa agtaaaaaac  24300
aggtctctgc gctccctcac ccgcagctgt ctgtatcaca agagcgaaga ccagcttcgg  24360
cgcacgctgg aggacgctga ggcactcttc agcaaatact gcgcgctcac tcttaaggac  24420
tagctccgcg cccttctcga atttaggcgg gaacgcctac gtcatcgcag cgccgccgtc  24480
atgagcaagg acattcccac gccatacatg tggagctatc agccgcagat gggactcgcg  24540
gcgggcgcct cccaggatta ctccacccgc atgaactggc tcagtgccgg cccacacatg  24600
atctcacagg ttaatgacat ccgcacccat cgaaaccaaa tattggtgga gcaggcggca  24660
attaccacca cgccccgcaa taatcccaac cccagggagt ggcccgcgtc cctggtgtat  24720
caggaaattc ccggccccac caccgtacta cttccgcgtg attcccaggc cgaagtccaa  24780
atgactaact caggggcaca gctcgcgggc ggctgtcgtc acagggtgcg gcctcctcgc  24840
cagggtataa ctcacctgaa gatccgaggc agaggtattc agctcaacga cgagtcggtg  24900
agctcctcgc tcggtctcag acctgacggg accttccaga tagccggagc cggccgatct  24960
tccttcacgc cccgccaggc gtacctgact ctgcagagct cgtcctcggc gccgcgctcg  25020
ggcggcatcg ggactctcca gttcgtgcag gagtttgtgc cctcggtcta cttcaacccc  25080
ttctcgggct ctcccggtcg ctacccggac cagttcatcc cgaactttga cgccgcgagg  25140
gactcggtgg acggctacga ctgaatgtcg ggtggacccg gtgcagagca acttcgcctg  25200
aagcaccttg accactgccg ccgccctcag tgctttgccc gctgtcagac cggtgagttc  25260
cagtactttt ccctgcccga ctcgcacccg gacggcccgg cgcacggggt gcgcttttc  25320
atcccgagtc aggtccgctc taccctaatc agggagttca ccgcccgtcc cctactggcg  25380
gagttggaaa aggggccttc tatcctaacc attgcctgca tctgctctaa ccctggatta  25440
caccaagatc tttgctgtca tttgtgtgct gagtataata aaggctgaga tcagaatcta  25500
ctcgggctcc tgtcgccatc ctgtcaacgc caccgtccaa gcccggcccg atcagcccga  25560
ggtgaacctc acctgcggtc tgcaccggcg cctgaggaaa tacctagctt ggtactacaa  25620
cagcactccc tttgtggttt acaacagctt tgaccaggac ggggtctcac tgagggataa  25680
cctctcgaac ctgagctact ccatcaggaa gaacaacacc ctcgagctac ttcctcctta  25740
cctgcccggg acttaccagt gtgtcaccgg tccctgcacc cacacccacc tgttgatcgt  25800
aaacgactct cttccgagaa cagacctcaa taactcctct ccgcagttcc ccagaacagg  25860
aggtgagctc aggaaacccc gggtaaagaa gggtggacaa gagttaacac ttgtggggtt  25920
tctggtgtat gtgacgctgg tggtggctct tttgattaag gcttttcctt ccatgtctga  25980
```

-continued

```
actatccctc ttcttttatg aacaactcga ctagtgctaa cgggacccta cccaacgaat  26040
cgggattgaa tatcggtaac caggttgcag tttcactttt gattaccttc atagtcctct  26100
tcctgctagt gctgtcgctt ctgtgcctgc ggatcggggg ctgctgcatc cacgtttata  26160
tctggtgctg gctgtttaga aggttcggag accaccgcag gtagaataaa caaacctaga  26220
cctagaaatg gacggtctct gcagcgagca acgcatacta gagaggcgcc ggcaaaaagc  26280
agagctcgag cgtcttaaac aagagctcca agacgccgtg gccatacacc agtgcaaaaa  26340
agggctcttc tgtctggtaa aacaggccac gctcacctat gaaaaaacag gtgacaccca  26400
ccgcctagga tacaagctgc ccacacagcg ccaaaagttt gcccttatga taggtgaaca  26460
acccatcacc gtgacccagc actccgtgga gacagaaggc tgcattcatg ctccctgcag  26520
gggcgctgac tgcctctaca ccttgatcaa aaccctttgc ggtctcagag accttatccc  26580
tttcaattga tcataactgt aatcaataaa aatcactta cttgaaatct gatagcaagc  26640
ctctgtccaa tttttcagc aacacttcct tcccctcttc ccaactctgg tactctaggc  26700
gcctcctagc tgcaaacttc ctccacagtc tgaagggaat gtcagattcc tcctcctcct  26760
gtccctccgc acccacgatc ttcatgttgt tgcagatgaa gcgcaccaaa acgtctgacg  26820
agagcttcaa ccccgtgtac ccctatgaca cggaaaacgg tcctccctcc gtccctttcc  26880
tcacccctcc cttcgtgtct cccgatggat tccaagagag cccccccggg gtcctgtctc  26940
tgaacctggc cgagcccctg gtcacttccc acggcatgct cgccctgaaa atgggaagtg  27000
gcctctccct ggacgacgcc ggcaacctca cctctcaaga tgtcaccacc actacccctc  27060
ccctgaaaaa aaccaagacc aacctcagcc tagaaacctc agcccccctg actgtgagca  27120
cctcaggcgc cctcacccta gcagccgccg ttcccctggc ggtggccggc acctccctca  27180
ccatgcaatc agaggccccc ctgacagtcc aagatgcaaa actcaccctg gccaccaagg  27240
gcccccctgac cgtgtctgaa ggcaaactgg ccttgcagac ctcggccccg ctgacggccg  27300
ctgacagcag cgccctcacc gttagcgcca caccacccat cagtgtaagc agtggaagtt  27360
tgggcttaga catggaagac cccatgtata ctcatgatgg aaaactggga ataagaattg  27420
gaggcccact gagagtagta gacagcctgc acacactgac tgtagttacc ggaaatggaa  27480
tagctgtaga taacaatgcc ctccaaacta gagttacggg cgccctgggt tatgacacat  27540
caggaaacct acaactgaga gccgcggggg gtatgcgaat tgatgcaaat ggccaactta  27600
tccttgatgt ggcataccca tttgatgctc aaaacaatct cagccttaga cttggtcagg  27660
gacccctgta tgtaaacaca gaccacaacc tagatttgaa ttgcaacaga ggtctgacca  27720
caactaccac caacaacaca aaaaaacttg aaactaaaat tggctcaggc ttagactatg  27780
ataccaatgg tgctgtcatt attaaacttg gtactggtgt aagctttgac agcacaggcg  27840
ccctaactgt gggaaacact ggcgatgata aactgactct gtggacaacc ccagacccat  27900
ctccaaattg cagaattcac gcagacaaag actgcaagtt tactctagtc ctaactaagt  27960
gtggaagtca aatcctggct tctgtcgccg ccctagcggt gtcaggaaat ctggcttcaa  28020
taacaggcac cgttgccagc gttaccatct ttctcagatt tgatcagaat ggagtgctta  28080
tggaaaactc ctccctagac aagcagtact ggaacttcag aaatggtaac tcaaccaatg  28140
ccacccccta caccaatgca gttgggttca tgccaaacct cgcagcatac cccaagacac  28200
agagccagac tgctaaaaac aacattgtaa gtcaggttta cttgaatggg gacaaatcca  28260
aacccatgac ccttaccatt accctcaatg gaactaatga atccagtgaa actagccagg  28320
```

-continued tgagtcacta ctccatgtca tttacatggg cttgggagag tgggcaatat gccaccgaaa 28380
cctttgccac caattccttt accttctctt acattgctga acaataaaga aagcacagag 28440
atgcttgttt ttgatttcaa aattgtgtgc ttttatttat tttcaagctt acagtatttc 28500
cagtagtcat tcgaatagag cttaatgaaa ctgcatgaga acccttccac atagcttaaa 28560
ttatcaccag tgcaaatgga gaaaaatcaa catacctttt tatccagata tcacagaacc 28620
ctagtattca acctgccacc tccctcccaa cacacagagt acacagtcct ttctccccgg 28680
ctggccttaa aaagcatcat atcatgggta acagacatat tcttaggtgt tatattccac 28740
acggtttcct gtcgagccaa acgctcatca gtgatattaa taaactcccc gggcagctca 28800
cttaagttca tgtcgctgtc cagctgctga gccacaggct gctgtccaac ttgcggttgc 28860
ttaacgggcg gcgaaggaga agtccacgcc tacatggggg tagagtcata atcgtgcatc 28920
aggatagggc ggtggtgctg cagcagcgcg cgaataaact gctgccgccg ccgctccgtc 28980
ctgcaggaat acaacatggc agtggtctcc tcagcgatga ttcgcaccgc ccgcagcata 29040
aggcgccttg tcctccgggc acagcagcgc accctgatct cacttaaatc agcacagtaa 29100
ctgcagcaca gcaccacaat attgttcaaa atcccacagt gcaaggcgct gtatccaaag 29160
ctcatggcgg ggaccacaga acccacgtgg ccatcatacc acaagcgcag gtagattaag 29220
tggcgacccc tcataaacac gctggacata aacattacct cttttggcat gttgtaattc 29280
accacctccc ggtaccatat aaacctctga ttaaacatgg cgccatccac caccatccta 29340
aaccagctgg ccaaaacctg cccgccggct atacactgca gggaaccggg actggaacaa 29400
tgacagtgga gagcccagga ctcgtaacca tggatcatca tgctcgtcat gatatcaatg 29460
ttggcacaac acaggcacac gtgcatacac ttcctcagga ttacaagctc ctcccgcgtt 29520
agaaccatat cccagggaac aacccattcc tgaatcagcg taaatcccac actgcaggga 29580
agacctcgca cgtaactcac gttgtgcatt gtcaaagtgt tacattcggg cagcagcgga 29640
tgatcctcca gtatggtagc gcgggtttct gtctcaaaag gaggtagacg atccctactg 29700
tacggagtgc gccgagacaa ccgagatcgt gttggtcgta gtgtcatgcc aaatggaacg 29760
ccggacgtag tcatatttcc tccagcagaa ccaagtgcgc gcgtggcagc tatccttgcg 29820
tcttctgtct cgccgcctgc cccgctcggt gtagtagttg taatacagcc actccctcag 29880
accgtcaagg cgctccctgg cgtccggatc tataacaaca ccatcctgca gcgccgccct 29940
gatgacatcc accaccgtag agtatgccaa gcccagccag gaaatgcact cactttgaca 30000
gcgagagata ggaggagcgg gaagagatgg aagaaccatg atagtaaaag aacttttatt 30060
ccaatcgatc ctctacaatg tcaaagtgta gatctatcag atggcactgg tctcctccgc 30120
tgagtcgatc aaaaataaca gctaaaccac aaacaacacg attggtcaaa tgctgcacaa 30180
gggcttgcag cataaaatcg cctcgaaagt ccaccgcaag cataacatca aagccaccgc 30240
ccctatcatg atctatgata aaaaccccac agctatccac cagacccata tagttttcat 30300
ctctccatcg tgaaaaaata tttacaagct cctcctttaa atcacctcca accaattcaa 30360
aaagttgagc cagaccgccc tccaccttca ttttcagcat gcgcatcatg attgcaaaaa 30420
ttcaggctcc tcagacacct gtataagatt gagaagcgga acattaacat caatgtttcg 30480
ctcgcgaaga tcgcgcctca gtgcaagcat gatataatcc cacaggtcgg agcggatcag 30540
cgaggacatc tccccgccag gaaccaactc aacggagcct atgctgatta taatacgcat 30600
attcggggct atgctaacca gcacggcccc caaataggcg tactgcatag gcggcgacaa 30660
aaagtgaaca gtttgggtta aaaaatcagg caaacactcg cgcaaaaaag caagaacatc 30720

```
ataaccatgc tcatgcaaat agatgcaagt aagctcagga acgaccacag aaaaatgcac  30780
aatttttctc tcaaacatga ctgcgagccc tgcaaaaaat aaaaaagaaa cattacacaa  30840
gagtagcctg tcttacaatg ggatagacta ctctaaccaa cataagacgg gccacgacat  30900
cgcccgcgtg gccataaaaa aaattatccg tgtgattaaa aagaagcaca gatagctggc  30960
cagtcatatc cggagtcatc acgtgcgaac ccgtgtagac ccccgggttg gacacatcgg  31020
ccaaagaaag aaagcggcca atgtatcccg gaggaatgat aacactaaga cgaagataca  31080
acagaataac cccatggggg ggaataacaa agttagtagg tgaataaaaa cgataaacac  31140
ccgaaactcc ctcctgcgta ggcaaaatag cgccctcccc ttccaaaaca acatacagcg  31200
cttccacagc agccatgaca aaagactcaa aacactcaaa agactcagtc ttaccaggaa  31260
aataaaagca ctctcacagc accagcacta atcagagtgt gaagagggcc aagtgccgaa  31320
cgagtatata taggaattaa aaatgacgta aatgtgtaaa ggtcaaaaaa cgcccagaaa  31380
aatacacaga ccaacgcccg aaacgaaaac ccgcgaaaaa atacccagaa gttcctcaac  31440
aaccgccact tccgctttcc cacgatacgt cacttcctcg aaaatagcaa actacatttc  31500
ccacatgtac aaaaccgaaa ccactcccct tgtcaccgcc cacaacttac atcttaatta  31560
acaaacgtca aagcctacgt cagccgcccc gcctcgcccc gcccacctca ttatcatatt  31620
ggccacaatc caaaataagg tatattattg atgatgattt aaatattatg cggtgtgaaa  31680
taccgcacag atgcgtaagg agaaaatacc gcatcaggcg ctcttccgct tcctcgctca  31740
ctgactcgct gcgctcggtc gttcggctgc ggcgagcggt atcagctcac tcaaaggcgg  31800
taatacggtt atccacagaa tcaggggata acgcaggaaa gaacatgtga gcaaaaggcc  31860
agcaaaaggc caggaaccgt aaaaaggccg cgttgctggc gtttttccat aggctccgcc  31920
cccctgacga gcatcacaaa aatcgacgct caagtcagag gtggcgaaac ccgacaggac  31980
tataaagata ccaggcgttt ccccctggaa gctccctcgt gcgctctcct gttccgaccc  32040
tgccgcttac cggatacctg tccgcctttc tcccttcggg aagcgtggcg ctttctcata  32100
gctcacgctg taggtatctc agttcggtgt aggtcgttcg ctccaagctg ggctgtgtgc  32160
acgaaccccc cgttcagccc gaccgctgcg ccttatccgg taactatcgt cttgagtcca  32220
acccggtaag acacgactta tcgccactgg cagcagccac tggtaacagg attagcagag  32280
cgaggtatgt aggcggtgct acagagttct tgaagtggtg gcctaactac ggctacacta  32340
gaaggacagt atttggtatc tgcgctctgc tgaagccagt taccttcgga aaaagagttg  32400
gtagctcttg atccggcaaa caaaccaccg ctggtagcgg tggttttttt gtttgcaagc  32460
agcagattac gcgcagaaaa aaaggatctc aagaagatcc tttgatcttt tctacggggt  32520
ctgacgctca gtggaacgaa aactcacgtt aagggatttt ggtcatgaga ttatcaaaaa  32580
ggatcttcac ctagatcctt ttaaattaaa aatgaagttt taaatcaatc taaagtatat  32640
atgagtaaac ttggtctgac agttaccaat gcttaatcag tgaggcacct atctcagcga  32700
tctgtctatt tcgttcatcc atagttgcct gactccccgt cgtgtagata actacgatac  32760
gggagggctt accatctggc cccagtgctg caatgatacc gcgagaccca cgctcaccgg  32820
ctccagattt atcagcaata aaccagccag ccggaagggc cgagcgcaga agtggtcctg  32880
caactttatc cgcctccatc cagtctatta attgttgccg ggaagctaga gtaagtagtt  32940
cgccagttaa tagtttgcgc aacgttgttg ccattgctgc aggcatcgtg gtgtcacgct  33000
cgtcgtttgg tatggcttca ttcagctccg gttcccaacg atcaaggcga gttacatgat  33060
```

cccccatgtt gtgcaaaaaa gcggttagct ccttcggtcc tccgatcgtt gtcagaagta 33120
agttggccgc agtgttatca ctcatggtta tggcagcact gcataattct cttactgtca 33180
tgccatccgt aagatgcttt tctgtgactg gtgagtactc aaccaagtca ttctgagaat 33240
agtgtatgcg gcgaccgagt tgctcttgcc cggcgtcaac acgggataat accgcgccac 33300
atagcagaac tttaaaagtg ctcatcattg gaaaacgttc ttcggggcga aaactctcaa 33360
ggatcttacc gctgttgaga tccagttcga tgtaacccac tcgtgcaccc aactgatctt 33420
cagcatcttt tactttcacc agcgtttctg ggtgagcaaa aacaggaagg caaaatgccg 33480
caaaaaaggg aataagggcg acacggaaat gttgaatact catactcttc ctttttcaat 33540
attattgaag catttatcag ggttattgtc tcatgagcgg atacatattt gaatgtattt 33600
agaaaaataa acaaataggg gttccgcgca catttccccg aaaagtgcca cctgacgtct 33660
aagaaaccat tattatcatg acattaacct ataaaaatag gcgtatcacg aggccctttc 33720
gtcttcaaga attgatttaa at 33742

<210> SEQ ID NO 11
<211> LENGTH: 31807
<212> TYPE: DNA
<213> ORGANISM: Artificial Sequence
<220> FEATURE:
<223> OTHER INFORMATION: BZ1/BZ28 Ad vector

<400> SEQUENCE: 11
catcatcaat aatatacctt attttggatt gtggccaata tgataatgag gtgggcgggg 60
cgaggcgggg cgggtgacgt aggacgtgcg agtagggttg ggaggtgtgg cggaagtgtg 120
gcatttgtaa gtgggaggag cttacatgca agcttccgtc gcggaaaatg tgacgttttt 180
tatgagcgcc gcctacctcc ggaagtgcca attttcgcgc gctttttacc ggatatcgta 240
gtaattttgg gcgggaccat gtaagatttg gccattttcg cgcgaaaagt gaaacgggga 300
agtgaaaact gaataatagg gcgttagtca tagcgcgtaa tatttaccga gggccgaggg 360
actttgaccg attacgtgga ggactcgccc aggtgttttt tacgtgaatt tccgcgttcc 420
gggtcaaagt ctccgttttt attgtcaccg tcatttgacg cggagggtat ttaaacccgc 480
tgcgctccta gcgatcgctg atgagaccag gaccaggtgc cgaccctgcg agtgcggcgg 540
caagcacatg agaaatcagc ctgtgatgtt ggatgtgacc gaggagctta ggcctgacca 600
tctggtgctg gcctgcacca gggccgagtt tgggtctagc gatgaggata ccgattgagg 660
tgggtaaggt gggcgtggct agcagggtgg gcgtgtataa attgggggtc taaggggtct 720
ctctgtttgt cttgcaacag ccgccgccat gagcgacacc ggcaacagct ttgatggaag 780
catctttagc cctatctga cagtgcgcat gcctcactgg gccggagtgc gtcagaatgt 840
gatgggttcc aacgtggatg gacgtcccgt tctgccttca aattcgtcta cgatggccta 900
cgcgaccgtg ggaggaactc cgctggacgc cgcgacctcc gccgccgcct ccgccgccgc 960
cgcgaccgcg cgcagcatgg ctacggacct ttacagctct ttggtggcga gcagcgcggc 1020
ctctcgcgcg tctgctcggg atgaaaaact gactgctctg ctgcttaaac tggaagactt 1080
gacccgggag ctgggtcaac tgacccagca ggtctccagc ttgcgtgaga gcagccttgc 1140
ctccccctaa tggcccataa tataaataaa agccagtctg tttggattaa gcaagtgtat 1200
gttctttatt taactctccg cgcgcggtaa gcccgggacc agcggtctcg gtcgtttagg 1260
gtgcggtgga ttctttccaa cacgtggtac aggtggctct ggatgtttag atacatgggc 1320
atgagtccat ccctggggtg gaggtagcac cactgcagag cttcgtgctc gggggtggtg 1380

-continued

```
ttgtatatga tccagtcgta gcaggagcgc tgggcgtggt gctgaaaaat gtccttaagc   1440
aagaggctta tagctagggg gaggcccttg gtgtaagtgt ttacaaatct gcttagctgg   1500
gaggggtgca tccgggggga tatgatgtgc atcttggact ggatttttag gttggctatg   1560
ttcccaccca gatcccttct gggattcatg ttgtgcagga ccaccagcac ggtatatcca   1620
gtgcacttgg gaaatttatc gtggagctta gacgggaatg catggaagaa cttggagacg   1680
cccttgtggc ctcccagatt ttccatacat tcgtccatga tgatggcaat gggcccgtgg   1740
gaagctgcct gagcaaaaac gtttctggca tcgctcacat cgtagttatg ttccagggtg   1800
aggtcatcat aggacatctt tacaaatcgg gggcggaggg tcccggactg ggggatgatg   1860
gtaccctcgg gccccggggc gtagttcccc tcacagatct gcatctccca ggctttcatt   1920
tcagagggag ggatcatatc cacctgcggg gcgatgaaaa agacagtttc tggcgcaggg   1980
gagattaact gggatgagag caggtttctg agcagctgtg actttccaca gccggtgggc   2040
ccatatatca cgcctatcac cggctgcagc tggtagttaa gagagctgca gctgccgtcc   2100
tcccggagca ggggggccac ctcgttgagc atatccctga cgtggatgtt ctccctgacc   2160
agttccgcca gaaggcgctc gccgcccagc gaaagcagct cttgcaagga agcaaaattt   2220
ttcagcggtt tcaggccatc ggccgtgggc atgtttttca gcgtctgggt cagcagctcc   2280
agcctgtccc agagctcggt gatgtgctct acggcatctc gatccagcag atctcctcgt   2340
ttcgcgggtt ggggcggctt tcgctgtagg gcaccagccg atgggcgtcc agcggggcca   2400
gagtcatgtc cttccatggg cgcagagtcc tcgtcagggt ggtctgggtc acggtgaagg   2460
ggtgcgctcc gggttgggca ctggccaggg tgcgcttgag gctggttctg ctggtgctga   2520
atcgctgccg ctcttcgccc tgcgcgtcgg ccaggtagca tttgaccatg gtctcgtagt   2580
cgagaccctc ggcggcgtgc cccttggcgc ggagctttcc cttggaggtg gcgccgcacg   2640
aggggcactg caggctcttc agggcgtaga gcttgggagc gagaaacacg gactctgggg   2700
agtaggcgtc cgcgccgcag gccgcgcaga ccgtctcgca ttccaccagc caagtgagtt   2760
ccgggcggtc agggtcaaaa accaggttgc cccatgcttt tttgatgcgt ttcttacctc   2820
ggctctccat gaggcggtgt cccttctcgg tgacgaagag gctgtccgtg tccccgtaga   2880
ccgacttcag ggcctgtct  tccagcggag tgcctctgtc ctcctcgtag agaaactctg   2940
accactctga gacgaaggcc cgtgtccagg ccaggacgaa ggaggccacg tgggaggggt   3000
agcggtcgtt gtccactagc gggtccacct tctccagggt gtgcagacac atgtccccct   3060
cctccgcgtc cagaaaagtg attggcttat aggtgtagga cacgtgaccg ggggttcccg   3120
acgggggggt ataaaagggg gtgggcgccc tttcatcttc actctcttcc gcatcgctgt   3180
ctgcgagagc cagctgctgg ggtaagtatt ccctttcaaa ggcgggcatg acctcagcgc   3240
tcaggttgtc agtttctaaa aatgaggagg atttgatgtt cacctgtccg gaagtgatac   3300
ctttgagggt acctgggtcc atctggtcag aaaacactat ttttttgttg tcaagcttgg   3360
tggcgaacga cccgtagagg gcgttggaga gcagcttggc aatggagcgc agggtctggt   3420
ttttgtcgcg gtcggctcgc tccttggccg cgatgttgag ttgcacgtat tcgcgggcca   3480
cgcacttcca ctcggggaag acggtggtgc gctcgtctgg gatcaggcgc accctccagc   3540
cgcggttgtg cagggtgacc atgtcgacgc tggtggcgac ctcaccgcgc agacgctcgt   3600
tggtccagca gaggcggccg cctttgcgcg agcagaaggg gggtaggggg tccagctggt   3660
cctcgtttgg ggggtccgcg tcgatggtaa agaccccggg gagcaggcgc gggtcaaagt   3720
```

-continued

```
agtcgatctt gcaagcttgc atgtccagag cccgctgcca ttcgcgggcg gcgagcgcgc   3780
gctcgtaggg gttgaggggc gggccccagg gcatggggtg ggtgagcgcg gaggcgtaca   3840
tgccgcagat gtcatacacg tacaggggtt ccctgaggat accgaggtag gtggggtagc   3900
agcgcccccc gcggatgctg gcgcgcacgt agtcatagag ctcgtgggag ggggccagca   3960
tgttgagccc aaggttggtg cgctgggggc gctcggcgcg gaagacgatc tgtctgaaga   4020
tggcatggga gttggaggag atggtgggtc gctggaagac gttgaagctt gcttcttgca   4080
agcccacgga gtccctgacg aaggaggcgt aggactcgcg cagcttgtgc accagctcgg   4140
cggtgacctg gacgtcgagc gcgcagtagt cgagggtctc gcggatgatg tcatacttat   4200
cctcccccctt ctttttccac agctcgcggt tgaggacgaa ctcttcgcgg tctttccagt   4260
actcttggag gggaaacccg tccgtgtccg aacggtaaga gcctagcatg tagaactggt   4320
tgacggcctg gtaggggcag cagcccttct ccacgggcag cgcgtaggcc tgcgccgcct   4380
tgcggaggga ggtgtgggta agggcgaaag tgtccctgac catgactttg aggtattgat   4440
gtctgaagtc tgtgtcatcg cagccgccct gttcccacag ggtgtagtcc gtgcgctttt   4500
tggagcgcgg gttgggcagg gagaaggtga ggtcattgaa gaggatcttc cccgctcgag   4560
gcatgaagtt tctggtgatg cgaaagggcc ctgggaccga ggagcggttg ttgatgacct   4620
gggcggccag gacgatctcg tcaaagccgt ttatgttgtg gcccacgatg tagagctcca   4680
ggaagcgggg ctggcccttg atggagggga gctttttaag ttcctcgtag gtaagctcct   4740
cgggcgattc caggccgtgc tcctccaggg cccagtcttg caagtgaggg ttggccgcca   4800
ggaaggatcg ccagaggtcg cgggccatga gggtctgcag gcggtcgcgg aaggttctga   4860
actgccgccc tacggccatc ttttcggggg tgatgcagta gaaggtgagg gggtctttct   4920
cccaggggtc ccatctgagc tcttgggcga ggtcgcgcgc ggcggcgacc agagcctcgt   4980
cgcccccccag tttcatgacc agcatgaagg gcacgagctg cttgccaaag gctcccatcc   5040
aagtgtaggt ctctacatcg taggtgacaa agaggcgctc cgtgcgagga tgagagccga   5100
tcgggaagaa ctggatctcc cgccaccagt tggaggattg gctgttgatg tggtgaaagt   5160
agaagtcccg tctgcgggcc gagcactcgt gctggctttt gtaaaagcga ccgcagtact   5220
ggcagcgctg cacgggttgt atatcttgca cgaggtgaac ctggcgacct ctgacgagga   5280
agcgcagcgg gaatctaagt cccccgcctg ggtcccgtg tggctggtgg tcttctactt   5340
tggttgtctg gccgccagca tctgtctcct ggagggcgat ggtggagcag accaccacgc   5400
cgcgagagcc gcaggtccag atctcggcgc tcggcgggcg gagtttgatg acgacatcgc   5460
gcacattgga gctgtccatg gtctccagct cccgcggcgg caggtcagcc gggagttcct   5520
ggaggttcac ctcgcagaga cggtcaagg cgcggacagt gttgagatgg tatctgattt   5580
caaggggcgt gttggaggcg gagtcgatgg cttgcagaag gccgcagccc cggggggcca   5640
cgatggttcc ccgcggggcg cgaggggagg cggaagctgg gggtgtgttc agaagcggtg   5700
acgcgggcgg gcccccggag gtaggggggg ttccggcccc acaggcatgg gcggcagggg   5760
cacgtcttcg ccgcgcgcgg gcaggggctg gtgctggctc cggagagcgc ttgcgtgcgc   5820
gacgacgcga cggttggtgt cctgtatctg gcgcctctga gtgaagacca cgggtcccgt   5880
gaccttgaac ctgaaagaga gttcgacaga atcaatctcg gcatcgttga cagcggcctg   5940
gcgcaggatc tcctgcacgt cgcccgagtt gtcctggtag gcgatctctg ccatgaactg   6000
ctcgatctct tcctcctgga gatctcctcg tccggcgcgc tccacggtgg ccgccaggtc   6060
gttggagatg cgacccatga gctgcgagaa ggcgttgagg ccgccctcgt tccagacccg   6120
```

-continued gctgtagacc acgcccccct cggcgtcgcg ggcgcgcatg accacctggg ccaggttgag 6180
ctccacgtgt cgcgtgaaga cggcgtagtt gcgcaggcgc tggaaaaggt agttcagggt 6240
ggtggcggtg tgttcggcga cgaagaagta catgacccag cgccgcaacg tggattcatt 6300
gatgtccccc aaggcctcca ggcgctccat ggcctcgtag aagtccacgg cgaagttgaa 6360
aaactgggag ttgcgagcgg acacggtcaa ctcctcctcc agaagacgga tgagctcggc 6420
gacagtgtcg cgcacctcgc gctcgaaggc cacgggggc gcttcttcct cttccacctc 6480
ttcttccatg attgcttctt cttcctcagc cgggacggga gggggcggcg gcgggggagg 6540
ggcgcggcgg cggcggcggc gcaccggcag gcggtcgatg aagcgctcga tcatctcccc 6600
ccgcatgcgg cgcatggtct cggtgacggc gcggccgttc tcccgggggc gcagctcaaa 6660
gacgccgcct ctcatctcgc cgcggggcgg gcggccgtga ggtagcgaga cggcgctgac 6720
tatgcatctt aacaattgct gtgtaggtac gccgccaagg gacctgattg agtccagatc 6780
caccggatcc gaaaaccttt ggaggaaagc gtctatccag tcgcagtcgc aaggtaggct 6840
gagcaccgtg gcgggcgggg gcgggtcggg agagttcctg gcggagatgc tgctgatgat 6900
gtaattaaag taggcggtct tgagaaggcg gatggtggac aggagcacca tgtctttggg 6960
tccggcctgt tggatgcgga ggcggtcggc catgccccag gcctcgttct gacaccggcg 7020
caggtctttg tagtagtctt gcatgagtct ttccaccggc acctcttctc cttcctcttc 7080
tccatctcgc cggtggtttc tcgcgccgcc catgcgcgtg accccaaagc ccctgagcgg 7140
ctgcagcagg gccaggtcgg cgaccacgcg ctcggccaag atggcctgct gtacctgagt 7200
gagggtcctc tcgaagtcat ccatgtccac gaagcggtgg taggcgcccg tgttgatggt 7260
gtaggtgcag ttggccatga cggaccagtt gacggtctgg tgtcccggct gcgagagctc 7320
cgtgtaccgc aggcgcgaga aggcgcggga atcgaacacg tagtcgttgc aagtccgcac 7380
cagatactgg tagcccacca ggaagtgcgg cggaggttgg cgatagaggg gccagcgctg 7440
ggtggcgggg gcgccgggcg ccaggtcttc cagcatgagg cggtggtatc cgtagatgta 7500
cctggacatc caggtgatgc cggcggcggt ggtggtggcg cgcgcgtagt cgcggacccg 7560
gttccagatg tttcgcaggg gcgagaagtg ttccatggtc ggcacgctct ggccggtgag 7620
gcgcgcgcag tcgttgacgc tctatacaca cacaaaaacg aaagcgttta cagggctttc 7680
gttctgtagc ctggaggaaa gtaaatgggt tgggttgcgg tgtgccccgg ttcgagacca 7740
agctgagctc ggccggctga agccgcagct aacgtggtat tggcagtccc gtctcgaccc 7800
aggccctgta tcctccagga tacggtcgag agcccttttg ctttcttggc caagcgcccg 7860
tggcgcgatc tgggatagat ggtcgcgatg agaggacaaa agcggctcgc ttccgtagtc 7920
tggagaaaca atcgccaggg ttgcgttgcg gcgtaccccg gttcgagccc ctatggcggc 7980
ttggatcggc cggaaccgcg gctaacgtgg gctgtggcag ccccgtcctc aggaccccgc 8040
cagccgactt ctccagttac gggagcgagc cccttttgtt ttttattttt tagatgcatc 8100
ccgtgctgcg gcagatgcgc ccctcgcccc ggcccgatca gcagcagcaa cagcaggcat 8160
gcagaccccc ctctcctcta cccgccccgg tcaccacggc cgcggcggcc gtgtccggcg 8220
cggggggcgc gctggagtca gatgagccac cgcggcggcg acctaggcag tatctggact 8280
tggaagaggg cgagggactg gcgcggctgg gggcgagctc tccagagcgc cacccgcggg 8340
tgcagttgaa aagggacgcg cgcgaggcgt acctgccgcg gcagaacctg tttcgcgacc 8400
gcgggggcga ggagcccgag gagatgcgag actgcaggtt ccaagcgggg cgcgagctgc 8460
gccgcgggtt ggacagacag cgcctgctgc gcgaggagga ctttgagccc gacacgcaga 8520
cgggcatcag ccccgcgcgc gcgcacgtgg ccgcggccga cctggtgacc gcctacgagc 8580
agacggtgaa ccaggagcgc aacttccaaa aaagcttcaa caaccacgtg cgcacgctgg 8640
tggcgcgcga ggaggtgacc ctgggtctca tgcatctgtg ggacctggtg gaggcgatcg 8700
tgcagaaccc cagcagcaag cccctgaccg cgcagctgtt cctggtggtg cagcacagca 8760
gggacaacga ggccttcagg gaggcgctgc tgaacatcac cgagccggag gggcgctggc 8820
tcctggacct gataaacatc ctgcagagca tagtggtgca ggagcgcagc ctgagcctgg 8880
ccgagaaggt ggcggccatt aactattcta tgctgagctt gggcaagttc tacgcccgca 8940
agatctacaa gaccccctac gtgcccatag acaaggaggt gaagatagac agcttctaca 9000
tgcgcatggc gctaaaggtg ctgaccctga gcgacgacct gggagtgtac cgcaacgagc 9060
gcatccacaa ggccgtgagc gccagccggc ggcgcgagct gagcgaccgc gagctgatgc 9120
acagtctgca gcgcgcgctc accggcgcgg gcgagggcga cagggaggtc gagtcctact 9180
tcgacatggg ggctgacctg cactggcagc cgagccgccg cgccctggag gcggcggggg 9240
cgtatggcgg cccccctggcg gccgatgacg aggaagagga ggactatgag ctagaggagg 9300
gcgagtacct ggaggactga cctggctggt ggtgttttgg tatagatgca agatccgaac 9360
gtggcggacc cggcggtccg ggcggcgctg cagagccagc cgtccggcat taactcctct 9420
gacgactggg ccgcggccat gggtcgcatc atggccctga ccgcgcgcaa ccccgaggcc 9480
ttcaggcagc agcctcaggc taaccggctg gcggccatct tggaagcggt agtgcccgcg 9540
cgctccaacc ccacccacga gaaggtgctg gccatagtca acgcgctggc ggagagcagg 9600
gccatccggg cggacgaggc cggactggtg tacgatgcgc tgctgcagcg ggtggcgcgg 9660
tacaacagcg gcaacgtgca gaccaacctg gaccgcctgg tgacggacgt gcgcgaggcc 9720
gtggcgcagc gcgagcgctt gcatcaggac ggtaacctgg gctcgctggt ggcgctaaac 9780
gccttcctca gcacccagcc ggccaacgta ccgcgggggc aggaggacta caccaacttc 9840
ttgagcgcgc tgcggctgat ggtgaccgag gtccctcaga gcgaggtgta ccagtcgggg 9900
cccgactact tcttccagac cagcagacag ggcttgcaaa ccgtgaacct gagccaggct 9960
ttcaagaacc tgcgggggct gtggggagtg aaagcgccca ccggcgaccg agctacggtg 10020
tccagcctgc taacccccaa ctcgcgcctg ctgctgctgc tgatcgcgcc cttcacggac 10080
agcgggagcg tctcgcggga gacctatctg ggccacctgc tgacgctgta ccgcgaggcc 10140
atcgggcagg cgcaggtgga cgagcacacc ttccaagaga tcaccagcgt gagccacgcg 10200
ctggggcagg aggacacggg cagcctgcag gcgaccctga actacctgct gaccaacagg 10260
cggcagaaga ttcccacgct gcacagcctg acccaggagg aggagcgcat cttgcgctac 10320
gtgcagcaga gcgtgagcct gaacctgatg cgcgacggcg tgacgcccag cgtggcgctg 10380
gacatgaccg cgcgcaacat ggaaccgggc atgtacgctt cccagcggcc gttcatcaac 10440
cgcctgatgg actacttgca tcgggcggcg gccgtgaacc ccgagtactt caccaatgcc 10500
attctgaatc cccactggat gcccccctccg ggtttctaca acggagactt cgaggtgcct 10560
gaggtcaatg atgggttcct ctgggatgac atggatgaca gtgtgttctc ccccaacccg 10620
ctgcgcgccg cgtctctgcg attgaaggag ggctctgaca gggaaggacc gaggagtctg 10680
gcctcctccc tggctctggg ggcggtgggc gccacgggcg cggcggcgcg gggcagcagc 10740
cccttcccca gcctggcaga ctctctgaat agcgggcggg tgagcaggcc ccgcttgcta 10800
ggcgaggagg agtatctgaa caactccctg ctgcagcccg tgagggacaa aaacgctcag 10860

-continued

```
cgacagcagt ttcccaacaa cgggatagag agcctggtgg acaagatgtc cagatggaag  10920
acatatgcgc aggagtacaa ggagtgggag gaccgccagc cgcggcccct gccgcccccct  10980
agacagcgct ggcagcggcg cgcgtccaac cgccgctgga gacagggacc cgaggacgat  11040
gatgactctg cagatgacag cagcgtgttg gacctgggcg ggagcgggaa cccctttttcg  11100
cacctgcgcc cacgcctggg caagatgttt taaaagagaa aaataaaact caccaaggcc  11160
atggcgacga gcgttggttt tttgttccct tccttagtat gcggcgcgcg gcgatgttcg  11220
aggaggggcc tccccctct tacgagagcg cgatgggaat ttctcctgcg gcgcccctgc  11280
agcctcccta cgtgcctcct cggtacctgc aacctacagg ggggagaaat agcatctgtt  11340
actctgagct gcagcccctg tacgatacca ccagactgta cctggtggac aacaagtccg  11400
cggacgtggc ctccctgaac taccagaacg accacagcga tttttgacc acggtgatcc  11460
aaaacaacga cttcacccca accgaggcca gtacccagac cataaacctg gacaacaggt  11520
cgaactgggg cggcgacctg aagaccatcc tgcacaccaa catgcccaac gtgaacgagt  11580
tcatgtttac caactctttt aaggcgcggg ttatggtggc gcgcgagcag ggggaggcga  11640
agtacgagtg ggtggacttc acgctgcccg agggcaacta ctcagagacc atgactattg  11700
acctgatgaa caatgcgatc gtggaacact acctgaaagt gggcaggcag aacggggtga  11760
aggagagcga tatcggggtc aagtttgaca ccagaaactt tcgtctgggc tgggaccccg  11820
tgaccgggct ggtcatgccg gggtctaca ccaacgaggc ctttcatccc gatatagtgc  11880
tcctgcccgg ctgtggggtg gactttaccc agagccggct gagcaacctg ctgggcgttc  11940
gcaagcggca acctttccag gagggtttca agatcaccta tgaggatctg gagggggca  12000
acattcccgc gctccttgat ctggacgcct acgaggagag cttgaaaccc gaggagagcg  12060
ctggcgacag cggcgagagt ggcgaggagc aagccggcgg cggtggcagc gcgtcggtag  12120
aaaacgaaag tactcccgca gtggcggcag acgctgcgga ggtcgagcca gaggccatgc  12180
agcaggacgc agaggagggc gcacaggagg gcgcgcagga ggacatgaac gatggggaga  12240
tcaggggaga cactttcgcc acccggggcg aagaaaaaga ggcagaggcg gtggcggcga  12300
cggtggaagc cgaaaccgag gcagaggcag agcccaagac cgaagttatg gaagacatga  12360
atgatggaga acgtaggggt gacacgtttg ccacccgggg cgaagagaag gcggcggagg  12420
cagaagccgc ggctgaggag gcggctgcgg ctgcggccga ggctgaggct gcggctgagg  12480
ctaaggtcga agccgatgtt gcggttgagg ctcaggctga ggaggaggag gcggcgactg  12540
aagcagttaa ggaaaaggcc caggcagagc aggaagagaa aaaacctgtc attcaacctc  12600
taaaagaaga tagcaaaaag cgcagttaca acgtcatcga gggcagcacc tttacccagt  12660
accgcagctg gtacctggcg tacaactacg gcgacccggt caagggggtg cgctcgtgga  12720
ccctgctctg cacgccggac gtcacctgcg gctccgagca gatgtattgg tcgctgccaa  12780
acatgatgca agacccggtg accttccgct ccacgcggca ggttagcaac ttcccggtgg  12840
tgggcgccga actgctgccc gtgcactcca agagttttta caacgagcag gccgtctact  12900
cccagctgat ccgccaggcc acctctctga cccacgtgtt caatcgcttt cccgagaacc  12960
agattttggc gcgcccgccg gcccccacca tcaccaccgt cagtgaaaac gttcctgccc  13020
tcacagatca cgggacgcta ccgctgcgca acagcatctc aggagtccag cgagtgacca  13080
ttactgacgc cagacgccgg acctgcccct acgtttacaa ggccttgggc atagtctcgc  13140
cgcgcgtcct ctccagtcgc actttttaaa atacatctac cctcacgctt caaaatcatg  13200
```

-continued tccgtactca tctcacccag caacaacacc ggctgggggc tgcgcgcgcc cagcaagatg 13260
tttggagggg cgaggaaacg ctccgagcag cacccagtgc gcgtgcgcgg ccactaccgc 13320
gcgccctggg gagcgcacaa gcgcgggcgc gcagggcgca ccactgtgga cgacgccatt 13380
gactccgtag tggagcaggc gcgccactac acacccggcg cgccgtccgc ccccgccgtg 13440
tccaccgtgg acgaggcgat cgagagcgtg gtacagggcg cgcggcacta tgccaacctt 13500
aaaaatcgac gccgtcgcgt ggctcgccgc catcgccgga gaccccgggc caccgccgcc 13560
gcgcgccttg ctaaggctct gctcaggcgc gccaggcgaa ctggccgccg ggccgccatg 13620
agggccgcac ggcgggctgc cgccagcgcg gccgccgcgg ccccacgggc acgaaggcgc 13680
gcggccgctg ccgccgccgc cgccatttcc agcttggcct cgacgcggcg cggtaacata 13740
tactgggtgc gcgactcggt aaccggcacg cgggtacccg tgcgctttcg ccccccgcgg 13800
aattagcaca agacaacata cacactgagt ctcctgctgt tgtgtatccc agcggcgacc 13860
gtcagcagcg gcgacatgtc caagcgcaaa attaaagaag agatgctcca ggtcatcgcg 13920
ccggagatct atgggccccc gaagaaggag gaggatgatt acaagccccg caagctaaag 13980
cgggtcaaaa agaaaaagaa agatgatgac gttgacgagg cggtggagtt tgtccgccgc 14040
atggcgccca ggcgccccgt gcagtggaag ggtcggcgcg tgcagcgagt cctgcgcccc 14100
ggcaccgcgg tggtctttac gcccggcgag cgttccacgc gcactttcaa gcgggtgtac 14160
gatgaggtgt acggcgacga ggatctgttg gagcaggcca accatcgctt tggggagttt 14220
gcatatggga aacggccccg cgagagccta aaagaggacc tgctggcgct accgctggac 14280
gagggcaatc ccaccccgag tctgaagccg gtaaccctgc aacaggtgct gcctttgagc 14340
gcgcccagcg agcagaagcg agggttgaag cgcgagggcg gggacctggc acccaccgtg 14400
cagttgatgg tgcccaagcg gcagaagctg gaggacgtgc tggagaaaat gaaagtagag 14460
cccgggatcc agcccgaaat caaggtccgc cccatcaagc aggtggcgcc cggcgtggga 14520
gtccagaccg tggacgttag gattcccacg gaggagatgg aaacccaaac cgccactccc 14580
tcttcggcgg ctagcgccac caccggctcc gcttcggtag aggtgcagac ggacccctgg 14640
ctagccgccg ccgccccggc cgcccccgt tcgcgcgggc gcaagagaaa ttatccagcg 14700
gccagcgcgc tcatgcccca gtacgcactg catccatcca tcgcgcccac ccccggctac 14760
cgcgggtact cgtaccgccc gcgcagatca gccggcaccc gcggccgccg ccgccgtgcg 14820
accacaacca gccgccgccg tcgccgccgc cgccagccag tgctgacccc cgtgtctgta 14880
aggaaggtgg ctcgctcggg gagcacgctg gtggtgccca gagcgcgcta ccaccccagc 14940
attgtttaaa gccggtctct gtatggttct tgcagatatg gccctcactt gtcgcctccg 15000
cttcccggtg ccgggatacc gaggaagaac tcaccgccgc agaggcatgg cgggcagtgg 15060
tctccgcggc ggccgtcgcc atcgccggcg cgcaaagagc aggcgcatgc gcggcggtgt 15120
gctgcccttc ctaatcccgc taatcgccgc ggcgatcggt gccgtgcccg ggatcgcctc 15180
cgtggccctg caggcgtccc agaaacattg actcttgcaa ccttgcaagc ttgcattttt 15240
tggaggaaaa aataaaaagt ctagactctc acgctcgctt ggtcctgtga ctattttgta 15300
gaaaaaagat ggaagacatc aactttgcgt cgctggcccc gcgtcacggc tcgcgcccgt 15360
tcatgggaga ctggacagat atcggcacca gcaatatgag cggtggcgcc ttcagctggg 15420
gcagtctgtg gagtggcctt aaaaattttg gttccaccat taagaactat ggcaacaaag 15480
cgtggaacag cagcacgggt cagatgctga gagacaagtt gaaagagcag aacttccagg 15540
agaaggtggc acagggcctg gcctctggca tcagcggggt ggtggacata gctaaccagg 15600

-continued

```
ccgtgcagaa aaagataaac agtcatctgg acccccgccc tcaggtggag gaaacgcctc  15660
cagccatgga gacggtgtct cccgagggca aaggcgaaaa gcgcccgcgg cccgacaggg  15720
aagagaccct ggtgtcacac accgaggagc cgccctctta cgaggaggca gtcaaggccg  15780
gcctgcccac cactcgcccc atagctccca tggccaccgg tgtggtgggt cacaggcaac  15840
acacccccgc gacactagat ctgcccccgc cgtccgagcc gactcgccag ccaaaggcgg  15900
tgacggtgcc cgctccctcc acttccgccg ccaacagagt gcctctgcgc cgcgctgcga  15960
gcggcccccg ggcctcgcga gtcagcggca actggcagag cacactgaac agcatcgtgg  16020
gcctgggagt gaggagtgtg aagcgccgcc gttgctactg aatgagcaag ctagctaacg  16080
tgttgtatgt gtgtatgcgt cctatgtcgc cgccagagga gctgttgagc cgccggcgcc  16140
gtctgcactc cagcgaattt caagatggcg accccatcga tgatgcctca gtggtcgtac  16200
atgcacatct cgggccagga cgcttcggag tacctgagcc ccgggctggt gcagttcgcc  16260
cgcgccacag acacctactt caacatgagt aacaagttca ggaaccccac tgtggcgccc  16320
acccacgatg tgaccacgga ccggtcgcag cgcctgacgc tgcggttcat ccccgtggat  16380
cgggaggaca ccgcttactc ttacaaggcg cggttcacgc tggccgtggg cgacaaccgc  16440
gtgctggaca tggcctccac ttactttgac atccgggggg tgctggacag ggcccccact  16500
ttcaagccct actcgggcac tgcctacaac tccctggccc ccaagggcgc tcccaattct  16560
tgcgagtggg aggaggaaac acaaaatgag gtacaagcca atgaagaaca actagcagaa  16620
gaagaggatg aagaaatggc tcaagaggat cagcagccta ctaaaaaaac ccatgtatat  16680
gctcaggcac ctctttctgg cgaacagatt accaaagatg gcttgcaaat aggagctgaa  16740
gttacaggag aaacatcaaa gcccattttt gcagacaaga cattccaacc agaacctcag  16800
ataggagagt ctcaatggaa tgaggccgat gctacagtag caggaggtag ggttttgaaa  16860
aagactaccc ctatgaaacc ttgctatgga tcctatgcca gacctaccaa tgccaatgga  16920
gggcagggga tacttgaggc aaatgctaaa ggggaactcg aatctaaagt tgagatgcag  16980
tttttctcta acaccacaac tcttaatgta agagacggtg aaaatggcct taaaccaaaa  17040
gtagtgctgt atagcgaaga tgtcaacctg gaatcccctg acactcatct gtcttacaag  17100
cccaaaaaag atgatgttaa tgccaaaatc atgttgggtc agcaagccat gcccaacaga  17160
cccaacctca ttggatttag agataatttc attgggctca tgtattacaa cagcactgga  17220
aacatgggag tgctggcggg tcaggcctct cagttgaatg ctgtggtgga cttgcaggat  17280
agaaacacgg aactgtcata tcagcttatg cttgattcca ttggagatag aaccagatac  17340
ttttccatgt ggaaccaggc agtggatagc tatgacccag atgttagaat cattgaaaac  17400
catggggtgg aggatgagct gcccaactac tgttttccct tgggcggtat aggaattaca  17460
gatacatacc aggccataaa agcagccaat ggtggagatg ctactacgtg gtctgctgat  17520
aacacatttg cagaccgcaa cgaaataggg gtgggaaaca acttcgccat ggagatcaac  17580
atccaggcca acctctggag aaacttcctc tatgcgaacg tgggactcta cctgccagac  17640
aagctcaagt acaaccccac caacgtggac atctctgaca accccaacac ctatgactac  17700
atgaacaagc gggtggtggc ccccggcctg gtggactgct ttgtcaatgt gggagccagg  17760
tggtccctgg actacatgga caacgtcaac cccttcaacc accaccgcaa tgcgggtctg  17820
cgctaccgct ccatgatcct gggcaacggg cgctatgtgc ccttccacat ccaggtaccc  17880
cagaagttct ttgccatcaa gaacctcctg ctcctgcccg gctcctacac ctacgagtgg  17940
```

-continued

```
aacttcagga aggatgtaaa catggtccta cagagctctc tgggcaatga ccttagggta  18000
gatggggcca gcatcaagtt tgacagcatc accctctatg ctacattttt ccccatggcc  18060
cacaacaccg cctccacgct tgaggccatg ctgagaaacg acaccaacga ccagtccttc  18120
aatgactacc tctctggggc caacatgctc tacccaatcc cagccaaggc caccaacgtg  18180
cccatctcca tcccctctcg caactgggcc gcctttagag gctgggcctt tacccgcctt  18240
aagaccaagg agacccccctc cctgggctcg ggttttgatc cctactttgt ttactcggga  18300
tccatcccct acctggatgg caccttctac ctcaaccaca ctttcaagaa gatatccatc  18360
atgtatgact cctccgtcag ctggccgggc aacgaccgct tgctcacccc caatgagttc  18420
gaggtcaagc gcgccgtgga cggcgagggc tacaacgtgg cccagtgcaa catgaccaag  18480
gactggttcc tggtgcagat gctggccaac tacaacatag gctaccaggg cttctacatc  18540
ccagagagct acaaggacag gatgtattcc ttcttcagaa atttccaacc catgagccga  18600
caggtggtgg acgagaccaa ttacaaggac tatcaggcca ttggcatcac ccaccagcac  18660
aacaactcgg gtttcgtggg ctacctggcg cccaccatgc gcgagggaca ggcctacccc  18720
gccaacttcc cctacccccct gataggcaag accgcggtcg acagcgtcac ccagaaaaag  18780
ttcctctgcg accgcaccct ctggcgcatc cccttctcta gcaactttat gtccatgggt  18840
gcgctcacgg acctgggcca aaacctgctt tatgccaact ctgcccatgc gctggacatg  18900
acttttgagg tggaccccat ggacgagccc acccttctct atattgtgtt tgaagtgttc  18960
gacgtggtca gagtgcacca gccgcaccgc ggtgtcatcg agaccgtgta cctgcgtacg  19020
cccttctcag ccggcaacgc caccacctaa ggagacagcg ccgccgcctg catgactggt  19080
tccaccgagc aagagctcag ggccatcgcc agagacctgg gatgcggacc ctatttttg  19140
ggcacctatg acaaacgctt cccgggtttt atctcccgag acaagctcgc ctgcgccatc  19200
gtcaacacgg ccgcgcgcga gaccgggggc gtgcactggc tggcctttgg ctgggacccg  19260
cgctctaaaa cttgctacct ctttgacccc tttggcttct ccgatcagcg cctcaggcag  19320
atttatgagt ttgagtacga ggggctgttg cgccgcagcg cgcttgcctc ctcgcccgac  19380
cgctgcatca cccttgagaa gtccaccgag accgtgcagg ggccccactc ggccgcctgc  19440
ggtctcttct gttgcatgtt tttgcacgcc tttgtgcact ggcctcagag tcccatggat  19500
cgcaacccca ccatgaactt gctaaaggga gtgcccaacg ccatgctcca gagcccccag  19560
gtcctgccca ccctgcgccg caaccaggaa cagctctacc gcttcctgga gcgccactcc  19620
ccctacttcc gcagccacag cgcgcgcatc cgggggggcca cctcttttg ccacttgcaa  19680
gaaaacatgc aagacggaaa atgatgtaca gcatgctttt aataaatgta aagactgtgc  19740
actttattta tacacgggct ctttctggtt atttattcaa caccgccgtc gccatctaga  19800
aatcgaaagg gttctgccgc gcgtcgccgt gcgccacggg cagagacacg ttgcgatact  19860
ggaagcggct cgcccacttg aactcgggca ccaccatgcg gggcagtggt tcctcgggga  19920
aattctcgct ccacagggtg cgggtcagct gcagcgcgct caggaggtcg ggagccgaga  19980
tcttgaagtc gcagttgggg ccggaaccct gcgcgcgcga gttgcggtac acggggttgc  20040
agcactggaa caccagcagg gccggattat tcacgctggc cagcaggctc tcgtcgctaa  20100
tcatgtcgct gtccagatcc tccgcgttgc tcagggcgaa tggggtcatc ttgcagacct  20160
gcctgcccag gaaaggcggg agcccaggct tgccgttaca gtcgcagcgc aggggcatta  20220
gcaggtgccc acggcccgac tgcgcctgcg ggtacaacgc gcgcatgaag gcttcgatct  20280
gcctaaaagc cacctgggtc ttggctccct ccgaaaagaa catcccacag gacttgctgg  20340
```

```
agaactggtt cgcgggacag ctggcatcgt gcaggcagca gcgcgcgtca gtgttggcga  20400
tctgcaccac gttgcgaccc caccggtttt tcactatctt ggccttggaa gcctgctcct  20460
ttagcgcgcg ctggccgttc tcgctggtca catccatctc tatcacctgt tccttgttga  20520
tcatgtttgt cccgtgcaga cactttaggt cgccctccgt ctgggtgcag cggtgctccc  20580
acagcgcgca accggtgggc tcccaatttt tgtgggtcac ccccgcgtag gcctgcaggt  20640
aggcctgcag gaagcgcccc atcatggtca taaaggtctt ctggctcgta aaggtcagct  20700
gcaggccgcg atgctcttcg ttcagccagg tcttgcagat ggcggccagc gcctcggtct  20760
gctcgggcag catcttaaaa tttgtcttca ggtcgttatc cacgtggtac ttgtccatca  20820
tggcacgcgc cgcctccatg cccttctccc aggcggacac catgggcagg cttagggggt  20880
ttatcacttc cagcggcgag gacaccgtac tttcgatttc ttcttcctcc ccctcttccc  20940
ggcgcgcgcc cccgctgttg cgcgctctta ccgcctgcac caaggggtcg tcttcaggca  21000
agcgccgcac cgagcgcttg ccgcccttga cctgcttgat cagtaccggc gggttgctga  21060
agcccaccat ggtcagcgcc gcctgctctt cttcgtcttc gctgtctacc actatttctg  21120
gggaggggct tctccgctct gcggcaaagg cggcggatcg cttctttttt ttcttgggag  21180
ccgccgcgat ggagtccgcc acggcgaccg aggtcgaggg cgtggggctg ggggtgcgcg  21240
gcaccagggc ctcgtcgccc tcggactctt cctctgactc caggcggcgg cggagtcgct  21300
tctttggggg cgcgcgcgtt agcggcggcg gagacgggga cggggacggg gacgggacgc  21360
cctccacagg gggcggtctt cgcgcagacc cgcggccgcg ctcgggggtc ttctcgcgct  21420
ggtcttggtc ccgactggcc attgtatcct cctcctccta ggcagagaga cataaggagt  21480
ctatcatgca agtcgagaag gaggagagct taaccacccc ctctgagacc gccgtcgccg  21540
tcgcccccgc taccgccgac gcgcccgcca caccgagcga cacccccgcg gacccccccg  21600
ccgacgcacc cctgttcgag gaagcggccg tggagcagga cccgggcttt gtctcggcag  21660
aggaggattt gcaagaggag gaggataagg aggagaagcc ctcagtgcca aaagatcata  21720
aagagcaaga cgagcacgac gcagacgcac accagggtga agtcgggcgg ggggacggag  21780
ggcatggcgg cgccgactac ctagacgaag gaaacgacgt gctcttgaag cacctgcatc  21840
gtcagtgcgc cattgtctgc gacgctctgc aggagcgcag cgaggtgccc ctcagcgtgg  21900
cggaggtcag ccgcgcctac gagctcagcc tcttttcccc ccgggtgccc ccccgccgcc  21960
gcgaaaacgg cacatgcgag cccaacccgc gcctcaactt ctaccccgcc tttgtggtgc  22020
ccgaggtcct ggccacctat cacatcttct ttcaaaattg caagatcccc atctcgtgcc  22080
gcgccaaccg tagccgcgcc gataagatgc tggccctgcg ccagggcgac cacatacctg  22140
atatcgccgc tttggaagat gtgccaaaga tcttcgaggg tctgggtcgc aacgagaagc  22200
gggcagcaaa ctctctgcaa caggaaaaca gcgaaaatga gagtcacact ggagcgctgg  22260
tggagctgga gggcgacaac gcccgcctgg cggtgctcaa gcgcagcatc gaggtcaccc  22320
actttgccta ccccgcgctc aacctgcccc ccaaagtcat gaacgcggtc atggacgggc  22380
taatcatgcg ccgcggccgg ccccttgctc cagatgcaaa cttgcatgag gagaccgagg  22440
acggtcagcc cgtggtcagc gacgagcagc tgacgcgctg gctggaaacc gcggaccccg  22500
ccgaactgga ggagcggcgc aagatgatga tggccgcggt gctggtcacc gtagagctgg  22560
agtgtctgca gcgcttcttc ggcgaccccg agatgcagag aaaggtcgag gagaccctac  22620
actacacctt ccgccagggc tacgtgcgcc aggcttgcaa gatctccaac gtggagctca  22680
```

-continued gcaacctggt gtcctacctg ggcatcttgc atgaaaaccg ccttgggcag agcgtgctac 22740
actccaccct gcgcggggag gcgcgccgcg actacgtgcg cgactgcgtt tacctcttcc 22800
tctgctacac ctggcagacg gccatggggg tctggcagca gtgcctggag gagcgcaacc 22860
tcaaggagct ggagaagctc ctgcagcgcg cgctcaaaga cctctggacg ggctacaacg 22920
agcgctcggt ggccgccgcg ctggccgacc tcatcttccc cgagcgcctg ctcaaaactc 22980
tccagcaggg gctgcccgac ttcaccagcc aaagcatgtt gcaaaatttt aggaacttta 23040
tcctggagcg ttctggcatc ctacccgcca cctgctgcgc cctgcccagc gactttgtcc 23100
ccctcgtgta ccgcgagtgc cccccgccgc tgtggggcca ctgctacctg ttccaactgg 23160
ccaactacct gtcctaccac gcggacctca tggaagactc cagcggcgag gggctcatgg 23220
agtgccactg ccgctgcaac ctctgcacgc cccaccgctc cctggtctgc aacacccaac 23280
tgctcagcga gagtcagatt atcggtacct tcgagctaca gggtccgtcc tcctcagacg 23340
agaagtccgc ggctccgggg ctaaaactca ctccggggct gtggacttcc gcctacctgc 23400
gcaaatttgt acctgaagac taccacgccc acgagatcag gttttacgag gaccaatccc 23460
gcccgcccaa ggcggagctg accgcctgcg tcatcaccca gggcgagatc ctaggccaat 23520
tgcaagccat ccaaaaagcc cgccaagagt tttgctgag aaagggtcgg ggggtgtatc 23580
tggaccccca gtcgggtgag gagctcaacc cggttccccc gctgccgccg ccgcgggacc 23640
ttgcttccca ggataagcat cgccatggct cccagaaaga agcagcagcg gccgccactg 23700
ccgccacccc acacgctgga ggaagaggag gaatactggg acagtcaggc agaggaggtt 23760
tcggacgagg aggagccgga gacggagatg gaagagtggg aggaggacag cttagacgag 23820
gaggcttccg aagccgaaga ggcaggcgca acaccgtcac cctcggccgc agcccccctcg 23880
caggcgcccc cgaagtccgc tcccagcatc agcagcaaca gcagcgctat aacctccgct 23940
cctccaccgc cgcgacccac ggccgaccgc agacccaacc gtagatggga caccaccgga 24000
accggggccg gtaagtcctc cgggaaaggc aagcaagcgc agcgccaagg ctaccgctcg 24060
tggcgcgctc acaagaacgc catagtcgct tgcttgcaag actgcggggg gaacatctcc 24120
ttcgcccgcc gcttcctgct cttccaccac ggtgtggcct tcccccgtaa cgtcctgcat 24180
tactaccgtc atctctacag cccctactgc ggcggcagtg agccagaggc ggccggcggc 24240
agcggcgccc gtttcggtgc ctaggaagac ccagggcaag acttcagcca agaaactcgc 24300
ggcggccgcg gcgaacgcgg tcgcgggggc cctgcgcctg acggtgaacg aacccctgtc 24360
gacccgcgaa ctgaggaacc gaatcttccc cactctctat gccatcttcc agcagagcag 24420
agggcaggat caggaactga aagtaaaaaa caggtctctg cgctccctca cccgcagctg 24480
tctgtatcac aagagcgaag accagcttcg gcgcacgctg gaggacgctg aggcactctt 24540
cagcaaatac tgcgcgctca ctcttaagga ctagctccgc gcccttctcg aatttaggcg 24600
ggaacgccta cgtcatcgca gcgccgccgt catgagcaag gacattccca cgccatacat 24660
gtggagctat cagccgcaga tgggactcgc ggcgggcgcc tcccaggatt actccacccg 24720
catgaactgg ctcagtgccg gcccacacat gatctcacag gttaatgaca tccgcaccca 24780
tcgaaaccaa atattggtgg agcaggcggc aattaccacc acgccccgca ataatcccaa 24840
ccccagggag tggcccgcgt ccctggtgta tcaggaaatt cccggcccca ccaccgtact 24900
acttccgcgt gattcccagg ccgaagtcca aatgactaac tcaggggcac agctcgcggg 24960
cggctgtcgt cacagggtgc ggcctcctcg ccagggtata actcacctga agatccgagg 25020
cagaggtatt cagctcaacg acgagtcggt gagctcctcg ctcggtctca gacctgacgg 25080

-continued gaccttccag atagccggag ccggccgatc ttccttcacg ccccgccagg cgtacctgac 25140
tctgcagagc tcgtcctcgg cgccgcgctc gggcggcatc gggactctcc agttcgtgca 25200
ggagtttgtg ccctcggtct acttcaaccc cttctcgggc tctcccggtc gctacccgga 25260
ccagttcatc ccgaactttg acgccgcgag ggactcggtg gacggctacg actgaatgtc 25320
gggtggaccc ggtgcagagc aacttcgcct gaagcacctt gaccactgcc gccgccctca 25380
gtgctttgcc cgctgtcaga ccggtgagtt ccagtacttt tccctgcccg actcgcaccc 25440
ggacggcccg gcgcacgggg tgcgcttttt catcccgagt caggtccgct ctaccctaat 25500
cagggagttc accgcccgtc ccctactggc ggagttggaa aaggggcctt ctatcctaac 25560
cattgcctgc atctgctcta accctggatt acaccaagat ctttgctgtc atttgtgtgc 25620
tgagtataat aaaggctgag atcagaatct actcgggctc ctgtcgccat cctgtcaacg 25680
ccaccgtcca agcccggccc gatcagcccg aggtgaacct cacctgcggt ctgcaccggc 25740
gcctgaggaa atacctagct tggtactaca acagcactcc ctttgtggtt tacaacagct 25800
ttgaccagga cggggtctca ctgagggata acctctcgaa cctgagctac tccatcagga 25860
agaacaacac cctcgagcta cttcctcctt acctgcccgg gacttaccag tgtgtcaccg 25920
gtccctgcac ccacacccac ctgttgatcg taaacgactc tcttccgaga acagacctca 25980
ataactcctc tccgcagttc cccagaacag gaggtgagct caggaaaccc cgggtaaaga 26040
agggtggaca agagttaaca cttgtggggt ttctggtgta tgtgacgctg gtggtggctc 26100
ttttgattaa ggcttttcct tccatgtctg aactatccct cttcttttat gaacaactcg 26160
actagtgcta acgggaccct acccaacgaa tcgggattga atatcggtaa ccaggttgca 26220
gtttcacttt tgattacctt catagtcctc ttcctgctag tgctgtcgct tctgtgcctg 26280
cggatcgggg gctgctgcat ccacgtttat atctggtgct ggctgtttag aaggttcgga 26340
gaccaccgca ggtagaataa acaaacctag acctagaaat ggacggtctc tgcagcgagc 26400
aacgcatact agagaggcgc cggcaaaaag cagagctcga gcgtcttaaa caagagctcc 26460
aagacgccgt ggccatacac cagtgcaaaa aagggctctt ctgtctggta aaacaggcca 26520
cgctcaccta tgaaaaaaca ggtgacaccc accgcctagg atacaagctg cccacacagc 26580
gccaaaagtt tgcccttatg ataggtgaac aacccatcac cgtgacccag cactccgtgg 26640
agacagaagg ctgcattcat gctccctgca ggggcgctga ctgcctctac accttgatca 26700
aaaccctttg cggtctcaga gaccttatcc ctttcaattg atcataactg taatcaataa 26760
aaaatcactt acttgaaatc tgatagcaag cctctgtcca attttttcag caacacttcc 26820
ttcccctctt cccaactctg gtactctagg cgcctcctag ctgcaaactt cctccacagt 26880
ctgaagggaa tgtcagattc ctcctcctcc tgtccctccg cacccacgat cttcatgttg 26940
ttgcagatga agcgcaccaa aacgtctgac gagagcttca accccgtgta cccctatgac 27000
acggaaaacg gtcctccctc cgtccctttc ctcacccctc ccttcgtgtc tcccgatgga 27060
ttccaagaga gcccccccgg ggtcctgtct ctgaacctgg ccgagcccct ggtcacttcc 27120
cacggcatgc tcgccctgaa aatgggaagt ggcctctccc tggacgacgc cggcaacctc 27180
acctctcaag atgtcaccac cactacccct cccctgaaaa aaaccaagac caacctcagc 27240
ctagaaacct cagcccccct gactgtgagc acctcaggcg ccctcaccct agcagccgcc 27300
gttcccctgg cggtggccgg cacctccctc accatgcaat cagaggcccc cctgacagtc 27360
caagatgcaa aactcaccct ggccaccaag ggcccccctga ccgtgtctga aggcaaactg 27420
gccttgcaga cctcggcccc gctgacggcc gctgacagca gcgccctcac cgttagcgcc 27480
acaccaccca tcagtgtaag cagtggaagt ttgggcttag acatggaaga ccccatgtat 27540
actcatgatg gaaaactggg aataagaatt ggaggcccac tgagagtagt agacagcctg 27600
cacacactga ctgtagttac cggaaatgga atagctgtag ataacaatgc cctccaaact 27660
agagttacgg gcgccctggg ttatgacaca tcaggaaacc tacaactgag agccgcgggg 27720
ggtatgcgaa ttgatgcaaa tggccaactt atccttgatg tggcataccc atttgatgct 27780
caaaacaatc tcagccttag acttggtcag ggacccctgt atgtaaacac agaccacaac 27840
ctagatttga attgcaacag aggtctgacc acaactacca ccaacaacac aaaaaaactt 27900
gaaactaaaa ttggctcagg cttagactat gataccaatg gtgctgtcat tattaaactt 27960
ggtactggtg taagctttga cagcacaggc gccctaactg tgggaaacac tggcgatgat 28020
aaactgactc tgtggacaac cccagaccca tctccaaatt gcagaattca cgcagacaaa 28080
gactgcaagt ttactctagt cctaactaag tgtggaagtc aaatcctggc ttctgtcgcc 28140
gccctagcgg tgtcaggaaa tctggcttca ataacaggca ccgttgccag cgttaccatc 28200
tttctcagat ttgatcagaa tggagtgctt atggaaaact cctccctaga caagcagtac 28260
tggaacttca gaaatggtaa ctcaaccaat gccacccccct acaccaatgc agttgggttc 28320
atgccaaacc tcgcagcata ccccaagaca cagagccaga ctgctaaaaa caacattgta 28380
agtcaggttt acttgaatgg ggacaaatcc aaacccatga cccttaccat taccctcaat 28440
ggaactaatg aatccagtga aactagccag gtgagtcact actccatgtc atttacatgg 28500
gcttgggaga gtgggcaata tgccaccgaa acctttgcca ccaattcctt taccttctct 28560
tacattgctg aacaataaag aaagcacaga gatgcttgtt tttgatttca aaattgtgtg 28620
cttttattta ttttcaagct tacagtattt ccagtagtca ttcgaataga gcttaatgaa 28680
actgcatgag aacccttcca catagcttaa attatcacca gtgcaaatgg agaaaaatca 28740
acataccttt ttatccagat atcacagaac cctagtattc aacctgccac ctccctccca 28800
acacacagag tacacagtcc tttctccccg gctggcctta aaaagcatca tatcatgggt 28860
aacagacata ttcttaggtg ttatattcca cacggtttcc tgtcgagcca aacgctcatc 28920
agtgatatta ataaactccc cgggcagctc acttaagttc atgtcgctgt ccagctgctg 28980
agccacaggc tgctgtccaa cttgcggttg cttaacgggc ggcgaaggag aagtccacgc 29040
ctacatgggg gtagagtcat aatcgtgcat caggataggg cggtggtgct gcagcagcgc 29100
gcgaataaac tgctgccgcc gccgctccgt cctgcaggaa tacaacatgg cagtggtctc 29160
ctcagcgatg attcgcaccg cccgcagcat aaggcgcctt gtcctccggg cacagcagcg 29220
caccctgatc tcacttaaat cagcacagta actgcagcac agcaccacaa tattgttcaa 29280
aatcccacag tgcaaggcgc tgtatccaaa gctcatggcg gggaccacag aacccacgtg 29340
gccatcatac cacaagcgca ggtagattaa gtggcgaccc ctcataaaca cgctggacat 29400
aaacattacc tcttttggca tgttgtaatt caccacctcc cggtaccata taaacctctg 29460
attaaacatg gcgccatcca ccaccatcct aaaccagctg gccaaaacct gcccgccggc 29520
tatacactgc agggaaccgg gactggaaca atgacagtgg agagcccagg actcgtaacc 29580
atggatcatc atgctcgtca tgatatcaat gttggcacaa cacaggcaca cgtgcataca 29640
cttcctcagg attacaagct cctcccgcgt tagaaccata tcccagggaa caacccattc 29700
ctgaatcagc gtaaatccca cactgcaggg aagacctcgc acgtaactca cgttgtgcat 29760
tgtcaaagtg ttacattcgg gcagcagcgg atgatcctcc agtatggtag cgcgggtttc 29820

```
tgtctcaaaa ggaggtagac gatccctact gtacggagtg cgccgagaca accgagatcg  29880
tgttggtcgt agtgtcatgc caaatggaac gccggacgta gtcatatttc ctccagcaga  29940
accaagtgcg cgcgtggcag ctatccttgc gtcttctgtc tcgccgcctg ccccgctcgg  30000
tgtagtagtt gtaatacagc cactccctca gaccgtcaag gcgctccctg gcgtccggat  30060
ctataacaac accatcctgc agcgccgccc tgatgacatc caccaccgta gagtatgcca  30120
agcccagcca ggaaatgcac tcactttgac agcgagagat aggaggagcg ggaagagatg  30180
gaagaaccat gatagtaaaa gaacttttat tccaatcgat cctctacaat gtcaaagtgt  30240
agatctatca gatggcactg gtctcctccg ctgagtcgat caaaaataac agctaaacca  30300
caaacaacac gattggtcaa atgctgcaca agggcttgca gcataaaatc gcctcgaaag  30360
tccaccgcaa gcataacatc aaagccaccg cccctatcat gatctatgat aaaaacccca  30420
cagctatcca ccagacccat atagttttca tctctccatc gtgaaaaaat atttacaagc  30480
tcctccttta aatcacctcc aaccaattca aaaagttgag ccagaccgcc ctccaccttc  30540
attttcagca tgcgcatcat gattgcaaaa attcaggctc ctcagacacc tgtataagat  30600
tgagaagcgg aacattaaca tcaatgtttc gctcgcgaag atcgcgcctc agtgcaagca  30660
tgatataatc ccacaggtcg gagcggatca gcgaggacat ctccccgcca ggaaccaact  30720
caacggagcc tatgctgatt ataatacgca tattcggggc tatgctaacc agcacggccc  30780
ccaaataggc gtactgcata ggcggcgaca aaaagtgaac agtttgggtt aaaaaatcag  30840
gcaaacactc gcgcaaaaaa gcaagaacat cataaccatg ctcatgcaaa tagatgcaag  30900
taagctcagg aacgaccaca gaaaaatgca caatttttct ctcaaacatg actgcgagcc  30960
ctgcaaaaaa taaaaaagaa acattacaca agagtagcct gtcttacaat gggatagact  31020
actctaacca acataagacg ggccacgaca tcgcccgcgt ggccataaaa aaaattatcc  31080
gtgtgattaa aaagaagcac agatagctgg ccagtcatat ccggagtcat cacgtgcgaa  31140
cccgtgtaga cccccgggtt ggacacatcg gccaaagaaa gaaagcggcc aatgtatccc  31200
ggaggaatga taacactaag acgaagatac aacagaataa ccccatgggg gggaataaca  31260
aagttagtag gtgaataaaa acgataaaca cccgaaactc cctcctgcgt aggcaaaata  31320
gcgccctccc cttccaaaac aacatacagc gcttccacag cagccatgac aaaagactca  31380
aaacactcaa aagactcagt cttaccagga aaataaaagc actctcacag caccagcact  31440
aatcagagtg tgaagagggc caagtgccga acgagtatat ataggaatta aaaatgacgt  31500
aaatgtgtaa aggtcaaaaa acgcccagaa aaatacacag accaacgccc gaaacgaaaa  31560
cccgcgaaaa aatacccaga agttcctcaa caaccgccac ttccgctttc ccacgatacg  31620
tcacttcctc gaaaatagca aactacattt cccacatgta caaaaccgaa accactcccc  31680
ttgtcaccgc ccacaactta catcttaatt aacaaacgtc aaagcctacg tcagccgccc  31740
cgcctcgccc cgcccacctc attatcatat tggccacaat ccaaaataag gtatattatt  31800
gatgatg                                                             31807
```

<210> SEQ ID NO 12
<211> LENGTH: 31656
<212> TYPE: DNA
<213> ORGANISM: Artificial Sequence
<220> FEATURE:
<223> OTHER INFORMATION: BZ1/BZ28.5IXP Ad vector

<400> SEQUENCE: 12

-continued

```
catcatcaat aatatacctt attttggatt gtggccaata tgataatgag gtgggcgggg      60
cgaggcgggg cgggtgacgt aggacgtgcg agtagggttg ggaggtgtgg cggaagtgtg     120
gcatttgtaa gtgggaggag cttacatgca agcttccgtc gcggaaaatg tgacgttttt     180
tatgagcgcc gcctacctcc ggaagtgcca attttcgcgc gctttttacc ggatatcgta     240
gtaattttgg gcgggaccat gtaagatttg gccattttcg cgcgaaaagt gaaacgggga     300
agtgaaaact gaataatagg gcgttagtca tagcgcgtaa tatttaccga gggccgaggg     360
actttgaccg attacgtgga ggactcgccc aggtgttttt tacgtgaatt tccgcgttcc     420
gggtcaaagt ctccgttttt attgtcaccg tcatttgacg cggagggtat ttaaacccgc     480
tgcgctccta gcgatcgcgg tactgaaatg tgtgggcgtg gcttaagggt gggaaagaat     540
atataaggtg ggggtcttat gtagttttgt atctgttttg cagcagccgc cgccgccatg     600
agcgacaccg gcaacagctt tgatggaagc atctttagcc cctatctgac agtgcgcatg     660
cctcactggg ccggagtgcg tcagaatgtg atgggttcca acgtggatgg acgtcccgtt     720
ctgccttcaa attcgtctac gatggcctac gcgaccgtgg gaggaactcc gctggacgcc     780
gcgacctccg ccgccgcctc cgccgccgcc gcgaccgcgc gcagcatggc tacggacctt     840
tacagctctt tggtggcgag cagcgcggcc tctcgcgcgt ctgctcggga tgaaaaactg     900
actgctctgc tgcttaaact ggaagacttg acccgggagc tgggtcaact gacccagcag     960
gtctccagct tgcgtgagag cagccttgcc tccccctaat ggcccataat ataaataaaa    1020
gccagtctgt ttggattaag caagtgtatg ttctttattt aactctccgc gcgcggtaag    1080
cccgggacca gcggtctcgg tcgtttaggg tgcggtggat tctttccaac acgtggtaca    1140
ggtggctctg gatgtttaga tacatgggca tgagtccatc cctggggtgg aggtagcacc    1200
actgcagagc ttcgtgctcg gggtggtgt tgtatatgat ccagtcgtag caggagcgct     1260
gggcgtggtg ctgaaaaatg tccttaagca agaggcttat agctaggggg aggcccttgg    1320
tgtaagtgtt tacaaatctg cttagctggg aggggtgcat ccggggggat atgatgtgca    1380
tcttggactg gatttttagg ttggctatgt tcccacccag atcccttctg ggattcatgt    1440
tgtgcaggac caccagcacg gtatatccag tgcacttggg aaatttatcg tggagcttag    1500
acgggaatgc atggaagaac ttggagacgc ccttgtggcc tcccagattt tccatacatt    1560
cgtccatgat gatggcaatg ggcccgtggg aagctgcctg agcaaaaacg tttctggcat    1620
cgctcacatc gtagttatgt tccagggtga ggtcatcata ggacatcttt acaaatcggg    1680
ggcggagggt cccggactgg gggatgatgg taccctcggg ccccggggcg tagttcccct    1740
cacagatctg catctcccag gctttcattt cagagggagg gatcatatcc acctgcgggg    1800
cgatgaaaaa gacagtttct ggcgcagggg agattaactg ggatgagagc aggtttctga    1860
gcagctgtga ctttccacag ccggtgggcc catatatcac gcctatcacc ggctgcagct    1920
ggtagttaag agagctgcag ctgccgtcct cccggagcag gggggccacc tcgttgagca    1980
tatccctgac gtggatgttc tccctgacca gttccgccag aaggcgctcg ccgcccagcg    2040
aaagcagctc ttgcaaggaa gcaaaatttt tcagcggttt caggccatcg gccgtgggca    2100
tgtttttcag cgtctgggtc agcagctcca gcctgtccca gagctcggtg atgtgctcta    2160
cggcatctcg atccagcaga tctcctcgtt tcgcgggttg ggcggcttt cgctgtaggg     2220
caccagccga tgggcgtcca gcggggccag agtcatgtcc ttccatgggc gcagagtcct    2280
cgtcagggtg gtctgggtca cggtgaaggg gtgcgctccg ggttgggcac tggccagggt    2340
gcgcttgagg ctggttctgc tggtgctgaa tcgctgccgc tcttcgccct gcgcgtcggc    2400
```

```
caggtagcat ttgaccatgg tctcgtagtc gagaccctcg gcggcgtgcc ccttggcgcg   2460
gagctttccc ttggaggtgg cgccgcacga ggggcactgc aggctcttca gggcgtagag   2520
cttgggagcg agaaacacgg actctgggga gtaggcgtcc gcgccgcagg ccgcgcagac   2580
cgtctcgcat tccaccagcc aagtgagttc cgggcggtca gggtcaaaaa ccaggttgcc   2640
cccatgcttt ttgatgcgtt tcttacctcg gctctccatg aggcggtgtc ccttctcggt   2700
gacgaagagg ctgtccgtgt ccccgtagac cgacttcagg ggcctgtctt ccagcggagt   2760
gcctctgtcc tcctcgtaga gaaactctga ccactctgag acgaaggccc gtgtccaggc   2820
caggacgaag gaggccacgt gggaggggta gcggtcgttg tccactagcg ggtccacctt   2880
ctccagggtg tgcagacaca tgtccccctc ctccgcgtcc agaaaagtga ttggcttata   2940
ggtgtaggac acgtgaccgg gggttcccga cggggggggta taaaaggggg tgggcgccct   3000
ttcatcttca ctctcttccg catcgctgtc tgcgagagcc agctgctggg gtaagtattc   3060
cctttcaaag gcgggcatga cctcagcgct caggttgtca gtttctaaaa atgaggagga   3120
tttgatgttc acctgtccgg aagtgatacc tttgagggta cctgggtcca tctggtcaga   3180
aaacactatt tttttgttgt caagcttggt ggcgaacgac ccgtagaggg cgttggagag   3240
cagcttggca atggagcgca gggtctggtt tttgtcgcgg tcggctcgct ccttggccgc   3300
gatgttgagt tgcacgtatt cgcgggccac gcacttccac tcggggaaga cggtggtgcg   3360
ctcgtctggg atcaggcgca ccctccagcc gcggttgtgc agggtgacca tgtcgacgct   3420
ggtggcgacc tcaccgcgca gacgctcgtt ggtccagcag aggcggccgc ctttgcgcga   3480
gcagaagggg ggtagggggt ccagctggtc ctcgtttggg gggtccgcgt cgatggtaaa   3540
gaccccgggg agcaggcgcg ggtcaaagta gtcgatcttg caagcttgca tgtccagagc   3600
ccgctgccat tcgcgggcgg cgagcgcgcg ctcgtagggg ttgaggggcg ggccccaggg   3660
catggggtgg gtgagcgcgg aggcgtacat gccgcagatg tcatacacgt acaggggttc   3720
cctgaggata ccgaggtagg tggggtagca gcgccccccg cggatgctgg cgcgcacgta   3780
gtcatagagc tcgtgggagg gggccagcat gttgagccca aggttggtgc gctgggggcg   3840
ctcggcgcgg aagacgatct gtctgaagat ggcatgggag ttggaggaga tggtgggtcg   3900
ctggaagacg ttgaagcttg cttcttgcaa gcccacggag tccctgacga aggaggcgta   3960
ggactcgcgc agcttgtgca ccagctcggc ggtgacctgg acgtcgagcg cgcagtagtc   4020
gagggtctcg cggatgatgt catacttatc ctcccccttc tttttccaca gctcgcggtt   4080
gaggacgaac tcttcgcggt ctttccagta ctcttggagg ggaaacccgt ccgtgtccga   4140
acggtaagag cctagcatgt agaactggtt gacggcctgg taggggcagc agcccttctc   4200
cacgggcagc gcgtaggcct gcgccgcctt gcggagggag gtgtgggtaa gggcgaaagt   4260
gtccctgacc atgactttga ggtattgatg tctgaagtct gtgtcatcgc agccgccctg   4320
ttcccacagg gtgtagtccg tgcgcttttt ggagcgcggg ttgggcaggg agaaggtgag   4380
gtcattgaag aggatcttcc ccgctcgagg catgaagttt ctggtgatgc gaaagggccc   4440
tgggaccgag gagcggttgt tgatgacctg ggcggccagg acgatctcgt caaagccgtt   4500
tatgttgtgg cccacgatgt agagctccag gaagcggggc tggcccttga tggaggggag   4560
ctttttaagt tcctcgtagg taagctcctc gggcgattcc aggccgtgct cctccagggc   4620
ccagtcttgc aagtgagggt tggccgccag gaaggatcgc cagaggtcgc gggccatgag   4680
ggtctgcagg cggtcgcgga aggttctgaa ctgccgccct acggccatct tttcgggggt   4740
```

-continued gatgcagtag aaggtgaggg ggtctttctc ccaggggtcc catctgagct cttgggcgag 4800
gtcgcgcgcg gcggcgacca gagcctcgtc gccccccagt ttcatgacca gcatgaaggg 4860
cacgagctgc ttgccaaagg ctcccatcca agtgtaggtc tctacatcgt aggtgacaaa 4920
gaggcgctcc gtgcgaggat gagagccgat cgggaagaac tggatctccc gccaccagtt 4980
ggaggattgg ctgttgatgt ggtgaaagta gaagtcccgt ctgcgggccg agcactcgtg 5040
ctggcttttg taaaagcgac cgcagtactg gcagcgctgc acgggttgta tatcttgcac 5100
gaggtgaacc tggcgacctc tgacgaggaa gcgcagcggg aatctaagtc ccccgcctgg 5160
ggtcccgtgt ggctggtggt cttctacttt ggttgtctgg ccgccagcat ctgtctcctg 5220
gagggcgatg gtggagcaga ccaccacgcc gcgagagccg caggtccaga tctcggcgct 5280
cggcgggcgg agtttgatga cgacatcgcg cacattggag ctgtccatgg tctccagctc 5340
ccgcggcggc aggtcagccg ggagttcctg gaggttcacc tcgcagagac gggtcaaggc 5400
gcggacagtg ttgagatggt atctgatttc aaggggcgtg ttggaggcgg agtcgatggc 5460
ttgcagaagg ccgcagcccc ggggggccac gatggttccc cgcggggcgc gaggggaggc 5520
ggaagctggg ggtgtgttca gaagcggtga cgcgggcggg cccccggagg taggggggt 5580
tccggcccca caggcatggg cggcaggggc acgtcttcgc cgcgcgcggg caggggctgg 5640
tgctggctcc ggagagcgct tgcgtgcgcg acgacgcgac ggttggtgtc ctgtatctgg 5700
cgcctctgag tgaagaccac gggtcccgtg accttgaacc tgaaagagag ttcgacagaa 5760
tcaatctcgg catcgttgac agcggcctgg cgcaggatct cctgcacgtc gcccgagttg 5820
tcctggtagg cgatctctgc catgaactgc tcgatctctt cctcctggag atctcctcgt 5880
ccggcgcgct ccacggtggc cgccaggtcg ttggagatgc gacccatgag ctgcgagaag 5940
gcgttgaggc cgccctcgtt ccagacccgg ctgtagacca cgccccccctc ggcgtcgcgg 6000
gcgcgcatga ccacctgggc caggttgagc tccacgtgtc gcgtgaagac ggcgtagttg 6060
cgcaggcgct ggaaaaggta gttcagggtg gtggcggtgt gttcggcgac gaagaagtac 6120
atgacccagc gccgcaacgt ggattcattg atgtccccca aggcctccag gcgctccatg 6180
gcctcgtaga agtccacggc gaagttgaaa aactgggagt tgcgagcgga cacggtcaac 6240
tcctcctcca gaagacggat gagctcggcg acagtgtcgc gcacctcgcg ctcgaaggcc 6300
acggggggcg cttcttcctc ttccacctct tcttccatga ttgcttcttc ttcctcagcc 6360
gggacgggag gggcggcgg cgggggaggg gcgcggcggc ggcggcggcg caccggcagg 6420
cggtcgatga agcgctcgat catctccccc cgcatgcggc gcatggtctc ggtgacggcg 6480
cggccgttct cccgggggcg cagctcaaag acgccgcctc tcatctcgcc gcggggcggg 6540
cggccgtgag gtagcgagac ggcgctgact atgcatctta acaattgctg tgtaggtacg 6600
ccgccaaggg acctgattga gtccagatcc accggatccg aaaacctttg gaggaaagcg 6660
tctatccagt cgcagtcgca aggtaggctg agcaccgtgg cgggcggggg cgggtcggga 6720
gagttcctgg cggagatgct gctgatgatg taattaaagt aggcggtctt gagaaggcgg 6780
atggtggaca ggagcaccat gtctttgggt ccggcctgtt ggatgcggag gcggtcggcc 6840
atgccccagg cctcgttctg acaccggcgc aggtctttgt agtagtcttg catgagtctt 6900
tccaccggca cctcttctcc ttcctcttct ccatctcgcc ggtggtttct cgcgccgccc 6960
atgcgcgtga ccccaaagcc cctgagcggc tgcagcaggg ccaggtcggc gaccacgcgc 7020
tcggccaaga tggcctgctg tacctgagtg agggtcctct cgaagtcatc catgtccacg 7080
aagcggtggt aggcgcccgt gttgatggtg taggtgcagt tggccatgac ggaccagttg 7140

-continued

```
acggtctggt gtcccggctg cgagagctcc gtgtaccgca ggcgcgagaa ggcgcgggaa   7200
tcgaacacgt agtcgttgca agtccgcacc agatactggt agcccaccag gaagtgcggc   7260
ggaggttggc gatagagggg ccagcgctgg gtggcggggg cgccgggcgc caggtcttcc   7320
agcatgaggc ggtggtatcc gtagatgtac ctggacatcc aggtgatgcc ggcggcggtg   7380
gtggtggcgc gcgcgtagtc gcggacccgg ttccagatgt ttcgcagggg cgagaagtgt   7440
tccatggtcg gcacgctctg gccggtgagg cgcgcgcagt cgttgacgct ctatacacac   7500
acaaaaacga aagcgtttac agggctttcg ttctgtagcc tggaggaaag taaatgggtt   7560
gggttgcggt gtgccccggt tcgagaccaa gctgagctcg gccggctgaa gccgcagcta   7620
acgtggtatt ggcagtcccg tctcgaccca ggccctgtat cctccaggat acggtcgaga   7680
gcccttttgc tttcttggcc aagcgcccgt ggcgcgatct gggatagatg gtcgcgatga   7740
gaggacaaaa gcggctcgct tccgtagtct ggagaaacaa tcgccagggt tgcgttgcgg   7800
cgtaccccgg ttcgagcccc tatggcggct tggatcggcc ggaaccgcgg ctaacgtggg   7860
ctgtggcagc cccgtcctca ggaccccgcc agccgacttc tccagttacg ggagcgagcc   7920
ccttttgttt tttatttttt agatgcatcc cgtgctgcgg cagatgcgcc cctcgccccg   7980
gcccgatcag cagcagcaac agcaggcatg cagaccccc tctcctctac ccgccccggt   8040
caccacggcc gcggcggccg tgtccggcgc ggggggcgcg ctggagtcag atgagccacc   8100
gcggcggcga cctaggcagt atctggactt ggaagagggc gagggactgg cgcggctggg   8160
ggcgagctct ccagagcgcc acccgcgggt gcagttgaaa agggacgcgc gcgaggcgta   8220
cctgccgcgg cagaacctgt ttcgcgaccg cgggggcgag gagcccgagg agatgcgaga   8280
ctgcaggttc caagcggggc gcgagctgcg ccgcgggttg gacagacagc gcctgctgcg   8340
cgaggaggac tttgagcccg acacgcagac gggcatcagc cccgcgcgcg cgcacgtggc   8400
cgcggccgac ctggtgaccg cctacgagca gacggtgaac caggagcgca acttccaaaa   8460
aagcttcaac aaccacgtgc gcacgctggt ggcgcgcgag gaggtgaccc tgggtctcat   8520
gcatctgtgg gacctggtgg aggcgatcgt gcagaacccc agcagcaagc ccctgaccgc   8580
gcagctgttc ctggtggtgc agcacagcag ggacaacgag gccttcaggg aggcgctgct   8640
gaacatcacc gagccggagg ggcgctggct cctggacctg ataaacatcc tgcagagcat   8700
agtggtgcag gagcgcagcc tgagcctggc cgagaaggtg gcggccatta actattctat   8760
gctgagcttg ggcaagttct acgcccgcaa gatctacaag acccccctacg tgcccataga   8820
caaggaggtg aagatagaca gcttctacat gcgcatggcg ctaaaggtgc tgaccctgag   8880
cgacgacctg ggagtgtacc gcaacgagcg catccacaag gccgtgagcg ccagccggcg   8940
gcgcgagctg agcgaccgcg agctgatgca cagtctgcag cgcgcgctca ccggcgcggg   9000
cgagggcgac agggaggtcg agtcctactt cgacatgggg gctgacctgc actggcagcc   9060
gagccgccgc gccctggagg cggcgggggc gtatggcggc cccctggcgg ccgatgacga   9120
ggaagaggag gactatgagc tagaggaggg cgagtacctg gaggactgac ctggctggtg   9180
gtgttttggt atagatgcaa gatccgaacg tggcggaccc ggcggtccgg gcggcgctgc   9240
agagccagcc gtccggcatt aactcctctg acgactgggc cgcggccatg ggtcgcatca   9300
tggccctgac cgcgcgcaac cccgaggcct tcaggcagca gcctcaggct aaccggctgg   9360
cggccatctt ggaagcggta gtgcccgcgc gctccaaccc cacccacgag aaggtgctgg   9420
ccatagtcaa cgcgctggcg gagagcaggg ccatccgggc ggacgaggcc ggactggtgt   9480
```

```
acgatgcgct gctgcagcgg gtggcgcggt acaacagcgg caacgtgcag accaacctgg   9540
accgcctggt gacggacgtg cgcgaggccg tggcgcagcg cgagcgcttg catcaggacg   9600
gtaacctggg ctcgctggtg gcgctaaacg ccttcctcag cacccagccg gccaacgtac   9660
cgcgggggca ggaggactac accaacttct tgagcgcgct gcggctgatg gtgaccgagg   9720
tccctcagag cgaggtgtac cagtcggggc ccgactactt cttccagacc agcagacagg   9780
gcttgcaaac cgtgaacctg agccaggctt tcaagaacct gcgggggctg tggggagtga   9840
aagcgcccac cggcgaccga gctacggtgt ccagcctgct aacccccaac tcgcgcctgc   9900
tgctgctgct gatcgcgccc ttcacggaca gcgggagcgt ctcgcgggag acctatctgg   9960
gccacctgct gacgctgtac cgcgaggcca tcgggcaggc gcaggtggac gagcacacct  10020
tccaagagat caccagcgtg agccacgcgc tggggcagga ggacacgggc agcctgcagg  10080
cgaccctgaa ctacctgctg accaacaggc ggcagaagat tcccacgctg cacagcctga  10140
cccaggagga ggagcgcatc ttgcgctacg tgcagcagag cgtgagcctg aacctgatgc  10200
gcgacggcgt gacgcccagc gtggcgctgg acatgaccgc gcgcaacatg gaaccgggca  10260
tgtacgcttc ccagcggccg ttcatcaacc gcctgatgga ctacttgcat cgggcggcgg  10320
ccgtgaaccc cgagtacttc accaatgcca ttctgaatcc ccactggatg ccccctccgg  10380
gtttctacaa cggagacttc gaggtgcctg aggtcaatga tgggttcctc tgggatgaca  10440
tggatgacag tgtgttctcc cccaacccgc tgcgcgccgc gtctctgcga ttgaaggagg  10500
gctctgacag ggaaggaccg aggagtctgg cctcctccct ggctctgggg gcggtgggcg  10560
ccacgggcgc ggcggcgcgg ggcagcagcc ccttccccag cctggcagac tctctgaata  10620
gcgggcgggt gagcaggccc cgcttgctag gcgaggagga gtatctgaac aactccctgc  10680
tgcagcccgt gagggacaaa aacgctcagc gacagcagtt tcccaacaac gggatagaga  10740
gcctggtgga caagatgtcc agatggaaga catatgcgca ggagtacaag gagtgggagg  10800
accgccagcc gcggcccctg ccgcccccta gacagcgctg gcagcggcgc gcgtccaacc  10860
gccgctggag acagggaccc gaggacgatg atgactctgc agatgacagc agcgtgttgg  10920
acctgggcgg gagcgggaac cccttttcgc acctgcgccc acgcctgggc aagatgtttt  10980
aaaagagaaa aataaaactc accaaggcca tggcgacgag cgttggtttt ttgttccctt  11040
ccttagtatg cggcgcgcgg cgatgttcga ggaggggcct ccccccctctt acgagagcgc  11100
gatgggaatt tctcctgcgg cgcccctgca gcctccctac gtgcctcctc ggtacctgca  11160
acctacaggg gggagaaata gcatctgtta ctctgagctg cagcccctgt acgataccac  11220
cagactgtac ctggtggaca acaagtccgc ggacgtggcc tccctgaact accagaacga  11280
ccacagcgat tttttgacca cggtgatcca aaacaacgac ttcaccccaa ccgaggccag  11340
tacccagacc ataaacctgg acaacaggtc gaactggggc ggcgacctga agaccatcct  11400
gcacaccaac atgcccaacg tgaacgagtt catgtttacc aactctttta aggcgcgggt  11460
tatggtggcg cgcgagcagg gggaggcgaa gtacgagtgg gtggacttca cgctgcccga  11520
gggcaactac tcagagacca tgactattga cctgatgaac aatgcgatcg tggaacacta  11580
cctgaaagtg ggcaggcaga acggggtgaa ggagagcgat atcggggtca agtttgacac  11640
cagaaacttt cgtctgggct gggaccccgt gaccgggctg gtcatgccgg gggtctacac  11700
caacgaggcc tttcatcccg atatagtgct cctgcccggc tgtggggtgg actttaccca  11760
gagccggctg agcaacctgc tgggcgttcg caagcggcaa cctttccagg agggtttcaa  11820
gatcacctat gaggatctgg aggggggcaa cattcccgcg ctccttgatc tggacgccta  11880
```

cgaggagagc ttgaaacccg aggagagcgc tggcgacagc ggcgagagtg gcgaggagca 11940
agccggcggc ggtggcagcg cgtcggtaga aaacgaaagt actcccgcag tggcggcaga 12000
cgctgcggag gtcgagccag aggccatgca gcaggacgca gaggagggcg cacaggaggg 12060
cgcgcaggag gacatgaacg atggggagat caggggagac actttcgcca cccggggcga 12120
agaaaaagag gcagaggcgg tggcggcgac ggtggaagcc gaaaccgagg cagaggcaga 12180
gcccaagacc gaagttatgg aagacatgaa tgatggagaa cgtaggggtg acacgtttgc 12240
cacccggggc gaagagaagg cggcggaggc agaagccgcg gctgaggagg cggctgcggc 12300
tgcggccgag gctgaggctg cggctgaggc taaggtcgaa gccgatgttg cggttgaggc 12360
tcaggctgag gaggaggagg cggcgactga agcagttaag gaaaaggccc aggcagagca 12420
ggaagagaaa aaacctgtca ttcaacctct aaaagaagat agcaaaaagc gcagttacaa 12480
cgtcatcgag ggcagcacct ttacccagta ccgcagctgg tacctggcgt acaactacgg 12540
cgacccggtc aagggggtgc gctcgtggac cctgctctgc acgccggacg tcacctgcgg 12600
ctccgagcag atgtattggt cgctgccaaa catgatgcaa gacccggtga ccttccgctc 12660
cacgcggcag gttagcaact tcccggtggt gggcgccgaa ctgctgcccg tgcactccaa 12720
gagtttttac aacgagcagg ccgtctactc ccagctgatc cgccaggcca cctctctgac 12780
ccacgtgttc aatcgctttc ccgagaacca gattttggcg cgcccgccgg cccccaccat 12840
caccaccgtc agtgaaaacg ttcctgccct cacagatcac gggacgctac cgctgcgcaa 12900
cagcatctca ggagtccagc gagtgaccat tactgacgcc agacgccgga cctgccccta 12960
cgtttacaag gccttgggca tagtctcgcc gcgcgtcctc tccagtcgca ctttttaaaa 13020
tacatctacc ctcacgcttc aaaatcatgt ccgtactcat ctcacccagc aacaacaccg 13080
gctgggggct gcgcgcgccc agcaagatgt ttggaggggc gaggaaacgc tccgagcagc 13140
acccagtgcg cgtgcgcggc cactaccgcg cgccctgggg agcgcacaag cgcgggcgcg 13200
cagggcgcac cactgtggac gacgccattg actccgtagt ggagcaggcg cgccactaca 13260
cacccggcgc gccgtccgcc cccgccgtgt ccaccgtgga cgaggcgatc gagagcgtgg 13320
tacagggcgc gcggcactat gccaacctta aaaatcgacg ccgtcgcgtg gctcgccgcc 13380
atcgccggag accccgggcc accgccgccg cgcgccttgc taaggctctg ctcaggcgcg 13440
ccaggcgaac tggccgccgg gccgccatga gggccgcacg gcgggctgcc gccagcgcgg 13500
ccgccgcggc cccacgggca cgaaggcgcg cggccgctgc cgccgccgcc gccatttcca 13560
gcttggcctc gacgcggcgc ggtaacatat actgggtgcg cgactcggta accggcacgc 13620
gggtacccgt gcgctttcgc cccccgcgga attagcacaa gacaacatac acactgagtc 13680
tcctgctgtt gtgtatccca gcggcgaccg tcagcagcgg cgacatgtcc aagcgcaaaa 13740
ttaaagaaga gatgctccag gtcatcgcgc cggagatcta tgggcccccg aagaaggagg 13800
aggatgatta caagccccgc aagctaaagc gggtcaaaaa gaaaaagaaa gatgatgacg 13860
ttgacgaggc ggtggagttt gtccgccgca tggcgcccag gcgccccgtg cagtggaagg 13920
gtcggcgcgt gcagcgagtc ctgcgccccg gcaccgcggt ggtctttacg cccggcgagc 13980
gttccacgcg cactttcaag cgggtgtacg atgaggtgta cggcgacgag gatctgttgg 14040
agcaggccaa ccatcgcttt ggggagtttg catatgggaa acggccccgc gagagcctaa 14100
aagaggacct gctggcgcta ccgctggacg agggcaatcc caccccgagt ctgaagccgg 14160
taaccctgca acaggtgctg cctttgagcg cgcccagcga gcagaagcga gggttgaagc 14220

-continued

```
gcgagggcgg ggacctggca cccaccgtgc agttgatggt gcccaagcgg cagaagctgg  14280
aggacgtgct ggagaaaatg aaagtagagc ccgggatcca gcccgaaatc aaggtccgcc  14340
ccatcaagca ggtggcgccc ggcgtgggag tccagaccgt ggacgttagg attcccacgg  14400
aggagatgga aacccaaacc gccactccct cttcggcggc tagcgccacc accggctccg  14460
cttcggtaga ggtgcagacg gacccctggc tagccgccgc cgccccggcc gcccccgtt  14520
cgcgcgggcg caagagaaat tatccagcgg ccagcgcgct catgccccag tacgcactgc  14580
atccatccat cgcgcccacc cccggctacc gcgggtactc gtaccgcccg cgcagatcag  14640
ccggcacccg cggccgccgc cgccgtgcga ccacaaccag ccgccgccgt cgccgccgcc  14700
gccagccagt gctgaccccc gtgtctgtaa ggaaggtggc tcgctcgggg agcacgctgg  14760
tggtgcccag agcgcgctac caccccagca ttgtttaaag ccggtctctg tatggttctt  14820
gcagatatgg ccctcacttg tcgcctccgc ttcccggtgc cgggataccg aggaagaact  14880
caccgccgca gaggcatggc gggcagtggt ctccgcggcg gccgtcgcca tcgccggcgc  14940
gcaaagagca ggcgcatgcg cggcggtgtg ctgcccttcc taatcccgct aatcgccgcg  15000
gcgatcggtg ccgtgcccgg gatcgcctcc gtggccctgc aggcgtccca gaaacattga  15060
ctcttgcaac cttgcaagct tgcatttttt ggaggaaaaa ataaaaagtc tagactctca  15120
cgctcgcttg gtcctgtgac tattttgtag aaaaaagatg gaagacatca actttgcgtc  15180
gctggccccg cgtcacggct cgcgcccgtt catgggagac tggacagata tcggcaccag  15240
caatatgagc ggtggcgcct tcagctgggg cagtctgtgg agtggcctta aaaattttgg  15300
ttccaccatt aagaactatg gcaacaaagc gtggaacagc agcacgggtc agatgctgag  15360
agacaagttg aaagagcaga acttccagga gaaggtggca cagggcctgg cctctggcat  15420
cagcggggtg gtggacatag ctaaccaggc cgtgcagaaa aagataaaca gtcatctgga  15480
cccccgccct caggtggagg aaacgcctcc agccatggag acggtgtctc ccgagggcaa  15540
aggcgaaaag cgcccgcggc ccgacaggga agagaccctg gtgtcacaca ccgaggagcc  15600
gccctcttac gaggaggcag tcaaggccgg cctgcccacc actcgcccca tagctcccat  15660
ggccaccggt gtggtgggtc acaggcaaca cacccccgcg acactagatc tgcccccgcc  15720
gtccgagccg actcgccagc caaaggcggt gacggtgccc gctccctcca cttccgccgc  15780
caacagagtg cctctgcgcc gcgctgcgag cggcccccgg gcctcgcgag tcagcggcaa  15840
ctggcagagc acactgaaca gcatcgtggg cctgggagtg aggagtgtga agcgccgccg  15900
ttgctactga atgagcaagc tagctaacgt gttgtatgtg tgtatgcgtc ctatgtcgcc  15960
gccagaggag ctgttgagcc gccggcgccg tctgcactcc agcgaatttc aagatggcga  16020
ccccatcgat gatgcctcag tggtcgtaca tgcacatctc gggccaggac gcttcggagt  16080
acctgagccc cgggctggtg cagttcgccc gcgccacaga cacctacttc aacatgagta  16140
acaagttcag gaaccccact gtggcgccca cccacgatgt gaccacggac cggtcgcagc  16200
gcctgacgct gcggttcatc cccgtggatc gggaggacac cgcttactct tacaaggcgc  16260
ggttcacgct ggccgtgggc gacaaccgcg tgctggacat ggcctccact tactttgaca  16320
tccgggggt gctggacagg ggccccactt tcaagcccta ctcgggcact gcctacaact  16380
ccctggcccc caagggcgct cccaattctt gcgagtggga ggaggaaaca caaaatgagg  16440
tacaagccaa tgaagaacaa ctagcagaag aagaggatga agaaatggct caagaggatc  16500
agcagcctac taaaaaaacc catgtatatg ctcaggcacc tctttctggc gaacagatta  16560
ccaaagatgg cttgcaaata ggagctgaag ttacaggaga aacatcaaag cccatttttg  16620
```

```
cagacaagac attccaacca gaacctcaga taggagagtc tcaatggaat gaggccgatg  16680
ctacagtagc aggaggtagg gttttgaaaa agactacccc tatgaaacct tgctatggat  16740
cctatgccag acctaccaat gccaatggag ggcaggggat acttgaggca aatgctaaag  16800
gggaactcga atctaaagtt gagatgcagt ttttctctaa caccacaact cttaatgtaa  16860
gagacggtga aaatggcctt aaaccaaaag tagtgctgta tagcgaagat gtcaacctgg  16920
aatcccctga cactcatctg tcttacaagc ccaaaaaaga tgatgttaat gccaaaatca  16980
tgttgggtca gcaagccatg cccaacagac ccaacctcat tggatttaga gataatttca  17040
ttgggctcat gtattacaac agcactggaa acatgggagt gctggcgggt caggcctctc  17100
agttgaatgc tgtggtggac ttgcaggata gaaacacgga actgtcatat cagcttatgc  17160
ttgattccat tggagataga accagatact ttccatgtg gaaccaggca gtggatagct  17220
atgacccaga tgttagaatc attgaaaacc atggggtgga ggatgagctg cccaactact  17280
gttttccctt gggcggtata ggaattacag atacatacca ggccataaaa gcagccaatg  17340
gtggagatgc tactacgtgg tctgctgata acacatttgc agaccgcaac gaaatagggg  17400
tgggaaacaa cttcgccatg gagatcaaca tccaggccaa cctctggaga aacttcctct  17460
atgcgaacgt gggactctac ctgccagaca agctcaagta caaccccacc aacgtggaca  17520
tctctgacaa ccccaacacc tatgactaca tgaacaagcg ggtggtggcc cccggcctgg  17580
tggactgctt tgtcaatgtg ggagccaggt ggtccctgga ctacatggac aacgtcaacc  17640
ccttcaacca ccaccgcaat gcgggtctgc gctaccgctc catgatcctg ggcaacgggc  17700
gctatgtgcc cttccacatc caggtacccc agaagttctt tgccatcaag aacctcctgc  17760
tcctgcccgg ctcctacacc tacgagtgga acttcaggaa ggatgtaaac atggtcctac  17820
agagctctct gggcaatgac cttagggtag atggggccag catcaagttt gacagcatca  17880
ccctctatgc tacatttttc cccatggccc acaacaccgc ctccacgctt gaggccatgc  17940
tgagaaacga caccaacgac cagtccttca atgactacct ctctggggcc aacatgctct  18000
acccaatccc agccaaggcc accaacgtgc ccatctccat cccctctcgc aactgggccg  18060
cctttagagg ctgggccttt acccgcctta agaccaagga gacccccctcc ctgggctcgg  18120
gttttgatcc ctactttgtt tactcgggat ccatccccta cctggatggc accttctacc  18180
tcaaccacac tttcaagaag atatccatca tgtatgactc ctccgtcagc tggccgggca  18240
acgaccgctt gctcaccccc aatgagttcg aggtcaagcg cgccgtggac ggcgagggct  18300
acaacgtggc ccagtgcaac atgaccaagg actggttcct ggtgcagatg ctggccaact  18360
acaacatagg ctaccagggc ttctacatcc cagagagcta caaggacagg atgtattcct  18420
tcttcagaaa tttccaaccc atgagccgac aggtggtgga cgagaccaat tacaaggact  18480
atcaggccat tggcatcacc caccagcaca acaactcggg tttcgtgggc tacctggcgc  18540
ccaccatgcg cgagggacag gcctaccccg ccaacttccc ctaccccctg ataggcaaga  18600
ccgcggtcga cagcgtcacc cagaaaaagt tcctctgcga ccgcaccctc tggcgcatcc  18660
ccttctctag caactttatg tccatgggtg cgctcacgga cctgggccaa aacctgcttt  18720
atgccaactc tgcccatgcg ctggacatga cttttgaggt ggaccccatg gacgagccca  18780
cccttctcta tattgtgttt gaagtgttcg acgtggtcag agtgcaccag ccgcaccgcg  18840
gtgtcatcga gaccgtgtac ctgcgtacgc ccttctcagc cggcaacgcc accacctaag  18900
gagacagcgc cgccgcctgc atgactggtt ccaccgagca agagctcagg gccatcgcca  18960
```

-continued gagacctggg atgcggaccc tattttttgg gcacctatga caaacgcttc ccgggtttta 19020
tctcccgaga caagctcgcc tgcgccatcg tcaacacggc cgcgcgcgag accgggggcg 19080
tgcactggct ggcctttggc tgggacccgc gctctaaaac ttgctacctc tttgacccct 19140
ttggcttctc cgatcagcgc ctcaggcaga tttatgagtt tgagtacgag ggctgttgc 19200 gccgcagcgc gcttgcctcc tcgcccgacc gctgcatcac ccttgagaag tccaccgaga 19260
ccgtgcaggg gccccactcg gccgcctgcg gtctcttctg ttgcatgttt ttgcacgcct 19320
ttgtgcactg gcctcagagt cccatggatc gcaaccccac catgaacttg ctaaagggag 19380
tgcccaacgc catgctccag agcccccagg tcctgcccac cctgcgccgc aaccaggaac 19440
agctctaccg cttcctggag cgccactccc cctacttccg cagccacagc gcgcgcatcc 19500
ggggggccac ctctttttgc cacttgcaag aaaacatgca agacggaaaa tgatgtacag 19560
catgctttta ataaatgtaa agactgtgca ctttatttat acacgggctc tttctggtta 19620
tttattcaac accgccgtcg ccatctagaa atcgaaaggg ttctgccgcg cgtcgccgtg 19680
cgccacgggc agagacacgt tgcgatactg gaagcggctc gcccacttga actcgggcac 19740
caccatgcgg ggcagtggtt cctcggggaa attctcgctc cacagggtgc gggtcagctg 19800
cagcgcgctc aggaggtcgg gagccgagat cttgaagtcg cagttggggc cggaaccctg 19860
cgcgcgcgag ttgcggtaca cggggttgca gcactggaac accagcaggg ccggattatt 19920
cacgctggcc agcaggctct cgtcgctaat catgtcgctg tccagatcct ccgcgttgct 19980
cagggcgaat ggggtcatct tgcagacctg cctgcccagg aaaggcggga gcccaggctt 20040
gccgttacag tcgcagcgca ggggcattag caggtgccca cggcccgact gcgcctgcgg 20100
gtacaacgcg cgcatgaagg cttcgatctg cctaaaagcc acctgggtct tggctccctc 20160
cgaaaagaac atcccacagg acttgctgga gaactggttc gcgggacagc tggcatcgtg 20220
caggcagcag cgcgcgtcag tgttggcgat ctgcaccacg ttgcgacccc accggttttt 20280
cactatcttg gccttggaag cctgctcctt tagcgcgcgc tggccgttct cgctggtcac 20340
atccatctct atcacctgtt ccttgttgat catgtttgtc ccgtgcagac actttaggtc 20400
gccctccgtc tgggtgcagc ggtgctccca cagcgcgcaa ccggtgggct cccaattttt 20460
gtgggtcacc cccgcgtagg cctgcaggta ggcctgcagg aagcgcccca tcatggtcat 20520
aaaggtcttc tggctcgtaa aggtcagctg caggccgcga tgctcttcgt tcagccaggt 20580
cttgcagatg gcggccagcg cctcggtctg ctcgggcagc atcttaaaat ttgtcttcag 20640
gtcgttatcc acgtggtact tgtccatcat ggcacgcgcc gcctccatgc ccttctccca 20700
ggcggacacc atgggcaggc ttagggggtt tatcacttcc agcggcgagg acaccgtact 20760
ttcgatttct tcttcctccc cctcttcccg gcgcgcgccc ccgctgttgc gcgctcttac 20820
cgcctgcacc aaggggtcgt cttcaggcaa gcgccgcacc gagcgcttgc cgcccttgac 20880
ctgcttgatc agtaccggcg ggttgctgaa gcccaccatg gtcagcgccg cctgctcttc 20940
ttcgtcttcg ctgtctacca ctatttctgg ggaggggctt ctccgctctg cggcaaaggc 21000
ggcggatcgc ttcttttttt tcttgggagc cgccgcgatg gagtccgcca cggcgaccga 21060
ggtcgagggc gtggggctgg gggtgcgcgg caccagggcc tcgtcgccct cggactcttc 21120
ctctgactcc aggcggcggc ggagtcgctt ctttgggggc gcgcgcgtta gcggcggcgg 21180
agacggggac ggggacgggg acgggacgcc ctccacaggg ggcggtcttc gcgcagaccc 21240
gcggccgcgc tcgggggtct tctcgcgctg gtcttggtcc cgactggcca ttgtatcctc 21300
ctcctcctag gcagagagac ataaggagtc tatcatgcaa gtcgagaagg aggagagctt 21360

-continued

```
aaccaccccc tctgagaccg ccgtcgccgt cgccccccgct accgccgacg cgcccgccac  21420
accgagcgac accccccgcgg acccccccgc cgacgcaccc ctgttcgagg aagcggccgt  21480
ggagcaggac ccgggctttg tctcggcaga ggaggatttg caagaggagg aggataagga  21540
ggagaagccc tcagtgccaa aagatcataa agagcaagac gagcacgacg cagacgcaca  21600
ccagggtgaa gtcgggcggg gggacggagg gcatggcggc gccgactacc tagacgaagg  21660
aaacgacgtg ctcttgaagc acctgcatcg tcagtgcgcc attgtctgcg acgctctgca  21720
ggagcgcagc gaggtgcccc tcagcgtggc ggaggtcagc cgcgcctacg agctcagcct  21780
cttttccccc cgggtgcccc cccgccgccg cgaaaacggc acatgcgagc ccaacccgcg  21840
cctcaacttc taccccgcct ttgtggtgcc cgaggtcctg gccacctatc acatcttctt  21900
tcaaaattgc aagatcccca tctcgtgccg cgccaaccgt agccgcgccg ataagatgct  21960
ggccctgcgc cagggcgacc acatacctga tatcgccgct ttggaagatg tgccaaagat  22020
cttcgagggt ctgggtcgca acgagaagcg ggcagcaaac tctctgcaac aggaaaacag  22080
cgaaaatgag agtcacactg gagcgctggt ggagctggag ggcgacaacg cccgcctggc  22140
ggtgctcaag cgcagcatcg aggtcaccca ctttgcctac cccgcgctca acctgccccc  22200
caaagtcatg aacgcggtca tggacgggct aatcatgcgc cgcggccggc cccttgctcc  22260
agatgcaaac ttgcatgagg agaccgagga cggtcagccc gtggtcagcg acgagcagct  22320
gacgcgctgg ctggaaaccg cggaccccgc cgaactggag gagcggcgca agatgatgat  22380
ggccgcggtg ctggtcaccg tagagctgga gtgtctgcag cgcttcttcg gcgaccccga  22440
gatgcagaga aaggtcgagg agaccctaca ctacaccttc cgccagggct acgtgcgcca  22500
ggcttgcaag atctccaacg tggagctcag caacctggtg tcctacctgg gcatcttgca  22560
tgaaaaccgc cttgggcaga gcgtgctaca ctccaccctg cgcggggagg cgcgccgcga  22620
ctacgtgcgc gactgcgttt acctcttcct ctgctacacc tggcagacgg ccatgggggt  22680
ctggcagcag tgcctggagg agcgcaacct caaggagctg gagaagctcc tgcagcgcgc  22740
gctcaaagac ctctggacgg gctacaacga gcgctcggtg gccgccgcgc tggccgacct  22800
catcttcccc gagcgcctgc tcaaaactct ccagcagggg ctgcccgact tcaccagcca  22860
aagcatgttg caaaatttta ggaactttat cctggagcgt tctggcatcc tacccgccac  22920
ctgctgcgcc ctgcccagcg actttgtccc cctcgtgtac cgcgagtgcc ccccgccgct  22980
gtggggccac tgctacctgt tccaactggc caactacctg tcctaccacg cggacctcat  23040
ggaagactcc agcggcgagg ggctcatgga gtgccactgc cgctgcaacc tctgcacgcc  23100
ccaccgctcc ctggtctgca acacccaact gctcagcgag agtcagatta tcggtacctt  23160
cgagctacag ggtccgtcct cctcagacga gaagtccgcg gctccggggc taaaactcac  23220
tccggggctg tggacttccg cctacctgcg caaatttgta cctgaagact accacgccca  23280
cgagatcagg ttttacgagg accaatcccg cccgcccaag gcggagctga ccgcctgcgt  23340
catcacccag ggcgagatcc taggccaatt gcaagccatc caaaaagccc gccaagagtt  23400
tttgctgaga aagggtcggg gggtgtatct ggacccccag tcgggtgagg agctcaaccc  23460
ggttcccccg ctgccgccgc cgcgggacct tgcttcccag gataagcatc gccatggctc  23520
ccagaaagaa gcagcagcgg ccgccactgc cgccacccca cacgctggag gaagaggagg  23580
aatactggga cagtcaggca gaggaggttt cggacgagga ggagccggag acggagatgg  23640
aagagtggga ggaggacagc ttagacgagg aggcttccga agccgaagag gcaggcgcaa  23700
```

```
caccgtcacc ctcggccgca gccccctcgc aggcgccccc gaagtccgct cccagcatca  23760
gcagcaacag cagcgctata acctccgctc ctccaccgcc gcgacccacg gccgaccgca  23820
gacccaaccg tagatgggac accaccggaa ccggggccgg taagtcctcc gggaaaggca  23880
agcaagcgca gcgccaaggc taccgctcgt ggcgcgctca caagaacgcc atagtcgctt  23940
gcttgcaaga ctgcgggggg aacatctcct tcgcccgccg cttcctgctc ttccaccacg  24000
gtgtggcctt cccccgtaac gtcctgcatt actaccgtca tctctacagc ccctactgcg  24060
gcggcagtga gccagaggcg gccggcggca gcggcgcccg tttcggtgcc taggaagacc  24120
cagggcaaga cttcagccaa gaaactcgcg gcggccgcgg cgaacgcggt cgcgggggcc  24180
ctgcgcctga cggtgaacga acccctgtcg acccgcgaac tgaggaaccg aatcttcccc  24240
actctctatg ccatcttcca gcagagcaga gggcaggatc aggaactgaa agtaaaaaac  24300
aggtctctgc gctccctcac ccgcagctgt ctgtatcaca agagcgaaga ccagcttcgg  24360
cgcacgctgg aggacgctga ggcactcttc agcaaatact gcgcgctcac tcttaaggac  24420
tagctccgcg cccttctcga atttaggcgg gaacgcctac gtcatcgcag cgccgccgtc  24480
atgagcaagg acattcccac gccatacatg tggagctatc agccgcagat gggactcgcg  24540
gcgggcgcct cccaggatta ctccacccgc atgaactggc tcagtgccgg cccacacatg  24600
atctcacagg ttaatgacat ccgcacccat cgaaaccaaa tattggtgga gcaggcggca  24660
attaccacca cgccccgcaa taatcccaac cccagggagt ggcccgcgtc cctggtgtat  24720
caggaaattc ccggccccac caccgtacta cttccgcgtg attcccaggc cgaagtccaa  24780
atgactaact caggggcaca gctcgcgggc ggctgtcgtc acagggtgcg gcctcctcgc  24840
cagggtataa ctcacctgaa gatccgaggc agaggtattc agctcaacga cgagtcggtg  24900
agctcctcgc tcggtctcag acctgacggg accttccaga tagccggagc cggccgatct  24960
tccttcacgc cccgccaggc gtacctgact ctgcagagct cgtcctcggc gccgcgctcg  25020
ggcggcatcg ggactctcca gttcgtgcag gagtttgtgc cctcggtcta cttcaacccc  25080
ttctcgggct ctcccggtcg ctacccggac cagttcatcc cgaactttga cgccgcgagg  25140
gactcggtgg acggctacga ctgaatgtcg ggtggacccg gtgcagagca acttcgcctg  25200
aagcaccttg accactgccg ccgccctcag tgctttgccc gctgtcagac cggtgagttc  25260
cagtactttt ccctgcccga ctcgcacccg gacggcccgg cgcacggggt gcgcttttc   25320
atcccgagtc aggtccgctc taccctaatc agggagttca ccgcccgtcc cctactggcg  25380
gagttggaaa aggggccttc tatcctaacc attgcctgca tctgctctaa ccctggatta  25440
caccaagatc tttgctgtca tttgtgtgct gagtataata aaggctgaga tcagaatcta  25500
ctcgggctcc tgtcgccatc ctgtcaacgc caccgtccaa gcccggcccg atcagcccga  25560
ggtgaacctc acctgcggtc tgcaccggcg cctgaggaaa tacctagctt ggtactacaa  25620
cagcactccc tttgtggttt acaacagctt tgaccaggac ggggtctcac tgagggataa  25680
cctctcgaac ctgagctact ccatcaggaa gaacaacacc ctcgagctac ttcctcctta  25740
cctgcccggg acttaccagt gtgtcaccgg tccctgcacc cacacccacc tgttgatcgt  25800
aaacgactct cttccgagaa cagacctcaa taactcctct ccgcagttcc ccagaacagg  25860
aggtgagctc aggaaacccc gggtaaagaa gggtggacaa gagttaacac ttgtggggtt  25920
tctggtgtat gtgacgctgg tggtggctct tttgattaag gcttttcctt ccatgtctga  25980
actatccctc ttcttttatg aacaactcga ctagtgctaa cgggacccta cccaacgaat  26040
cgggattgaa tatcggtaac caggttgcag tttcactttt gattaccttc atagtcctct  26100
```

-continued

```
tcctgctagt gctgtcgctt ctgtgcctgc ggatcggggg ctgctgcatc cacgtttata  26160
tctggtgctg gctgtttaga aggttcggag accaccgcag gtagaataaa caaacctaga  26220
cctagaaatg gacggtctct gcagcgagca acgcatacta gagaggcgcc ggcaaaaagc  26280
agagctcgag cgtcttaaac aagagctcca agacgccgtg gccatacacc agtgcaaaaa  26340
agggctcttc tgtctggtaa aacaggccac gctcacctat gaaaaaacag gtgacaccca  26400
ccgcctagga tacaagctgc ccacacagcg ccaaaagttt gcccttatga taggtgaaca  26460
acccatcacc gtgacccagc actccgtgga gacagaaggc tgcattcatg ctccctgcag  26520
gggcgctgac tgcctctaca ccttgatcaa aaccctttgc ggtctcagag accttatccc  26580
tttcaattga tcataactgt aatcaataaa aaatcactta cttgaaatct gatagcaagc  26640
ctctgtccaa tttttcagc aacacttcct tcccctcttc ccaactctgg tactctaggc  26700
gcctcctagc tgcaaacttc ctccacagtc tgaagggaat gtcagattcc tcctcctcct  26760
gtccctccgc acccacgatc ttcatgttgt tgcagatgaa gcgcaccaaa acgtctgacg  26820
agagcttcaa ccccgtgtac ccctatgaca cggaaaacgg tcctccctcc gtccctttcc  26880
tcacccctcc cttcgtgtct cccgatggat tccaagagag cccccccggg gtcctgtctc  26940
tgaacctggc cgagcccctg gtcacttccc acggcatgct cgccctgaaa atgggaagtg  27000
gcctctccct ggacgacgcc ggcaacctca cctctcaaga tgtcaccacc actacccctc  27060
ccctgaaaaa aaccaagacc aacctcagcc tagaaacctc agccccctg actgtgagca  27120
cctcaggcgc cctcacccta gcagccgccg ttcccctggc ggtggccggc acctccctca  27180
ccatgcaatc agaggccccc ctgacagtcc aagatgcaaa actcaccctg gccaccaagg  27240
gcccctgac cgtgtctgaa ggcaaactgg ccttgcagac ctcggccccg ctgacggccg  27300
ctgacagcag cgccctcacc gttagcgcca caccacccat cagtgtaagc agtggaagtt  27360
tgggcttaga catggaagac cccatgtata ctcatgatgg aaaactggga ataagaattg  27420
gaggcccact gagagtagta gacagcctgc acacactgac tgtagttacc ggaaatggaa  27480
tagctgtaga taacaatgcc ctccaaacta gagttacggg cgccctgggt tatgacacat  27540
caggaaacct acaactgaga gccgcggggg gtatgcgaat tgatgcaaat ggccaactta  27600
tccttgatgt ggcataccca tttgatgctc aaaacaatct cagccttaga cttggtcagg  27660
gacccctgta tgtaaacaca gaccacaacc tagatttgaa ttgcaacaga ggtctgacca  27720
caactaccac caacaacaca aaaaaacttg aaactaaaat tggctcaggc ttagactatg  27780
ataccaatgg tgctgtcatt attaaacttg gtactggtgt aagctttgac agcacaggcg  27840
ccctaactgt gggaaacact ggcgatgata aactgactct gtggacaacc ccagacccat  27900
ctccaaattg cagaattcac gcagacaaag actgcaagtt tactctagtc ctaactaagt  27960
gtggaagtca aatcctggct tctgtcgccg ccctagcggt gtcaggaaat ctggcttcaa  28020
taacaggcac cgttgccagc gttaccatct ttctcagatt tgatcagaat ggagtgctta  28080
tggaaaactc ctccctagac aagcagtact ggaacttcag aaatggtaac tcaaccaatg  28140
ccaccccta caccaatgca gttgggttca tgccaaacct cgcagcatac cccaagacac  28200
agagccagac tgctaaaaac aacattgtaa gtcaggttta cttgaatggg gacaaatcca  28260
aacccatgac ccttaccatt accctcaatg gaactaatga atccagtgaa actagccagg  28320
tgagtcacta ctccatgtca tttacatggg cttgggagag tgggcaatat gccaccgaaa  28380
cctttgccac caattccttt accttctctt acattgctga acaataaaga aagcacagag  28440
```

-continued

```
atgcttgttt ttgatttcaa aattgtgtgc ttttatttat tttcaagctt acagtatttc  28500
cagtagtcat tcgaatagag cttaatgaaa ctgcatgaga acccttccac atagcttaaa  28560
ttatcaccag tgcaaatgga gaaaaatcaa catacctttt tatccagata tcacagaacc  28620
ctagtattca acctgccacc tccctcccaa cacacagagt acacagtcct ttctccccgg  28680
ctggccttaa aaagcatcat atcatgggta acagacatat tcttaggtgt tatattccac  28740
acggtttcct gtcgagccaa acgctcatca gtgatattaa taaactcccc gggcagctca  28800
cttaagttca tgtcgctgtc cagctgctga gccacaggct gctgtccaac ttgcggttgc  28860
ttaacgggcg gcgaaggaga agtccacgcc tacatggggg tagagtcata atcgtgcatc  28920
aggatagggc ggtggtgctg cagcagcgcg cgaataaact gctgccgccg ccgctccgtc  28980
ctgcaggaat acaacatggc agtggtctcc tcagcgatga ttcgcaccgc ccgcagcata  29040
aggcgccttg tcctccgggc acagcagcgc accctgatct cacttaaatc agcacagtaa  29100
ctgcagcaca gcaccacaat attgttcaaa atcccacagt gcaaggcgct gtatccaaag  29160
ctcatggcgg ggaccacaga acccacgtgg ccatcatacc acaagcgcag gtagattaag  29220
tggcgacccc tcataaacac gctggacata aacattacct cttttggcat gttgtaattc  29280
accacctccc ggtaccatat aaacctctga ttaaacatgg cgccatccac caccatccta  29340
aaccagctgg ccaaaacctg cccgccggct atacactgca gggaaccggg actggaacaa  29400
tgacagtgga gagcccagga ctcgtaacca tggatcatca tgctcgtcat gatatcaatg  29460
ttggcacaac acaggcacac gtgcatacac ttcctcagga ttacaagctc ctcccgcgtt  29520
agaaccatat cccagggaac aacccattcc tgaatcagcg taaatcccac actgcaggga  29580
agacctcgca cgtaactcac gttgtgcatt gtcaaagtgt tacattcggg cagcagcgga  29640
tgatcctcca gtatggtagc gcgggtttct gtctcaaaag gaggtagacg atccctactg  29700
tacggagtgc gccgagacaa ccgagatcgt gttggtcgta gtgtcatgcc aaatggaacg  29760
ccggacgtag tcatatttcc tccagcagaa ccaagtgcgc gcgtggcagc tatccttgcg  29820
tcttctgtct cgccgcctgc cccgctcggt gtagtagttg taatacagcc actccctcag  29880
accgtcaagg cgctccctgg cgtccggatc tataacaaca ccatcctgca gcgccgccct  29940
gatgacatcc accaccgtag agtatgccaa gcccagccag gaaatgcact cactttgaca  30000
gcgagagata ggaggagcgg gaagagatgg aagaaccatg atagtaaaag aacttttatt  30060
ccaatcgatc ctctacaatg tcaaagtgta gatctatcag atggcactgg tctcctccgc  30120
tgagtcgatc aaaaataaca gctaaaccac aaacaacacg attggtcaaa tgctgcacaa  30180
gggcttgcag cataaaatcg cctcgaaagt ccaccgcaag cataacatca aagccaccgc  30240
ccctatcatg atctatgata aaaaccccac agctatccac cagacccata tagttttcat  30300
ctctccatcg tgaaaaaata tttacaagct cctcctttaa atcacctcca accaattcaa  30360
aaagttgagc cagaccgccc tccaccttca ttttcagcat gcgcatcatg attgcaaaaa  30420
ttcaggctcc tcagacacct gtataagatt gagaagcgga acattaacat caatgtttcg  30480
ctcgcgaaga tcgcgcctca gtgcaagcat gatataatcc cacaggtcgg agcggatcag  30540
cgaggacatc tccccgccag gaaccaactc aacggagcct atgctgatta taatacgcat  30600
attcggggct atgctaacca gcacggcccc caaataggcg tactgcatag gcggcgacaa  30660
aaagtgaaca gtttgggtta aaaaatcagg caaacactcg cgcaaaaaag caagaacatc  30720
ataaccatgc tcatgcaaat agatgcaagt aagctcagga acgaccacag aaaaatgcac  30780
aatttttctc tcaaacatga ctgcgagccc tgcaaaaaat aaaaaagaaa cattacacaa  30840
```

```
gagtagcctg tcttacaatg ggatagacta ctctaaccaa cataagacgg gccacgacat  30900

cgcccgcgtg gccataaaaa aaattatccg tgtgattaaa aagaagcaca gatagctggc  30960

cagtcatatc cggagtcatc acgtgcgaac ccgtgtagac ccccgggttg gacacatcgg  31020

ccaaagaaag aaagcggcca atgtatcccg gaggaatgat aacactaaga cgaagataca  31080

acagaataac cccatggggg ggaataacaa agttagtagg tgaataaaaa cgataaacac  31140

ccgaaactcc ctcctgcgta ggcaaaatag cgccctcccc ttccaaaaca acatacagcg  31200

cttccacagc agccatgaca aaagactcaa aacactcaaa agactcagtc ttaccaggaa  31260

aataaaagca ctctcacagc accagcacta atcagagtgt gaagagggcc aagtgccgaa  31320

cgagtatata taggaattaa aaatgacgta aatgtgtaaa ggtcaaaaaa cgcccagaaa  31380

aatacacaga ccaacgcccg aaacgaaaac ccgcgaaaaa atacccagaa gttcctcaac  31440

aaccgccact tccgctttcc cacgatacgt cacttcctcg aaaatagcaa actacatttc  31500

ccacatgtac aaaaccgaaa ccactcccct tgtcaccgcc cacaacttac atcttaatta  31560

acaaacgtca aagcctacgt cagccgcccc gcctcgcccc gcccacctca ttatcatatt  31620

ggccacaatc caaaataagg tatattattg atgatg                            31656
```

<210> SEQ ID NO 13
<211> LENGTH: 10158
<212> TYPE: DNA
<213> ORGANISM: Artificial Sequence
<220> FEATURE:
<223> OTHER INFORMATION: BZ1/BZ28 intermediate plasmid 1

<400> SEQUENCE: 13

```
catcatcaat aatatacctt attttggatt gtggccaata tgataatgag gtgggcgggg     60

cgaggcgggg cgggtgacgt aggacgtgcg agtagggttg ggaggtgtgg cggaagtgtg    120

gcatttgtaa gtgggaggag cttacatgca agcttccgtc gcggaaaatg tgacgttttt    180

tatgagcgcc gcctacctcc ggaagtgcca attttcgcgc gctttttacc ggatatcgta    240

gtaattttgg gcgggaccat gtaagatttg gccattttcg cgcgaaaagt gaaacgggga    300

agtgaaaact gaataatagg gcgttagtca tagcgcgtaa tatttaccga gggccgaggg    360

actttgaccg attacgtgga ggactcgccc aggtgttttt tacgtgaatt tccgcgttcc    420

gggtcaaagt ctccgttttt attgtcaccg tcatttgacg cggagggtat ttaaacccgc    480

tgcgctccta gcgatcgctg atgagaccag gaccaggtgc cgaccctgcg agtgcggcgg    540

caagcacatg agaaatcagc ctgtgatgtt ggatgtgacc gaggagctta ggcctgacca    600

tctggtgctg gcctgcacca gggccgagtt tgggtctagc gatgaggata ccgattgagg    660

tgggtaaggt gggcgtggct agcagggtgg gcgtgtataa attgggggtc taaggggtct    720

ctctgtttgt cttgcaacag ccgccgcatg agcgacaccg gcaacagctt tgatggaagc    780

atctttagcc cctatctgac agtgcgcatg cctcactggg ccggagtgcg tcagaatgtg    840

atgggttcca acgtggatgg acgtcccgtt ctgccttcaa attcgtctac gatggcctac    900

gcgaccgtgg gaggaactcc gctggacgcc gcgacctccg ccgccgcctc cgccgccgcc    960

gcgaccgcgc gcagcatggc tacggacctt tacagctctt tggtggcgag cagcgcggcc   1020

tctcgcgcgt ctgctcggga tgaaaaactg actgctctgc tgcttaaact ggaagacttg   1080

acccgggagc tgggtcaact gacccagcag gtctccagct tgcgtgagag cagccttgcc   1140

tccccctaat ggcccataat ataaataaaa gccagtctgt ttggattaag caagtgtatg   1200
```

-continued

```
ttctttattt aactctccgc gcgcggtaag cccgggacca gcggtctcgg tcgtttaggg   1260
tgcggtggat tctttccaac acgtggtaca ggtggctctg gatgtttaga tacatgggca   1320
tgagtccatc cctggggtgg aggtagcacc actgcagagc ttcgtgctcg gggtggtgt    1380
tgtatatgat ccagtcgtag caggagcgct gggcgtggtg ctgaaaaatg tccttaagca   1440
agaggcttat agctaggggg aggcccttgg tgtaagtgtt tacaaatctg cttagctggg   1500
aggggtgcat ccggggggat atgatgtgca tcttggactg gatttttagg ttggctatgt   1560
tcccacccag atcccttctg ggattcatgt tgtgcaggac caccagcacg gtatatccag   1620
tgcacttggg aaatttatcg tggagcttag acgggaatgc atggaagaac ttggagacgc   1680
ccttgtggcc tcccagattt tccatacatt cgtccatgat gatggcaatg ggcccgtggg   1740
aagctgcctg agcaaaaacg tttctggcat cgctcacatc gtagttatgt tccagggtga   1800
ggtcatcata ggacatcttt acaaatcggg ggcggagggt cccggactgg gggatgatgg   1860
tacgtattgg tcgctgccaa acatgatgca agacccggtg accttccgct ccacgcggca   1920
ggttagcaac ttcccggtgg tgggcgccga actgctgccc gtgcactcca agagttttta   1980
caacgagcag gccgtctact cccagctgat ccgccaggcc acctctctga cccacgtgtt   2040
caatcgcttt cccgagaacc agattttggc gcgcccgccg gcccccacca tcaccaccgt   2100
cagtgaaaac gttcctgccc tcacagatca cgggacgcta ccgctgcgca acagcatctc   2160
aggagtccag cgagtgacca ttactgacgc cagacgccgg acctgcccct acgtttaaac   2220
gactctcttc cgagaacaga cctcaataac tcctctccgc agttccccag aacaggaggt   2280
gagctcagga aaccccgggt aaagaagggt ggacaagagt taacacttgt ggggtttctg   2340
gtgtatgtga cgctggtggt ggctcttttg attaaggctt ttccttccat gtctgaacta   2400
tccctcttct tttatgaaca actcgactag tgctaacggg accctaccca acgaatcggg   2460
attgaatatc ggtaaccagg ttgcagtttc acttttgatt accttcatag tcctcttcct   2520
gctagtgctg tcgcttctgt gcctgcggat cgggggctgc tgcatccacg tttatatctg   2580
gtgctggctg tttagaaggt tcggagacca ccgcaggtag aataaacaaa cctagaccta   2640
gaaatggacg gtctctgcag cgagcaacgc atactagaga ggcgccggca aaaagcagag   2700
ctcgagcgtc ttaaacaaga gctccaagac gccgtggcca tacaccagtg caaaaaaggg   2760
ctcttctgtc tggtaaaaca ggccacgctc acctatgaaa aaacaggtga cacccaccgc   2820
ctaggataca agctgcccac acagcgccaa aagtttgccc ttatgatagg tgaacaaccc   2880
atcaccgtga cccagcactc cgtggagaca gaaggctgca ttcatgctcc ctgcaggggc   2940
gctgactgcc tctacacctt gatcaaaacc ctttgcggtc tcagagacct tatccctttc   3000
aattgatcat aactgtaatc aataaaaaat cacttacttg aaatctgata gcaagcctct   3060
gtccaatttt ttcagcaaca cttccttccc ctcttcccaa ctctggtact ctaggcgcct   3120
cctagctgca aacttcctcc acagtctgaa gggaatgtca gattcctcct cctcctgtcc   3180
ctccgcaccc acgatcttca tgttgttgca gatgaagcgc accaaaacgt ctgacgagag   3240
cttcaacccc gtgtacccct atgacacgga aaacggtcct ccctccgtcc ctttcctcac   3300
ccctcccttc gtgtctcccg atggattcca agagagcccc cccggggtcc tgtctctgaa   3360
cctggccgag cccctggtca cttcccacgg catgctcgcc ctgaaaatgg gaagtggcct   3420
ctccctggac gacgccggca acctcacctc tcaagatgtc accaccacta cccctcccct   3480
gaaaaaaacc aagaccaacc tcagcctaga aacctcagcc cccctgactg tgagcacctc   3540
aggcgccctc accctagcag ccgccgttcc cctggcggtg gccggcacct ccctcaccat   3600
```

-continued

```
gcaatcagag gccccccctga cagtccaaga tgcaaaactc accctggcca ccaagggccc   3660
cctgaccgtg tctgaaggca aactggcctt gcagacctcg gccccgctga cggccgctga   3720
cagcagcgcc ctcaccgtta gcgccacacc acccatcagt gtaagcagtg gaagtttggg   3780
cttagacatg gaagacccca tgtatactca tgatggaaaa ctgggaataa gaattggagg   3840
cccactgaga gtagtagaca gcctgcacac actgactgta gttaccggaa atggaatagc   3900
tgtagataac aatgccctcc aaactagagt tacgggcgcc ctgggttatg acacatcagg   3960
aaacctacaa ctgagagccg cgggggggtat gcgaattgat gcaaatggcc aacttatcct   4020
tgatgtggca tacccatttg atgctcaaaa caatctcagc cttagacttg gtcagggacc   4080
cctgtatgta aacacagacc acaacctaga tttgaattgc aacagaggtc tgaccacaac   4140
taccaccaac aacacaaaaa aacttgaaac taaaattggc tcaggcttag actatgatac   4200
caatggtgct gtcattatta aacttggtac tggtgtaagc tttgacagca caggcgccct   4260
aactgtggga aacactggcg atgataaact gactctgtgg acaaccccag acccatctcc   4320
aaattgcaga attcacgcag acaaagactg caagtttact ctagtcctaa ctaagtgtgg   4380
aagtcaaatc ctggcttctg tcgccgccct agcggtgtca ggaaatctgg cttcaataac   4440
aggcaccgtt gccagcgtta ccatctttct cagatttgat cagaatggag tgcttatgga   4500
aaactcctcc ctagacaagc agtactggaa cttcagaaat ggtaactcaa ccaatgccac   4560
cccctacacc aatgcagttg ggttcatgcc aaacctcgca gcatacccca agacacagag   4620
ccagactgct aaaaacaaca ttgtaagtca ggtttacttg aatggggaca aatccaaacc   4680
catgaccctt accattaccc tcaatggaac taatgaatcc agtgaaacta gccaggtgag   4740
tcactactcc atgtcattta catgggcttg ggagagtggg caatatgcca ccgaaacctt   4800
tgccaccaat tcctttacct tctcttacat tgctgaacaa taaagaaagc acagagatgc   4860
ttgtttttga tttcaaaatt gtgtgctttt atttattttc aagcttacag tatttccagt   4920
agtcattcga atagagctta atgaaactgc atgagaaccc ttccacatag cttaaattat   4980
caccagtgca aatggagaaa aatcaacata cctttttatc cagatatcac agaaccctag   5040
tattcaacct gccacctccc tcccaacaca cagagtacac agtcctttct ccccggctgg   5100
ccttaaaaag catcatatca tgggtaacag acatattctt aggtgttata ttccacacgg   5160
tttcctgtcg agccaaacgc tcatcagtga tattaataaa ctccccgggc agctcactta   5220
agttcatgtc gctgtccagc tgctgagcca caggctgctg tccaacttgc ggttgcttaa   5280
cgggcggcga aggagaagtc cacgcctaca tgggggtaga gtcataatcg tgcatcagga   5340
tagggcggtg gtgctgcagc agcgcgcgaa taaactgctg ccgccgccgc tccgtcctgc   5400
aggaatacaa catggcagtg gtctcctcag cgatgattcg caccgcccgc agcataaggc   5460
gccttgtcct ccgggcacag cagcgcaccc tgatctcact taaatcagca cagtaactgc   5520
agcacagcac cacaatattg ttcaaaatcc cacagtgcaa ggcgctgtat ccaaagctca   5580
tggcggggac cacagaaccc acgtggccat cataccacaa gcgcaggtag attaagtggc   5640
gacccctcat aaacacgctg gacataaaca ttacctcttt tggcatgttg taattcacca   5700
cctcccggta ccatataaac ctctgattaa acatggcgcc atccaccacc atcctaaacc   5760
agctggccaa aacctgcccg ccggctatac actgcaggga accgggactg gaacaatgac   5820
agtggagagc ccaggactcg taaccatgga tcatcatgct cgtcatgata tcaatgttgg   5880
cacaacacag gcacacgtgc atacacttcc tcaggattac aagctcctcc cgcgttagaa   5940
```

-continued

```
ccatatccca gggaacaacc cattcctgaa tcagcgtaaa tcccacactg cagggaagac   6000
ctcgcacgta actcacgttg tgcattgtca aagtgttaca ttcgggcagc agcggatgat   6060
cctccagtat ggtagcgcgg gtttctgtct caaaaggagg tagacgatcc ctactgtacg   6120
gagtgcgccg agacaaccga gatcgtgttg gtcgtagtgt catgccaaat ggaacgccgg   6180
acgtagtcat atttcctcca gcagaaccaa gtgcgcgcgt ggcagctatc cttgcgtctt   6240
ctgtctcgcc gcctgccccg ctcggtgtag tagttgtaat acagccactc cctcagaccg   6300
tcaaggcgct ccctggcgtc cggatctata acaacaccat cctgcagcgc cgccctgatg   6360
acatccacca ccgtagagta tgccaagccc agccaggaaa tgcactcact ttgacagcga   6420
gagataggag gagcgggaag agatggaaga accatgatag taaaagaact tttattccaa   6480
tcgatcctct acaatgtcaa agtgtagatc tatcagatgg cactggtctc ctccgctgag   6540
tcgatcaaaa ataacagcta aaccacaaac aacacgattg gtcaaatgct gcacaagggc   6600
ttgcagcata aaatcgcctc gaaagtccac cgcaagcata acatcaaagc caccgcccct   6660
atcatgatct atgataaaaa ccccacagct atccaccaga cccatatagt tttcatctct   6720
ccatcgtgaa aaaatattta caagctcctc ctttaaatca cctccaacca attcaaaaag   6780
ttgagccaga ccgccctcca ccttcatttt cagcatgcgc atcatgattg caaaaattca   6840
ggctcctcag acacctgtat aagattgaga agcggaacat taacatcaat gtttcgctcg   6900
cgaagatcgc gcctcagtgc aagcatgata taatcccaca ggtcggagcg gatcagcgag   6960
gacatctccc cgccaggaac caactcaacg gagcctatgc tgattataat acgcatattc   7020
ggggctatgc taaccagcac ggcccccaaa taggcgtact gcataggcgg cgacaaaaag   7080
tgaacagttt gggttaaaaa atcaggcaaa cactcgcgca aaaaagcaag aacatcataa   7140
ccatgctcat gcaaatagat gcaagtaagc tcaggaacga ccacagaaaa atgcacaatt   7200
tttctctcaa acatgactgc gagccctgca aaaaataaaa aagaaacatt acacaagagt   7260
agcctgtctt acaatgggat agactactct aaccaacata agacgggcca cgacatcgcc   7320
cgcgtggcca taaaaaaaat tatccgtgtg attaaaaaga agcacagata gctggccagt   7380
catatccgga gtcatcacgt gcgaacccgt gtagaccccc gggttggaca catcggccaa   7440
agaaagaaag cggccaatgt atcccggagg aatgataaca ctaagacgaa gatacaacag   7500
aataacccca tggggggGaa taacaaagtt agtaggtgaa taaaaacgat aaacacccga   7560
aactccctcc tgcgtaggca aaatagcgcc ctccccttcc aaaacaacat acagcgcttc   7620
cacagcagcc atgacaaaag actcaaaaca ctcaaaagac tcagtcttac caggaaaata   7680
aaagcactct cacagcacca gcactaatca gagtgtgaag agggccaagt gccgaacgag   7740
tatatatagg aattaaaaat gacgtaaatg tgtaaaggtc aaaaaacgcc cagaaaaata   7800
cacagaccaa cgcccgaaac gaaaacccgc gaaaaaatac ccagaagttc ctcaacaacc   7860
gccacttccg ctttcccacg atacgtcact tcctcgaaaa tagcaaacta catttcccac   7920
atgtacaaaa ccgaaaccac tccccttgtc accgcccaca acttacatct taattaacaa   7980
acgtcaaagc ctacgtcagc cgccccgcct cgccccgccc acctcattat catattggcc   8040
acaatccaaa ataaggtata ttattgatga tgatttaaat attatgcggt gtgaaatacc   8100
gcacagatgc gtaaggagaa aataccgcat caggcgctct tccgcttcct cgctcactga   8160
ctcgctgcgc tcggtcgttc ggctgcggcg agcggtatca gctcactcaa aggcggtaat   8220
acggttatcc acagaatcag gggataacgc aggaaagaac atgtgagcaa aaggccagca   8280
aaaggccagg aaccgtaaaa aggccgcgtt gctggcgttt ttccataggc tccgcccccc   8340
```

tgacgagcat cacaaaaatc gacgctcaag tcagaggtgg cgaaacccga caggactata 8400
aagataccag gcgtttcccc ctggaagctc cctcgtgcgc tctcctgttc cgaccctgcc 8460
gcttaccgga tacctgtccg cctttctccc ttcgggaagc gtggcgcttt ctcatagctc 8520
acgctgtagg tatctcagtt cggtgtaggt cgttcgctcc aagctgggct gtgtgcacga 8580
accccccgtt cagcccgacc gctgcgcctt atccggtaac tatcgtcttg agtccaaccc 8640
ggtaagacac gacttatcgc cactggcagc agccactggt aacaggatta gcagagcgag 8700
gtatgtaggc ggtgctacag agttcttgaa gtggtggcct aactacggct acactagaag 8760
gacagtattt ggtatctgcg ctctgctgaa gccagttacc ttcggaaaaa gagttggtag 8820
ctcttgatcc ggcaaacaaa ccaccgctgg tagcggtggt ttttttgttt gcaagcagca 8880
gattacgcgc agaaaaaaag gatctcaaga agatcctttg atcttttcta cggggtctga 8940
cgctcagtgg aacgaaaact cacgttaagg gattttggtc atgagattat caaaaaggat 9000
cttcacctag atccttttaa attaaaaatg aagttttaaa tcaatctaaa gtatatatga 9060
gtaaacttgg tctgacagtt accaatgctt aatcagtgag gcacctatct cagcgatctg 9120
tctatttcgt tcatccatag ttgcctgact ccccgtcgtg tagataacta cgatacggga 9180
gggcttacca tctggcccca gtgctgcaat gataccgcga gacccacgct caccggctcc 9240
agatttatca gcaataaacc agccagccgg aagggccgag cgcagaagtg gtcctgcaac 9300
tttatccgcc tccatccagt ctattaattg ttgccgggaa gctagagtaa gtagttcgcc 9360
agttaatagt ttgcgcaacg ttgttgccat tgctgcaggc atcgtggtgt cacgctcgtc 9420
gtttggtatg gcttcattca gctccggttc ccaacgatca aggcgagtta catgatcccc 9480
catgttgtgc aaaaaagcgg ttagctcctt cggtcctccg atcgttgtca gaagtaagtt 9540
ggccgcagtg ttatcactca tggttatggc agcactgcat aattctctta ctgtcatgcc 9600
atccgtaaga tgcttttctg tgactggtga gtactcaacc aagtcattct gagaatagtg 9660
tatgcggcga ccgagttgct cttgcccggc gtcaacacgg gataataccg cgccacatag 9720
cagaacttta aaagtgctca tcattggaaa acgttcttcg gggcgaaaac tctcaaggat 9780
cttaccgctg ttgagatcca gttcgatgta acccactcgt gcacccaact gatcttcagc 9840
atcttttact ttcaccagcg tttctgggtg agcaaaaaca ggaaggcaaa atgccgcaaa 9900
aaagggaata agggcgacac ggaaatgttg aatactcata ctcttccttt ttcaatatta 9960
ttgaagcatt tatcagggtt attgtctcat gagcggatac atatttgaat gtatttagaa 10020
aaataaacaa ataggggttc cgcgcacatt tccccgaaaa gtgccacctg acgtctaaga 10080
aaccattatt atcatgacat taacctataa aaataggcgt atcacgaggc cctttcgtct 10140
tcaagaattg atttaaat 10158

<210> SEQ ID NO 14
<211> LENGTH: 2927
<212> TYPE: DNA
<213> ORGANISM: Artificial Sequence
<220> FEATURE:
<223> OTHER INFORMATION: BZ1/BZ28.5IXP Ad vector fragment

<400> SEQUENCE: 14
gcgatcgcgg tactgaaatg tgtgggcgtg gcttaagggt gggaaagaat atataaggtg 60
ggggtcttat gtagttttgt atctgttttg cagcagccgc cgccgccatg agcgacaccg 120
gcaacagctt tgatggaagc atctttagcc cctatctgac agtgcgcatg cctcactggg 180

-continued

```
ccggagtgcg tcagaatgtg atgggttcca acgtggatgg acgtcccgtt ctgccttcaa    240
attcgtctac gatggcctac gcgaccgtgg gaggaactcc gctggacgcc gcgacctccg    300
ccgccgcctc cgccgccgcc gcgaccgcgc gcagcatggc tacggacctt tacagctctt    360
tggtggcgag cagcgcggcc tctcgcgcgt ctgctcggga tgaaaaactg actgctctgc    420
tgcttaaact ggaagacttg acccgggagc tgggtcaact gacccagcag gtctccagct    480
tgcgtgagag cagccttgcc tccccctaat ggcccataat ataaataaaa gccagtctgt    540
ttggattaag caagtgtatg ttctttattt aactctccgc gcgcggtaag cccgggacca    600
gcggtctcgg tcgtttaggg tgcggtggat tctttccaac acgtggtaca ggtggctctg    660
gatgtttaga tacatgggca tgagtccatc cctggggtgg aggtagcacc actgcagagc    720
ttcgtgctcg gggtggtgt tgtatatgat ccagtcgtag caggagcgct gggcgtggtg    780
ctgaaaaatg tccttaagca agaggcttat agctaggggg aggcccttgg tgtaagtgtt    840
tacaaatctg cttagctggg aggggtgcat ccggggggat atgatgtgca tcttggactg    900
gatttttagg ttggctatgt tcccacccag atcccttctg ggattcatgt tgtgcaggac    960
caccagcacg gtatatccag tgcacttggg aaatttatcg tggagcttag acgggaatgc   1020
atggaagaac ttggagacgc ccttgtggcc tcccagattt tccatacatt cgtccatgat   1080
gatggcaatg ggcccgtggg aagctgcctg agcaaaaacg tttctggcat cgctcacatc   1140
gtagttatgt tccagggtga ggtcatcata ggacatcttt acaaatcggg ggcggagggt   1200
cccggactgg gggatgatgg taccctcggg ccccggggcg tagttcccct cacagatctg   1260
catctcccag gctttcattt cagagggagg gatcatatcc acctgcgggg cgatgaaaaa   1320
gacagtttct ggcgcagggg agattaactg ggatgagagc aggtttctga gcagctgtga   1380
ctttccacag ccggtgggcc catatatcac gcctatcacc ggctgcagct ggtagttaag   1440
agagctgcag ctgccgtcct cccggagcag gggggccacc tcgttgagca tatccctgac   1500
gtggatgttc tccctgacca gttccgccag aaggcgctcg ccgcccagcg aaagcagctc   1560
ttgcaaggaa gcaaaatttt tcagcggttt caggccatcg gccgtgggca tgtttttcag   1620
cgtctgggtc agcagctcca gcctgtccca gagctcggtg atgtgctcta cggcatctcg   1680
atccagcaga tctcctcgtt tcgcgggttg ggcggcttt cgctgtaggg caccagccga   1740
tgggcgtcca gcggggccag agtcatgtcc ttccatgggc gcagagtcct cgtcagggtg   1800
gtctgggtca cggtgaaggg gtgcgctccg ggttgggcac tggccagggt gcgcttgagg   1860
ctggttctgc tggtgctgaa tcgctgccgc tcttcgccct gcgcgtcggc caggtagcat   1920
ttgaccatgg tctcgtagtc gagaccctcg gcggcgtgcc ccttggcgcg gagctttccc   1980
ttggaggtgg cgccgcacga ggggcactgc aggctcttca gggcgtagag cttgggagcg   2040
agaaacacgg actctgggga gtaggcgtcc gcgccgcagg ccgcgcagac cgtctcgcat   2100
tccaccagcc aagtgagttc cgggcggtca gggtcaaaaa ccaggttgcc cccatgcttt   2160
ttgatgcgtt tcttacctcg gctctccatg aggcggtgtc ccttctcggt gacgaagagg   2220
ctgtccgtgt ccccgtagac cgacttcagg ggcctgtctt ccagcggagt gcctctgtcc   2280
tcctcgtaga gaaactctga ccactctgag acgaaggccc gtgtccaggc caggacgaag   2340
gaggccacgt gggaggggta gcggtcgttg tccactagcg ggtccacctt ctccagggtg   2400
tgcagacaca tgtccccctc ctccgcgtcc agaaaagtga ttggcttata ggtgtaggac   2460
acgtgaccgg gggttcccga cggggggta taaaaggggg tgggcgccct ttcatcttca   2520
ctctcttccg catcgctgtc tgcgagagcc agctgctggg gtaagtattc cctttcaaag   2580
```

-continued gcgggcatga cctcagcgct caggttgtca gtttctaaaa atgaggagga tttgatgttc 2640
acctgtccgg aagtgatacc tttgagggta cctgggtcca tctggtcaga aaacactatt 2700
tttttgttgt caagcttggt ggcgaacgac ccgtagaggg cgttggagag cagcttggca 2760
atggagcgca gggtctggtt tttgtcgcgg tcggctcgct ccttggccgc gatgttgagt 2820
tgcacgtatt cgcgggccac gcacttccac tcggggaaga cggtggtgcg ctcgtctggg 2880
atcaggcgca ccctccagcc gcggttgtgc agggtgacca tgtcgac 2927

<210> SEQ ID NO 15
<211> LENGTH: 36563
<212> TYPE: DNA
<213> ORGANISM: Artificial Sequence
<220> FEATURE:
<223> OTHER INFORMATION: pBZ1_BZ28F.Fluc

<400> SEQUENCE: 15
catcatcaat aatatacctt attttggatt gtggccaata tgataatgag gtgggcgggg 60
cgaggcgggg cgggtgacgt aggacgtgcg agtagggttg ggaggtgtgg cggaagtgtg 120
gcatttgtaa gtgggaggag cttacatgca agcttccgtc gcggaaaatg tgacgttttt 180
tatgagcgcc gcctacctcc ggaagtgcca attttcgcgc gctttttacc ggatatcgta 240
gtaattttgg gcgggaccat gtaagatttg gccattttcg cgcgaaaagt gaaacgggga 300
agtgaaaact gaataatagg gcgttagtca tagcgcgtaa tatttaccga gggccgaggg 360
actttgaccg attacgtgga ggactcgccc aggtgttttt tacgtgaatt tccgcgttcc 420
gggtcaaagt ctccgttttt attgtcaccg tcatttgacg cggagggtat ttaaacccgc 480
tgcgctccta gcgatcgctc aatattggcc attagccata ttattcattg gttatatagc 540
ataaatcaat attggctatt ggccattgca tacgttgtat ccatatcata atatgtacat 600
ttatattggc tcatgtccaa cattaccgcc atgttgacat tgattattga ctagttatta 660
atagtaatca attacggggt cattagttca tagcccatat atggagttcc gcgttacata 720
acttacggta aatggcccgc ctggctgacc gcccaacgac ccccgcccat tgacgtcaat 780
aatgacgtat gttcccatag taacgccaat agggactttc cattgacgtc aatgggtgga 840
gtatttacgg taaactgccc acttggcagt acatcaagtg tatcatatgc caagtacgcc 900
ccctattgac gtcaatgacg gtaaatggcc cgcctggcat tatgcccagt acatgacctt 960
atgggacttt cctacttggc agtacatcta cgtattagtc atcgctatta ccatggtgat 1020
gcggttttgg cagtacatca atgggcgtgg atagcggttt gactcacggg gatttccaag 1080
tctccacccc attgacgtca atgggagttt gttttggcac caaaatcaac gggactttcc 1140
aaaatgtcgt aacaactccg ccccattgac gcaaatgggc ggtaggcgtg tacggtggga 1200
ggtctatata agcagagctc gtttagtgaa ccgtcagatc gcctggagac gccatccacg 1260
ctgttttgac ctccatagaa gacaccggga ccgatccagc ctccgcggcc gggaacggtg 1320
cattggaagc ttggcattcc ggtactgttg gtaaagccac catggaagac gccaaaaaca 1380
taaagaaagg cccggcgcca ttctatccgc tggaagatgg aaccgctgga gagcaactgc 1440
ataaggctat gaagagatac gccctggttc ctggaacaat tgcttttaca gatgcacata 1500
tcgaggtgga catcacttac gctgagtact tcgaaatgtc cgttcggttg gcagaagcta 1560
tgaaacgata tgggctgaat acaaatcaca gaatcgtcgt atgcagtgaa aactctcttc 1620
aattctttat gccggtgttg ggcgcgttat ttatcggagt tgcagttgcg cccgcgaacg 1680

-continued

```
acatttataa tgaacgtgaa ttgctcaaca gtatgggcat ttcgcagcct accgtggtgt   1740
tcgtttccaa aaaggggttg caaaaaattt tgaacgtgca aaaaaagctc ccaatcatcc   1800
aaaaaattat tatcatggat tctaaaacgg attaccaggg atttcagtcg atgtacacgt   1860
tcgtcacatc tcatctacct cccggtttta atgaatacga ttttgtgcca gagtccttcg   1920
atagggacaa gacaattgca ctgatcatga actcctctgg atctactggt ctgcctaaag   1980
gtgtcgctct gcctcataga actgcctgcg tgagattctc gcatgccaga gatcctattt   2040
ttggcaatca aatcattccg gatactgcga ttttaagtgt tgttccattc catcacggtt   2100
ttggaatgtt tactacactc ggatatttga tatgtggatt tcgagtcgtc ttaatgtata   2160
gatttgaaga agagctgttt ctgaggagcc ttcaggatta caagattcaa agtgcgctgc   2220
tggtgccaac cctattctcc ttcttcgcca aaagcactct gattgacaaa tacgatttat   2280
ctaatttaca cgaaattgct tctggtggcg ctcccctctc taaggaagtc ggggaagcgg   2340
ttgccaagag gttccatctg ccaggtatca ggcaaggata tgggctcact gagactacat   2400
cagctattct gattacaccc gagggggatg ataaaccggg cgcggtcggt aaagttgttc   2460
cattttttga agcgaaggtt gtggatctgg ataccgggaa aacgctgggc gttaatcaaa   2520
gaggcgaact gtgtgtgaga ggtcctatga ttatgtccgg ttatgtaaac aatccggaag   2580
cgaccaacgc cttgattgac aaggatggat ggctacattc tggagacata gcttactggg   2640
acgaagacga acacttcttc atcgttgacc gcctgaagtc tctgattaag tacaaaggct   2700
atcaggtggc tcccgctgaa ttggaatcca tcttgctcca acaccccaac atcttcgacg   2760
caggtgtcgc aggtcttccc gacgatgacg ccggtgaact tcccgccgcc gttgttgttt   2820
tggagcacgg aaagacgatg acggaaaaag agatcgtgga ttacgtcgcc agtcaagtaa   2880
caaccgcgaa aaagttgcgc ggaggagttg tgtttgtgga cgaagtaccg aaaggtctta   2940
ccggaaaact cgacgcaaga aaaatcagag agatcctcat aaaggccaag aagggcggaa   3000
agatcgccgt gtaattctag acgagatccg aacttgttta ttgcagctta taatggttac   3060
aaataaagca atagcatcac aaatttcaca aataaagcat ttttttcact gcattctagt   3120
tgtggtttgt ccaaactcat caatgtatct tatcatgtct gcgatcgctg atgagaccag   3180
gaccaggtgc cgaccctgcg agtgcggcgg caagcacatg agaaatcagc ctgtgatgtt   3240
ggatgtgacc gaggagctta ggcctgacca tctggtgctg gcctgcacca gggccgagtt   3300
tgggtctagc gatgaggata ccgattgagg tgggtaaggt gggcgtggct agcagggtgg   3360
gcgtgtataa attgggggtc taaggggtct ctctgtttgt cttgcaacag ccgccgccat   3420
gagcgacacc ggcaacagct ttgatggaag catctttagc ccctatctga cagtgcgcat   3480
gcctcactgg gccggagtgc gtcagaatgt gatgggttcc aacgtggatg gacgtcccgt   3540
tctgccttca aattcgtcta cgatggccta cgcgaccgtg ggaggaactc cgctggacgc   3600
cgcgacctcc gccgccgcct ccgccgccgc cgcgaccgcg cgcagcatgg ctacggacct   3660
ttacagctct ttggtggcga gcagcgcggc ctctcgcgcg tctgctcggg atgaaaaact   3720
gactgctctg ctgcttaaac tggaagactt gacccgggag ctgggtcaac tgacccagca   3780
ggtctccagc ttgcgtgaga gcagccttgc ctccccctaa tggcccataa tataaataaa   3840
agccagtctg tttggattaa gcaagtgtat gttctttatt taactctccg cgcgcggtaa   3900
gcccgggacc agcggtctcg gtcgtttagg gtgcggtgga ttctttccaa cacgtggtac   3960
aggtggctct ggatgtttag atacatgggc atgagtccat ccctggggtg gaggtagcac   4020
cactgcagag cttcgtgctc gggggtggtg ttgtatatga tccagtcgta gcaggagcgc   4080
```

-continued tgggcgtggt gctgaaaaat gtccttaagc aagaggctta tagctagggg gaggcccttg 4140
gtgtaagtgt ttacaaatct gcttagctgg gaggggtgca tccgggggga tatgatgtgc 4200
atcttggact ggatttttag gttggctatg ttcccaccca gatcccttct gggattcatg 4260
ttgtgcagga ccaccagcac ggtatatcca gtgcacttgg gaaatttatc gtggagctta 4320
gacgggaatg catggaagaa cttggagacg cccttgtggc ctcccagatt ttccatacat 4380
tcgtccatga tgatggcaat gggcccgtgg gaagctgcct gagcaaaaac gtttctggca 4440
tcgctcacat cgtagttatg ttccagggtg aggtcatcat aggacatctt tacaaatcgg 4500
gggcggaggg tcccggactg ggggatgatg gtaccctcgg gccccggggc gtagttcccc 4560
tcacagatct gcatctccca ggctttcatt tcagagggag ggatcatatc cacctgcggg 4620
gcgatgaaaa agacagtttc tggcgcaggg gagattaact gggatgagag caggtttctg 4680
agcagctgtg actttccaca gccggtgggc ccatatatca cgcctatcac cggctgcagc 4740
tggtagttaa gagagctgca gctgccgtcc tcccggagca ggggggccac ctcgttgagc 4800
atatccctga cgtggatgtt ctccctgacc agttccgcca gaaggcgctc gccgcccagc 4860
gaaagcagct cttgcaagga agcaaaattt ttcagcggtt tcaggccatc ggccgtgggc 4920
atgtttttca gcgtctgggt cagcagctcc agcctgtccc agagctcggt gatgtgctct 4980
acggcatctc gatccagcag atctcctcgt ttcgcgggtt ggggcggctt tcgctgtagg 5040
gcaccagccg atgggcgtcc agcggggcca gagtcatgtc cttccatggg cgcagagtcc 5100
tcgtcagggt ggtctgggtc acggtgaagg ggtgcgctcc gggttgggca ctggccaggg 5160
tgcgcttgag gctggttctg ctggtgctga atcgctgccg ctcttcgccc tgcgcgtcgg 5220
ccaggtagca tttgaccatg gtctcgtagt cgagaccctc ggcggcgtgc cccttggcgc 5280
ggagctttcc cttggaggtg gcgccgcacg aggggcactg caggctcttc agggcgtaga 5340
gcttgggagc gagaaacacg gactctgggg agtaggcgtc cgcgccgcag gccgcgcaga 5400
ccgtctcgca ttccaccagc caagtgagtt ccgggcggtc agggtcaaaa accaggttgc 5460
ccccatgctt tttgatgcgt ttcttacctc ggctctccat gaggcggtgt cccttctcgg 5520
tgacgaagag gctgtccgtg tccccgtaga ccgacttcag ggcctgtct tccagcggag 5580 tgcctctgtc ctcctcgtag agaaactctg accactctga gacgaaggcc cgtgtccagg 5640
ccaggacgaa ggaggccacg tgggaggggt agcggtcgtt gtccactagc gggtccacct 5700
tctccagggt gtgcagacac atgtcccccct cctccgcgtc cagaaaagtg attggcttat 5760
aggtgtagga cacgtgaccg gggttcccg acgggggggt ataaaagggg gtgggcgccc 5820
tttcatcttc actctcttcc gcatcgctgt ctgcgagagc cagctgctgg ggtaagtatt 5880
ccctttcaaa ggcgggcatg acctcagcgc tcaggttgtc agtttctaaa aatgaggagg 5940
atttgatgtt cacctgtccg gaagtgatac ctttgagggt acctgggtcc atctggtcag 6000
aaaacactat ttttttgttg tcaagcttgg tggcgaacga cccgtagagg gcgttggaga 6060
gcagcttggc aatggagcgc agggtctggt ttttgtcgcg gtcggctcgc tccttggccg 6120
cgatgttgag ttgcacgtat tcgcgggcca cgcacttcca ctcggggaag acggtggtgc 6180
gctcgtctgg gatcaggcgc accctccagc cgcggttgtg cagggtgacc atgtcgacgc 6240
tggtggcgac ctcaccgcgc agacgctcgt tggtccagca gaggcggccg cctttgcgcg 6300
agcagaaggg gggtaggggg tccagctggt cctcgtttgg ggggtccgcg tcgatggtaa 6360
agaccccggg gagcaggcgc gggtcaaagt agtcgatctt gcaagcttgc atgtccagag 6420

-continued

```
cccgctgcca ttcgcgggcg gcgagcgcgc gctcgtaggg gttgaggggc gggccccagg   6480
gcatggggtg ggtgagcgcg gaggcgtaca tgccgcagat gtcatacacg tacaggggtt   6540
ccctgaggat accgaggtag gtggggtagc agcgcccccc gcggatgctg gcgcgcacgt   6600
agtcatagag ctcgtgggag ggggccagca tgttgagccc aaggttggtg cgctgggggc   6660
gctcggcgcg gaagacgatc tgtctgaaga tggcatggga gttggaggag atggtgggtc   6720
gctggaagac gttgaagctt gcttcttgca agcccacgga gtccctgacg aaggaggcgt   6780
aggactcgcg cagcttgtgc accagctcgg cggtgacctg gacgtcgagc gcgcagtagt   6840
cgagggtctc gcggatgatg tcatacttat cctcccctt cttttccac agctcgcggt    6900
tgaggacgaa ctcttcgcgg tctttccagt actcttggag gggaaacccg tccgtgtccg   6960
aacggtaaga gcctagcatg tagaactggt tgacggcctg gtaggggcag cagcccttct   7020
ccacgggcag cgcgtaggcc tgcgccgcct tgcggaggga ggtgtgggta agggcgaaag   7080
tgtccctgac catgactttg aggtattgat gtctgaagtc tgtgtcatcg cagccgccct   7140
gttcccacag ggtgtagtcc gtgcgctttt tggagcgcgg gttgggcagg gagaaggtga   7200
ggtcattgaa gaggatcttc cccgctcgag gcatgaagtt tctggtgatg cgaaagggcc   7260
ctgggaccga ggagcggttg ttgatgacct gggcggccag gacgatctcg tcaaagccgt   7320
ttatgttgtg gcccacgatg tagagctcca ggaagcgggg ctggcccttg atggagggga   7380
gctttttaag ttcctcgtag gtaagctcct cgggcgattc caggccgtgc tcctccaggg   7440
cccagtcttg caagtgaggg ttggccgcca ggaaggatcg ccagaggtcg cgggccatga   7500
gggtctgcag gcggtcgcgg aaggttctga actgccgccc tacggccatc ttttcggggg   7560
tgatgcagta gaaggtgagg gggtctttct cccaggggtc ccatctgagc tcttgggcga   7620
ggtcgcgcgc ggcggcgacc agagcctcgt cgccccccag tttcatgacc agcatgaagg   7680
gcacgagctg cttgccaaag gctcccatcc aagtgtaggt ctctacatcg taggtgacaa   7740
agaggcgctc cgtgcgagga tgagagccga tcgggaagaa ctggatctcc cgccaccagt   7800
tggaggattg gctgttgatg tggtgaaagt agaagtcccg tctgcgggcc gagcactcgt   7860
gctggctttt gtaaaagcga ccgcagtact ggcagcgctg cacgggttgt atatcttgca   7920
cgaggtgaac ctggcgacct ctgacgagga agcgcagcgg gaatctaagt cccccgcctg   7980
gggtcccgtg tggctggtgg tcttctactt tggttgtctg gccgccagca tctgtctcct   8040
ggagggcgat ggtggagcag accaccacgc cgcgagagcc gcaggtccag atctcggcgc   8100
tcggcgggcg gagtttgatg acgacatcgc gcacattgga gctgtccatg gtctccagct   8160
cccgcggcgg caggtcagcc gggagttcct ggaggttcac ctcgcagaga cgggtcaagg   8220
cgcggacagt gttgagatgg tatctgattt caaggggcgt gttggaggcg gagtcgatgg   8280
cttgcagaag gccgcagccc cgggggcca cgatggttcc ccgcggggcg cgaggggagg    8340
cggaagctgg gggtgtgttc agaagcggtg acgcgggcgg gcccccggag gtaggggggg   8400
ttccggcccc acaggcatgg gcggcagggg cacgtcttcg ccgcgcgcgg gcaggggctg   8460
gtgctggctc cggagagcgc ttgcgtgcgc gacgacgcga cggttggtgt cctgtatctg   8520
gcgcctctga gtgaagacca cgggtcccgt gaccttgaac ctgaaagaga gttcgacaga   8580
atcaatctcg gcatcgttga cagcggcctg gcgcaggatc tcctgcacgt cgcccgagtt   8640
gtcctggtag gcgatctctg ccatgaactg ctcgatctct tcctcctgga gatctcctcg   8700
tccggcgcgc tccacggtgg ccgccaggtc gttggagatg cgacccatga gctgcgagaa   8760
ggcgttgagg ccgccctcgt tccagacccg gctgtagacc acgcccccct cggcgtcgcg   8820
```

```
ggcgcgcatg accacctggg ccaggttgag ctccacgtgt cgcgtgaaga cggcgtagtt   8880
gcgcaggcgc tggaaaaggt agttcagggt ggtggcggtg tgttcggcga cgaagaagta   8940
catgacccag cgccgcaacg tggattcatt gatgtccccc aaggcctcca ggcgctccat   9000
ggcctcgtag aagtccacgg cgaagttgaa aaactgggag ttgcgagcgg acacggtcaa   9060
ctcctcctcc agaagacgga tgagctcggc gacagtgtcg cgcacctcgc gctcgaaggc   9120
cacgggggc gcttcttcct cttccacctc ttcttccatg attgcttctt cttcctcagc   9180
cgggacggga gggggcggcg gcgggggagg ggcgcggcgg cggcggcggc gcaccggcag   9240
gcggtcgatg aagcgctcga tcatctcccc ccgcatgcgg cgcatggtct cggtgacggc   9300
gcggccgttc tcccgggggc gcagctcaaa gacgccgcct ctcatctcgc cgcggggcgg   9360
gcggccgtga ggtagcgaga cggcgctgac tatgcatctt aacaattgct gtgtaggtac   9420
gccgccaagg gacctgattg agtccagatc caccggatcc gaaaaccttt ggaggaaagc   9480
gtctatccag tcgcagtcgc aaggtaggct gagcaccgtg gcgggcgggg gcgggtcggg   9540
agagttcctg gcggagatgc tgctgatgat gtaattaaag taggcggtct tgagaaggcg   9600
gatggtggac aggagcacca tgtctttggg tccggcctgt tggatgcgga ggcggtcggc   9660
catgccccag gcctcgttct gacaccggcg caggtctttg tagtagtctt gcatgagtct   9720
ttccaccggc acctcttctc cttcctcttc tccatctcgc cggtggtttc tcgcgccgcc   9780
catgcgcgtg accccaaagc ccctgagcgg ctgcagcagg gccaggtcgg cgaccacgcg   9840
ctcggccaag atggcctgct gtacctgagt gagggtcctc tcgaagtcat ccatgtccac   9900
gaagcggtgg taggcgcccg tgttgatggt gtaggtgcag ttggccatga cggaccagtt   9960
gacggtctgg tgtcccggct gcgagagctc cgtgtaccgc aggcgcgaga aggcgcggga  10020
atcgaacacg tagtcgttgc aagtccgcac cagatactgg tagcccacca ggaagtgcgg  10080
cggaggttgg cgatagaggg gccagcgctg ggtggcgggg gcgccgggcg ccaggtcttc  10140
cagcatgagg cggtggtatc cgtagatgta cctggacatc caggtgatgc cggcggcggt  10200
ggtggtggcg cgcgcgtagt cgcggacccg gttccagatg tttcgcaggg gcgagaagtg  10260
ttccatggtc ggcacgctct ggccggtgag gcgcgcgcag tcgttgacgc tctatacaca  10320
cacaaaaacg aaagcgttta cagggctttc gttctgtagc ctggaggaaa gtaaatgggt  10380
tgggttgcgg tgtgccccgg ttcgagacca agctgagctc ggccggctga agccgcagct  10440
aacgtggtat tggcagtccc gtctcgaccc aggccctgta tcctccagga tacggtcgag  10500
agccctttttg ctttcttggc caagcgcccg tggcgcgatc tgggatagat ggtcgcgatg  10560
agaggacaaa agcggctcgc ttccgtagtc tggagaaaca atcgccaggg ttgcgttgcg  10620
gcgtaccccg gttcgagccc ctatggcggc ttggatcggc cggaaccgcg gctaacgtgg  10680
gctgtggcag ccccgtcctc aggaccccgc cagccgactt ctccagttac gggagcgagc  10740
cccttttgtt ttttattttt tagatgcatc ccgtgctgcg gcagatgcgc ccctcgcccc  10800
ggcccgatca gcagcagcaa cagcaggcat gcagaccccc ctctcctcta cccgccccgg  10860
tcaccacggc cgcggcggcc gtgtccggcg cggggggcgc gctggagtca gatgagccac  10920
cgcggcggcg acctaggcag tatctggact tggaagaggg cgagggactg gcgcggctgg  10980
gggcgagctc tccagagcgc cacccgcggg tgcagttgaa aagggacgcg cgcgaggcgt  11040
acctgccgcg gcagaacctg tttcgcgacc gcgggggcga ggagcccgag gagatgcgag  11100
actgcaggtt ccaagcgggg cgcgagctgc gccgcgggtt ggacagacag cgcctgctgc  11160
```

-continued gcgaggagga ctttgagccc gacacgcaga cgggcatcag ccccgcgcgc gcgcacgtgg 11220
ccgcggccga cctggtgacc gcctacgagc agacggtgaa ccaggagcgc aacttccaaa 11280
aaagcttcaa caaccacgtg cgcacgctgg tggcgcgcga ggaggtgacc ctgggtctca 11340
tgcatctgtg ggacctggtg gaggcgatcg tgcagaaccc cagcagcaag cccctgaccg 11400
cgcagctgtt cctggtggtg cagcacagca gggacaacga ggccttcagg gaggcgctgc 11460
tgaacatcac cgagccggag gggcgctggc tcctggacct gataaacatc ctgcagagca 11520
tagtggtgca ggagcgcagc ctgagcctgg ccgagaaggt ggcggccatt aactattcta 11580
tgctgagctt gggcaagttc tacgcccgca agatctacaa gaccccctac gtgcccatag 11640
acaaggaggt gaagatagac agcttctaca tgcgcatggc gctaaaggtg ctgaccctga 11700
gcgacgacct gggagtgtac cgcaacgagc gcatccacaa ggccgtgagc gccagccggc 11760
ggcgcgagct gagcgaccgc gagctgatgc acagtctgca gcgcgcgctc accggcgcgg 11820
gcgagggcga cagggaggtc gagtcctact tcgacatggg ggctgacctg cactggcagc 11880
cgagccgccg cgccctggag gcggcggggg cgtatggcgg cccccctggcg gccgatgacg 11940 aggaagagga ggactatgag ctagaggagg gcgagtacct ggaggactga cctggctggt 12000
ggtgttttgg tatagatgca agatccgaac gtggcggacc cggcggtccg ggcggcgctg 12060
cagagccagc cgtccggcat taactcctct gacgactggg ccgcggccat gggtcgcatc 12120
atggccctga ccgcgcgcaa ccccgaggcc ttcaggcagc agcctcaggc taaccggctg 12180
gcggccatct tggaagcggt agtgcccgcg cgctccaacc ccacccacga gaaggtgctg 12240
gccatagtca acgcgctggc ggagagcagg gccatccggg cggacgaggc cggactggtg 12300
tacgatgcgc tgctgcagcg ggtggcgcgg tacaacagcg gcaacgtgca gaccaacctg 12360
gaccgcctgg tgacggacgt gcgcgaggcc gtggcgcagc gcgagcgctt gcatcaggac 12420
ggtaacctgg gctcgctggt ggcgctaaac gccttcctca gcacccagcc ggccaacgta 12480
ccgcgggggc aggaggacta caccaacttc ttgagcgcgc tgcggctgat ggtgaccgag 12540
gtccctcaga gcgaggtgta ccagtcgggg cccgactact tcttccagac cagcagacag 12600
ggcttgcaaa ccgtgaacct gagccaggct ttcaagaacc tgcgggggct gtggggagtg 12660
aaagcgccca ccggcgaccg agctacggtg tccagcctgc taacccccaa ctcgcgcctg 12720
ctgctgctgc tgatcgcgcc cttcacggac agcgggagcg tctcgcggga gacctatctg 12780
ggccacctgc tgacgctgta ccgcgaggcc atcgggcagg cgcaggtgga cgagcacacc 12840
ttccaagaga tcaccagcgt gagccacgcg ctggggcagg aggacacggg cagcctgcag 12900
gcgaccctga actacctgct gaccaacagg cggcagaaga ttcccacgct gcacagcctg 12960
acccaggagg aggagcgcat cttgcgctac gtgcagcaga gcgtgagcct gaacctgatg 13020
cgcgacggcg tgacgcccag cgtggcgctg gacatgaccg cgcgcaacat ggaaccgggc 13080
atgtacgctt cccagcggcc gttcatcaac cgcctgatgg actacttgca tcgggcggcg 13140
gccgtgaacc ccgagtactt caccaatgcc attctgaatc cccactggat gccccctccg 13200
ggtttctaca acggagactt cgaggtgcct gaggtcaatg atgggttcct ctgggatgac 13260
atggatgaca gtgtgttctc ccccaacccg ctgcgcgccg cgtctctgcg attgaaggag 13320
ggctctgaca gggaaggacc gaggagtctg gcctcctccc tggctctggg ggcggtgggc 13380
gccacgggcg cggcggcgcg gggcagcagc cccttcccca gcctggcaga ctctctgaat 13440
agcgggcggg tgagcaggcc ccgcttgcta ggcgaggagg agtatctgaa caactccctg 13500
ctgcagcccg tgagggacaa aaacgctcag cgacagcagt ttcccaacaa cgggatagag 13560
agcctggtgg acaagatgtc cagatggaag acatatgcgc aggagtacaa ggagtgggag 13620
gaccgccagc cgcggcccct gccgccccct agacagcgct ggcagcggcg cgcgtccaac 13680
cgccgctgga gacagggacc cgaggacgat gatgactctg cagatgacag cagcgtgttg 13740
gacctgggcg ggagcgggaa cccctttcg cacctgcgcc cacgcctggg caagatgttt 13800
taaaagagaa aaataaaact caccaaggcc atggcgacga gcgttggttt tttgttccct 13860
tccttagtat gcggcgcgcg gcgatgttcg aggaggggcc tcccccctct tacgagagcg 13920
cgatgggaat ttctcctgcg gcgcccctgc agcctcccta cgtgcctcct cggtacctgc 13980
aacctacagg ggggagaaat agcatctgtt actctgagct gcagcccctg tacgatacca 14040
ccagactgta cctggtggac aacaagtccg cggacgtggc ctccctgaac taccagaacg 14100
accacagcga ttttttgacc acggtgatcc aaaacaacga cttcacccca accgaggcca 14160
gtacccagac cataaacctg gacaacaggt cgaactgggg cggcgacctg aagaccatcc 14220
tgcacaccaa catgcccaac gtgaacgagt tcatgtttac caactctttt aaggcgcggg 14280
ttatggtggc gcgcgagcag ggggaggcga agtacgagtg ggtggacttc acgctgcccg 14340
agggcaacta ctcagagacc atgactattg acctgatgaa caatgcgatc gtggaacact 14400
acctgaaagt gggcaggcag aacggggtga aggagagcga tatcggggtc aagtttgaca 14460
ccagaaactt tcgtctgggc tgggaccccg tgaccgggct ggtcatgccg gggtctaca 14520
ccaacgaggc ctttcatccc gatatagtgc tcctgcccgg ctgtggggtg gactttaccc 14580
agagccggct gagcaacctg ctgggcgttc gcaagcggca acctttccag gagggtttca 14640
agatcaccta tgaggatctg gagggggca acattcccgc gctccttgat ctggacgcct 14700
acgaggagag cttgaaaccc gaggagagcg ctggcgacag cggcgagagt ggcgaggagc 14760
aagccggcgg cggtggcagc gcgtcggtag aaaacgaaag tactcccgca gtggcggcag 14820
acgctgcgga ggtcgagcca gaggccatgc agcaggacgc agaggagggc gcacaggagg 14880
gcgcgcagga ggacatgaac gatggggaga tcaggggaga cactttcgcc acccggggcg 14940
aagaaaaaga ggcagaggcg gtggcggcga cggtggaagc cgaaaccgag gcagaggcag 15000
agcccaagac cgaagttatg gaagacatga atgatggaga acgtaggggt gacacgtttg 15060
ccacccgggg cgaagagaag gcggcggagg cagaagccgc ggctgaggag gcggctgcgg 15120
ctgcggccga ggctgaggct gcggctgagg ctaaggtcga agccgatgtt gcggttgagg 15180
ctcaggctga ggaggaggag gcggcgactg aagcagttaa ggaaaaggcc caggcagagc 15240
aggaagagaa aaaacctgtc attcaacctc taaaagaaga tagcaaaaag cgcagttaca 15300
acgtcatcga gggcagcacc tttacccagt accgcagctg gtacctggcg tacaactacg 15360
gcgacccggt caagggggtg cgctcgtgga ccctgctctg cacgccggac gtcacctgcg 15420
gctccgagca gatgtattgg tcgctgccaa acatgatgca agacccggtg accttccgct 15480
ccacgcggca ggttagcaac ttcccggtgg tgggcgccga actgctgccc gtgcactcca 15540
agagttttta caacgagcag gccgtctact cccagctgat ccgccaggcc acctctctga 15600
cccacgtgtt caatcgcttt cccgagaacc agattttggc gcgcccgccg gcccccacca 15660
tcaccaccgt cagtgaaaac gttcctgccc tcacagatca cgggacgcta ccgctgcgca 15720
acagcatctc aggagtccag cgagtgacca ttactgacgc cagacgccgg acctgcccct 15780
acgtttacaa ggccttgggc atagtctcgc cgcgcgtcct ctccagtcgc actttttaaa 15840
atacatctac cctcacgctt caaaatcatg tccgtactca tctcacccag caacaacacc 15900

-continued ggctgggggc tgcgcgcgcc cagcaagatg tttggagggg cgaggaaacg ctccgagcag 15960
cacccagtgc gcgtgcgcgg ccactaccgc gcgccctggg gagcgcacaa gcgcgggcgc 16020
gcagggcgca ccactgtgga cgacgccatt gactccgtag tggagcaggc gcgccactac 16080
acacccggcg cgccgtccgc ccccgccgtg tccaccgtgg acgaggcgat cgagagcgtg 16140
gtacagggcg cgcggcacta tgccaacctt aaaaatcgac gccgtcgcgt ggctcgccgc 16200
catcgccgga gaccccgggc caccgccgcc gcgcgccttg ctaaggctct gctcaggcgc 16260
gccaggcgaa ctggccgccg ggccgccatg agggccgcac ggcgggctgc cgccagcgcg 16320
gccgccgcgg ccccacgggc acgaaggcgc gcggccgctg ccgccgccgc cgccatttcc 16380
agcttggcct cgacgcggcg cggtaacata tactgggtgc gcgactcggt aaccggcacg 16440
cgggtacccg tgcgctttcg ccccccgcgg aattagcaca agacaacata cacactgagt 16500
ctcctgctgt tgtgtatccc agcggcgacc gtcagcagcg gcgacatgtc caagcgcaaa 16560
attaaagaag agatgctcca ggtcatcgcg ccggagatct atgggccccc gaagaaggag 16620
gaggatgatt acaagccccg caagctaaag cgggtcaaaa agaaaaagaa agatgatgac 16680
gttgacgagg cggtggagtt tgtccgccgc atggcgccca ggcgccccgt gcagtggaag 16740
ggtcggcgcg tgcagcgagt cctgcgcccc ggcaccgcgg tggtctttac gcccggcgag 16800
cgttccacgc gcactttcaa gcgggtgtac gatgaggtgt acggcgacga ggatctgttg 16860
gagcaggcca accatcgctt tggggagttt gcatatggga aacggccccg cgagagccta 16920
aaagaggacc tgctggcgct accgctggac gagggcaatc ccaccccgag tctgaagccg 16980
gtaaccctgc aacaggtgct gcctttgagc gcgcccagcg agcagaagcg agggttgaag 17040
cgcgagggcg gggacctggc acccaccgtg cagttgatgg tgcccaagcg gcagaagctg 17100
gaggacgtgc tggagaaaat gaaagtagag cccgggatcc agcccgaaat caaggtccgc 17160
cccatcaagc aggtggcgcc cggcgtggga gtccagaccg tggacgttag gattcccacg 17220
gaggagatgg aaacccaaac cgccactccc tcttcggcgg ctagcgccac caccggctcc 17280
gcttcggtag aggtgcagac ggacccctgg ctagccgccg ccgcccccggc cgcccccccgt 17340
tcgcgcgggc gcaagagaaa ttatccagcg gccagcgcgc tcatgcccca gtacgcactg 17400
catccatcca tcgcgcccac cccccggctac cgcgggtact cgtaccgccc gcgcagatca 17460
gccggcaccc gcggccgccg ccgccgtgcg accacaacca gccgccgccg tcgccgccgc 17520
cgccagccag tgctgacccc cgtgtctgta aggaaggtgg ctcgctcggg gagcacgctg 17580
gtggtgccca gagcgcgcta ccaccccagc attgtttaaa gccggtctct gtatggttct 17640
tgcagatatg gccctcactt gtcgcctccg cttcccggtg ccgggatacc gaggaagaac 17700
tcaccgccgc agaggcatgg cgggcagtgg tctccgcggc ggccgtcgcc atcgccggcg 17760
cgcaaagagc aggcgcatgc gcggcggtgt gctgcccttc ctaatcccgc taatcgccgc 17820
ggcgatcggt gccgtgcccg ggatcgcctc cgtggccctg caggcgtccc agaaacattg 17880
actcttgcaa ccttgcaagc ttgcattttt tggaggaaaa aataaaaagt ctagactctc 17940
acgctcgctt ggtcctgtga ctattttgta gaaaaaagat ggaagacatc aactttgcgt 18000
cgctggcccc gcgtcacggc tcgcgcccgt tcatgggaga ctggacagat atcggcacca 18060
gcaatatgag cggtggcgcc ttcagctggg gcagtctgtg gagtggcctt aaaaattttg 18120
gttccaccat taagaactat ggcaacaaag cgtggaacag cagcacgggt cagatgctga 18180
gagacaagtt gaaagagcag aacttccagg agaaggtggc acagggcctg gcctctggca 18240
tcagcggggt ggtggacata gctaaccagg ccgtgcagaa aaagataaac agtcatctgg 18300
acccccgccc tcaggtggag gaaacgcctc cagccatgga gacggtgtct cccgagggca 18360
aaggcgaaaa gcgcccgcgg cccgacaggg aagagaccct ggtgtcacac accgaggagc 18420
cgccctctta cgaggaggca gtcaaggccg gcctgcccac cactcgcccc atagctccca 18480
tggccaccgg tgtggtgggt cacaggcaac acacccccgc gacactagat ctgcccccgc 18540
cgtccgagcc gactcgccag ccaaaggcgg tgacggtgcc cgctccctcc acttccgccg 18600
ccaacagagt gcctctgcgc cgcgctgcga gcggccccg ggcctcgcga gtcagcggca 18660
actggcagag cacactgaac agcatcgtgg gcctgggagt gaggagtgtg aagcgccgcc 18720
gttgctactg aatgagcaag ctagctaacg tgttgtatgt gtgtatgcgt cctatgtcgc 18780
cgccagagga gctgttgagc cgccggcgcc gtctgcactc cagcgaattt caagatggcg 18840
accccatcga tgatgcctca gtggtcgtac atgcacatct cgggccagga cgcttcggag 18900
tacctgagcc ccgggctggt gcagttcgcc cgcgccacag acacctactt caacatgagt 18960
aacaagttca ggaaccccac tgtggcgccc acccacgatg tgaccacgga ccggtcgcag 19020
cgcctgacgc tgcggttcat ccccgtggat cgggaggaca ccgcttactc ttacaaggcg 19080
cggttcacgc tggccgtggg cgacaaccgc gtgctggaca tggcctccac ttactttgac 19140
atccgggggg tgctggacag ggccccact ttcaagccct actcgggcac tgcctacaac 19200
tccctggccc ccaagggcgc tcccaattct tgcgagtggg aggaggaaac acaaaatgag 19260
gtacaagcca atgaagaaca actagcagaa gaagaggatg aagaaatggc tcaagaggat 19320
cagcagccta ctaaaaaaac ccatgtatat gctcaggcac ctctttctgg cgaacagatt 19380
accaaagatg gcttgcaaat aggagctgaa gttacaggag aaacatcaaa gcccattttt 19440
gcagacaaga cattccaacc agaacctcag ataggagagt ctcaatggaa tgaggccgat 19500
gctacagtag caggaggtag ggttttgaaa aagactaccc ctatgaaacc ttgctatgga 19560
tcctatgcca gacctaccaa tgccaatgga gggcagggga tacttgaggc aaatgctaaa 19620
ggggaactcg aatctaaagt tgagatgcag tttttctcta acaccacaac tcttaatgta 19680
agagacggtg aaaatggcct taaaccaaaa gtagtgctgt atagcgaaga tgtcaacctg 19740
gaatcccctg acactcatct gtcttacaag cccaaaaaag atgatgttaa tgccaaaatc 19800
atgttgggtc agcaagccat gcccaacaga cccaacctca ttggatttag agataatttc 19860
attgggctca tgtattacaa cagcactgga aacatgggag tgctggcggg tcaggcctct 19920
cagttgaatg ctgtggtgga cttgcaggat agaaacacgg aactgtcata tcagcttatg 19980
cttgattcca ttggagatag aaccagatac ttttccatgt ggaaccaggc agtggatagc 20040
tatgacccag atgttagaat cattgaaaac catggggtgg aggatgagct gcccaactac 20100
tgttttccct tgggcggtat aggaattaca gatacatacc aggccataaa agcagccaat 20160
ggtggagatg ctactacgtg gtctgctgat aacacatttg cagaccgcaa cgaaataggg 20220
gtgggaaaca acttcgccat ggagatcaac atccaggcca acctctggag aaacttcctc 20280
tatgcgaacg tgggactcta cctgccagac aagctcaagt acaaccccac caacgtggac 20340
atctctgaca accccaacac ctatgactac atgaacaagc gggtggtggc ccccggcctg 20400
gtggactgct ttgtcaatgt gggagccagg tggtccctgg actacatgga caacgtcaac 20460
cccttcaacc accaccgcaa tgcgggtctg cgctaccgct ccatgatcct gggcaacggg 20520
cgctatgtgc ccttccacat ccaggtaccc cagaagttct ttgccatcaa gaacctcctg 20580
ctcctgcccg gctcctacac ctacgagtgg aacttcagga aggatgtaaa catggtccta 20640

-continued cagagctctc tgggcaatga ccttagggta gatggggcca gcatcaagtt tgacagcatc 20700
accctctatg ctacattttt ccccatggcc cacaacaccg cctccacgct tgaggccatg 20760
ctgagaaacg acaccaacga ccagtccttc aatgactacc tctctggggc caacatgctc 20820
tacccaatcc cagccaaggc caccaacgtg cccatctcca tcccctctcg caactgggcc 20880
gcctttagag gctgggcctt tacccgcctt aagaccaagg agacccccctc cctgggctcg 20940
ggttttgatc cctactttgt ttactcggga tccatcccct acctggatgg caccttctac 21000
ctcaaccaca ctttcaagaa gatatccatc atgtatgact cctccgtcag ctggccgggc 21060
aacgaccgct tgctcacccc caatgagttc gaggtcaagc gcgccgtgga cggcgagggc 21120
tacaacgtgg cccagtgcaa catgaccaag gactggttcc tggtgcagat gctggccaac 21180
tacaacatag gctaccaggg cttctacatc ccagagagct acaaggacag gatgtattcc 21240
ttcttcagaa atttccaacc catgagccga caggtggtgg acgagaccaa ttacaaggac 21300
tatcaggcca ttggcatcac ccaccagcac aacaactcgg gtttcgtggg ctacctggcg 21360
cccaccatgc gcgagggaca ggcctacccc gccaacttcc cctacccccct gataggcaag 21420
accgcggtcg acagcgtcac ccagaaaaag ttcctctgcg accgcaccct ctggcgcatc 21480
cccttctcta gcaactttat gtccatgggt gcgctcacgg acctgggcca aaacctgctt 21540
tatgccaact ctgcccatgc gctggacatg acttttgagg tggaccccat ggacgagccc 21600
acccttctct atattgtgtt tgaagtgttc gacgtggtca gagtgcacca gccgcaccgc 21660
ggtgtcatcg agaccgtgta cctgcgtacg cccttctcag ccggcaacgc caccacctaa 21720
ggagacagcg ccgccgcctg catgactggt tccaccgagc aagagctcag ggccatcgcc 21780
agagacctgg gatgcggacc ctatttttg ggcacctatg acaaacgctt cccgggtttt 21840
atctcccgag acaagctcgc ctgcgccatc gtcaacacgg ccgcgcgcga gaccgggggc 21900
gtgcactggc tggcctttgg ctgggacccg cgctctaaaa cttgctacct ctttgacccc 21960
tttggcttct ccgatcagcg cctcaggcag atttatgagt ttgagtacga ggggctgttg 22020
cgccgcagcg cgcttgcctc ctcgcccgac cgctgcatca cccttgagaa gtccaccgag 22080
accgtgcagg ggccccactc ggccgcctgc ggtctcttct gttgcatgtt tttgcacgcc 22140
tttgtgcact ggcctcagag tcccatggat cgcaacccca ccatgaactt gctaaaggga 22200
gtgcccaacg ccatgctcca gagcccccag gtcctgccca ccctgcgccg caaccaggaa 22260
cagctctacc gcttcctgga gcgccactcc ccctacttcc gcagccacag cgcgcgcatc 22320
cggggggcca cctcttttg ccacttgcaa gaaaacatgc aagacggaaa atgatgtaca 22380
gcatgctttt aataaatgta aagactgtgc actttattta tacacgggct ctttctggtt 22440
atttattcaa caccgccgtc gccatctaga aatcgaaagg gttctgccgc gcgtcgccgt 22500
gcgccacggg cagagacacg ttgcgatact ggaagcggct cgcccacttg aactcgggca 22560
ccaccatgcg gggcagtggt tcctcgggga aattctcgct ccacagggtg cgggtcagct 22620
gcagcgcgct caggaggtcg ggagccgaga tcttgaagtc gcagttgggg ccggaaccct 22680
gcgcgcgcga gttgcggtac acggggttgc agcactggaa caccagcagg gccggattat 22740
tcacgctggc cagcaggctc tcgtcgctaa tcatgtcgct gtccagatcc tccgcgttgc 22800
tcagggcgaa tggggtcatc ttgcagacct gcctgcccag gaaaggcggg agcccaggct 22860
tgccgttaca gtcgcagcgc aggggcatta gcaggtgccc acggcccgac tgcgcctgcg 22920
ggtacaacgc gcgcatgaag gcttcgatct gcctaaaagc cacctgggtc ttggctccct 22980
ccgaaaagaa catcccacag gacttgctgg agaactggtt cgcgggacag ctggcatcgt 23040

```
gcaggcagca gcgcgcgtca gtgttggcga tctgcaccac gttgcgaccc caccggtttt  23100
tcactatctt ggccttggaa gcctgctcct ttagcgcgcg ctggccgttc tcgctggtca  23160
catccatctc tatcacctgt tccttgttga tcatgtttgt cccgtgcaga cactttaggt  23220
cgccctccgt ctgggtgcag cggtgctccc acagcgcgca accggtgggc tcccaatttt  23280
tgtgggtcac ccccgcgtag gcctgcaggt aggcctgcag gaagcgcccc atcatggtca  23340
taaaggtctt ctggctcgta aaggtcagct gcaggccgcg atgctcttcg ttcagccagg  23400
tcttgcagat ggcggccagc gcctcggtct gctcgggcag catcttaaaa tttgtcttca  23460
ggtcgttatc cacgtggtac ttgtccatca tggcacgcgc cgcctccatg cccttctccc  23520
aggcggacac catgggcagg cttagggggt ttatcacttc cagcggcgag gacaccgtac  23580
tttcgatttc ttcttcctcc ccctcttccc ggcgcgcgcc cccgctgttg cgcgctctta  23640
ccgcctgcac caaggggtcg tcttcaggca agcgccgcac cgagcgcttg ccgcccttga  23700
cctgcttgat cagtaccggc gggttgctga agcccaccat ggtcagcgcc gcctgctctt  23760
cttcgtcttc gctgtctacc actatttctg gggaggggct tctccgctct gcggcaaagg  23820
cggcggatcg cttctttttt ttcttgggag ccgccgcgat ggagtccgcc acggcgaccg  23880
aggtcgaggg cgtggggctg ggggtgcgcg gcaccagggc ctcgtcgccc tcggactctt  23940
cctctgactc caggcggcgg cggagtcgct tctttggggg cgcgcgcgtt agcggcggcg  24000
gagacgggga cggggacggg gacgggacgc cctccacagg gggcggtctt cgcgcagacc  24060
cgcggccgcg ctcgggggtc ttctcgcgct ggtcttggtc ccgactggcc attgtatcct  24120
cctcctccta ggcagagaga cataaggagt ctatcatgca agtcgagaag gaggagagct  24180
taaccacccc ctctgagacc gccgtcgccg tcgcccccgc taccgccgac gcgcccgcca  24240
caccgagcga cacccccgcg gacccccccg ccgacgcacc cctgttcgag gaagcggccg  24300
tggagcagga cccgggcttt gtctcggcag aggaggattt gcaagaggag gaggataagg  24360
aggagaagcc ctcagtgcca aaagatcata aagagcaaga cgagcacgac gcagacgcac  24420
accagggtga agtcgggcgg ggggacggag ggcatggcgg cgccgactac ctagacgaag  24480
gaaacgacgt gctcttgaag cacctgcatc gtcagtgcgc cattgtctgc gacgctctgc  24540
aggagcgcag cgaggtgccc ctcagcgtgg cggaggtcag ccgcgcctac gagctcagcc  24600
tcttttcccc ccgggtgccc ccccgccgcc gcgaaaacgg cacatgcgag cccaacccgc  24660
gcctcaactt ctaccccgcc tttgtggtgc ccgaggtcct ggccacctat cacatcttct  24720
ttcaaaattg caagatcccc atctcgtgcc gcgccaaccg tagccgcgcc gataagatgc  24780
tggccctgcg ccagggcgac cacatacctg atatcgccgc tttggaagat gtgccaaaga  24840
tcttcgaggg tctgggtcgc aacgagaagc gggcagcaaa ctctctgcaa caggaaaaca  24900
gcgaaaatga gagtcacact ggagcgctgg tggagctgga gggcgacaac gcccgcctgg  24960
cggtgctcaa gcgcagcatc gaggtcaccc actttgccta ccccgcgctc aacctgcccc  25020
ccaaagtcat gaacgcggtc atggacgggc taatcatgcg ccgcggccgg ccccttgctc  25080
cagatgcaaa cttgcatgag gagaccgagg acggtcagcc cgtggtcagc gacgagcagc  25140
tgacgcgctg gctggaaacc gcggaccccg ccgaactgga ggagcggcgc aagatgatga  25200
tggccgcggt gctggtcacc gtagagctgg agtgtctgca gcgcttcttc ggcgaccccg  25260
agatgcagag aaaggtcgag gagaccctac actacacctt ccgccagggc tacgtgcgcc  25320
aggcttgcaa gatctccaac gtggagctca gcaacctggt gtcctacctg ggcatcttgc  25380
```

-continued

```
atgaaaaccg ccttgggcag agcgtgctac actccaccct gcgcggggag gcgcgccgcg  25440
actacgtgcg cgactgcgtt tacctcttcc tctgctacac ctggcagacg gccatggggg  25500
tctggcagca gtgcctggag gagcgcaacc tcaaggagct ggagaagctc ctgcagcgcg  25560
cgctcaaaga cctctggacg ggctacaacg agcgctcggt ggccgccgcg ctggccgacc  25620
tcatcttccc cgagcgcctg ctcaaaactc tccagcaggg gctgcccgac ttcaccagcc  25680
aaagcatgtt gcaaaatttt aggaacttta tcctggagcg ttctggcatc ctacccgcca  25740
cctgctgcgc cctgcccagc gactttgtcc ccctcgtgta ccgcgagtgc cccccgccgc  25800
tgtggggcca ctgctacctg ttccaactgg ccaactacct gtcctaccac gcggacctca  25860
tggaagactc cagcggcgag ggctcatgg agtgccactg ccgctgcaac ctctgcacgc  25920
cccaccgctc cctggtctgc aacacccaac tgctcagcga gagtcagatt atcggtacct  25980
tcgagctaca gggtccgtcc tcctcagacg agaagtccgc ggctccgggg ctaaaactca  26040
ctccggggct gtggacttcc gcctacctgc gcaaatttgt acctgaagac taccacgccc  26100
acgagatcag gttttacgag gaccaatccc gcccgcccaa ggcggagctg accgcctgcg  26160
tcatcaccca gggcgagatc ctaggccaat tgcaagccat ccaaaaagcc cgccaagagt  26220
tttgctgag aaagggtcgg ggggtgtatc tggaccccca gtcgggtgag gagctcaacc  26280
cggttccccc gctgccgccg ccgcgggacc ttgcttccca ggataagcat cgccatggct  26340
cccagaaaga agcagcagcg gccgccactg ccgccacccc acacgctgga ggaagaggag  26400
gaatactggg acagtcaggc agaggaggtt tcggacgagg aggagccgga gacggagatg  26460
gaagagtggg aggaggacag cttagacgag gaggcttccg aagccgaaga ggcaggcgca  26520
acaccgtcac cctcggccgc agccccctcg caggcgcccc cgaagtccgc tcccagcatc  26580
agcagcaaca gcagcgctat aacctccgct cctccaccgc cgcgacccac ggccgaccgc  26640
agacccaacc gtagatggga caccaccgga accggggccg gtaagtcctc cgggaaaggc  26700
aagcaagcgc agcgccaagg ctaccgctcg tggcgcgctc acaagaacgc catagtcgct  26760
tgcttgcaag actgcggggg gaacatctcc ttcgcccgcc gcttcctgct cttccaccac  26820
ggtgtggcct tcccccgtaa cgtcctgcat tactaccgtc atctctacag cccctactgc  26880
ggcggcagtg agccagaggc ggccggcggc agcggcgccc gtttcggtgc ctaggaagac  26940
ccagggcaag acttcagcca agaaactcgc ggcggccgcg gcgaacgcgg tcgcgggggc  27000
cctgcgcctg acggtgaacg aacccctgtc gacccgcgaa ctgaggaacc gaatcttccc  27060
cactctctat gccatcttcc agcagagcag agggcaggat caggaactga aagtaaaaaa  27120
caggtctctg cgctccctca cccgcagctg tctgtatcac aagagcgaag accagcttcg  27180
gcgcacgctg gaggacgctg aggcactctt cagcaaatac tgcgcgctca ctcttaagga  27240
ctagctccgc gcccttctcg aatttaggcg ggaacgccta cgtcatcgca gcgccgccgt  27300
catgagcaag gacattccca cgccatacat gtggagctat cagccgcaga tgggactcgc  27360
ggcgggcgcc tcccaggatt actccacccg catgaactgg ctcagtgccg gcccacacat  27420
gatctcacag gttaatgaca tccgcaccca tcgaaaccaa atattggtgg agcaggcggc  27480
aattaccacc acgccccgca ataatcccaa ccccagggag tggcccgcgt ccctggtgta  27540
tcaggaaatt cccggcccca ccaccgtact acttccgcgt gattcccagg ccgaagtcca  27600
aatgactaac tcaggggcac agctcgcggg cggctgtcgt cacagggtgc ggcctcctcg  27660
ccagggtata actcacctga agatccgagg cagaggtatt cagctcaacg acgagtcggt  27720
gagctcctcg ctcggtctca gacctgacgg gaccttccag atagccggag ccggccgatc  27780
```

ttccttcacg ccccgccagg cgtacctgac tctgcagagc tcgtcctcgg cgccgcgctc 27840
gggcggcatc gggactctcc agttcgtgca ggagtttgtg ccctcggtct acttcaaccc 27900
cttctcgggc tctcccggtc gctacccgga ccagttcatc ccgaactttg acgccgcgag 27960
ggactcggtg gacggctacg actgaatgtc gggtggaccc ggtgcagagc aacttcgcct 28020
gaagcacctt gaccactgcc gccgccctca gtgctttgcc cgctgtcaga ccggtgagtt 28080
ccagtacttt tccctgcccg actcgcaccc ggacggcccg gcgcacgggg tgcgcttttt 28140
catcccgagt caggtccgct ctaccctaat cagggagttc accgcccgtc ccctactggc 28200
ggagttggaa aaggggcctt ctatcctaac cattgcctgc atctgctcta accctggatt 28260
acaccaagat ctttgctgtc atttgtgtgc tgagtataat aaaggctgag atcagaatct 28320
actcgggctc ctgtcgccat cctgtcaacg ccaccgtcca agcccggccc gatcagcccg 28380
aggtgaacct cacctgcggt ctgcaccggc gcctgaggaa atacctagct tggtactaca 28440
acagcactcc ctttgtggtt tacaacagct ttgaccagga cggggtctca ctgagggata 28500
acctctcgaa cctgagctac tccatcagga agaacaacac cctcgagcta cttcctcctt 28560
acctgcccgg gacttaccag tgtgtcaccg gtccctgcac ccacacccac ctgttgatcg 28620
taaacgactc tcttccgaga acagacctca ataactcctc tccgcagttc cccagaacag 28680
gaggtgagct caggaaaccc cgggtaaaga agggtggaca agagttaaca cttgtggggt 28740
ttctggtgta tgtgacgctg gtggtggctc ttttgattaa ggcttttcct tccatgtctg 28800
aactatccct cttcttttat gaacaactcg actagtgcta acgggaccct acccaacgaa 28860
tcgggattga atatcggtaa ccaggttgca gtttcacttt tgattacctt catagtcctc 28920
ttcctgctag tgctgtcgct tctgtgcctg cggatcgggg gctgctgcat ccacgtttat 28980
atctggtgct ggctgtttag aaggttcgga gaccaccgca ggtagaataa acaaacctag 29040
acctagaaat ggacggtctc tgcagcgagc aacgcatact agagaggcgc cggcaaaaag 29100
cagagctcga gcgtcttaaa caagagctcc aagacgccgt ggccatacac cagtgcaaaa 29160
aagggctctt ctgtctggta aaacaggcca cgctcaccta tgaaaaaaca ggtgacaccc 29220
accgcctagg atacaagctg cccacacagc gccaaaagtt tgcccttatg ataggtgaac 29280
aacccatcac cgtgacccag cactccgtgg agacagaagg ctgcattcat gctccctgca 29340
ggggcgctga ctgcctctac accttgatca aaaccctttg cggtctcaga gaccttatcc 29400
ctttcaattg atcataactg taatcaataa aaaatcactt acttgaaatc tgatagcaag 29460
cctctgtcca attttttcag caacacttcc ttcccctctt cccaactctg gtactctagg 29520
cgcctcctag ctgcaaactt cctccacagt ctgaagggaa tgtcagattc ctcctcctcc 29580
tgtccctccg cacccacgat cttcatgttg ttgcagatga agcgcaccaa aacgtctgac 29640
gagagcttca accccgtgta cccctatgac acggaaaacg gtcctccctc cgtccctttc 29700
ctcacccctc ccttcgtgtc tcccgatgga ttccaagaga gcccccccgg ggtcctgtct 29760
ctgaacctgg ccgagcccct ggtcacttcc cacggcatgc tcgccctgaa aatgggaagt 29820
ggcctctccc tggacgacgc cggcaacctc acctctcaag atgtcaccac cactacccct 29880
cccctgaaaa aaaccaagac caacctcagc ctagaaacct cagcccccct gactgtgagc 29940
acctcaggcg ccctcaccct agcagccgcc gttcccctgg cggtggccgg cacctccctc 30000
accatgcaat cagaggcccc cctgacagtc caagatgcaa aactcaccct ggccaccaag 30060
ggcccccctga ccgtgtctga aggcaaactg gccttgcaga cctcggcccc gctgacggcc 30120

-continued

```
gctgacagca gcgccctcac cgttagcgcc acaccaccca tcagtgtaag cagtggaagt  30180
ttgggcttag acatggaaga ccccatgtat actcatgatg gaaaactggg aataagaatt  30240
ggaggcccac tgagagtagt agacagcctg cacacactga ctgtagttac cggaaatgga  30300
atagctgtag ataacaatgc cctccaaact agagttacgg gcgccctggg ttatgacaca  30360
tcaggaaacc tacaactgag agccgcgggg ggtatgcgaa ttgatgcaaa tggccaactt  30420
atccttgatg tggcataccc atttgatgct caaaacaatc tcagccttag acttggtcag  30480
ggacccctgt atgtaaacac agaccacaac ctagatttga attgcaacag aggtctgacc  30540
acaactacca ccaacaacac aaaaaaactt gaaactaaaa ttggctcagg cttagactat  30600
gataccaatg gtgctgtcat tattaaactt ggtactggtg taagctttga cagcacaggc  30660
gccctaactg tgggaaacac tggcgatgat aaactgactc tgtggacaac cccagaccca  30720
tctccaaatt gcagaattca cgcagacaaa gactgcaagt ttactctagt cctaactaag  30780
tgtggaagtc aaatcctggc ttctgtcgcc gccctagcgg tgtcaggaaa tctggcttca  30840
ataacaggca ccgttgccag cgttaccatc tttctcagat ttgatcagaa tggagtgctt  30900
atggaaaact cctccctaga caagcagtac tggaacttca gaaatggtaa ctcaaccaat  30960
gccacccccct acaccaatgc agttgggttc atgccaaacc tcgcagcata ccccaagaca  31020
cagagccaga ctgctaaaaa caacattgta agtcaggttt acttgaatgg ggacaaatcc  31080
aaacccatga cccttaccat taccctcaat ggaactaatg aatccagtga aactagccag  31140
gtgagtcact actccatgtc atttacatgg gcttgggaga gtgggcaata tgccaccgaa  31200
acctttgcca ccaattcctt taccttctct tacattgctg aacaataaag aaagcacaga  31260
gatgcttgtt tttgatttca aaattgtgtg cttttattta ttttcaagct tacagtattt  31320
ccagtagtca ttcgaataga gcttaatgaa actgcatgag aacccttcca catagcttaa  31380
attatcacca gtgcaaatgg agaaaaatca acatacctttt ttatccagat atcacagaac  31440
cctagtattc aacctgccac ctccctccca acacacagag tacacagtcc tttctccccg  31500
gctggcctta aaaagcatca tatcatgggt aacagacata ttcttaggtg ttatattcca  31560
cacggtttcc tgtcgagcca aacgctcatc agtgatatta ataaactccc cgggcagctc  31620
acttaagttc atgtcgctgt ccagctgctg agccacaggc tgctgtccaa cttgcggttg  31680
cttaacgggc ggcgaaggag aagtccacgc ctacatgggg gtagagtcat aatcgtgcat  31740
caggataggg cggtggtgct gcagcagcgc gcgaataaac tgctgccgcc gccgctccgt  31800
cctgcaggaa tacaacatgg cagtggtctc ctcagcgatg attcgcaccg cccgcagcat  31860
aaggcgcctt gtcctccggg cacagcagcg caccctgatc tcacttaaat cagcacagta  31920
actgcagcac agcaccacaa tattgttcaa aatcccacag tgcaaggcgc tgtatccaaa  31980
gctcatggcg gggaccacag aacccacgtg gccatcatac cacaagcgca ggtagattaa  32040
gtggcgaccc ctcataaaca cgctggacat aaacattacc tcttttggca tgttgtaatt  32100
caccacctcc cggtaccata taaacctctg attaaacatg gcgccatcca ccaccatcct  32160
aaaccagctg gccaaaacct gcccgccggc tatacactgc agggaaccgg gactggaaca  32220
atgacagtgg agagcccagg actcgtaacc atggatcatc atgctcgtca tgatatcaat  32280
gttggcacaa cacaggcaca cgtgcataca cttcctcagg attacaagct cctcccgcgt  32340
tagaaccata tcccagggaa caacccattc ctgaatcagc gtaaatccca cactgcaggg  32400
aagacctcgc acgtaactca cgttgtgcat tgtcaaagtg ttacattcgg gcagcagcgg  32460
atgatcctcc agtatggtag cgcgggtttc tgtctcaaaa ggaggtagac gatccctact  32520
```

```
gtacggagtg cgccgagaca accgagatcg tgttggtcgt agtgtcatgc caaatggaac  32580
gccggacgta gtcatatttc ctccagcaga accaagtgcg cgcgtggcag ctatccttgc  32640
gtcttctgtc tcgccgcctg ccccgctcgg tgtagtagtt gtaatacagc cactccctca  32700
gaccgtcaag gcgctccctg gcgtccggat ctataacaac accatcctgc agcgccgccc  32760
tgatgacatc caccaccgta gagtatgcca agcccagcca ggaaatgcac tcactttgac  32820
agcgagagat aggaggagcg ggaagagatg gaagaaccat gatagtaaaa gaacttttat  32880
tccaatcgat cctctacaat gtcaaagtgt agatctatca gatggcactg gtctcctccg  32940
ctgagtcgat caaaaataac agctaaacca caaacaacac gattggtcaa atgctgcaca  33000
agggcttgca gcataaaatc gcctcgaaag tccaccgcaa gcataacatc aaagccaccg  33060
cccctatcat gatctatgat aaaaacccca cagctatcca ccagacccat atagttttca  33120
tctctccatc gtgaaaaaat atttacaagc tcctccttta aatcacctcc aaccaattca  33180
aaaagttgag ccagaccgcc ctccaccttc attttcagca tgcgcatcat gattgcaaaa  33240
attcaggctc ctcagacacc tgtataagat tgagaagcgg aacattaaca tcaatgtttc  33300
gctcgcgaag atcgcgcctc agtgcaagca tgatataatc ccacaggtcg gagcggatca  33360
gcgaggacat ctccccgcca ggaaccaact caacggagcc tatgctgatt ataatacgca  33420
tattcggggc tatgctaacc agcacggccc ccaaataggc gtactgcata ggcggcgaca  33480
aaaagtgaac agtttgggtt aaaaaatcag gcaaacactc gcgcaaaaaa gcaagaacat  33540
cataaccatg ctcatgcaaa tagatgcaag taagctcagg aacgaccaca gaaaaatgca  33600
caatttttct ctcaaacatg actgcgagcc ctgcaaaaaa taaaaaagaa acattacaca  33660
agagtagcct gtcttacaat gggatagact actctaacca acataagacg ggccacgaca  33720
tcgcccgcgt ggccataaaa aaaattatcc gtgtgattaa aaagaagcac agatagctgg  33780
ccagtcatat ccggagtcat cacgtgcgaa cccgtgtaga cccccgggtt ggacacatcg  33840
gccaaagaaa gaaagcggcc aatgtatccc ggaggaatga taacactaag acgaagatac  33900
aacagaataa ccccatgggg gggaataaca aagttagtag gtgaataaaa acgataaaca  33960
cccgaaactc cctcctgcgt aggcaaaata gcgccctccc cttccaaaac aacatacagc  34020
gcttccacag cagccatgac aaaagactca aaacactcaa aagactcagt cttaccagga  34080
aaataaaagc actctcacag caccagcact aatcagagtg tgaagagggc caagtgccga  34140
acgagtatat ataggaatta aaaatgacgt aaatgtgtaa aggtcaaaaa acgcccagaa  34200
aaatacacag accaacgccc gaaacgaaaa cccgcgaaaa aatacccaga agttcctcaa  34260
caaccgccac ttccgctttc ccacgatacg tcacttcctc gaaaatagca aactacattt  34320
cccacatgta caaaaccgaa accactcccc ttgtcaccgc ccacaactta catcttaatt  34380
aacaaacgtc aaagcctacg tcagccgccc cgcctcgccc cgcccacctc attatcatat  34440
tggccacaat ccaaaataag gtatattatt gatgatgatt taaatattat gcggtgtgaa  34500
ataccgcaca gatgcgtaag gagaaaatac cgcatcaggc gctcttccgc ttcctcgctc  34560
actgactcgc tgcgctcggt cgttcggctg cggcgagcgg tatcagctca ctcaaaggcg  34620
gtaatacggt tatccacaga atcaggggat aacgcaggaa agaacatgtg agcaaaaggc  34680
cagcaaaagg ccaggaaccg taaaaaggcc gcgttgctgg cgtttttcca taggctccgc  34740
ccccctgacg agcatcacaa aaatcgacgc tcaagtcaga ggtggcgaaa cccgacagga  34800
ctataaagat accaggcgtt tccccctgga agctccctcg tgcgctctcc tgttccgacc  34860
```

ctgccgctta ccggatacct gtccgccttt ctcccttcgg gaagcgtggc gctttctcat 34920
agctcacgct gtaggtatct cagttcggtg taggtcgttc gctccaagct gggctgtgtg 34980
cacgaacccc ccgttcagcc cgaccgctgc gccttatccg gtaactatcg tcttgagtcc 35040
aacccggtaa gacacgactt atcgccactg gcagcagcca ctggtaacag gattagcaga 35100
gcgaggtatg taggcggtgc tacagagttc ttgaagtggt ggcctaacta cggctacact 35160
agaaggacag tatttggtat ctgcgctctg ctgaagccag ttaccttcgg aaaaagagtt 35220
ggtagctctt gatccggcaa acaaaccacc gctggtagcg gtggtttttt tgtttgcaag 35280
cagcagatta cgcgcagaaa aaaaggatct caagaagatc ctttgatctt ttctacgggg 35340
tctgacgctc agtggaacga aaactcacgt taagggattt tggtcatgag attatcaaaa 35400
aggatcttca cctagatcct tttaaattaa aaatgaagtt ttaaatcaat ctaaagtata 35460
tatgagtaaa cttggtctga cagttaccaa tgcttaatca gtgaggcacc tatctcagcg 35520
atctgtctat ttcgttcatc catagttgcc tgactccccg tcgtgtagat aactacgata 35580
cgggagggct taccatctgg ccccagtgct gcaatgatac cgcgagaccc acgctcaccg 35640
gctccagatt tatcagcaat aaaccagcca gccggaaggg ccgagcgcag aagtggtcct 35700
gcaactttat ccgcctccat ccagtctatt aattgttgcc gggaagctag agtaagtagt 35760
tcgccagtta atagtttgcg caacgttgtt gccattgctg caggcatcgt ggtgtcacgc 35820
tcgtcgtttg gtatggcttc attcagctcc ggttcccaac gatcaaggcg agttacatga 35880
tcccccatgt tgtgcaaaaa agcggttagc tccttcggtc ctccgatcgt tgtcagaagt 35940
aagttggccg cagtgttatc actcatggtt atggcagcac tgcataattc tcttactgtc 36000
atgccatccg taagatgctt ttctgtgact ggtgagtact caaccaagtc attctgagaa 36060
tagtgtatgc ggcgaccgag ttgctcttgc ccggcgtcaa cacgggataa taccgcgcca 36120
catagcagaa ctttaaaagt gctcatcatt ggaaaacgtt cttcggggcg aaaactctca 36180
aggatcttac cgctgttgag atccagttcg atgtaaccca ctcgtgcacc caactgatct 36240
tcagcatctt ttactttcac cagcgtttct gggtgagcaa aaacaggaag gcaaaatgcc 36300
gcaaaaaagg gaataagggc gacacggaaa tgttgaatac tcatactctt cctttttcaa 36360
tattattgaa gcatttatca gggttattgt ctcatgagcg gatacatatt tgaatgtatt 36420
tagaaaaata aacaaatagg ggttccgcgc acatttcccc gaaaagtgcc acctgacgtc 36480
taagaaacca ttattatcat gacattaacc tataaaaata ggcgtatcac gaggcccttt 36540
cgtcttcaag aattgattta aat 36563

<210> SEQ ID NO 16
<211> LENGTH: 37555
<212> TYPE: DNA
<213> ORGANISM: Artificial Sequence
<220> FEATURE:
<223> OTHER INFORMATION: pBZ1_BZ28F.RSVF-2A-GLuc

<400> SEQUENCE: 16
catcatcaat aatatacctt attttggatt gtggccaata tgataatgag gtgggcgggg 60
cgaggcgggg cgggtgacgt aggacgtgcg agtagggttg ggaggtgtgg cggaagtgtg 120
gcatttgtaa gtgggaggag cttacatgca agcttccgtc gcggaaaatg tgacgttttt 180
tatgagcgcc gcctacctcc ggaagtgcca attttcgcgc gctttttacc ggatatcgta 240
gtaattttgg gcgggaccat gtaagatttg gccattttcg cgcgaaaagt gaaacgggga 300
agtgaaaact gaataatagg gcgttagtca tagcgcgtaa tatttaccga gggccgaggg 360

-continued

```
actttgaccg attacgtgga ggactcgccc aggtgttttt tacgtgaatt tccgcgttcc    420
gggtcaaagt ctccgttttt attgtcaccg tcatttgacg cggagggtat ttaaacccgc    480
tgcgctccta gcgatcgctc aatattggcc attagccata ttattcattg gttatatagc    540
ataaatcaat attggctatt ggccattgca tacgttgtat ccatatcata atatgtacat    600
ttatattggc tcatgtccaa cattaccgcc atgttgacat tgattattga ctagttatta    660
atagtaatca attacggggt cattagttca tagcccatat atggagttcc gcgttacata    720
acttacggta aatggcccgc ctggctgacc gcccaacgac ccccgcccat tgacgtcaat    780
aatgacgtat gttcccatag taacgccaat agggactttc cattgacgtc aatgggtgga    840
gtatttacgg taaactgccc acttggcagt acatcaagtg tatcatatgc caagtacgcc    900
ccctattgac gtcaatgacg gtaaatggcc cgcctggcat tatgcccagt acatgacctt    960
atgggacttt cctacttggc agtacatcta cgtattagtc atcgctatta ccatggtgat   1020
gcggttttgg cagtacatca atgggcgtgg atagcggttt gactcacggg gatttccaag   1080
tctccacccc attgacgtca atgggagttt gttttggcac caaaatcaac gggactttcc   1140
aaaatgtcgt aacaactccg ccccattgac gcaaatgggc ggtaggcgtg tacggtggga   1200
ggtctatata agcagagctc gtttagtgaa ccgtcagatc gcctggagac gccatccacg   1260
ctgttttgac ctccatagaa gacaccggga ccgatccagc ctccgcggtt ggccgtgctc   1320
ttcctgacgg gtaggtgtcc cctaacctag ggagccaacc atcgggggc cttctcccta   1380
aatccccgtg gcccaccctc ctgggcagag gcagcaggtt tctcactggc cccctctccc   1440
ccacctccaa gcttggcctt tcggctcaga tctcagccca cagctggcct gatctgggtc   1500
tcccctccca ccctcaggga gccaggctcg gcatttcgtc gacatggaac tgctgatcct   1560
gaaggccaac gccatcacca ccatcctgac cgccgtgacc ttctgcttcg ccagcggcca   1620
gaacatcacc gaggaattct accagagcac ctgtagcgcc gtgtccaagg gctacctgag   1680
cgccctgcgg accggctggt acaccagcgt gatcaccatc gagctgagca acatcaaaaa   1740
gaacaagtgc aacggcaccg acgccaaaat caagctgatc aagcaggaac tggacaagta   1800
caagaacgcc gtgaccgagc tgcagctgct gatgcagagc acccccgcca ccaacaaccg   1860
ggccagacgg gagctgcccc ggttcatgaa ctacaccctg aacaacgcca aaaagaccaa   1920
cgtgaccctg agcaagaagc ggaagcggcg gttcctgggc ttcctgctgg gcgtgggcag   1980
cgccattgct agcggagtgg ctgtgtctaa ggtgctgcac ctggaaggcg aagtgaacaa   2040
gatcaagtcc gccctgctga gcaccaacaa ggccgtggtg tccctgagca acggcgtgtc   2100
cgtgctgacc agcaaggtgc tggatctgaa gaactacatc gacaagcagc tgctgcccat   2160
cgtgaacaag cagagctgca gcatcagcaa catcgagaca gtgatcgagt tccagcagaa   2220
gaacaaccgg ctgctggaaa tcacccgcga gttcagcgtg aacgccggcg tgaccacccc   2280
cgtgtccacc tacatgctga ccaacagcga gctgctgagc ctgatcaacg acatgcccat   2340
caccaacgac cagaaaaagc tgatgagcaa caacgtgcag atcgtgcggc agcagagcta   2400
ctccatcatg tccatcatca aagaagaggt gctggcctac gtggtgcagc tgcccctgta   2460
cggcgtgatc gacacccccct gctggaagct gcacaccagc cccctgtgca ccaccaacac   2520
caaagagggc agcaacatct gcctgacccg gaccgaccgg ggctggtact gcgataatgc   2580
cggcagcgtg tcattctttc cacaagccga gacatgcaag gtgcagagca accgggtgtt   2640
ctgcgacacc atgaacagcc tgaccctgcc cagcgaggtg aacctgtgca acgtggacat   2700
```

-continued cttcaaccct aagtacgact gcaagatcat gacctccaag accgacgtgt ccagctccgt 2760
gatcacctcc ctgggcgcca tcgtgtcctg ctacggcaag accaagtgca ccgccagcaa 2820
caagaaccgg ggcatcatca agaccttcag caacggctgc gactacgtgt ccaacaaggg 2880
cgtggacacc gtgtccgtgg gcaacaccct gtactacgtg aacaaacagg aaggcaagag 2940
cctgtacgtg aagggcgagc ccatcatcaa cttctacgac cccctggtgt tccccagcga 3000
cgagttcgac gccagcatca gccaggtcaa cgagaagatc aaccagagcc tggccttcat 3060
cagaaagagc gacgagctgc tgcacaatgt gaatgccgtg aagtccacca ccaatatcat 3120
gatcaccaca atcatcatcg tgatcatcgt catcctgctg tccctgatcg ccgtgggcct 3180
gctgctgtac tgcaaggccc ggtccacccc tgtgaccctg tccaaggacc agctgagcgg 3240
catcaacaat atcgccttct ccaacggacg cgtgaccgag ctgctttacc ggatgaagcg 3300
ggctgagaca tattgcccga gaccccctgtt ggcaatccat cctactgagg ctcgccacaa 3360
acagaaaatc gtggcccccg tcaaacagac actcaatttt gacttgttga aacttgcagg 3420
agatgttgag tcaaaccccg ggcctatggg cgtcaaggtc ctgttcgctc tgatttgtat 3480
cgctgtcgct gaagctaagc caaccgagaa taatgaagac tttaatatcg tggccgtggc 3540
ttctaacttc gctaccacag acctggatgc agacagggga aagctgccag gcaagaaact 3600
gcccctggag gtcctgaagg agatggaagc aaatgcccgg aaagccgggt gcacaagagg 3660
atgcctgatt tgtctgagcc acatcaagtg cactcctaag atgaagaagt tcatccccgg 3720
ccggtgccat acctacgagg gcgataagga atccgcccag ggaggaatcg gagaggctat 3780
cgtggatatt cccgaaatcc ctggcttcaa agacctggag cccatggaac agtttattgc 3840
acaggtggat ctgtgcgtcg actgtactac cggatgcctg aagggactgg caaacgtcca 3900
gtgtagcgac ctgctgaaga aatggctgcc tcagcgatgt gctacatttg ccagcaagat 3960
tcagggccag gtggacaaga ttaagggagc aggaggcgac tgataattct agacgagatc 4020
cgaacttgtt tattgcagct tataatggtt acaaataaag caatagcatc acaaatttca 4080
caaataaagc atttttttca ctgcattcta gttgtggttt gtccaaactc atcaatgtat 4140
cttatcatgt ctgcgatcgc tgatgagacc aggaccaggt gccgaccctg cgagtgcggc 4200
ggcaagcaca tgagaaatca gcctgtgatg ttggatgtga ccgaggagct taggcctgac 4260
catctggtgc tggcctgcac cagggccgag tttgggtcta gcgatgagga taccgattga 4320
ggtgggtaag gtgggcgtgg ctagcagggt gggcgtgtat aaattggggg tctaaggggt 4380
ctctctgttt gtcttgcaac agccgccgcc atgagcgaca ccggcaacag ctttgatgga 4440
agcatcttta gcccctatct gacagtgcgc atgcctcact gggccggagt gcgtcagaat 4500
gtgatgggtt ccaacgtgga tggacgtccc gttctgcctt caaattcgtc tacgatggcc 4560
tacgcgaccg tgggaggaac tccgctggac gccgcgacct ccgccgccgc ctccgccgcc 4620
gccgcgaccg cgcgcagcat ggctacggac ctttacagct ctttggtggc gagcagcgcg 4680
gcctctcgcg cgtctgctcg ggatgaaaaa ctgactgctc tgctgcttaa actggaagac 4740
ttgacccggg agctgggtca actgacccag caggtctcca gcttgcgtga gagcagcctt 4800
gcctccccct aatggcccat aatataaata aaagccagtc tgtttggatt aagcaagtgt 4860
atgttcttta tttaactctc cgcgcgcggt aagcccggga ccagcggtct cggtcgttta 4920
gggtgcggtg gattctttcc aacacgtggt acaggtggct ctggatgttt agatacatgg 4980
gcatgagtcc atccctgggg tggaggtagc accactgcag agcttcgtgc tcgggggtgg 5040
tgttgtatat gatccagtcg tagcaggagc gctgggcgtg gtgctgaaaa atgtccttaa 5100

-continued gcaagaggct tatagctagg gggaggccct tggtgtaagt gtttacaaat ctgcttagct 5160
gggaggggtg catccggggg gatatgatgt gcatcttgga ctggattttt aggttggcta 5220
tgttcccacc cagatccctt ctgggattca tgttgtgcag gaccaccagc acggtatatc 5280
cagtgcactt gggaaattta tcgtggagct tagacgggaa tgcatggaag aacttggaga 5340
cgcccttgtg gcctcccaga ttttccatac attcgtccat gatgatggca atgggcccgt 5400
gggaagctgc ctgagcaaaa acgtttctgg catcgctcac atcgtagtta tgttccaggg 5460
tgaggtcatc ataggacatc tttacaaatc gggggcggag ggtcccggac tgggggatga 5520
tggtaccctc gggccccggg gcgtagttcc cctcacagat ctgcatctcc caggctttca 5580
tttcagaggg agggatcata tccacctgcg gggcgatgaa aaagacagtt tctggcgcag 5640
gggagattaa ctgggatgag agcaggtttc tgagcagctg tgactttcca cagccggtgg 5700
gcccatatat cacgcctatc accggctgca gctggtagtt aagagagctg cagctgccgt 5760
cctcccggag caggggggcc acctcgttga gcatatccct gacgtggatg ttctccctga 5820
ccagttccgc cagaaggcgc tcgccgccca gcgaaagcag ctcttgcaag gaagcaaaat 5880
ttttcagcgg tttcaggcca tcggccgtgg gcatgttttt cagcgtctgg gtcagcagct 5940
ccagcctgtc ccagagctcg gtgatgtgct ctacggcatc tcgatccagc agatctcctc 6000
gtttcgcggg ttggggcggc tttcgctgta gggcaccagc cgatgggcgt ccagcggggc 6060
cagagtcatg tccttccatg ggcgcagagt cctcgtcagg gtggtctggg tcacggtgaa 6120
ggggtgcgct ccgggttggg cactggccag ggtgcgcttg aggctggttc tgctggtgct 6180
gaatcgctgc cgctcttcgc cctgcgcgtc ggccaggtag catttgacca tggtctcgta 6240
gtcgagaccc tcggcggcgt gccccttggc gcggagcttt cccttggagg tggcgccgca 6300
cgaggggcac tgcaggctct tcagggcgta gagcttggga gcgagaaaca cggactctgg 6360
ggagtaggcg tccgcgccgc aggccgcgca gaccgtctcg cattccacca gccaagtgag 6420
ttccgggcgg tcagggtcaa aaaccaggtt gcccccatgc tttttgatgc gtttcttacc 6480
tcggctctcc atgaggcggt gtcccttctc ggtgacgaag aggctgtccg tgtccccgta 6540
gaccgacttc aggggcctgt cttccagcgg agtgcctctg tcctcctcgt agagaaactc 6600
tgaccactct gagacgaagg cccgtgtcca ggccaggacg aaggaggcca cgtgggaggg 6660
gtagcggtcg ttgtccacta gcgggtccac cttctccagg gtgtgcagac acatgtcccc 6720
ctcctccgcg tccagaaaag tgattggctt ataggtgtag gacacgtgac cgggggttcc 6780
cgacgggggg gtataaaagg gggtgggcgc cctttcatct tcactctctt ccgcatcgct 6840
gtctgcgaga gccagctgct ggggtaagta ttccctttca aaggcgggca tgacctcagc 6900
gctcaggttg tcagtttcta aaaatgagga ggatttgatg ttcacctgtc cggaagtgat 6960
acctttgagg gtacctgggt ccatctggtc agaaaacact atttttttgt tgtcaagctt 7020
ggtggcgaac gacccgtaga gggcgttgga gagcagcttg gcaatggagc gcagggtctg 7080
gtttttgtcg cggtcggctc gctccttggc cgcgatgttg agttgcacgt attcgcgggc 7140
cacgcacttc cactcgggga agacggtggt gcgctcgtct gggatcaggc gcaccctcca 7200
gccgcggttg tgcagggtga ccatgtcgac gctggtggcg acctcaccgc gcagacgctc 7260
gttggtccag cagaggcggc cgcctttgcg cgagcagaag gggggtaggg ggtccagctg 7320
gtcctcgttt ggggggtccg cgtcgatggt aaagaccccg gggagcaggc gcgggtcaaa 7380
gtagtcgatc ttgcaagctt gcatgtccag agcccgctgc cattcgcggg cggcgagcgc 7440

-continued

```
gcgctcgtag gggttgaggg gcgggcccca gggcatgggg tgggtgagcg cggaggcgta   7500
catgccgcag atgtcataca cgtacagggg ttccctgagg ataccgaggt aggtggggta   7560
gcagcgcccc ccgcggatgc tggcgcgcac gtagtcatag agctcgtggg agggggccag   7620
catgttgagc ccaaggttgg tgcgctgggg gcgctcggcg cggaagacga tctgtctgaa   7680
gatggcatgg gagttggagg agatggtggg tcgctggaag acgttgaagc ttgcttcttg   7740
caagcccacg gagtccctga cgaaggaggc gtaggactcg cgcagcttgt gcaccagctc   7800
ggcggtgacc tggacgtcga gcgcgcagta gtcgagggtc tcgcggatga tgtcatactt   7860
atcctccccc ttctttttcc acagctcgcg gttgaggacg aactcttcgc ggtctttcca   7920
gtactcttgg aggggaaacc cgtccgtgtc cgaacggtaa gagcctagca tgtagaactg   7980
gttgacggcc tggtaggggc agcagccctt ctccacgggc agcgcgtagg cctgcgccgc   8040
cttgcggagg gaggtgtggg taagggcgaa agtgtccctg accatgactt tgaggtattg   8100
atgtctgaag tctgtgtcat cgcagccgcc ctgttcccac agggtgtagt ccgtgcgctt   8160
tttggagcgc gggttgggca gggagaaggt gaggtcattg aagaggatct tccccgctcg   8220
aggcatgaag tttctggtga tgcgaaaggg ccctgggacc gaggagcggt tgttgatgac   8280
ctgggcggcc aggacgatct cgtcaaagcc gtttatgttg tggcccacga tgtagagctc   8340
caggaagcgg ggctggccct tgatggaggg gagcttttta agttcctcgt aggtaagctc   8400
ctcgggcgat tccaggccgt gctcctccag ggcccagtct tgcaagtgag ggttggccgc   8460
caggaaggat cgccagaggt cgcgggccat gagggtctgc aggcggtcgc ggaaggttct   8520
gaactgccgc cctacggcca tcttttcggg ggtgatgcag tagaaggtga gggggtcttt   8580
ctcccagggg tcccatctga gctcttgggc gaggtcgcgc gcggcggcga ccagagcctc   8640
gtcgcccccc agtttcatga ccagcatgaa gggcacgagc tgcttgccaa aggctcccat   8700
ccaagtgtag gtctctacat cgtaggtgac aaagaggcgc tccgtgcgag gatgagagcc   8760
gatcgggaag aactggatct cccgccacca gttggaggat tggctgttga tgtggtgaaa   8820
gtagaagtcc cgtctgcggg ccgagcactc gtgctggctt ttgtaaaagc gaccgcagta   8880
ctggcagcgc tgcacgggtt gtatatcttg cacgaggtga acctggcgac ctctgacgag   8940
gaagcgcagc gggaatctaa gtcccccgcc tggggtcccg tgtggctggt ggtcttctac   9000
tttggttgtc tggccgccag catctgtctc ctggagggcg atggtggagc agaccaccac   9060
gccgcgagag ccgcaggtcc agatctcggc gctcggcggg cggagtttga tgacgacatc   9120
gcgcacattg gagctgtcca tggtctccag ctcccgcggc ggcaggtcag ccgggagttc   9180
ctggaggttc acctcgcaga gacgggtcaa ggcgcggaca gtgttgagat ggtatctgat   9240
ttcaaggggc gtgttggagg cggagtcgat ggcttgcaga aggccgcagc cccgggggc   9300
cacgatggtt ccccgcgggg cgcgagggga ggcggaagct gggggtgtgt tcagaagcgg   9360
tgacgcgggc gggcccccgg aggtaggggg ggttccggcc ccacaggcat gggcggcagg   9420
ggcacgtctt cgccgcgcgc gggcaggggc tggtgctggc tccggagagc gcttgcgtgc   9480
gcgacgacgc gacggttggt gtcctgtatc tggcgcctct gagtgaagac cacgggtccc   9540
gtgaccttga acctgaaaga gagttcgaca gaatcaatct cggcatcgtt gacagcggcc   9600
tggcgcagga tctcctgcac gtcgcccgag ttgtcctggt aggcgatctc tgccatgaac   9660
tgctcgatct cttcctcctg gagatctcct cgtccggcgc gctccacggt ggccgccagg   9720
tcgttggaga tgcgacccat gagctgcgag aaggcgttga ggccgccctc gttccagacc   9780
cggctgtaga ccacgccccc ctcggcgtcg cgggcgcgca tgaccacctg ggccaggttg   9840
```

agctccacgt gtcgcgtgaa gacggcgtag ttgcgcaggc gctggaaaag gtagttcagg 9900
gtggtggcgg tgtgttcggc gacgaagaag tacatgaccc agcgccgcaa cgtggattca 9960
ttgatgtccc ccaaggcctc caggcgctcc atggcctcgt agaagtccac ggcgaagttg 10020
aaaaactggg agttgcgagc ggacacggtc aactcctcct ccagaagacg gatgagctcg 10080
gcgacagtgt cgcgcacctc gcgctcgaag gccacggggg gcgcttcttc ctcttccacc 10140
tcttcttcca tgattgcttc ttcttcctca gccgggacgg gagggggcgg cggcggggga 10200
ggggcgcggc ggcggcggcg gcgcaccggc aggcggtcga tgaagcgctc gatcatctcc 10260
ccccgcatgc ggcgcatggt ctcggtgacg gcgcggccgt tctcccgggg gcgcagctca 10320
aagacgccgc ctctcatctc gccgcggggc gggcggccgt gaggtagcga gacggcgctg 10380
actatgcatc ttaacaattg ctgtgtaggt acgccgccaa gggacctgat tgagtccaga 10440
tccaccggat ccgaaaacct ttggaggaaa gcgtctatcc agtcgcagtc gcaaggtagg 10500
ctgagcaccg tggcgggcgg gggcgggtcg ggagagttcc tggcggagat gctgctgatg 10560
atgtaattaa agtaggcggt cttgagaagg cggatggtgg acaggagcac catgtctttg 10620
ggtccggcct gttggatgcg gaggcggtcg gccatgcccc aggcctcgtt ctgacaccgg 10680
cgcaggtctt tgtagtagtc ttgcatgagt ctttccaccg gcacctcttc tccttcctct 10740
tctccatctc gccggtggtt tctcgcgccg cccatgcgcg tgaccccaaa gcccctgagc 10800
ggctgcagca gggccaggtc ggcgaccacg cgctcggcca agatggcctg ctgtacctga 10860
gtgagggtcc tctcgaagtc atccatgtcc acgaagcggt ggtaggcgcc cgtgttgatg 10920
gtgtaggtgc agttggccat gacggaccag ttgacggtct ggtgtcccgg ctgcgagagc 10980
tccgtgtacc gcaggcgcga gaaggcgcgg gaatcgaaca cgtagtcgtt gcaagtccgc 11040
accagatact ggtagcccac caggaagtgc ggcggaggtt ggcgatagag gggccagcgc 11100
tgggtggcgg gggcgccggg cgccaggtct tccagcatga ggcggtggta tccgtagatg 11160
tacctggaca tccaggtgat gccggcggcg gtggtggtgg cgcgcgcgta gtcgcggacc 11220
cggttccaga tgtttcgcag gggcgagaag tgttccatgg tcggcacgct ctggccggtg 11280
aggcgcgcgc agtcgttgac gctctataca cacacaaaaa cgaaagcgtt tacagggctt 11340
tcgttctgta gcctggagga aagtaaatgg gttgggttgc ggtgtgcccc ggttcgagac 11400
caagctgagc tcggccggct gaagccgcag ctaacgtggt attggcagtc ccgtctcgac 11460
ccaggccctg tatcctccag gatacggtcg agagcccttt tgctttcttg gccaagcgcc 11520
cgtggcgcga tctgggatag atggtcgcga tgagaggaca aaagcggctc gcttccgtag 11580
tctggagaaa caatcgccag ggttgcgttg cggcgtaccc cggttcgagc ccctatggcg 11640
gcttggatcg gccggaaccg cggctaacgt gggctgtggc agccccgtcc tcaggacccc 11700
gccagccgac ttctccagtt acgggagcga gccccttttg ttttttattt tttagatgca 11760
tcccgtgctg cggcagatgc gcccctcgcc ccggcccgat cagcagcagc aacagcaggc 11820
atgcagaccc ccctctcctc tacccgcccc ggtcaccacg gccgcggcgg ccgtgtccgg 11880
cgcggggggc gcgctggagt cagatgagcc accgcggcgg cgacctaggc agtatctgga 11940
cttggaagag ggcgagggac tggcgcggct gggggcgagc tctccagagc gccacccgcg 12000
ggtgcagttg aaaagggacg cgcgcgaggc gtacctgccg cggcagaacc tgtttcgcga 12060
ccgcgggggc gaggagcccg aggagatgcg agactgcagg ttccaagcgg ggcgcgagct 12120
gcgccgcggg ttggacagac agcgcctgct gcgcgaggag gactttgagc ccgacacgca 12180

-continued gacgggcatc agccccgcgc gcgcgcacgt ggccgcggcc gacctggtga ccgcctacga 12240
gcagacggtg aaccaggagc gcaacttcca aaaaagcttc aacaaccacg tgcgcacgct 12300
ggtggcgcgc gaggaggtga ccctgggtct catgcatctg tgggacctgg tggaggcgat 12360
cgtgcagaac cccagcagca agcccctgac cgcgcagctg ttcctggtgg tgcagcacag 12420
cagggacaac gaggccttca gggaggcgct gctgaacatc accgagccgg aggggcgctg 12480
gctcctggac ctgataaaca tcctgcagag catagtggtg caggagcgca gcctgagcct 12540
ggccgagaag gtggcggcca ttaactattc tatgctgagc ttgggcaagt tctacgcccg 12600
caagatctac aagaccccct acgtgcccat agacaaggag gtgaagatag acagcttcta 12660
catgcgcatg gcgctaaagg tgctgaccct gagcgacgac ctgggagtgt accgcaacga 12720
gcgcatccac aaggccgtga gcgccagccg gcggcgcgag ctgagcgacc gcgagctgat 12780
gcacagtctg cagcgcgcgc tcaccggcgc gggcgagggc gacagggagg tcgagtccta 12840
cttcgacatg gggggctgacc tgcactggca gccgagccgc cgcgccctgg aggcggcggg 12900
ggcgtatggc ggcccccctgg cggccgatga cgaggaagag gaggactatg agctagagga 12960
gggcgagtac ctggaggact gacctggctg gtggtgtttt ggtatagatg caagatccga 13020
acgtggcgga cccggcggtc cgggcggcgc tgcagagcca gccgtccggc attaactcct 13080
ctgacgactg ggccgcggcc atgggtcgca tcatggccct gaccgcgcgc aaccccgagg 13140
ccttcaggca gcagcctcag gctaaccggc tggcggccat cttggaagcg gtagtgcccg 13200
cgcgctccaa ccccacccac gagaaggtgc tggccatagt caacgcgctg gcggagagca 13260
gggccatccg ggcggacgag gccggactgg tgtacgatgc gctgctgcag cgggtggcgc 13320
ggtacaacag cggcaacgtg cagaccaacc tggaccgcct ggtgacggac gtgcgcgagg 13380
ccgtggcgca gcgcgagcgc ttgcatcagg acggtaacct gggctcgctg gtggcgctaa 13440
acgccttcct cagcacccag ccggccaacg taccgcgggg gcaggaggac tacaccaact 13500
tcttgagcgc gctgcggctg atggtgaccg aggtccctca gagcgaggtg taccagtcgg 13560
ggcccgacta cttcttccag accagcagac agggcttgca aaccgtgaac ctgagccagg 13620
ctttcaagaa cctgcggggg ctgtggggag tgaaagcgcc caccggcgac cgagctacgg 13680
tgtccagcct gctaaccccc aactcgcgcc tgctgctgct gctgatcgcg cccttcacgg 13740
acagcgggag cgtctcgcgg gagacctatc tgggccacct gctgacgctg taccgcgagg 13800
ccatcgggca ggcgcaggtg gacgagcaca ccttccaaga gatcaccagc gtgagccacg 13860
cgctggggca ggaggacacg ggcagcctgc aggcgaccct gaactacctg ctgaccaaca 13920
ggcggcagaa gattcccacg ctgcacagcc tgacccagga ggaggagcgc atcttgcgct 13980
acgtgcagca gagcgtgagc ctgaacctga tgcgcgacgg cgtgacgccc agcgtggcgc 14040
tggacatgac cgcgcgcaac atggaaccgg gcatgtacgc ttcccagcgg ccgttcatca 14100
accgcctgat ggactacttg catcgggcgg cggccgtgaa ccccgagtac ttcaccaatg 14160
ccattctgaa tccccactgg atgcccccctc cgggtttcta caacggagac ttcgaggtgc 14220
ctgaggtcaa tgatgggttc ctctgggatg acatggatga cagtgtgttc tcccccaacc 14280
cgctgcgcgc cgcgtctctg cgattgaagg agggctctga cagggaagga ccgaggagtc 14340
tggcctcctc cctggctctg gggggcggtgg gcgccacggg cgcggcggcg cggggcagca 14400
gccccttccc cagcctggca gactctctga atagcgggcg ggtgagcagg ccccgcttgc 14460
taggcgagga ggagtatctg aacaactccc tgctgcagcc cgtgagggac aaaaacgctc 14520
agcgacagca gtttcccaac aacgggatag agagcctggt ggacaagatg tccagatgga 14580

-continued

```
agacatatgc gcaggagtac aaggagtggg aggaccgcca gccgcggccc ctgccgcccc  14640
ctagacagcg ctggcagcgg cgcgcgtcca accgccgctg gagacaggga cccgaggacg  14700
atgatgactc tgcagatgac agcagcgtgt tggacctggg cgggagcggg aacccctttt  14760
cgcacctgcg cccacgcctg ggcaagatgt tttaaaagag aaaaataaaa ctcaccaagg  14820
ccatggcgac gagcgttggt tttttgttcc cttccttagt atgcggcgcg cggcgatgtt  14880
cgaggagggg cctcccccct cttacgagag cgcgatggga atttctcctg cggcgcccct  14940
gcagcctccc tacgtgcctc ctcggtacct gcaacctaca gggggggagaa atagcatctg  15000
ttactctgag ctgcagcccc tgtacgatac caccagactg tacctggtgg acaacaagtc  15060
cgcggacgtg gcctccctga actaccagaa cgaccacagc gattttttga ccacggtgat  15120
ccaaaacaac gacttcaccc caaccgaggc cagtacccag accataaacc tggacaacag  15180
gtcgaactgg ggcggcgacc tgaagaccat cctgcacacc aacatgccca acgtgaacga  15240
gttcatgttt accaactctt ttaaggcgcg ggttatggtg gcgcgcgagc agggggaggc  15300
gaagtacgag tgggtggact tcacgctgcc cgagggcaac tactcagaga ccatgactat  15360
tgacctgatg aacaatgcga tcgtggaaca ctacctgaaa gtgggcaggc agaacggggt  15420
gaaggagagc gatatcgggg tcaagtttga caccagaaac tttcgtctgg gctgggaccc  15480
cgtgaccggg ctggtcatgc cgggggtcta caccaacgag gcctttcatc ccgatatagt  15540
gctcctgccc ggctgtgggg tggactttac ccagagccgg ctgagcaacc tgctgggcgt  15600
tcgcaagcgg caacctttcc aggagggttt caagatcacc tatgaggatc tggagggggg  15660
caacattccc gcgctccttg atctggacgc ctacgaggag agcttgaaac ccgaggagag  15720
cgctggcgac agcggcgaga gtggcgagga gcaagccggc ggcggtggca gcgcgtcggt  15780
agaaaacgaa agtactcccg cagtggcggc agacgctgcg gaggtcgagc cagaggccat  15840
gcagcaggac gcagaggagg gcgcacagga gggcgcgcag gaggacatga acgatgggga  15900
gatcagggga gacactttcg ccacccgggg cgaagaaaaa gaggcagagg cggtggcggc  15960
gacggtggaa gccgaaaccg aggcagaggc agagcccaag accgaagtta tggaagacat  16020
gaatgatgga gaacgtaggg gtgacacgtt tgccacccgg ggcgaagaga aggcggcgga  16080
ggcagaagcc gcggctgagg aggcggctgc ggctgcggcc gaggctgagg ctgcggctga  16140
ggctaaggtc gaagccgatg ttgcggttga ggctcaggct gaggaggagg aggcggcgac  16200
tgaagcagtt aaggaaaagg cccaggcaga gcaggaagag aaaaaacctg tcattcaacc  16260
tctaaaagaa gatagcaaaa agcgcagtta caacgtcatc gagggcagca cctttaccca  16320
gtaccgcagc tggtacctgg cgtacaacta cggcgacccg gtcaaggggg tgcgctcgtg  16380
gaccctgctc tgcacgccgg acgtcacctg cggctccgag cagatgtatt ggtcgctgcc  16440
aaacatgatg caagacccgg tgaccttccg ctccacgcgg caggttagca acttcccggt  16500
ggtgggcgcc gaactgctgc ccgtgcactc caagagtttt tacaacgagc aggccgtcta  16560
ctcccagctg atccgccagg ccacctctct gacccacgtg ttcaatcgct ttcccgagaa  16620
ccagattttg gcgcgcccgc cggcccccac catcaccacc gtcagtgaaa acgttcctgc  16680
cctcacagat cacgggacgc taccgctgcg caacagcatc tcaggagtcc agcgagtgac  16740
cattactgac gccagacgcc ggacctgccc ctacgtttac aaggccttgg gcatagtctc  16800
gccgcgcgtc ctctccagtc gcactttttta aaatacatct accctcacgc ttcaaaatca  16860
tgtccgtact catctcaccc agcaacaaca ccggctgggg gctgcgcgcg cccagcaaga  16920
```

-continued

```
tgtttggagg ggcgaggaaa cgctccgagc agcacccagt gcgcgtgcgc ggccactacc  16980
gcgcgccctg gggagcgcac aagcgcgggc gcgcagggcg caccactgtg gacgacgcca  17040
ttgactccgt agtggagcag gcgcgccact acacacccgg cgcgccgtcc gcccccgccg  17100
tgtccaccgt ggacgaggcg atcgagagcg tggtacaggg cgcgcggcac tatgccaacc  17160
ttaaaaatcg acgccgtcgc gtggctcgcc gccatcgccg gagaccccgg gccaccgccg  17220
ccgcgcgcct tgctaaggct ctgctcaggc gcgccaggcg aactggccgc cgggccgcca  17280
tgagggccgc acggcgggct gccgccagcg cggccgccgc ggccccacgg gcacgaaggc  17340
gcgcggccgc tgccgccgcc gccgccattt ccagcttggc ctcgacgcgg cgcggtaaca  17400
tatactgggt gcgcgactcg gtaaccggca cgcgggtacc cgtgcgcttt cgcccccgc  17460
ggaattagca caagacaaca tacacactga gtctcctgct gttgtgtatc ccagcggcga  17520
ccgtcagcag cggcgacatg tccaagcgca aaattaaaga agagatgctc caggtcatcg  17580
cgccggagat ctatgggccc ccgaagaagg aggaggatga ttacaagccc cgcaagctaa  17640
agcgggtcaa aaagaaaaag aaagatgatg acgttgacga ggcggtggag tttgtccgcc  17700
gcatggcgcc caggcgcccc gtgcagtgga agggtcggcg cgtgcagcga gtcctgcgcc  17760
ccggcaccgc ggtggtcttt acgcccggcg agcgttccac gcgcactttc aagcgggtgt  17820
acgatgaggt gtacggcgac gaggatctgt tggagcaggc caaccatcgc tttggggagt  17880
ttgcatatgg gaaacggccc cgcgagagcc taaaagagga cctgctggcg ctaccgctgg  17940
acgagggcaa tcccaccccg agtctgaagc cggtaaccct gcaacaggtg ctgcctttga  18000
gcgcgcccag cgagcagaag cgagggttga agcgcgaggg cggggacctg gcacccaccg  18060
tgcagttgat ggtgcccaag cggcagaagc tggaggacgt gctggagaaa atgaaagtag  18120
agcccgggat ccagcccgaa atcaaggtcc gccccatcaa gcaggtggcg cccggcgtgg  18180
gagtccagac cgtggacgtt aggattccca cggaggagat ggaaacccaa accgccactc  18240
cctcttcggc ggctagcgcc accaccggct ccgcttcggt agaggtgcag acggacccct  18300
ggctagccgc cgccgccccg gccgcccccc gttcgcgcgg gcgcaagaga aattatccag  18360
cggccagcgc gctcatgccc cagtacgcac tgcatccatc catcgcgccc acccccggct  18420
accgcgggta ctcgtaccgc ccgcgcagat cagccggcac ccgcggccgc cgccgccgtg  18480
cgaccacaac cagccgccgc cgtcgccgcc gccgccagcc agtgctgacc cccgtgtctg  18540
taaggaaggt ggctcgctcg gggagcacgc tggtggtgcc cagagcgcgc taccacccca  18600
gcattgttta aagccggtct ctgtatggtt cttgcagata tggccctcac ttgtcgcctc  18660
cgcttcccgg tgccgggata ccgaggaaga actcaccgcc gcagaggcat ggcgggcagt  18720
ggtctccgcg gcggccgtcg ccatcgccgg cgcgcaaaga gcaggcgcat gcgcggcggt  18780
gtgctgccct tcctaatccc gctaatcgcc gcggcgatcg gtgccgtgcc cgggatcgcc  18840
tccgtggccc tgcaggcgtc ccagaaacat tgactcttgc aaccttgcaa gcttgcattt  18900
tttggaggaa aaaataaaaa gtctagactc tcacgctcgc ttggtcctgt gactattttg  18960
tagaaaaaag atggaagaca tcaactttgc gtcgctggcc ccgcgtcacg gctcgcgccc  19020
gttcatggga gactggacag atatcggcac cagcaatatg agcggtggcg ccttcagctg  19080
gggcagtctg tggagtggcc ttaaaaattt tggttccacc attaagaact atggcaacaa  19140
agcgtggaac agcagcacgg gtcagatgct gagagacaag ttgaaagagc agaacttcca  19200
ggagaaggtg gcacagggcc tggcctctgg catcagcggg gtggtggaca tagctaacca  19260
ggccgtgcag aaaaagataa acagtcatct ggacccccgc cctcaggtgg aggaaacgcc  19320
```

-continued

```
tccagccatg gagacggtgt ctcccgaggg caaaggcgaa aagcgcccgc ggcccgacag  19380
ggaagagacc ctggtgtcac acaccgagga gccgccctct tacgaggagg cagtcaaggc  19440
cggcctgccc accactcgcc ccatagctcc catggccacc ggtgtggtgg gtcacaggca  19500
acacaccccc gcgacactag atctgccccc gccgtccgag ccgactcgcc agccaaaggc  19560
ggtgacggtg cccgctccct ccacttccgc cgccaacaga gtgcctctgc gccgcgctgc  19620
gagcggcccc cgggcctcgc gagtcagcgg caactggcag agcacactga acagcatcgt  19680
gggcctggga gtgaggagtg tgaagcgccg ccgttgctac tgaatgagca agctagctaa  19740
cgtgttgtat gtgtgtatgc gtcctatgtc gccgccagag gagctgttga gccgccggcg  19800
ccgtctgcac tccagcgaat ttcaagatgg cgaccccatc gatgatgcct cagtggtcgt  19860
acatgcacat ctcgggccag gacgcttcgg agtacctgag ccccgggctg gtgcagttcg  19920
cccgcgccac agacacctac ttcaacatga gtaacaagtt caggaacccc actgtggcgc  19980
ccacccacga tgtgaccacg gaccggtcgc agcgcctgac gctgcggttc atccccgtgg  20040
atcgggagga caccgcttac tcttacaagg cgcggttcac gctggccgtg ggcgacaacc  20100
gcgtgctgga catggcctcc acttactttg acatccgggg ggtgctggac aggggcccca  20160
ctttcaagcc ctactcgggc actgcctaca actccctggc ccccaagggc gctcccaatt  20220
cttgcgagtg ggaggaggaa acacaaaatg aggtacaagc caatgaagaa caactagcag  20280
aagaagagga tgaagaaatg gctcaagagg atcagcagcc tactaaaaaa acccatgtat  20340
atgctcaggc acctctttct ggcgaacaga ttaccaaaga tggcttgcaa ataggagctg  20400
aagttacagg agaaacatca aagcccattt ttgcagacaa gacattccaa ccagaacctc  20460
agataggaga gtctcaatgg aatgaggccg atgctacagt agcaggaggt agggttttga  20520
aaaagactac ccctatgaaa ccttgctatg gatcctatgc cagacctacc aatgccaatg  20580
gagggcaggg gatacttgag gcaaatgcta aaggggaact cgaatctaaa gttgagatgc  20640
agtttttctc taacaccaca actcttaatg taagagacgg tgaaaatggc cttaaaccaa  20700
aagtagtgct gtatagcgaa gatgtcaacc tggaatcccc tgacactcat ctgtcttaca  20760
agcccaaaaa agatgatgtt aatgccaaaa tcatgttggg tcagcaagcc atgcccaaca  20820
gacccaacct cattggattt agagataatt tcattgggct catgtattac aacagcactg  20880
gaaacatggg agtgctggcg ggtcaggcct ctcagttgaa tgctgtggtg gacttgcagg  20940
atagaaacac ggaactgtca tatcagctta tgcttgattc cattggagat agaaccagat  21000
acttttccat gtggaaccag gcagtggata gctatgaccc agatgttaga atcattgaaa  21060
accatggggt ggaggatgag ctgcccaact actgttttcc cttgggcggt ataggaatta  21120
cagatacata ccaggccata aaagcagcca atggtggaga tgctactacg tggtctgctg  21180
ataacacatt tgcagaccgc aacgaaatag gggtgggaaa caacttcgcc atggagatca  21240
acatccaggc caacctctgg agaaacttcc tctatgcgaa cgtgggactc tacctgccag  21300
acaagctcaa gtacaacccc accaacgtgg acatctctga caaccccaac acctatgact  21360
acatgaacaa gcgggtggtg gcccccggcc tggtggactg ctttgtcaat gtgggagcca  21420
ggtggtccct ggactacatg gacaacgtca accccttcaa ccaccaccgc aatgcgggtc  21480
tgcgctaccg ctccatgatc ctgggcaacg ggcgctatgt gcccttccac atccaggtac  21540
cccagaagtt ctttgccatc aagaacctcc tgctcctgcc cggctcctac acctacgagt  21600
ggaacttcag gaaggatgta aacatggtcc tacagagctc tctgggcaat gaccttaggg  21660
```

```
tagatggggc cagcatcaag tttgacagca tcaccctcta tgctacattt ttccccatgg  21720
cccacaacac cgcctccacg cttgaggcca tgctgagaaa cgacaccaac gaccagtcct  21780
tcaatgacta cctctctggg gccaacatgc tctacccaat cccagccaag gccaccaacg  21840
tgcccatctc catcccctct cgcaactggg ccgcctttag aggctgggcc tttacccgcc  21900
ttaagaccaa ggagaccccc tccctgggct cgggttttga tccctacttt gtttactcgg  21960
gatccatccc ctacctggat ggcaccttct acctcaacca cactttcaag aagatatcca  22020
tcatgtatga ctcctccgtc agctggccgg gcaacgaccg cttgctcacc cccaatgagt  22080
tcgaggtcaa gcgcgccgtg gacggcgagg gctacaacgt ggcccagtgc aacatgacca  22140
aggactggtt cctggtgcag atgctggcca actacaacat aggctaccag ggcttctaca  22200
tcccagagag ctacaaggac aggatgtatt ccttcttcag aaatttccaa cccatgagcc  22260
gacaggtggt ggacgagacc aattacaagg actatcaggc cattggcatc acccaccagc  22320
acaacaactc gggtttcgtg ggctacctgg cgcccaccat gcgcgaggga caggcctacc  22380
ccgccaactt cccctacccc ctgataggca agaccgcggt cgacagcgtc acccagaaaa  22440
agttcctctg cgaccgcacc ctctggcgca tccccttctc tagcaacttt atgtccatgg  22500
gtgcgctcac ggacctgggc caaaacctgc tttatgccaa ctctgcccat gcgctggaca  22560
tgacttttga ggtggacccc atggacgagc ccacccttct ctatattgtg tttgaagtgt  22620
tcgacgtggt cagagtgcac cagccgcacc gcggtgtcat cgagaccgtg tacctgcgta  22680
cgcccttctc agccggcaac gccaccacct aaggagacag cgccgccgcc tgcatgactg  22740
gttccaccga gcaagagctc agggccatcg ccagagacct gggatgcgga ccctattttt  22800
tgggcaccta tgacaaacgc ttcccgggtt ttatctcccg agacaagctc gcctgcgcca  22860
tcgtcaacac ggccgcgcgc gagaccgggg gcgtgcactg gctggccttt ggctgggacc  22920
cgcgctctaa aacttgctac ctctttgacc cctttggctt ctccgatcag cgcctcaggc  22980
agatttatga gtttgagtac gaggggctgt tgcgccgcag cgcgcttgcc tcctcgcccg  23040
accgctgcat caccettgag aagtccaccg agaccgtgca ggggccccac tcggccgcct  23100
gcggtctctt ctgttgcatg tttttgcacg cctttgtgca ctggcctcag agtcccatgg  23160
atcgcaaccc caccatgaac ttgctaaagg gagtgcccaa cgccatgctc cagagccccc  23220
aggtcctgcc caccctgcgc cgcaaccagg aacagctcta ccgcttcctg gagcgccact  23280
ccccctactt ccgcagccac agcgcgcgca tccggggggc cacctctttt tgccacttgc  23340
aagaaaacat gcaagacgga aaatgatgta cagcatgctt ttaataaatg taaagactgt  23400
gcactttatt tatacacggg ctctttctgg ttatttattc aacaccgccg tcgccatcta  23460
gaaatcgaaa gggttctgcc gcgcgtcgcc gtgcgccacg ggcagagaca cgttgcgata  23520
ctggaagcgg ctcgcccact tgaactcggg caccaccatg cggggcagtg gttcctcggg  23580
gaaattctcg ctccacaggg tgcgggtcag ctgcagcgcg ctcaggaggt cgggagccga  23640
gatcttgaag tcgcagttgg ggccggaacc ctgcgcgcgc gagttgcggt acacggggtt  23700
gcagcactgg aacaccagca gggccggatt attcacgctg gccagcaggc tctcgtcgct  23760
aatcatgtcg ctgtccagat cctccgcgtt gctcagggcg aatggggtca tcttgcagac  23820
ctgcctgccc aggaaaggcg ggagcccagg cttgccgtta cagtcgcagc gcaggggcat  23880
tagcaggtgc ccacggcccg actgcgcctg cgggtacaac gcgcgcatga aggcttcgat  23940
ctgcctaaaa gccacctggg tcttggctcc ctccgaaaag aacatcccac aggacttgct  24000
ggagaactgg ttcgcgggac agctggcatc gtgcaggcag cagcgcgcgt cagtgttggc  24060
```

```
gatctgcacc acgttgcgac cccaccggtt tttcactatc ttggccttgg aagcctgctc  24120
ctttagcgcg cgctggccgt tctcgctggt cacatccatc tctatcacct gttccttgtt  24180
gatcatgttt gtcccgtgca gacactttag gtcgccctcc gtctgggtgc agcggtgctc  24240
ccacagcgcg caaccggtgg gctcccaatt tttgtgggtc acccccgcgt aggcctgcag  24300
gtaggcctgc aggaagcgcc ccatcatggt cataaaggtc ttctggctcg taaaggtcag  24360
ctgcaggccg cgatgctctt cgttcagcca ggtcttgcag atggcggcca gcgcctcggt  24420
ctgctcgggc agcatcttaa aatttgtctt caggtcgtta tccacgtggt acttgtccat  24480
catggcacgc gccgcctcca tgcccttctc ccaggcggac accatgggca ggcttagggg  24540
gtttatcact tccagcggcg aggacaccgt actttcgatt tcttcttcct ccccctcttc  24600
ccggcgcgcg cccccgctgt tgcgcgctct taccgcctgc accaaggggt cgtcttcagg  24660
caagcgccgc accgagcgct tgccgccctt gacctgcttg atcagtaccg gcgggttgct  24720
gaagcccacc atggtcagcg ccgcctgctc ttcttcgtct tcgctgtcta ccactatttc  24780
tggggagggg cttctccgct ctgcggcaaa ggcggcggat cgcttctttt ttttcttggg  24840
agccgccgcg atggagtccg ccacggcgac cgaggtcgag ggcgtggggc tgggggtgcg  24900
cggcaccagg gcctcgtcgc cctcggactc ttcctctgac tccaggcggc ggcggagtcg  24960
cttctttggg ggcgcgcgcg ttagcggcgg cggagacggg gacggggacg gggacgggac  25020
gccctccaca gggggcggtc ttcgcgcaga cccgcggccg cgctcggggg tcttctcgcg  25080
ctggtcttgg tcccgactgg ccattgtatc ctcctcctcc taggcagaga gacataagga  25140
gtctatcatg caagtcgaga aggaggagag cttaaccacc ccctctgaga ccgccgtcgc  25200
cgtcgccccc gctaccgccg acgcgcccgc cacaccgagc gacacccccg cggacccccc  25260
cgccgacgca cccctgttcg aggaagcggc cgtggagcag gacccgggct ttgtctcggc  25320
agaggaggat ttgcaagagg aggaggataa ggaggagaag ccctcagtgc caaaagatca  25380
taaagagcaa gacgagcacg acgcagacgc acaccagggt gaagtcgggc ggggggacgg  25440
agggcatggc ggcgccgact acctagacga aggaaacgac gtgctcttga agcacctgca  25500
tcgtcagtgc gccattgtct gcgacgctct gcaggagcgc agcgaggtgc ccctcagcgt  25560
ggcggaggtc agccgcgcct acgagctcag cctcttttcc ccccgggtgc ccccccgccg  25620
ccgcgaaaac ggcacatgcg agcccaaccc gcgcctcaac ttctaccccg cctttgtggt  25680
gcccgaggtc ctggccacct atcacatctt ctttcaaaat tgcaagatcc ccatctcgtg  25740
ccgcgccaac cgtagccgcg ccgataagat gctggccctg cgccagggcg accacatacc  25800
tgatatcgcc gctttggaag atgtgccaaa gatcttcgag ggtctgggtc gcaacgagaa  25860
gcgggcagca aactctctgc aacaggaaaa cagcgaaaat gagagtcaca ctggagcgct  25920
ggtggagctg gagggcgaca acgcccgcct ggcggtgctc aagcgcagca tcgaggtcac  25980
ccactttgcc taccccgcgc tcaacctgcc ccccaaagtc atgaacgcgg tcatggacgg  26040
gctaatcatg cgccgcggcc ggccccttgc tccagatgca aacttgcatg aggagaccga  26100
ggacggtcag cccgtggtca gcgacgagca gctgacgcgc tggctggaaa ccgcggaccc  26160
cgccgaactg gaggagcggc gcaagatgat gatggccgcg gtgctggtca ccgtagagct  26220
ggagtgtctg cagcgcttct tcggcgaccc cgagatgcag agaaaggtcg aggagaccct  26280
acactacacc ttccgccagg gctacgtgcg ccaggcttgc aagatctcca acgtggagct  26340
cagcaacctg gtgtcctacc tgggcatctt gcatgaaaac cgccttgggc agagcgtgct  26400
```

-continued

```
acactccacc ctgcgcgggg aggcgcgccg cgactacgtg cgcgactgcg tttacctctt  26460
cctctgctac acctggcaga cggccatggg ggtctggcag cagtgcctgg aggagcgcaa  26520
cctcaaggag ctggagaagc tcctgcagcg cgcgctcaaa gacctctgga cgggctacaa  26580
cgagcgctcg gtggccgccg cgctggccga cctcatcttc cccgagcgcc tgctcaaaac  26640
tctccagcag gggctgcccg acttcaccag ccaaagcatg ttgcaaaatt ttaggaactt  26700
tatcctggag cgttctggca tcctacccgc cacctgctgc gccctgccca gcgactttgt  26760
ccccctcgtg taccgcgagt gccccccgcc gctgtggggc cactgctacc tgttccaact  26820
ggccaactac ctgtcctacc acgcggacct catggaagac tccagcggcg aggggctcat  26880
ggagtgccac tgccgctgca acctctgcac gccccaccgc tccctggtct gcaacaccca  26940
actgctcagc gagagtcaga ttatcggtac cttcgagcta cagggtccgt cctcctcaga  27000
cgagaagtcc gcggctccgg ggctaaaact cactccgggg ctgtggactt ccgcctacct  27060
gcgcaaattt gtacctgaag actaccacgc ccacgagatc aggttttacg aggaccaatc  27120
ccgcccgccc aaggcggagc tgaccgcctg cgtcatcacc cagggcgaga tcctaggcca  27180
attgcaagcc atccaaaaag cccgccaaga gtttttgctg agaaagggtc ggggggtgta  27240
tctggacccc cagtcgggtg aggagctcaa cccggttccc ccgctgccgc cgccgcggga  27300
ccttgcttcc caggataagc atcgccatgg ctcccagaaa gaagcagcag cggccgccac  27360
tgccgccacc ccacacgctg gaggaagagg aggaatactg ggacagtcag gcagaggagg  27420
tttcggacga ggaggagccg gagacggaga tggaagagtg ggaggaggac agcttagacg  27480
aggaggcttc cgaagccgaa gaggcaggcg caacaccgtc accctcggcc gcagccccct  27540
cgcaggcgcc cccgaagtcc gctcccagca tcagcagcaa cagcagcgct ataacctccg  27600
ctcctccacc gccgcgaccc acggccgacc gcagacccaa ccgtagatgg gacaccaccg  27660
gaaccggggc cggtaagtcc tccgggaaag gcaagcaagc gcagcgccaa ggctaccgct  27720
cgtggcgcgc tcacaagaac gccatagtcg cttgcttgca agactgcggg gggaacatct  27780
ccttcgcccg ccgcttcctg ctcttccacc acggtgtggc cttcccccgt aacgtcctgc  27840
attactaccg tcatctctac agcccctact gcggcggcag tgagccagag gcggccggcg  27900
gcagcggcgc ccgtttcggt gcctaggaag acccagggca agacttcagc caagaaactc  27960
gcggcggccg cggcgaacgc ggtcgcgggg gccctgcgcc tgacggtgaa cgaacccctg  28020
tcgacccgcg aactgaggaa ccgaatcttc cccactctct atgccatctt ccagcagagc  28080
agagggcagg atcaggaact gaaagtaaaa aacaggtctc tgcgctccct cacccgcagc  28140
tgtctgtatc acaagagcga agaccagctt cggcgcacgc tggaggacgc tgaggcactc  28200
ttcagcaaat actgcgcgct cactcttaag gactagctcc gcgcccttct cgaatttagg  28260
cgggaacgcc tacgtcatcg cagcgccgcc gtcatgagca aggacattcc cacgccatac  28320
atgtggagct atcagccgca gatgggactc gcggcgggcg cctcccagga ttactccacc  28380
cgcatgaact ggctcagtgc cggcccacac atgatctcac aggttaatga catccgcacc  28440
catcgaaacc aaatattggt ggagcaggcg gcaattacca ccacgccccg caataatccc  28500
aaccccaggg agtggcccgc gtccctggtg tatcaggaaa ttcccggccc caccaccgta  28560
ctacttccgc gtgattccca ggccgaagtc caaatgacta actcaggggc acagctcgcg  28620
ggcggctgtc gtcacagggt gcggcctcct cgccagggta taactcacct gaagatccga  28680
ggcagaggta ttcagctcaa cgacgagtcg gtgagctcct cgctcggtct cagacctgac  28740
gggaccttcc agatagccgg agccggccga tcttccttca cgccccgcca ggcgtacctg  28800
```

actctgcaga gctcgtcctc ggcgccgcgc tcgggcggca tcgggactct ccagttcgtg 28860
caggagtttg tgccctcggt ctacttcaac cccttctcgg gctctcccgg tcgctacccg 28920
gaccagttca tcccgaactt tgacgccgcg agggactcgg tggacggcta cgactgaatg 28980
tcgggtggac ccggtgcaga gcaacttcgc ctgaagcacc ttgaccactg ccgccgccct 29040
cagtgctttg cccgctgtca gaccggtgag ttccagtact tttccctgcc cgactcgcac 29100
ccggacggcc cggcgcacgg ggtgcgcttt ttcatcccga gtcaggtccg ctctacccta 29160
atcagggagt tcaccgcccg tcccctactg gcggagttgg aaaaggggcc ttctatccta 29220
accattgcct gcatctgctc taaccctgga ttacaccaag atctttgctg tcatttgtgt 29280
gctgagtata ataaaggctg agatcagaat ctactcgggc tcctgtcgcc atcctgtcaa 29340
cgccaccgtc caagcccggc ccgatcagcc cgaggtgaac ctcacctgcg gtctgcaccg 29400
gcgcctgagg aaatacctag cttggtacta caacagcact ccctttgtgg tttacaacag 29460
ctttgaccag gacggggtct cactgaggga taacctctcg aacctgagct actccatcag 29520
gaagaacaac accctcgagc tacttcctcc ttacctgccc gggacttacc agtgtgtcac 29580
cggtccctgc acccacaccc acctgttgat cgtaaacgac tctcttccga gaacagacct 29640
caataactcc tctccgcagt tccccagaac aggaggtgag ctcaggaaac cccgggtaaa 29700
gaagggtgga caagagttaa cacttgtggg gtttctggtg tatgtgacgc tggtggtggc 29760
tcttttgatt aaggcttttc cttccatgtc tgaactatcc ctcttctttt atgaacaact 29820
cgactagtgc taacgggacc ctacccaacg aatcgggatt gaatatcggt aaccaggttg 29880
cagtttcact tttgattacc ttcatagtcc tcttcctgct agtgctgtcg cttctgtgcc 29940
tgcggatcgg gggctgctgc atccacgttt atatctggtg ctggctgttt agaaggttcg 30000
gagaccaccg caggtagaat aaacaaacct agacctagaa atggacggtc tctgcagcga 30060
gcaacgcata ctagagaggc gccggcaaaa agcagagctc gagcgtctta aacaagagct 30120
ccaagacgcc gtggccatac accagtgcaa aaaagggctc ttctgtctgg taaaacaggc 30180
cacgctcacc tatgaaaaaa caggtgacac ccaccgccta ggatacaagc tgcccacaca 30240
gcgccaaaag tttgccctta tgataggtga acaacccatc accgtgaccc agcactccgt 30300
ggagacagaa ggctgcattc atgctccctg caggggcgct gactgcctct acaccttgat 30360
caaaaccctt tgcggtctca gagaccttat ccctttcaat tgatcataac tgtaatcaat 30420
aaaaaatcac ttacttgaaa tctgatagca agcctctgtc caatttttttc agcaacactt 30480
ccttcccctc ttcccaactc tggtactcta ggcgcctcct agctgcaaac ttcctccaca 30540
gtctgaaggg aatgtcagat tcctcctcct cctgtccctc cgcacccacg atcttcatgt 30600
tgttgcagat gaagcgcacc aaaacgtctg acgagagctt caaccccgtg taccccctatg 30660
acacggaaaa cggtcctccc tccgtccctt tcctcacccc tcccttcgtg tctcccgatg 30720
gattccaaga gagccccccc ggggtcctgt ctctgaacct ggccgagccc ctggtcactt 30780
cccacggcat gctcgccctg aaaatgggaa gtggcctctc cctggacgac gccggcaacc 30840
tcacctctca agatgtcacc accactaccc ctcccctgaa aaaaaccaag accaacctca 30900
gcctagaaac ctcagccccc ctgactgtga gcacctcagg cgccctcacc ctagcagccg 30960
ccgttcccct ggcggtggcc ggcacctccc tcaccatgca atcagaggcc cccctgacag 31020
tccaagatgc aaaactcacc ctggccacca agggcccccct gaccgtgtct gaaggcaaac 31080
tggccttgca gacctcggcc ccgctgacgg ccgctgacag cagcgccctc accgttagcg 31140

-continued

```
ccacaccacc catcagtgta agcagtggaa gtttgggctt agacatggaa gaccccatgt  31200
atactcatga tggaaaactg ggaataagaa ttggaggccc actgagagta gtagacagcc  31260
tgcacacact gactgtagtt accggaaatg gaatagctgt agataacaat gccctccaaa  31320
ctagagttac gggcgccctg ggttatgaca catcaggaaa cctacaactg agagccgcgg  31380
ggggtatgcg aattgatgca aatggccaac ttatccttga tgtggcatac ccatttgatg  31440
ctcaaaacaa tctcagcctt agacttggtc agggacccct gtatgtaaac acagaccaca  31500
acctagattt gaattgcaac agaggtctga ccacaactac caccaacaac acaaaaaaac  31560
ttgaaactaa aattggctca ggcttagact atgataccaa tggtgctgtc attattaaac  31620
ttggtactgg tgtaagcttt gacagcacag gcgccctaac tgtgggaaac actggcgatg  31680
ataaactgac tctgtggaca accccagacc catctccaaa ttgcagaatt cacgcagaca  31740
aagactgcaa gtttactcta gtcctaacta agtgtggaag tcaaatcctg gcttctgtcg  31800
ccgccctagc ggtgtcagga aatctggctt caataacagg caccgttgcc agcgttacca  31860
tctttctcag atttgatcag aatggagtgc ttatggaaaa ctcctcccta gacaagcagt  31920
actggaactt cagaaatggt aactcaacca atgccacccc ctacaccaat gcagttgggt  31980
tcatgccaaa cctcgcagca taccccaaga cacagagcca gactgctaaa aacaacattg  32040
taagtcaggt ttacttgaat ggggacaaat ccaaacccat gacccttacc attaccctca  32100
atggaactaa tgaatccagt gaaactagcc aggtgagtca ctactccatg tcatttacat  32160
gggcttggga gagtgggcaa tatgccaccg aaacctttgc caccaattcc tttaccttct  32220
cttacattgc tgaacaataa agaaagcaca gagatgcttg tttttgattt caaaattgtg  32280
tgcttttatt tattttcaag cttacagtat ttccagtagt cattcgaata gagcttaatg  32340
aaactgcatg agaacccttc cacatagctt aaattatcac cagtgcaaat ggagaaaaat  32400
caacatacct ttttatccag atatcacaga accctagtat tcaacctgcc acctccctcc  32460
caacacacag agtacacagt cctttctccc cggctggcct taaaaagcat catatcatgg  32520
gtaacagaca tattcttagg tgttatattc cacacggttt cctgtcgagc caaacgctca  32580
tcagtgatat taataaactc cccgggcagc tcacttaagt tcatgtcgct gtccagctgc  32640
tgagccacag gctgctgtcc aacttgcggt tgcttaacgg gcggcgaagg agaagtccac  32700
gcctacatgg gggtagagtc ataatcgtgc atcaggatag ggcggtggtg ctgcagcagc  32760
gcgcgaataa actgctgccg ccgccgctcc gtcctgcagg aatacaacat ggcagtggtc  32820
tcctcagcga tgattcgcac cgcccgcagc ataaggcgcc ttgtcctccg ggcacagcag  32880
cgcaccctga tctcacttaa atcagcacag taactgcagc acagcaccac aatattgttc  32940
aaaatcccac agtgcaaggc gctgtatcca aagctcatgg cggggaccac agaacccacg  33000
tggccatcat accacaagcg caggtagatt aagtggcgac ccctcataaa cacgctggac  33060
ataaacatta cctcttttgg catgttgtaa ttcaccacct cccggtacca tataaacctc  33120
tgattaaaca tggcgccatc caccaccatc ctaaaccagc tggccaaaac ctgcccgccg  33180
gctatacact gcagggaacc gggactggaa caatgacagt ggagagccca ggactcgtaa  33240
ccatggatca tcatgctcgt catgatatca atgttggcac aacacaggca cacgtgcata  33300
cacttcctca ggattacaag ctcctcccgc gttagaacca tatcccaggg aacaacccat  33360
tcctgaatca gcgtaaatcc cacactgcag ggaagacctc gcacgtaact cacgttgtgc  33420
attgtcaaag tgttacattc gggcagcagc ggatgatcct ccagtatggt agcgcgggtt  33480
tctgtctcaa aaggaggtag acgatcccta ctgtacggag tgcgccgaga caaccgagat  33540
```

cgtgttggtc gtagtgtcat gccaaatgga acgccggacg tagtcatatt tcctccagca 33600
gaaccaagtg cgcgcgtggc agctatcctt gcgtcttctg tctcgccgcc tgccccgctc 33660
ggtgtagtag ttgtaataca gccactccct cagaccgtca aggcgctccc tggcgtccgg 33720
atctataaca acaccatcct gcagcgccgc cctgatgaca tccaccaccg tagagtatgc 33780
caagcccagc caggaaatgc actcactttg acagcgagag ataggaggag cgggaagaga 33840
tggaagaacc atgatagtaa aagaactttt attccaatcg atcctctaca atgtcaaagt 33900
gtagatctat cagatggcac tggtctcctc cgctgagtcg atcaaaaata acagctaaac 33960
cacaaacaac acgattggtc aaatgctgca caagggcttg cagcataaaa tcgcctcgaa 34020
agtccaccgc aagcataaca tcaaagccac cgcccctatc atgatctatg ataaaaaccc 34080
cacagctatc caccagaccc atatagtttt catctctcca tcgtgaaaaa atatttacaa 34140
gctcctcctt taaatcacct ccaaccaatt caaaaagttg agccagaccg ccctccacct 34200
tcattttcag catgcgcatc atgattgcaa aaattcaggc tcctcagaca cctgtataag 34260
attgagaagc ggaacattaa catcaatgtt tcgctcgcga agatcgcgcc tcagtgcaag 34320
catgatataa tcccacaggt cggagcggat cagcgaggac atctccccgc caggaaccaa 34380
ctcaacggag cctatgctga ttataatacg catattcggg gctatgctaa ccagcacggc 34440
cccaaatag gcgtactgca taggcggcga caaaaagtga acagtttggg ttaaaaaatc 34500
aggcaaacac tcgcgcaaaa aagcaagaac atcataacca tgctcatgca aatagatgca 34560
agtaagctca ggaacgacca cagaaaaatg cacaattttt ctctcaaaca tgactgcgag 34620
ccctgcaaaa aataaaaaag aaacattaca caagagtagc ctgtcttaca atgggataga 34680
ctactctaac caacataaga cgggccacga catcgcccgc gtggccataa aaaaaattat 34740
ccgtgtgatt aaaaagaagc acagatagct ggccagtcat atccggagtc atcacgtgcg 34800
aacccgtgta gacccccggg ttggacacat cggccaaaga aagaaagcgg ccaatgtatc 34860
ccggaggaat gataacacta agacgaagat acaacagaat aaccccatgg gggggaataa 34920
caaagttagt aggtgaataa aaacgataaa cacccgaaac tccctcctgc gtaggcaaaa 34980
tagcgccctc cccttccaaa acaacataca gcgcttccac agcagccatg acaaaagact 35040
caaaacactc aaaagactca gtcttaccag gaaaataaaa gcactctcac agcaccagca 35100
ctaatcagag tgtgaagagg gccaagtgcc gaacgagtat atataggaat taaaaatgac 35160
gtaaatgtgt aaaggtcaaa aaacgcccag aaaaatacac agaccaacgc ccgaaacgaa 35220
aacccgcgaa aaaataccca gaagttcctc aacaaccgcc acttccgctt tcccacgata 35280
cgtcacttcc tcgaaaatag caaactacat ttcccacatg tacaaaaccg aaaccactcc 35340
ccttgtcacc gcccacaact tacatcttaa ttaacaaacg tcaaagccta cgtcagccgc 35400
cccgcctcgc cccgcccacc tcattatcat attggccaca atccaaaata aggtatatta 35460
ttgatgatga tttaaatatt atgcggtgtg aaataccgca cagatgcgta aggagaaaat 35520
accgcatcag gcgctcttcc gcttcctcgc tcactgactc gctgcgctcg gtcgttcggc 35580
tgcggcgagc ggtatcagct cactcaaagg cggtaatacg gttatccaca gaatcagggg 35640
ataacgcagg aaagaacatg tgagcaaaag gccagcaaaa ggccaggaac cgtaaaaagg 35700
ccgcgttgct ggcgtttttc cataggctcc gcccccctga cgagcatcac aaaaatcgac 35760
gctcaagtca gaggtggcga aacccgacag gactataaag ataccaggcg tttccccctg 35820
gaagctccct cgtgcgctct cctgttccga ccctgccgct taccggatac ctgtccgcct 35880
ttctcccttc gggaagcgtg gcgctttctc atagctcacg ctgtaggtat ctcagttcgg 35940
tgtaggtcgt tcgctccaag ctgggctgtg tgcacgaacc ccccgttcag cccgaccgct 36000
gcgccttatc cggtaactat cgtcttgagt ccaacccggt aagacacgac ttatcgccac 36060
tggcagcagc cactggtaac aggattagca gagcgaggta tgtaggcggt gctacagagt 36120
tcttgaagtg gtggcctaac tacggctaca ctagaaggac agtatttggt atctgcgctc 36180
tgctgaagcc agttaccttc ggaaaaagag ttggtagctc ttgatccggc aaacaaacca 36240
ccgctggtag cggtggtttt tttgtttgca agcagcagat tacgcgcaga aaaaaaggat 36300
ctcaagaaga tcctttgatc ttttctacgg ggtctgacgc tcagtggaac gaaaactcac 36360
gttaagggat tttggtcatg agattatcaa aaaggatctt cacctagatc cttttaaatt 36420
aaaaatgaag ttttaaatca atctaaagta tatatgagta aacttggtct gacagttacc 36480
aatgcttaat cagtgaggca cctatctcag cgatctgtct atttcgttca tccatagttg 36540
cctgactccc cgtcgtgtag ataactacga tacgggaggg cttaccatct ggccccagtg 36600
ctgcaatgat accgcgagac ccacgctcac cggctccaga tttatcagca ataaaccagc 36660
cagccggaag ggccgagcgc agaagtggtc ctgcaacttt atccgcctcc atccagtcta 36720
ttaattgttg ccgggaagct agagtaagta gttcgccagt taatagtttg cgcaacgttg 36780
ttgccattgc tgcaggcatc gtggtgtcac gctcgtcgtt tggtatggct tcattcagct 36840
ccggttccca acgatcaagg cgagttacat gatcccccat gttgtgcaaa aaagcggtta 36900
gctccttcgg tcctccgatc gttgtcagaa gtaagttggc cgcagtgtta tcactcatgg 36960
ttatggcagc actgcataat tctcttactg tcatgccatc cgtaagatgc ttttctgtga 37020
ctggtgagta ctcaaccaag tcattctgag aatagtgtat gcggcgaccg agttgctctt 37080
gcccggcgtc aacacgggat aataccgcgc cacatagcag aactttaaaa gtgctcatca 37140
ttggaaaacg ttcttcgggg cgaaaactct caaggatctt accgctgttg agatccagtt 37200
cgatgtaacc cactcgtgca cccaactgat cttcagcatc ttttactttc accagcgttt 37260
ctgggtgagc aaaaacagga aggcaaaatg ccgcaaaaaa gggaataagg gcgacacgga 37320
aatgttgaat actcatactc ttcctttttc aatattattg aagcatttat cagggttatt 37380
gtctcatgag cggatacata tttgaatgta tttagaaaaa taaacaaata ggggttccgc 37440
gcacatttcc ccgaaaagtg ccacctgacg tctaagaaac cattattatc atgacattaa 37500
cctataaaaa taggcgtatc acgaggccct ttcgtcttca agaattgatt taaat 37555

<210> SEQ ID NO 17
<211> LENGTH: 34477
<212> TYPE: DNA
<213> ORGANISM: Artificial Sequence
<220> FEATURE:
<223> OTHER INFORMATION: BZ1/BZ28F.Fluc Ad vector

<400> SEQUENCE: 17
catcatcaat aatatacctt attttggatt gtggccaata tgataatgag gtgggcgggg 60
cgaggcgggg cgggtgacgt aggacgtgcg agtagggttg ggaggtgtgg cggaagtgtg 120
gcatttgtaa gtgggaggag cttacatgca agcttccgtc gcggaaaatg tgacgttttt 180
tatgagcgcc gcctacctcc ggaagtgcca attttcgcgc gctttttacc ggatatcgta 240
gtaattttgg gcgggaccat gtaagatttg gccattttcg cgcgaaaagt gaaacgggga 300
agtgaaaact gaataatagg gcgttagtca tagcgcgtaa tatttaccga gggccgaggg 360
actttgaccg attacgtgga ggactcgccc aggtgttttt tacgtgaatt tccgcgttcc 420

-continued

```
gggtcaaagt ctccgttttt attgtcaccg tcatttgacg cggagggtat ttaaacccgc    480
tgcgctccta gcgatcgctc aatattggcc attagccata ttattcattg gttatatagc    540
ataaatcaat attggctatt ggccattgca tacgttgtat ccatatcata atatgtacat    600
ttatattggc tcatgtccaa cattaccgcc atgttgacat tgattattga ctagttatta    660
atagtaatca attacggggt cattagttca tagcccatat atggagttcc gcgttacata    720
acttacggta aatggcccgc ctggctgacc gcccaacgac ccccgcccat tgacgtcaat    780
aatgacgtat gttcccatag taacgccaat agggactttc cattgacgtc aatgggtgga    840
gtatttacgg taaactgccc acttggcagt acatcaagtg tatcatatgc caagtacgcc    900
ccctattgac gtcaatgacg gtaaatggcc cgcctggcat tatgcccagt acatgacctt    960
atgggacttt cctacttggc agtacatcta cgtattagtc atcgctatta ccatggtgat   1020
gcggttttgg cagtacatca atgggcgtgg atagcggttt gactcacggg gatttccaag   1080
tctccacccc attgacgtca atgggagttt gttttggcac caaaatcaac gggactttcc   1140
aaaatgtcgt aacaactccg ccccattgac gcaaatgggc ggtaggcgtg tacggtggga   1200
ggtctatata agcagagctc gtttagtgaa ccgtcagatc gcctggagac gccatccacg   1260
ctgttttgac ctccatagaa gacaccggga ccgatccagc ctccgcggcc gggaacggtg   1320
cattggaagc ttggcattcc ggtactgttg gtaaagccac catggaagac gccaaaaaca   1380
taaagaaagg cccggcgcca ttctatccgc tggaagatgg aaccgctgga gagcaactgc   1440
ataaggctat gaagagatac gccctggttc ctggaacaat tgcttttaca gatgcacata   1500
tcgaggtgga catcacttac gctgagtact tcgaaatgtc cgttcggttg gcagaagcta   1560
tgaaacgata tgggctgaat acaaatcaca gaatcgtcgt atgcagtgaa aactctcttc   1620
aattctttat gccggtgttg ggcgcgttat ttatcggagt tgcagttgcg cccgcgaacg   1680
acatttataa tgaacgtgaa ttgctcaaca gtatgggcat ttcgcagcct accgtggtgt   1740
tcgtttccaa aaaggggttg caaaaaattt tgaacgtgca aaaaaagctc ccaatcatcc   1800
aaaaaattat tatcatggat tctaaaacgg attaccaggg atttcagtcg atgtacacgt   1860
tcgtcacatc tcatctacct cccggtttta atgaatacga ttttgtgcca gagtccttcg   1920
atagggacaa gacaattgca ctgatcatga actcctctgg atctactggt ctgcctaaag   1980
gtgtcgctct gcctcataga actgcctgcg tgagattctc gcatgccaga gatcctattt   2040
ttggcaatca aatcattccg gatactgcga ttttaagtgt tgttccattc catcacggtt   2100
ttggaatgtt tactacactc ggatatttga tatgtggatt tcgagtcgtc ttaatgtata   2160
gatttgaaga agagctgttt ctgaggagcc ttcaggatta caagattcaa agtgcgctgc   2220
tggtgccaac cctattctcc ttcttcgcca aaagcactct gattgacaaa tacgatttat   2280
ctaatttaca cgaaattgct tctggtggcg ctcccctctc taaggaagtc ggggaagcgg   2340
ttgccaagag gttccatctg ccaggtatca ggcaaggata tgggctcact gagactacat   2400
cagctattct gattacaccc gagggggatg ataaaccggg cgcggtcggt aaagttgttc   2460
catttttga agcgaaggtt gtggatctgg ataccgggaa aacgctgggc gttaatcaaa   2520
gaggcgaact gtgtgtgaga ggtcctatga ttatgtccgg ttatgtaaac aatccggaag   2580
cgaccaacgc cttgattgac aaggatggat ggctacattc tggagacata gcttactggg   2640
acgaagacga acacttcttc atcgttgacc gcctgaagtc tctgattaag tacaaaggct   2700
atcaggtggc tcccgctgaa ttggaatcca tcttgctcca acaccccaac atcttcgacg   2760
```

-continued caggtgtcgc aggtcttccc gacgatgacg ccggtgaact tcccgccgcc gttgttgttt 2820
tggagcacgg aaagacgatg acggaaaaag agatcgtgga ttacgtcgcc agtcaagtaa 2880
caaccgcgaa aaagttgcgc ggaggagttg tgtttgtgga cgaagtaccg aaaggtctta 2940
ccggaaaact cgacgcaaga aaaatcagag agatcctcat aaaggccaag aagggcggaa 3000
agatcgccgt gtaattctag acgagatccg aacttgttta ttgcagctta taatggttac 3060
aaataaagca atagcatcac aaatttcaca aataaagcat ttttttcact gcattctagt 3120
tgtggtttgt ccaaactcat caatgtatct tatcatgtct gcgatcgctg atgagaccag 3180
gaccaggtgc cgaccctgcg agtgcggcgg caagcacatg agaaatcagc ctgtgatgtt 3240
ggatgtgacc gaggagctta ggcctgacca tctggtgctg gcctgcacca gggccgagtt 3300
tgggtctagc gatgaggata ccgattgagg tgggtaaggt gggcgtggct agcagggtgg 3360
gcgtgtataa attgggggtc taaggggtct ctctgtttgt cttgcaacag ccgccgccat 3420
gagcgacacc ggcaacagct ttgatggaag catctttagc ccctatctga cagtgcgcat 3480
gcctcactgg gccggagtgc gtcagaatgt gatgggttcc aacgtggatg gacgtcccgt 3540
tctgccttca aattcgtcta cgatggccta cgcgaccgtg ggaggaactc cgctggacgc 3600
cgcgacctcc gccgccgcct ccgccgccgc cgcgaccgcg cgcagcatgg ctacggacct 3660
ttacagctct ttggtggcga gcagcgcggc ctctcgcgcg tctgctcggg atgaaaaact 3720
gactgctctg ctgcttaaac tggaagactt gacccgggag ctgggtcaac tgacccagca 3780
ggtctccagc ttgcgtgaga gcagccttgc ctccccctaa tggcccataa tataaataaa 3840
agccagtctg tttggattaa gcaagtgtat gttctttatt taactctccg cgcgcggtaa 3900
gcccgggacc agcggtctcg gtcgtttagg gtgcggtgga ttctttccaa cacgtggtac 3960
aggtggctct ggatgtttag atacatgggc atgagtccat ccctggggtg gaggtagcac 4020
cactgcagag cttcgtgctc gggggtggtg ttgtatatga tccagtcgta gcaggagcgc 4080
tgggcgtggt gctgaaaaat gtccttaagc aagaggctta tagctagggg gaggcccttg 4140
gtgtaagtgt ttacaaatct gcttagctgg gaggggtgca tccgggggga tatgatgtgc 4200
atcttggact ggatttttag gttggctatg ttcccaccca gatcccttct gggattcatg 4260
ttgtgcagga ccaccagcac ggtatatcca gtgcacttgg gaaatttatc gtggagctta 4320
gacgggaatg catggaagaa cttggagacg cccttgtggc ctcccagatt ttccatacat 4380
tcgtccatga tgatggcaat gggcccgtgg gaagctgcct gagcaaaaac gtttctggca 4440
tcgctcacat cgtagttatg ttccagggtg aggtcatcat aggacatctt tacaaatcgg 4500
gggcggaggg tcccggactg gggatgatg gtaccctcgg gccccggggc gtagttcccc 4560
tcacagatct gcatctccca ggctttcatt tcagagggag ggatcatatc cacctgcggg 4620
gcgatgaaaa agacagtttc tggcgcaggg gagattaact gggatgagag caggtttctg 4680
agcagctgtg actttccaca gccggtgggc ccatatatca cgcctatcac cggctgcagc 4740
tggtagttaa gagagctgca gctgccgtcc tcccggagca ggggggccac ctcgttgagc 4800
atatccctga cgtggatgtt ctccctgacc agttccgcca gaaggcgctc gccgcccagc 4860
gaaagcagct cttgcaagga agcaaaattt ttcagcggtt tcaggccatc ggccgtgggc 4920
atgtttttca gcgtctgggt cagcagctcc agcctgtccc agagctcggt gatgtgctct 4980
acggcatctc gatccagcag atctcctcgt ttcgcgggtt ggggcggctt tcgctgtagg 5040
gcaccagccg atgggcgtcc agcggggcca gagtcatgtc cttccatggg cgcagagtcc 5100
tcgtcagggt ggtctgggtc acggtgaagg ggtgcgctcc gggttgggca ctggccaggg 5160

-continued

```
tgcgcttgag gctggttctg ctggtgctga atcgctgccg ctcttcgccc tgcgcgtcgg   5220
ccaggtagca tttgaccatg gtctcgtagt cgagaccctc ggcggcgtgc cccttggcgc   5280
ggagctttcc cttggaggtg gcgccgcacg aggggcactg caggctcttc agggcgtaga   5340
gcttgggagc gagaaacacg gactctgggg agtaggcgtc cgcgccgcag gccgcgcaga   5400
ccgtctcgca ttccaccagc caagtgagtt ccgggcggtc agggtcaaaa accaggttgc   5460
ccccatgctt tttgatgcgt ttcttacctc ggctctccat gaggcggtgt cccttctcgg   5520
tgacgaagag gctgtccgtg tccccgtaga ccgacttcag ggcctgtct tccagcggag    5580
tgcctctgtc ctcctcgtag agaaactctg accactctga gacgaaggcc cgtgtccagg   5640
ccaggacgaa ggaggccacg tgggaggggt agcggtcgtt gtccactagc gggtccacct   5700
tctccagggt gtgcagacac atgtccccct cctccgcgtc cagaaaagtg attggcttat   5760
aggtgtagga cacgtgaccg ggggttcccg acgggggggt ataaaagggg gtgggcgccc   5820
tttcatcttc actctcttcc gcatcgctgt ctgcgagagc cagctgctgg ggtaagtatt   5880
ccctttcaaa ggcgggcatg acctcagcgc tcaggttgtc agtttctaaa aatgaggagg   5940
atttgatgtt cacctgtccg gaagtgatac ctttgagggt acctgggtcc atctggtcag   6000
aaaacactat ttttttgttg tcaagcttgg tggcgaacga cccgtagagg gcgttggaga   6060
gcagcttggc aatggagcgc agggtctggt ttttgtcgcg gtcggctcgc tccttggccg   6120
cgatgttgag ttgcacgtat tcgcgggcca cgcacttcca ctcggggaag acggtggtgc   6180
gctcgtctgg gatcaggcgc accctccagc cgcggttgtg cagggtgacc atgtcgacgc   6240
tggtggcgac ctcaccgcgc agacgctcgt tggtccagca gaggcggccg cctttgcgcg   6300
agcagaaggg gggtaggggg tccagctggt cctcgtttgg ggggtccgcg tcgatggtaa   6360
agaccccggg gagcaggcgc gggtcaaagt agtcgatctt gcaagcttgc atgtccagag   6420
cccgctgcca ttcgcgggcg gcgagcgcgc gctcgtaggg gttgaggggc gggccccagg   6480
gcatggggtg ggtgagcgcg gaggcgtaca tgccgcagat gtcatacacg tacaggggtt   6540
ccctgaggat accgaggtag gtggggtagc agcgcccccc gcggatgctg gcgcgcacgt   6600
agtcatagag ctcgtgggag ggggccagca tgttgagccc aaggttggtg cgctgggggc   6660
gctcggcgcg gaagacgatc tgtctgaaga tggcatggga gttggaggag atggtgggtc   6720
gctggaagac gttgaagctt gcttcttgca agcccacgga gtccctgacg aaggaggcgt   6780
aggactcgcg cagcttgtgc accagctcgg cggtgacctg gacgtcgagc gcgcagtagt   6840
cgagggtctc gcggatgatg tcatacttat cctcccccctt ctttttccac agctcgcggt  6900
tgaggacgaa ctcttcgcgg tctttccagt actcttggag gggaaacccg tccgtgtccg   6960
aacggtaaga gcctagcatg tagaactggt tgacggcctg gtaggggcag cagcccttct   7020
ccacgggcag cgcgtaggcc tgcgccgcct tgcggaggga ggtgtgggta agggcgaaag   7080
tgtccctgac catgactttg aggtattgat gtctgaagtc tgtgtcatcg cagccgccct   7140
gttcccacag ggtgtagtcc gtgcgctttt tggagcgcgg gttgggcagg gagaaggtga   7200
ggtcattgaa gaggatcttc cccgctcgag gcatgaagtt tctggtgatg cgaaagggcc   7260
ctgggaccga ggagcggttg ttgatgacct gggcggccag gacgatctcg tcaaagccgt   7320
ttatgttgtg gcccacgatg tagagctcca ggaagcgggg ctggcccttg atggagggga   7380
gctttttaag ttcctcgtag gtaagctcct cgggcgattc caggccgtgc tcctccaggg   7440
cccagtcttg caagtgaggg ttggccgcca ggaaggatcg ccagaggtcg cgggccatga   7500
```

-continued

```
gggtctgcag gcggtcgcgg aaggttctga actgccgccc tacggccatc ttttcggggg   7560
tgatgcagta gaaggtgagg gggtctttct cccaggggtc ccatctgagc tcttgggcga   7620
ggtcgcgcgc ggcggcgacc agagcctcgt cgcccccag tttcatgacc agcatgaagg    7680
gcacgagctg cttgccaaag gctcccatcc aagtgtaggt ctctacatcg taggtgacaa   7740
agaggcgctc cgtgcgagga tgagagccga tcgggaagaa ctggatctcc cgccaccagt   7800
tggaggattg gctgttgatg tggtgaaagt agaagtcccg tctgcgggcc gagcactcgt   7860
gctggctttt gtaaaagcga ccgcagtact ggcagcgctg cacgggttgt atatcttgca   7920
cgaggtgaac ctggcgacct ctgacgagga agcgcagcgg gaatctaagt cccccgcctg   7980
gggtcccgtg tggctggtgg tcttctactt tggttgtctg gccgccagca tctgtctcct   8040
ggagggcgat ggtggagcag accaccacgc cgcgagagcc gcaggtccag atctcggcgc   8100
tcggcgggcg gagtttgatg acgacatcgc gcacattgga gctgtccatg gtctccagct   8160
cccgcggcgg caggtcagcc gggagttcct ggaggttcac ctcgcagaga cgggtcaagg   8220
cgcggacagt gttgagatgg tatctgattt caaggggcgt gttggaggcg gagtcgatgg   8280
cttgcagaag gccgcagccc cggggggcca cgatggttcc ccgcggggcg cgaggggagg   8340
cggaagctgg gggtgtgttc agaagcggtg acgcgggcgg gcccccggag gtaggggggg   8400
ttccggcccc acaggcatgg gcggcagggg cacgtcttcg ccgcgcgcgg gcaggggctg   8460
gtgctggctc cggagagcgc ttgcgtgcgc gacgacgcga cggttggtgt cctgtatctg   8520
gcgcctctga gtgaagacca cgggtcccgt gaccttgaac ctgaaagaga gttcgacaga   8580
atcaatctcg gcatcgttga cagcggcctg gcgcaggatc tcctgcacgt cgcccgagtt   8640
gtcctggtag gcgatctctg ccatgaactg ctcgatctct tcctcctgga gatctcctcg   8700
tccggcgcgc tccacggtgg ccgccaggtc gttggagatg cgacccatga gctgcgagaa   8760
ggcgttgagg ccgccctcgt tccagacccg gctgtagacc acgccccct cggcgtcgcg     8820
ggcgcgcatg accacctggg ccaggttgag ctccacgtgt cgcgtgaaga cggcgtagtt   8880
gcgcaggcgc tggaaaaggt agttcagggt ggtggcggtg tgttcggcga cgaagaagta   8940
catgacccag cgccgcaacg tggattcatt gatgtccccc aaggcctcca ggcgctccat   9000
ggcctcgtag aagtccacgg cgaagttgaa aaactgggag ttgcgagcgg acacggtcaa   9060
ctcctcctcc agaagacgga tgagctcggc gacagtgtcg cgcacctcgc gctcgaaggc   9120
cacgggggc gcttcttcct cttccacctc ttcttccatg attgcttctt cttcctcagc    9180
cgggacggga gggggcggcg gcgggggagg ggcgcggcgg cggcggcggc gcaccggcag   9240
gcggtcgatg aagcgctcga tcatctcccc ccgcatgcgg cgcatggtct cggtgacggc   9300
gcggccgttc tcccgggggc gcagctcaaa gacgccgcct ctcatctcgc cgcggggcgg   9360
gcggccgtga ggtagcgaga cggcgctgac tatgcatctt aacaattgct gtgtaggtac   9420
gccgccaagg gacctgattg agtccagatc caccggatcc gaaaaccttt ggaggaaagc   9480
gtctatccag tcgcagtcgc aaggtaggct gagcaccgtg gcgggcgggg gcgggtcggg   9540
agagttcctg gcggagatgc tgctgatgat gtaattaaag taggcggtct tgagaaggcg   9600
gatggtggac aggagcacca tgtctttggg tccggcctgt tggatgcgga ggcggtcggc   9660
catgccccag gcctcgttct gacaccggcg caggtctttg tagtagtctt gcatgagtct   9720
ttccaccggc acctcttctc cttcctcttc tccatctcgc cggtggtttc tcgcgccgcc   9780
catgcgcgtg accccaaagc ccctgagcgg ctgcagcagg gccaggtcgg cgaccacgcg   9840
ctcggccaag atggcctgct gtacctgagt gagggtcctc tcgaagtcat ccatgtccac   9900
```

-continued gaagcggtgg taggcgcccg tgttgatggt gtaggtgcag ttggccatga cggaccagtt 9960
gacggtctgg tgtcccggct gcgagagctc cgtgtaccgc aggcgcgaga aggcgcggga 10020
atcgaacacg tagtcgttgc aagtccgcac cagatactgg tagcccacca ggaagtgcgg 10080
cggaggttgg cgatagaggg gccagcgctg ggtggcgggg gcgccgggcg ccaggtcttc 10140
cagcatgagg cggtggtatc cgtagatgta cctggacatc caggtgatgc cggcggcggt 10200
ggtggtggcg cgcgcgtagt cgcggacccg gttccagatg tttcgcaggg gcgagaagtg 10260
ttccatggtc ggcacgctct ggccggtgag gcgcgcgcag tcgttgacgc tctatacaca 10320
cacaaaaacg aaagcgttta cagggctttc gttctgtagc ctggaggaaa gtaaatgggt 10380
tgggttgcgg tgtgccccgg ttcgagacca agctgagctc ggccggctga agccgcagct 10440
aacgtggtat tggcagtccc gtctcgaccc aggccctgta tcctccagga tacggtcgag 10500
agcccttttg ctttcttggc caagcgcccg tggcgcgatc tgggatagat ggtcgcgatg 10560
agaggacaaa agcggctcgc ttccgtagtc tggagaaaca atcgccaggg ttgcgttgcg 10620
gcgtaccccg gttcgagccc ctatggcggc ttggatcggc cggaaccgcg gctaacgtgg 10680
gctgtggcag ccccgtcctc aggaccccgc cagccgactt ctccagttac gggagcgagc 10740
cccttttgtt ttttattttt tagatgcatc ccgtgctgcg gcagatgcgc ccctcgcccc 10800
ggcccgatca gcagcagcaa cagcaggcat gcagaccccc ctctcctcta cccgccccgg 10860
tcaccacggc cgcggcggcc gtgtccggcg cgggggcgc gctggagtca gatgagccac 10920
cgcggcggcg acctaggcag tatctggact tggaagaggg cgagggactg gcgcggctgg 10980
gggcgagctc tccagagcgc cacccgcggg tgcagttgaa aagggacgcg cgcgaggcgt 11040
acctgccgcg gcagaacctg tttcgcgacc gcgggggcga ggagcccgag gagatgcgag 11100
actgcaggtt ccaagcgggg cgcgagctgc gccgcgggtt ggacagacag cgcctgctgc 11160
gcgaggagga ctttgagccc gacacgcaga cgggcatcag ccccgcgcgc gcgcacgtgg 11220
ccgcggccga cctggtgacc gcctacgagc agacggtgaa ccaggagcgc aacttccaaa 11280
aaagcttcaa caaccacgtg cgcacgctgg tggcgcgcga ggaggtgacc ctgggtctca 11340
tgcatctgtg ggacctggtg gaggcgatcg tgcagaaccc cagcagcaag cccctgaccg 11400
cgcagctgtt cctggtggtg cagcacagca gggacaacga ggccttcagg gaggcgctgc 11460
tgaacatcac cgagccggag gggcgctggc tcctggacct gataaacatc ctgcagagca 11520
tagtggtgca ggagcgcagc ctgagcctgg ccgagaaggt ggcggccatt aactattcta 11580
tgctgagctt gggcaagttc tacgcccgca agatctacaa gacccccctac gtgcccatag 11640
acaaggaggt gaagatagac agcttctaca tgcgcatggc gctaaaggtg ctgaccctga 11700
gcgacgacct gggagtgtac cgcaacgagc gcatccacaa ggccgtgagc gccagccggc 11760
ggcgcgagct gagcgaccgc gagctgatgc acagtctgca gcgcgcgctc accggcgcgg 11820
gcgagggcga cagggaggtc gagtcctact tcgacatggg ggctgacctg cactggcagc 11880
cgagccgccg cgccctggag gcggcggggg cgtatggcgg ccccctggcg gccgatgacg 11940
aggaagagga ggactatgag ctagaggagg gcgagtacct ggaggactga cctggctggt 12000
ggtgttttgg tatagatgca agatccgaac gtggcggacc cggcggtccg ggcggcgctg 12060
cagagccagc cgtccggcat taactcctct gacgactggg ccgcggccat gggtcgcatc 12120
atggccctga ccgcgcgcaa ccccgaggcc ttcaggcagc agcctcaggc taaccggctg 12180
gcggccatct tggaagcggt agtgcccgcg cgctccaacc ccacccacga gaaggtgctg 12240

-continued gccatagtca acgcgctggc ggagagcagg gccatccggg cggacgaggc cggactggtg 12300
tacgatgcgc tgctgcagcg ggtggcgcgg tacaacagcg gcaacgtgca gaccaacctg 12360
gaccgcctgg tgacggacgt gcgcgaggcc gtggcgcagc gcgagcgctt gcatcaggac 12420
ggtaacctgg gctcgctggt ggcgctaaac gccttcctca gcacccagcc ggccaacgta 12480
ccgcgggggc aggaggacta caccaacttc ttgagcgcgc tgcggctgat ggtgaccgag 12540
gtccctcaga gcgaggtgta ccagtcgggg cccgactact tcttccagac cagcagacag 12600
ggcttgcaaa ccgtgaacct gagccaggct ttcaagaacc tgcgggggct gtggggagtg 12660
aaagcgccca ccggcgaccg agctacggtg tccagcctgc taacccccaa ctcgcgcctg 12720
ctgctgctgc tgatcgcgcc cttcacggac agcgggagcg tctcgcggga gacctatctg 12780
ggccacctgc tgacgctgta ccgcgaggcc atcgggcagg cgcaggtgga cgagcacacc 12840
ttccaagaga tcaccagcgt gagccacgcg ctggggcagg aggacacggg cagcctgcag 12900
gcgaccctga actacctgct gaccaacagg cggcagaaga ttcccacgct gcacagcctg 12960
acccaggagg aggagcgcat cttgcgctac gtgcagcaga gcgtgagcct gaacctgatg 13020
cgcgacggcg tgacgcccag cgtggcgctg gacatgaccg cgcgcaacat ggaaccgggc 13080
atgtacgctt cccagcggcc gttcatcaac cgcctgatgg actacttgca tcgggcggcg 13140
gccgtgaacc ccgagtactt caccaatgcc attctgaatc cccactggat gccccctccg 13200
ggtttctaca acggagactt cgaggtgcct gaggtcaatg atgggttcct ctgggatgac 13260
atggatgaca gtgtgttctc ccccaacccg ctgcgcgccg cgtctctgcg attgaaggag 13320
ggctctgaca gggaaggacc gaggagtctg gcctcctccc tggctctggg ggcggtgggc 13380
gccacgggcg cggcggcgcg gggcagcagc cccttcccca gcctggcaga ctctctgaat 13440
agcgggcggg tgagcaggcc ccgcttgcta ggcgaggagg agtatctgaa caactccctg 13500
ctgcagcccg tgagggacaa aaacgctcag cgacagcagt ttcccaacaa cgggatagag 13560
agcctggtgg acaagatgtc cagatggaag acatatgcgc aggagtacaa ggagtgggag 13620
gaccgccagc cgcggcccct gccgccccct agacagcgct ggcagcggcg cgcgtccaac 13680
cgccgctgga gacagggacc cgaggacgat gatgactctg cagatgacag cagcgtgttg 13740
gacctgggcg ggagcgggaa cccctttcg cacctgcgcc cacgcctggg caagatgttt 13800
taaaagagaa aaataaaact caccaaggcc atggcgacga gcgttggttt tttgttccct 13860
tccttagtat gcggcgcgcg gcgatgttcg aggaggggcc tccccccctct tacgagagcg 13920 cgatgggaat ttctcctgcg gcgcccctgc agcctcccta cgtgcctcct cggtacctgc 13980
aacctacagg ggggagaaat agcatctgtt actctgagct gcagcccctg tacgatacca 14040
ccagactgta cctggtggac aacaagtccg cggacgtggc ctccctgaac taccagaacg 14100
accacagcga tttttgacc acggtgatcc aaaacaacga cttcacccca accgaggcca 14160
gtacccagac cataaacctg gacaacaggt cgaactgggg cggcgacctg aagaccatcc 14220
tgcacaccaa catgcccaac gtgaacgagt tcatgtttac caactctttt aaggcgcggg 14280
ttatggtggc gcgcgagcag ggggaggcga agtacgagtg ggtggacttc acgctgcccg 14340
agggcaacta ctcagagacc atgactattg acctgatgaa caatgcgatc gtggaacact 14400
acctgaaagt gggcaggcag aacggggtga aggagagcga tatcggggtc aagtttgaca 14460
ccagaaactt tcgtctgggc tgggaccccg tgaccgggct ggtcatgccg gggtctaca 14520 ccaacgaggc ctttcatccc gatatagtgc tcctgcccgg ctgtggggtg gactttaccc 14580
agagccggct gagcaacctg ctgggcgttc gcaagcggca acctttccag gagggtttca 14640
agatcaccta tgaggatctg gagggggggca acattcccgc gctccttgat ctggacgcct 14700
acgaggagag cttgaaaccc gaggagagcg ctggcgacag cggcgagagt ggcgaggagc 14760
aagccggcgg cggtggcagc gcgtcggtag aaaacgaaag tactcccgca gtggcggcag 14820
acgctgcgga ggtcgagcca gaggccatgc agcaggacgc agaggagggc gcacaggagg 14880
gcgcgcagga ggacatgaac gatggggaga tcaggggaga cactttcgcc acccggggcg 14940
aagaaaaaga ggcagaggcg gtggcggcga cggtggaagc cgaaaccgag gcagaggcag 15000
agcccaagac cgaagttatg gaagacatga atgatggaga acgtaggggt gacacgtttg 15060
ccacccgggg cgaagagaag gcggcggagg cagaagccgc ggctgaggag gcggctgcgg 15120
ctgcggccga ggctgaggct gcggctgagg ctaaggtcga agccgatgtt gcggttgagg 15180
ctcaggctga ggaggaggag gcggcgactg aagcagttaa ggaaaaggcc caggcagagc 15240
aggaagagaa aaaacctgtc attcaacctc taaaagaaga tagcaaaaag cgcagttaca 15300
acgtcatcga gggcagcacc tttacccagt accgcagctg gtacctggcg tacaactacg 15360
gcgacccggt caagggggtg cgctcgtgga ccctgctctg cacgccggac gtcacctgcg 15420
gctccgagca gatgtattgg tcgctgccaa acatgatgca agacccggtg accttccgct 15480
ccacgcggca ggttagcaac ttcccggtgg tgggcgccga actgctgccc gtgcactcca 15540
agagtttttta caacgagcag gccgtctact cccagctgat ccgccaggcc acctctctga 15600
cccacgtgtt caatcgcttt cccgagaacc agattttggc gcgcccgccg gcccccacca 15660
tcaccaccgt cagtgaaaac gttcctgccc tcacagatca cgggacgcta ccgctgcgca 15720
acagcatctc aggagtccag cgagtgacca ttactgacgc cagacgccgg acctgcccct 15780
acgtttacaa ggccttgggc atagtctcgc cgcgcgtcct ctccagtcgc actttttaaa 15840
atacatctac cctcacgctt caaaatcatg tccgtactca tctcacccag caacaacacc 15900
ggctgggggc tgcgcgcgcc cagcaagatg tttggagggg cgaggaaacg ctccgagcag 15960
cacccagtgc gcgtgcgcgg ccactaccgc gcgccctggg gagcgcacaa gcgcgggcgc 16020
gcagggcgca ccactgtgga cgacgccatt gactccgtag tggagcaggc gcgccactac 16080
acacccggcg cgccgtccgc ccccgccgtg tccaccgtgg acgaggcgat cgagagcgtg 16140
gtacagggcg cgcggcacta tgccaacctt aaaaatcgac gccgtcgcgt ggctcgccgc 16200
catcgccgga gaccccgggc caccgccgcc gcgcgccttg ctaaggctct gctcaggcgc 16260
gccaggcgaa ctggccgccg ggccgccatg agggccgcac ggcgggctgc cgccagcgcg 16320
gccgccgcgg ccccacgggc acgaaggcgc gcggccgctg ccgccgccgc cgccatttcc 16380
agcttggcct cgacgcggcg cggtaacata tactgggtgc gcgactcggt aaccggcacg 16440
cgggtacccg tgcgctttcg ccccccgcgg aattagcaca agacaacata cacactgagt 16500
ctcctgctgt tgtgtatccc agcggcgacc gtcagcagcg gcgacatgtc caagcgcaaa 16560
attaaagaag agatgctcca ggtcatcgcg ccggagatct atgggccccc gaagaaggag 16620
gaggatgatt acaagccccg caagctaaag cgggtcaaaa agaaaaagaa agatgatgac 16680
gttgacgagg cggtggagtt tgtccgccgc atggcgccca ggcgccccgt gcagtggaag 16740
ggtcggcgcg tgcagcgagt cctgcgcccc ggcaccgcgg tggtctttac gcccggcgag 16800
cgttccacgc gcactttcaa gcgggtgtac gatgaggtgt acggcgacga ggatctgttg 16860
gagcaggcca accatcgctt tggggagttt gcatatggga aacggccccg cgagagccta 16920
aaagaggacc tgctggcgct accgctggac gagggcaatc ccaccccgag tctgaagccg 16980

-continued

```
gtaaccctgc aacaggtgct gcctttgagc gcgcccagcg agcagaagcg agggttgaag  17040
cgcgagggcg gggacctggc acccaccgtg cagttgatgg tgcccaagcg gcagaagctg  17100
gaggacgtgc tggagaaaat gaaagtagag cccgggatcc agcccgaaat caaggtccgc  17160
cccatcaagc aggtggcgcc cggcgtggga gtccagaccg tggacgttag gattcccacg  17220
gaggagatgg aaacccaaac cgccactccc tcttcggcgg ctagcgccac caccggctcc  17280
gcttcggtag aggtgcagac ggacccctgg ctagccgccg ccgcccggc cgcccccgt  17340
tcgcgcgggc gcaagagaaa ttatccagcg gccagcgcgc tcatgcccca gtacgcactg  17400
catccatcca tcgcgcccac ccccggctac cgcgggtact cgtaccgccc gcgcagatca  17460
gccggcaccc gcggccgccg ccgccgtgcg accacaacca gccgccgccg tcgccgccgc  17520
cgccagccag tgctgacccc cgtgtctgta aggaaggtgg ctcgctcggg gagcacgctg  17580
gtggtgccca gagcgcgcta ccaccccagc attgtttaaa gccggtctct gtatggttct  17640
tgcagatatg gccctcactt gtcgcctccg cttcccggtg ccgggatacc gaggaagaac  17700
tcaccgccgc agaggcatgg cgggcagtgg tctccgcggc ggccgtcgcc atcgccggcg  17760
cgcaaagagc aggcgcatgc gcggcggtgt gctgcccttc ctaatcccgc taatcgccgc  17820
ggcgatcggt gccgtgcccg ggatcgcctc cgtggccctg caggcgtccc agaaacattg  17880
actcttgcaa ccttgcaagc ttgcattttt tggaggaaaa aataaaaagt ctagactctc  17940
acgctcgctt ggtcctgtga ctattttgta gaaaaaagat ggaagacatc aactttgcgt  18000
cgctggcccc gcgtcacggc tcgcgcccgt tcatgggaga ctggacagat atcggcacca  18060
gcaatatgag cggtggcgcc ttcagctggg gcagtctgtg gagtggcctt aaaaattttg  18120
gttccaccat taagaactat ggcaacaaag cgtggaacag cagcacgggt cagatgctga  18180
gagacaagtt gaaagagcag aacttccagg agaaggtggc acagggcctg gcctctggca  18240
tcagcggggt ggtggacata gctaaccagg ccgtgcagaa aaagataaac agtcatctgg  18300
acccccgccc tcaggtggag gaaacgcctc cagccatgga gacggtgtct cccgagggca  18360
aaggcgaaaa gcgcccgcgg cccgacaggg aagagaccct ggtgtcacac accgaggagc  18420
cgccctctta cgaggaggca gtcaaggccg gcctgcccac cactcgcccc atagctccca  18480
tggccaccgg tgtggtgggt cacaggcaac acacccccgc gacactagat ctgcccccgc  18540
cgtccgagcc gactcgccag ccaaaggcgg tgacggtgcc cgctccctcc acttccgccg  18600
ccaacagagt gcctctgcgc cgcgctgcga gcggcccccg ggcctcgcga gtcagcggca  18660
actggcagag cacactgaac agcatcgtgg gcctgggagt gaggagtgtg aagcgccgcc  18720
gttgctactg aatgagcaag ctagctaacg tgttgtatgt gtgtatgcgt cctatgtcgc  18780
cgccagagga gctgttgagc cgccggcgcc gtctgcactc cagcgaattt caagatggcg  18840
accccatcga tgatgcctca gtggtcgtac atgcacatct cgggccagga cgcttcggag  18900
tacctgagcc ccgggctggt gcagttcgcc cgcgccacag acacctactt caacatgagt  18960
aacaagttca ggaaccccac tgtggcgccc acccacgatg tgaccacgga ccggtcgcag  19020
cgcctgacgc tgcggttcat ccccgtggat cgggaggaca ccgcttactc ttacaaggcg  19080
cggttcacgc tggccgtggg cgacaaccgc gtgctggaca tggcctccac ttactttgac  19140
atccgggggg tgctggacag gggccccact ttcaagccct actcgggcac tgcctacaac  19200
tccctggccc ccaagggcgc tcccaattct tgcgagtggg aggaggaaac acaaaatgag  19260
gtacaagcca atgaagaaca actagcagaa gaagaggatg aagaaatggc tcaagaggat  19320
cagcagccta ctaaaaaaac ccatgtatat gctcaggcac ctctttctgg cgaacagatt  19380
```

accaaagatg gcttgcaaat aggagctgaa gttacaggag aaacatcaaa gcccattttt 19440
gcagacaaga cattccaacc agaacctcag ataggagagt ctcaatggaa tgaggccgat 19500
gctacagtag caggaggtag ggttttgaaa aagactaccc ctatgaaacc ttgctatgga 19560
tcctatgcca gacctaccaa tgccaatgga gggcagggga tacttgaggc aaatgctaaa 19620
ggggaactcg aatctaaagt tgagatgcag tttttctcta acaccacaac tcttaatgta 19680
agagacggtg aaaatggcct taaaccaaaa gtagtgctgt atagcgaaga tgtcaacctg 19740
gaatcccctg acactcatct gtcttacaag cccaaaaaag atgatgttaa tgccaaaatc 19800
atgttgggtc agcaagccat gcccaacaga cccaacctca ttggatttag agataatttc 19860
attgggctca tgtattacaa cagcactgga aacatgggag tgctggcggg tcaggcctct 19920
cagttgaatg ctgtggtgga cttgcaggat agaaacacgg aactgtcata tcagcttatg 19980
cttgattcca ttggagatag aaccagatac ttttccatgt ggaaccaggc agtggatagc 20040
tatgacccag atgttagaat cattgaaaac catggggtgg aggatgagct gcccaactac 20100
tgttttccct tgggcggtat aggaattaca gatacatacc aggccataaa agcagccaat 20160
ggtggagatg ctactacgtg gtctgctgat aacacatttg cagaccgcaa cgaaataggg 20220
gtgggaaaca acttcgccat ggagatcaac atccaggcca acctctggag aaacttcctc 20280
tatgcgaacg tgggactcta cctgccagac aagctcaagt acaaccccac caacgtggac 20340
atctctgaca accccaacac ctatgactac atgaacaagc gggtggtggc ccccggcctg 20400
gtggactgct ttgtcaatgt gggagccagg tggtccctgg actacatgga caacgtcaac 20460
cccttcaacc accaccgcaa tgcgggtctg cgctaccgct ccatgatcct gggcaacggg 20520
cgctatgtgc ccttccacat ccaggtaccc cagaagttct ttgccatcaa gaacctcctg 20580
ctcctgcccg gctcctacac ctacgagtgg aacttcagga aggatgtaaa catggtccta 20640
cagagctctc tgggcaatga ccttagggta gatggggcca gcatcaagtt tgacagcatc 20700
accctctatg ctacattttt ccccatggcc cacaacaccg cctccacgct tgaggccatg 20760
ctgagaaacg acaccaacga ccagtccttc aatgactacc tctctggggc caacatgctc 20820
tacccaatcc cagccaaggc caccaacgtg cccatctcca tcccctctcg caactgggcc 20880
gcctttagag gctgggcctt tacccgcctt aagaccaagg agacccccctc cctgggctcg 20940
ggttttgatc cctactttgt ttactcggga tccatcccct acctggatgg caccttctac 21000
ctcaaccaca ctttcaagaa gatatccatc atgtatgact cctccgtcag ctggccgggc 21060
aacgaccgct tgctcacccc caatgagttc gaggtcaagc gcgccgtgga cggcgagggc 21120
tacaacgtgg cccagtgcaa catgaccaag gactggttcc tggtgcagat gctggccaac 21180
tacaacatag gctaccaggg cttctacatc ccagagagct acaaggacag gatgtattcc 21240
ttcttcagaa atttccaacc catgagccga caggtggtgg acgagaccaa ttacaaggac 21300
tatcaggcca ttggcatcac ccaccagcac aacaactcgg gtttcgtggg ctacctggcg 21360
cccaccatgc gcgagggaca ggcctacccc gccaacttcc cctacccccct gataggcaag 21420
accgcggtcg acagcgtcac ccagaaaaag ttcctctgcg accgcaccct ctggcgcatc 21480
cccttctcta gcaactttat gtccatgggt gcgctcacgg acctgggcca aaacctgctt 21540
tatgccaact ctgcccatgc gctggacatg acttttgagg tggaccccat ggacgagccc 21600
acccttctct atattgtgtt tgaagtgttc gacgtggtca gagtgcacca gccgcaccgc 21660
ggtgtcatcg agaccgtgta cctgcgtacg cccttctcag ccggcaacgc caccacctaa 21720

-continued

```
ggagacagcg ccgccgcctg catgactggt tccaccgagc aagagctcag ggccatcgcc  21780
agagacctgg gatgcggacc ctattttttg ggcacctatg acaaacgctt cccgggtttt  21840
atctcccgag acaagctcgc ctgcgccatc gtcaacacgg ccgcgcgcga gaccgggggc  21900
gtgcactggc tggcctttgg ctgggacccg cgctctaaaa cttgctacct ctttgacccc  21960
tttggcttct ccgatcagcg cctcaggcag atttatgagt ttgagtacga ggggctgttg  22020
cgccgcagcg cgcttgcctc ctcgcccgac cgctgcatca cccttgagaa gtccaccgag  22080
accgtgcagg ggccccactc ggccgcctgc ggtctcttct gttgcatgtt tttgcacgcc  22140
tttgtgcact ggcctcagag tcccatggat cgcaacccca ccatgaactt gctaaaggga  22200
gtgcccaacg ccatgctcca gagcccccag gtcctgccca ccctgcgccg caaccaggaa  22260
cagctctacc gcttcctgga gcgccactcc ccctacttcc gcagccacag cgcgcgcatc  22320
cggggggcca cctctttttg ccacttgcaa gaaaacatgc aagacggaaa atgatgtaca  22380
gcatgctttt aataaatgta aagactgtgc actttattta tacacgggct ctttctggtt  22440
atttattcaa caccgccgtc gccatctaga aatcgaaagg gttctgccgc gcgtcgccgt  22500
gcgccacggg cagagacacg ttgcgatact ggaagcggct cgcccacttg aactcgggca  22560
ccaccatgcg gggcagtggt tcctcgggga aattctcgct ccacagggtg cgggtcagct  22620
gcagcgcgct caggaggtcg ggagccgaga tcttgaagtc gcagttgggg ccggaaccct  22680
gcgcgcgcga gttgcggtac acggggttgc agcactggaa caccagcagg gccggattat  22740
tcacgctggc cagcaggctc tcgtcgctaa tcatgtcgct gtccagatcc tccgcgttgc  22800
tcagggcgaa tggggtcatc ttgcagacct gcctgcccag gaaaggcggg agcccaggct  22860
tgccgttaca gtcgcagcgc aggggcatta gcaggtgccc acggcccgac tgcgcctgcg  22920
ggtacaacgc gcgcatgaag gcttcgatct gcctaaaagc cacctgggtc ttggctccct  22980
ccgaaaagaa catcccacag gacttgctgg agaactggtt cgcgggacag ctggcatcgt  23040
gcaggcagca gcgcgcgtca gtgttggcga tctgcaccac gttgcgaccc caccggtttt  23100
tcactatctt ggccttggaa gcctgctcct ttagcgcgcg ctggccgttc tcgctggtca  23160
catccatctc tatcacctgt tccttgttga tcatgtttgt cccgtgcaga cactttaggt  23220
cgccctccgt ctgggtgcag cggtgctccc acagcgcgca accggtgggc tcccaatttt  23280
tgtgggtcac ccccgcgtag gcctgcaggt aggcctgcag gaagcgcccc atcatggtca  23340
taaaggtctt ctggctcgta aaggtcagct gcaggccgcg atgctcttcg ttcagccagg  23400
tcttgcagat ggcggccagc gcctcggtct gctcgggcag catcttaaaa tttgtcttca  23460
ggtcgttatc cacgtggtac ttgtccatca tggcacgcgc cgcctccatg cccttctccc  23520
aggcggacac catgggcagg cttagggggt ttatcacttc cagcggcgag gacaccgtac  23580
tttcgatttc ttcttcctcc ccctcttccc ggcgcgcgcc cccgctgttg cgcgctctta  23640
ccgcctgcac caaggggtcg tcttcaggca agcgccgcac cgagcgcttg ccgcccttga  23700
cctgcttgat cagtaccggc gggttgctga agcccaccat ggtcagcgcc gcctgctctt  23760
cttcgtcttc gctgtctacc actatttctg gggaggggct tctccgctct gcggcaaagg  23820
cggcggatcg cttctttttt ttcttgggag ccgccgcgat ggagtccgcc acggcgaccg  23880
aggtcgaggg cgtggggctg ggggtgcgcg gcaccagggc ctcgtcgccc tcggactctt  23940
cctctgactc caggcggcgg cggagtcgct tctttggggg cgcgcgcgtt agcggcggcg  24000
gagacgggga cggggacggg gacgggacgc cctccacagg gggcggtctt cgcgcagacc  24060
cgcggccgcg ctcgggggtc ttctcgcgct ggtcttggtc ccgactggcc attgtatcct  24120
```

```
cctcctccta ggcagagaga cataaggagt ctatcatgca agtcgagaag gaggagagct  24180
taaccacccc ctctgagacc gccgtcgccg tcgcccccgc taccgccgac gcgcccgcca  24240
caccgagcga cacccccgcg gacccccccg ccgacgcacc cctgttcgag gaagcggccg  24300
tggagcagga cccgggcttt gtctcggcag aggaggattt gcaagaggag gaggataagg  24360
aggagaagcc ctcagtgcca aaagatcata aagagcaaga cgagcacgac gcagacgcac  24420
accagggtga agtcgggcgg ggggacggag ggcatggcgg cgccgactac ctagacgaag  24480
gaaacgacgt gctcttgaag cacctgcatc gtcagtgcgc cattgtctgc gacgctctgc  24540
aggagcgcag cgaggtgccc ctcagcgtgg cggaggtcag ccgcgcctac gagctcagcc  24600
tcttttcccc ccgggtgccc ccccgccgcc gcgaaaacgg cacatgcgag cccaacccgc  24660
gcctcaactt ctaccccgcc tttgtggtgc ccgaggtcct ggccacctat cacatcttct  24720
ttcaaaattg caagatcccc atctcgtgcc gcgccaaccg tagccgcgcc gataagatgc  24780
tggccctgcg ccagggcgac cacatacctg atatcgccgc tttggaagat gtgccaaaga  24840
tcttcgaggg tctgggtcgc aacgagaagc gggcagcaaa ctctctgcaa caggaaaaca  24900
gcgaaaatga gagtcacact ggagcgctgg tggagctgga gggcgacaac gcccgcctgg  24960
cggtgctcaa gcgcagcatc gaggtcaccc actttgccta ccccgcgctc aacctgcccc  25020
ccaaagtcat gaacgcggtc atggacgggc taatcatgcg ccgcggccgg ccccttgctc  25080
cagatgcaaa cttgcatgag gagaccgagg acggtcagcc cgtggtcagc gacgagcagc  25140
tgacgcgctg gctggaaacc gcggaccccg ccgaactgga ggagcggcgc aagatgatga  25200
tggccgcggt gctggtcacc gtagagctgg agtgtctgca gcgcttcttc ggcgaccccg  25260
agatgcagag aaaggtcgag gagaccctac actacacctt ccgccagggc tacgtgcgcc  25320
aggcttgcaa gatctccaac gtggagctca gcaacctggt gtcctacctg ggcatcttgc  25380
atgaaaaccg ccttgggcag agcgtgctac actccaccct gcgcggggag gcgcgccgcg  25440
actacgtgcg cgactgcgtt tacctcttcc tctgctacac ctggcagacg gccatggggg  25500
tctggcagca gtgcctggag gagcgcaacc tcaaggagct ggagaagctc ctgcagcgcg  25560
cgctcaaaga cctctggacg ggctacaacg agcgctcggt ggccgccgcg ctggccgacc  25620
tcatcttccc cgagcgcctg ctcaaaactc tccagcaggg gctgcccgac ttcaccagcc  25680
aaagcatgtt gcaaaatttt aggaacttta tcctggagcg ttctggcatc ctacccgcca  25740
cctgctgcgc cctgcccagc gactttgtcc ccctcgtgta ccgcgagtgc cccccgccgc  25800
tgtggggcca ctgctacctg ttccaactgg ccaactacct gtcctaccac gcggacctca  25860
tggaagactc cagcggcgag ggctcatgg agtgccactg ccgctgcaac ctctgcacgc  25920
cccaccgctc cctggtctgc aacacccaac tgctcagcga gagtcagatt atcggtacct  25980
tcgagctaca gggtccgtcc tcctcagacg agaagtccgc ggctccgggg ctaaaactca  26040
ctccggggct gtggacttcc gcctacctgc gcaaatttgt acctgaagac taccacgccc  26100
acgagatcag gttttacgag gaccaatccc gcccgcccaa ggcggagctg accgcctgcg  26160
tcatcaccca gggcgagatc ctaggccaat tgcaagccat ccaaaaagcc cgccaagagt  26220
ttttgctgag aaagggtcgg ggggtgtatc tggaccccca gtcgggtgag gagctcaacc  26280
cggttccccc gctgccgccg ccgcgggacc ttgcttccca ggataagcat cgccatggct  26340
cccagaaaga agcagcagcg gccgccactg ccgccacccc acacgctgga ggaagaggag  26400
gaatactggg acagtcaggc agaggaggtt tcggacgagg aggagccgga gacggagatg  26460
```

-continued

```
gaagagtggg aggaggacag cttagacgag gaggcttccg aagccgaaga ggcaggcgca  26520
acaccgtcac cctcggccgc agccccctcg caggcgcccc cgaagtccgc tcccagcatc  26580
agcagcaaca gcagcgctat aacctccgct cctccaccgc cgcgacccac ggccgaccgc  26640
agacccaacc gtagatggga caccaccgga accggggccg gtaagtcctc cgggaaaggc  26700
aagcaagcgc agcgccaagg ctaccgctcg tggcgcgctc acaagaacgc catagtcgct  26760
tgcttgcaag actgcggggg gaacatctcc ttcgcccgcc gcttcctgct cttccaccac  26820
ggtgtggcct tcccccgtaa cgtcctgcat tactaccgtc atctctacag cccctactgc  26880
ggcggcagtg agccagaggc ggccggcggc agcggcgccc gtttcggtgc ctaggaagac  26940
ccagggcaag acttcagcca agaaactcgc ggcggccgcg gcgaacgcgg tcgcgggggc  27000
cctgcgcctg acggtgaacg aacccctgtc gacccgcgaa ctgaggaacc gaatcttccc  27060
cactctctat gccatcttcc agcagagcag agggcaggat caggaactga aagtaaaaaa  27120
caggtctctg cgctccctca cccgcagctg tctgtatcac aagagcgaag accagcttcg  27180
gcgcacgctg gaggacgctg aggcactctt cagcaaatac tgcgcgctca ctcttaagga  27240
ctagctccgc gcccttctcg aatttaggcg ggaacgccta cgtcatcgca gcgccgccgt  27300
catgagcaag gacattccca cgccatacat gtggagctat cagccgcaga tgggactcgc  27360
ggcgggcgcc tcccaggatt actccacccg catgaactgg ctcagtgccg gcccacacat  27420
gatctcacag gttaatgaca tccgcaccca tcgaaaccaa atattggtgg agcaggcggc  27480
aattaccacc acgccccgca ataatcccaa ccccagggag tggcccgcgt ccctggtgta  27540
tcaggaaatt cccggcccca ccaccgtact acttccgcgt gattcccagg ccgaagtcca  27600
aatgactaac tcaggggcac agctcgcggg cggctgtcgt cacagggtgc ggcctcctcg  27660
ccagggtata actcacctga agatccgagg cagaggtatt cagctcaacg acgagtcggt  27720
gagctcctcg ctcggtctca gacctgacgg gaccttccag atagccggag ccggccgatc  27780
ttccttcacg ccccgccagg cgtacctgac tctgcagagc tcgtcctcgg cgccgcgctc  27840
gggcggcatc gggactctcc agttcgtgca ggagtttgtg ccctcggtct acttcaaccc  27900
cttctcgggc tctcccggtc gctacccgga ccagttcatc ccgaactttg acgccgcgag  27960
ggactcggtg gacggctacg actgaatgtc gggtggaccc ggtgcagagc aacttcgcct  28020
gaagcacctt gaccactgcc gccgccctca gtgctttgcc cgctgtcaga ccggtgagtt  28080
ccagtacttt tccctgcccg actcgcaccc ggacggcccg gcgcacgggg tgcgcttttt  28140
catcccgagt caggtccgct ctaccctaat cagggagttc accgcccgtc ccctactggc  28200
ggagttggaa aaggggcctt ctatcctaac cattgcctgc atctgctcta accctggatt  28260
acaccaagat ctttgctgtc atttgtgtgc tgagtataat aaaggctgag atcagaatct  28320
actcgggctc ctgtcgccat cctgtcaacg ccaccgtcca agcccggccc gatcagcccg  28380
aggtgaacct cacctgcggt ctgcaccggc gcctgaggaa atacctagct tggtactaca  28440
acagcactcc ctttgtggtt tacaacagct ttgaccagga cggggtctca ctgagggata  28500
acctctcgaa cctgagctac tccatcagga agaacaacac cctcgagcta cttcctcctt  28560
acctgcccgg gacttaccag tgtgtcaccg gtccctgcac ccacacccac ctgttgatcg  28620
taaacgactc tcttccgaga acagacctca ataactcctc tccgcagttc cccagaacag  28680
gaggtgagct caggaaaccc cgggtaaaga agggtggaca agagttaaca cttgtggggt  28740
ttctggtgta tgtgacgctg gtggtggctc ttttgattaa ggcttttcct tccatgtctg  28800
aactatccct cttcttttat gaacaactcg actagtgcta acgggaccct acccaacgaa  28860
```

```
tcgggattga atatcggtaa ccaggttgca gtttcacttt tgattacctt catagtcctc  28920
ttcctgctag tgctgtcgct tctgtgcctg cggatcgggg gctgctgcat ccacgtttat  28980
atctggtgct ggctgtttag aaggttcgga gaccaccgca ggtagaataa acaaacctag  29040
acctagaaat ggacggtctc tgcagcgagc aacgcatact agagaggcgc cggcaaaaag  29100
cagagctcga gcgtcttaaa caagagctcc aagacgccgt ggccatacac cagtgcaaaa  29160
aagggctctt ctgtctggta aaacaggcca cgctcaccta tgaaaaaaca ggtgacaccc  29220
accgcctagg atacaagctg cccacacagc gccaaaagtt tgcccttatg ataggtgaac  29280
aacccatcac cgtgacccag cactccgtgg agacagaagg ctgcattcat gctccctgca  29340
ggggcgctga ctgcctctac accttgatca aaaccctttg cggtctcaga gaccttatcc  29400
ctttcaattg atcataactg taatcaataa aaaatcactt acttgaaatc tgatagcaag  29460
cctctgtcca attttttcag caacacttcc ttcccctctt cccaactctg gtactctagg  29520
cgcctcctag ctgcaaactt cctccacagt ctgaagggaa tgtcagattc ctcctcctcc  29580
tgtccctccg cacccacgat cttcatgttg ttgcagatga agcgcaccaa aacgtctgac  29640
gagagcttca accccgtgta cccctatgac acggaaaacg gtcctccctc cgtccctttc  29700
ctcacccctc ccttcgtgtc tcccgatgga ttccaagaga gcccccccgg ggtcctgtct  29760
ctgaacctgg ccgagcccct ggtcacttcc cacggcatgc tcgccctgaa aatgggaagt  29820
ggcctctccc tggacgacgc cggcaacctc acctctcaag atgtcaccac cactacccct  29880
cccctgaaaa aaaccaagac caacctcagc ctagaaacct cagccccccct gactgtgagc  29940
acctcaggcg ccctcaccct agcagccgcc gttcccctgg cggtggccgg cacctccctc  30000
accatgcaat cagaggcccc cctgacagtc caagatgcaa aactcaccct ggccaccaag  30060
ggcccccctga ccgtgtctga aggcaaactg gccttgcaga cctcggcccc gctgacggcc  30120
gctgacagca gcgccctcac cgttagcgcc acaccaccca tcagtgtaag cagtggaagt  30180
ttgggcttag acatggaaga ccccatgtat actcatgatg gaaaactggg aataagaatt  30240
ggaggcccac tgagagtagt agacagcctg cacacactga ctgtagttac cggaaatgga  30300
atagctgtag ataacaatgc cctccaaact agagttacgg gcgccctggg ttatgacaca  30360
tcaggaaacc tacaactgag agccgcgggg ggtatgcgaa ttgatgcaaa tggccaactt  30420
atccttgatg tggcataccc atttgatgct caaaacaatc tcagccttag acttggtcag  30480
ggacccctgt atgtaaacac agaccacaac ctagatttga attgcaacag aggtctgacc  30540
acaactacca ccaacaacac aaaaaaactt gaaactaaaa ttggctcagg cttagactat  30600
gataccaatg gtgctgtcat tattaaactt ggtactggtg taagctttga cagcacaggc  30660
gccctaactg tgggaaacac tggcgatgat aaactgactc tgtggacaac cccagaccca  30720
tctccaaatt gcagaattca cgcagacaaa gactgcaagt ttactctagt cctaactaag  30780
tgtggaagtc aaatcctggc ttctgtcgcc gccctagcgg tgtcaggaaa tctggcttca  30840
ataacaggca ccgttgccag cgttaccatc tttctcagat ttgatcagaa tggagtgctt  30900
atggaaaact cctccctaga caagcagtac tggaacttca gaaatggtaa ctcaaccaat  30960
gccacccccct acaccaatgc agttgggttc atgccaaacc tcgcagcata ccccaagaca  31020
cagagccaga ctgctaaaaa caacattgta agtcaggttt acttgaatgg ggacaaatcc  31080
aaacccatga cccttaccat taccctcaat ggaactaatg aatccagtga aactagccag  31140
gtgagtcact actccatgtc atttacatgg gcttgggaga gtgggcaata tgccaccgaa  31200
```

```
acctttgcca ccaattcctt taccttctct tacattgctg aacaataaag aaagcacaga  31260
gatgcttgtt tttgatttca aaattgtgtg cttttattta ttttcaagct tacagtattt  31320
ccagtagtca ttcgaataga gcttaatgaa actgcatgag aacccttcca catagcttaa  31380
attatcacca gtgcaaatgg agaaaaatca acataccttt ttatccagat atcacagaac  31440
cctagtattc aacctgccac ctccctccca acacacagag tacacagtcc tttctccccg  31500
gctggcctta aaaagcatca tatcatgggt aacagacata ttcttaggtg ttatattcca  31560
cacggtttcc tgtcgagcca aacgctcatc agtgatatta ataaactccc cgggcagctc  31620
acttaagttc atgtcgctgt ccagctgctg agccacaggc tgctgtccaa cttgcggttg  31680
cttaacgggc ggcgaaggag aagtccacgc ctacatgggg gtagagtcat aatcgtgcat  31740
caggataggg cggtggtgct gcagcagcgc gcgaataaac tgctgccgcc gccgctccgt  31800
cctgcaggaa tacaacatgg cagtggtctc ctcagcgatg attcgcaccg cccgcagcat  31860
aaggcgcctt gtcctccggg cacagcagcg caccctgatc tcacttaaat cagcacagta  31920
actgcagcac agcaccacaa tattgttcaa aatcccacag tgcaaggcgc tgtatccaaa  31980
gctcatggcg gggaccacag aacccacgtg gccatcatac cacaagcgca ggtagattaa  32040
gtggcgaccc ctcataaaca cgctggacat aaacattacc tcttttggca tgttgtaatt  32100
caccacctcc cggtaccata taaacctctg attaaacatg gcgccatcca ccaccatcct  32160
aaaccagctg gccaaaacct gcccgccggc tatacactgc agggaaccgg gactggaaca  32220
atgacagtgg agagcccagg actcgtaacc atggatcatc atgctcgtca tgatatcaat  32280
gttggcacaa cacaggcaca cgtgcataca cttcctcagg attacaagct cctcccgcgt  32340
tagaaccata tcccagggaa caacccattc ctgaatcagc gtaaatccca cactgcaggg  32400
aagacctcgc acgtaactca cgttgtgcat tgtcaaagtg ttacattcgg gcagcagcgg  32460
atgatcctcc agtatggtag cgcgggtttc tgtctcaaaa ggaggtagac gatccctact  32520
gtacggagtg cgccgagaca accgagatcg tgttggtcgt agtgtcatgc caaatggaac  32580
gccggacgta gtcatatttc ctccagcaga accaagtgcg cgcgtggcag ctatccttgc  32640
gtcttctgtc tcgccgcctg ccccgctcgg tgtagtagtt gtaatacagc cactccctca  32700
gaccgtcaag gcgctccctg gcgtccggat ctataacaac accatcctgc agcgccgccc  32760
tgatgacatc caccaccgta gagtatgcca agcccagcca ggaaatgcac tcactttgac  32820
agcgagagat aggaggagcg ggaagagatg gaagaaccat gatagtaaaa gaacttttat  32880
tccaatcgat cctctacaat gtcaaagtgt agatctatca gatggcactg gtctcctccg  32940
ctgagtcgat caaaaataac agctaaacca caaacaacac gattggtcaa atgctgcaca  33000
agggcttgca gcataaaatc gcctcgaaag tccaccgcaa gcataacatc aaagccaccg  33060
cccctatcat gatctatgat aaaaacccca cagctatcca ccagacccat atagttttca  33120
tctctccatc gtgaaaaaat atttacaagc tcctccttta aatcacctcc aaccaattca  33180
aaaagttgag ccagaccgcc ctccaccttc attttcagca tgcgcatcat gattgcaaaa  33240
attcaggctc ctcagacacc tgtataagat tgagaagcgg aacattaaca tcaatgtttc  33300
gctcgcgaag atcgcgcctc agtgcaagca tgatataatc ccacaggtcg gagcggatca  33360
gcgaggacat ctccccgcca ggaaccaact caacggagcc tatgctgatt ataatacgca  33420
tattcggggc tatgctaacc agcacggccc ccaaataggc gtactgcata ggcggcgaca  33480
aaaagtgaac agtttgggtt aaaaaatcag gcaaacactc gcgcaaaaaa gcaagaacat  33540
cataaccatg ctcatgcaaa tagatgcaag taagctcagg aacgaccaca gaaaaatgca  33600
```

caatttttct ctcaaacatg actgcgagcc ctgcaaaaaa taaaaaagaa acattacaca 33660
agagtagcct gtcttacaat gggatagact actctaacca acataagacg ggccacgaca 33720
tcgcccgcgt ggccataaaa aaaattatcc gtgtgattaa aaagaagcac agatagctgg 33780
ccagtcatat ccggagtcat cacgtgcgaa cccgtgtaga cccccgggtt ggacacatcg 33840
gccaaagaaa gaaagcggcc aatgtatccc ggaggaatga taacactaag acgaagatac 33900
aacagaataa ccccatgggg gggaataaca aagttagtag gtgaataaaa acgataaaca 33960
cccgaaactc cctcctgcgt aggcaaaata gcgccctccc cttccaaaac aacatacagc 34020
gcttccacag cagccatgac aaaagactca aaacactcaa aagactcagt cttaccagga 34080
aaataaaagc actctcacag caccagcact aatcagagtg tgaagagggc caagtgccga 34140
acgagtatat ataggaatta aaaatgacgt aaatgtgtaa aggtcaaaaa acgcccagaa 34200
aaatacacag accaacgccc gaaacgaaaa cccgcgaaaa aatacccaga agttcctcaa 34260
caaccgccac ttccgctttc ccacgatacg tcacttcctc gaaaatagca aactacattt 34320
cccacatgta caaaaccgaa accactcccc ttgtcaccgc ccacaactta catcttaatt 34380
aacaaacgtc aaagcctacg tcagccgccc cgcctcgccc cgcccacctc attatcatat 34440
tggccacaat ccaaaataag gtatattatt gatgatg 34477

<210> SEQ ID NO 18
<211> LENGTH: 35469
<212> TYPE: DNA
<213> ORGANISM: Artificial Sequence
<220> FEATURE:
<223> OTHER INFORMATION: BZ1/BZ28F.RSVF-2A-GLuc Ad vector

<400> SEQUENCE: 18
catcatcaat aatatacctt attttggatt gtggccaata tgataatgag gtgggcgggg 60
cgaggcgggg cgggtgacgt aggacgtgcg agtagggttg ggaggtgtgg cggaagtgtg 120
gcatttgtaa gtgggaggag cttacatgca agcttccgtc gcggaaaatg tgacgttttt 180
tatgagcgcc gcctacctcc ggaagtgcca attttcgcgc gctttttacc ggatatcgta 240
gtaattttgg gcgggaccat gtaagatttg gccattttcg cgcgaaaagt gaaacgggga 300
agtgaaaact gaataatagg gcgttagtca tagcgcgtaa tatttaccga gggccgaggg 360
actttgaccg attacgtgga ggactcgccc aggtgttttt tacgtgaatt tccgcgttcc 420
gggtcaaagt ctccgttttt attgtcaccg tcatttgacg cggagggtat ttaaacccgc 480
tgcgctccta gcgatcgctc aatattggcc attagccata ttattcattg gttatatagc 540
ataaatcaat attggctatt ggccattgca tacgttgtat ccatatcata atatgtacat 600
ttatattggc tcatgtccaa cattaccgcc atgttgacat tgattattga ctagttatta 660
atagtaatca attacggggt cattagttca tagcccatat atggagttcc gcgttacata 720
acttacggta aatggcccgc ctggctgacc gcccaacgac ccccgcccat tgacgtcaat 780
aatgacgtat gttcccatag taacgccaat agggactttc cattgacgtc aatgggtgga 840
gtatttacgg taaactgccc acttggcagt acatcaagtg tatcatatgc caagtacgcc 900
ccctattgac gtcaatgacg gtaaatggcc cgcctggcat tatgcccagt acatgacctt 960
atgggacttt cctacttggc agtacatcta cgtattagtc atcgctatta ccatggtgat 1020
gcggttttgg cagtacatca atgggcgtgg atagcggttt gactcacggg gatttccaag 1080
tctccacccc attgacgtca atgggagttt gttttggcac caaaatcaac gggactttcc 1140
aaaatgtcgt aacaactccg ccccattgac gcaaatgggc ggtaggcgtg tacggtggga 1200
ggtctatata agcagagctc gtttagtgaa ccgtcagatc gcctggagac gccatccacg 1260
ctgttttgac ctccatagaa gacaccggga ccgatccagc ctccgcggtt ggccgtgctc 1320
ttcctgacgg gtaggtgtcc cctaacctag ggagccaacc atcgggggc cttctcccta 1380 aatccccgtg gcccaccctc ctgggcagag gcagcaggtt tctcactggc cccctctccc 1440
ccacctccaa gcttggcctt tcggctcaga tctcagccca cagctggcct gatctgggtc 1500
tcccctccca ccctcaggga gccaggctcg gcatttcgtc gacatggaac tgctgatcct 1560
gaaggccaac gccatcacca ccatcctgac cgccgtgacc ttctgcttcg ccagcggcca 1620
gaacatcacc gaggaattct accagagcac ctgtagcgcc gtgtccaagg gctacctgag 1680
cgccctgcgg accggctggt acaccagcgt gatcaccatc gagctgagca acatcaaaaa 1740
gaacaagtgc aacggcaccg acgccaaaat caagctgatc aagcaggaac tggacaagta 1800
caagaacgcc gtgaccgagc tgcagctgct gatgcagagc acccccgcca ccaacaaccg 1860
ggccagacgg gagctgcccc ggttcatgaa ctacaccctg aacaacgcca aaaagaccaa 1920
cgtgaccctg agcaagaagc ggaagcggcg gttcctgggc ttcctgctgg gcgtgggcag 1980
cgccattgct agcggagtgg ctgtgtctaa ggtgctgcac ctggaaggcg aagtgaacaa 2040
gatcaagtcc gccctgctga gcaccaacaa ggccgtggtg tccctgagca acggcgtgtc 2100
cgtgctgacc agcaaggtgc tggatctgaa gaactacatc gacaagcagc tgctgcccat 2160
cgtgaacaag cagagctgca gcatcagcaa catcgagaca gtgatcgagt tccagcagaa 2220
gaacaaccgg ctgctggaaa tcacccgcga gttcagcgtg aacgccggcg tgaccacccc 2280
cgtgtccacc tacatgctga ccaacagcga gctgctgagc ctgatcaacg acatgcccat 2340
caccaacgac cagaaaaagc tgatgagcaa caacgtgcag atcgtgcggc agcagagcta 2400
ctccatcatg tccatcatca aagaagaggt gctggcctac gtggtgcagc tgcccctgta 2460
cggcgtgatc gacacccccct gctggaagct gcacaccagc cccctgtgca ccaccaacac 2520
caaagagggc agcaacatct gcctgacccg gaccgaccgg ggctggtact gcgataatgc 2580
cggcagcgtg tcattctttc cacaagccga gacatgcaag gtgcagagca accgggtgtt 2640
ctgcgacacc atgaacagcc tgaccctgcc cagcgaggtg aacctgtgca acgtggacat 2700
cttcaaccct aagtacgact gcaagatcat gacctccaag accgacgtgt ccagctccgt 2760
gatcacctcc ctgggcgcca tcgtgtcctg ctacggcaag accaagtgca ccgccagcaa 2820
caagaaccgg ggcatcatca agaccttcag caacggctgc gactacgtgt ccaacaaggg 2880
cgtggacacc gtgtccgtgg gcaacaccct gtactacgtg aacaaacagg aaggcaagag 2940
cctgtacgtg aagggcgagc ccatcatcaa cttctacgac cccctggtgt tccccagcga 3000
cgagttcgac gccagcatca gccaggtcaa cgagaagatc aaccagagcc tggccttcat 3060
cagaaagagc gacgagctgc tgcacaatgt gaatgccgtg aagtccacca ccaatatcat 3120
gatcaccaca atcatcatcg tgatcatcgt catcctgctg tccctgatcg ccgtgggcct 3180
gctgctgtac tgcaaggccc ggtccacccc tgtgaccctg tccaaggacc agctgagcgg 3240
catcaacaat atcgccttct ccaacggacg cgtgaccgag ctgctttacc ggatgaagcg 3300
ggctgagaca tattgcccga gacccctgtt ggcaatccat cctactgagg ctcgccacaa 3360
acagaaaatc gtggcccccg tcaaacagac actcaatttt gacttgttga aacttgcagg 3420
agatgttgag tcaaaccccg ggcctatggg cgtcaaggtc ctgttcgctc tgatttgtat 3480
cgctgtcgct gaagctaagc caaccgagaa taatgaagac tttaatatcg tggccgtggc 3540
ttctaacttc gctaccacag acctggatgc agacagggga aagctgccag gcaagaaact 3600
gcccctggag gtcctgaagg agatggaagc aaatgcccgg aaagccgggt gcacaagagg 3660
atgcctgatt tgtctgagcc acatcaagtg cactcctaag atgaagaagt tcatccccgg 3720
ccggtgccat acctacgagg gcgataagga atccgcccag ggaggaatcg gagaggctat 3780
cgtggatatt cccgaaatcc ctggcttcaa agacctggag cccatggaac agtttattgc 3840
acaggtggat ctgtgcgtcg actgtactac cggatgcctg aagggactgg caaacgtcca 3900
gtgtagcgac ctgctgaaga aatggctgcc tcagcgatgt gctacatttg ccagcaagat 3960
tcagggccag gtggacaaga ttaagggagc aggaggcgac tgataattct agacgagatc 4020
cgaacttgtt tattgcagct tataatggtt acaaataaag caatagcatc acaaatttca 4080
caaataaagc atttttttca ctgcattcta gttgtggttt gtccaaactc atcaatgtat 4140
cttatcatgt ctgcgatcgc tgatgagacc aggaccaggt gccgaccctg cgagtgcggc 4200
ggcaagcaca tgagaaatca gcctgtgatg ttggatgtga ccgaggagct taggcctgac 4260
catctggtgc tggcctgcac cagggccgag tttgggtcta gcgatgagga taccgattga 4320
ggtgggtaag gtgggcgtgg ctagcagggt gggcgtgtat aaattggggg tctaaggggt 4380
ctctctgttt gtcttgcaac agccgccgcc atgagcgaca ccggcaacag ctttgatgga 4440
agcatcttta gcccctatct gacagtgcgc atgcctcact gggccggagt gcgtcagaat 4500
gtgatgggtt ccaacgtgga tggacgtccc gttctgcctt caaattcgtc tacgatggcc 4560
tacgcgaccg tgggaggaac tccgctggac gccgcgacct ccgccgccgc ctccgccgcc 4620
gccgcgaccg cgcgcagcat ggctacggac ctttacagct ctttggtggc gagcagcgcg 4680
gcctctcgcg cgtctgctcg ggatgaaaaa ctgactgctc tgctgcttaa actggaagac 4740
ttgacccggg agctgggtca actgacccag caggtctcca gcttgcgtga gagcagcctt 4800
gcctccccct aatggcccat aatataaata aaagccagtc tgtttggatt aagcaagtgt 4860
atgttcttta tttaactctc cgcgcgcggt aagcccggga ccagcggtct cggtcgttta 4920
gggtgcggtg gattctttcc aacacgtggt acaggtggct ctggatgttt agatacatgg 4980
gcatgagtcc atccctgggg tggaggtagc accactgcag agcttcgtgc tcgggggtgg 5040
tgttgtatat gatccagtcg tagcaggagc gctgggcgtg gtgctgaaaa atgtccttaa 5100
gcaagaggct tatagctagg gggaggccct tggtgtaagt gtttacaaat ctgcttagct 5160
gggaggggtg catccggggg gatatgatgt gcatcttgga ctggattttt aggttggcta 5220
tgttcccacc cagatccctt ctgggattca tgttgtgcag gaccaccagc acggtatatc 5280
cagtgcactt gggaaattta tcgtggagct tagacgggaa tgcatggaag aacttggaga 5340
cgcccttgtg gcctcccaga ttttccatac attcgtccat gatgatggca atgggcccgt 5400
gggaagctgc ctgagcaaaa acgtttctgg catcgctcac atcgtagtta tgttccaggg 5460
tgaggtcatc ataggacatc tttacaaatc gggggcggag ggtcccggac tgggggatga 5520
tggtaccctc gggccccggg gcgtagttcc cctcacagat ctgcatctcc caggctttca 5580
tttcagaggg agggatcata tccacctgcg gggcgatgaa aaagacagtt tctggcgcag 5640
gggagattaa ctgggatgag agcaggtttc tgagcagctg tgactttcca cagccggtgg 5700
gcccatatat cacgcctatc accggctgca gctggtagtt aagagagctg cagctgccgt 5760
cctcccggag caggggggcc acctcgttga gcatatccct gacgtggatg ttctccctga 5820
ccagttccgc cagaaggcgc tcgccgccca gcgaaagcag ctcttgcaag gaagcaaaat 5880

-continued

```
ttttcagcgg tttcaggcca tcggccgtgg gcatgttttt cagcgtctgg gtcagcagct   5940
ccagcctgtc ccagagctcg gtgatgtgct ctacggcatc tcgatccagc agatctcctc   6000
gtttcgcggg ttggggcggc tttcgctgta gggcaccagc cgatgggcgt ccagcggggc   6060
cagagtcatg tccttccatg ggcgcagagt cctcgtcagg gtggtctggg tcacggtgaa   6120
ggggtgcgct ccgggttggg cactggccag ggtgcgcttg aggctggttc tgctggtgct   6180
gaatcgctgc cgctcttcgc cctgcgcgtc ggccaggtag catttgacca tggtctcgta   6240
gtcgagaccc tcggcggcgt gccccttggc gcggagcttt cccttggagg tggcgccgca   6300
cgaggggcac tgcaggctct tcagggcgta gagcttggga gcgagaaaca cggactctgg   6360
ggagtaggcg tccgcgccgc aggccgcgca gaccgtctcg cattccacca gccaagtgag   6420
ttccgggcgg tcagggtcaa aaaccaggtt gcccccatgc tttttgatgc gtttcttacc   6480
tcggctctcc atgaggcggt gtcccttctc ggtgacgaag aggctgtccg tgtccccgta   6540
gaccgacttc aggggcctgt cttccagcgg agtgcctctg tcctcctcgt agagaaactc   6600
tgaccactct gagacgaagg cccgtgtcca ggccaggacg aaggaggcca cgtgggaggg   6660
gtagcggtcg ttgtccacta gcgggtccac cttctccagg gtgtgcagac acatgtcccc   6720
ctcctccgcg tccagaaaag tgattggctt ataggtgtag gacacgtgac cgggggttcc   6780
cgacgggggg gtataaaagg gggtgggcgc cctttcatct tcactctctt ccgcatcgct   6840
gtctgcgaga gccagctgct ggggtaagta ttccctttca aaggcgggca tgacctcagc   6900
gctcaggttg tcagtttcta aaaatgagga ggatttgatg ttcacctgtc cggaagtgat   6960
acctttgagg gtacctgggt ccatctggtc agaaaacact atttttttgt tgtcaagctt   7020
ggtggcgaac gacccgtaga gggcgttgga gagcagcttg gcaatggagc gcagggtctg   7080
gtttttgtcg cggtcggctc gctccttggc cgcgatgttg agttgcacgt attcgcgggc   7140
cacgcacttc cactcgggga agacggtggt gcgctcgtct gggatcaggc gcaccctcca   7200
gccgcggttg tgcagggtga ccatgtcgac gctggtggcg acctcaccgc gcagacgctc   7260
gttggtccag cagaggcggc cgccctttgcg cgagcagaag gggggtaggg ggtccagctg   7320
gtcctcgttt ggggggtccg cgtcgatggt aaagaccccg gggagcaggc gcgggtcaaa   7380
gtagtcgatc ttgcaagctt gcatgtccag agcccgctgc cattcgcggg cggcgagcgc   7440
gcgctcgtag ggttgaggg gcgggcccca gggcatgggg tgggtgagcg cggaggcgta    7500
catgccgcag atgtcataca cgtacagggg ttccctgagg ataccgaggt aggtggggta   7560
gcagcgcccc ccgcggatgc tggcgcgcac gtagtcatag agctcgtggg agggggccag   7620
catgttgagc ccaaggttgg tgcgctgggg gcgctcggcg cggaagacga tctgtctgaa   7680
gatggcatgg gagttggagg agatggtggg tcgctggaag acgttgaagc ttgcttcttg   7740
caagcccacg gagtccctga cgaaggaggc gtaggactcg cgcagcttgt gcaccagctc   7800
ggcggtgacc tggacgtcga gcgcgcagta gtcgagggtc tcgcggatga tgtcatactt   7860
atcctccccc ttctttttcc acagctcgcg gttgaggacg aactcttcgc ggtctttcca   7920
gtactcttgg aggggaaacc cgtccgtgtc cgaacggtaa gagcctagca tgtagaactg   7980
gttgacggcc tggtaggggc agcagccctt ctccacgggc agcgcgtagg cctgcgccgc   8040
cttgcggagg gaggtgtggg taagggcgaa agtgtccctg accatgactt tgaggtattg   8100
atgtctgaag tctgtgtcat cgcagccgcc ctgttcccac agggtgtagt ccgtgcgctt   8160
tttggagcgc gggttgggca gggagaaggt gaggtcattg aagaggatct tccccgctcg   8220
aggcatgaag tttctggtga tgcgaaaggg ccctgggacc gaggagcggt tgttgatgac   8280
```

ctgggcggcc aggacgatct cgtcaaagcc gtttatgttg tggcccacga tgtagagctc 8340
caggaagcgg ggctggccct tgatggaggg gagcttttta agttcctcgt aggtaagctc 8400
ctcgggcgat tccaggccgt gctcctccag ggcccagtct tgcaagtgag ggttggccgc 8460
caggaaggat cgccagaggt cgcgggccat gagggtctgc aggcggtcgc ggaaggttct 8520
gaactgccgc cctacggcca tcttttcggg ggtgatgcag tagaaggtga gggggtcttt 8580
ctcccagggg tcccatctga gctcttgggc gaggtcgcgc gcggcggcga ccagagcctc 8640
gtcgcccccc agtttcatga ccagcatgaa gggcacgagc tgcttgccaa aggctcccat 8700
ccaagtgtag gtctctacat cgtaggtgac aaagaggcgc tccgtgcgag gatgagagcc 8760
gatcgggaag aactggatct cccgccacca gttggaggat tggctgttga tgtggtgaaa 8820
gtagaagtcc cgtctgcggg ccgagcactc gtgctggctt ttgtaaaagc gaccgcagta 8880
ctggcagcgc tgcacgggtt gtatatcttg cacgaggtga acctggcgac ctctgacgag 8940
gaagcgcagc gggaatctaa gtcccccgcc tggggtcccg tgtggctggt ggtcttctac 9000
tttggttgtc tggccgccag catctgtctc ctggagggcg atggtggagc agaccaccac 9060
gccgcgagag ccgcaggtcc agatctcggc gctcggcggg cggagtttga tgacgacatc 9120
gcgcacattg gagctgtcca tggtctccag ctcccgcggc ggcaggtcag ccgggagttc 9180
ctggaggttc acctcgcaga gacgggtcaa ggcgcggaca gtgttgagat ggtatctgat 9240
ttcaaggggc gtgttggagg cggagtcgat ggcttgcaga aggccgcagc cccgggggc 9300
cacgatggtt ccccgcgggg cgcgaggga ggcggaagct gggggtgtgt tcagaagcgg 9360
tgacgcgggc gggcccccgg aggtaggggg ggttccggcc ccacaggcat gggcggcagg 9420
ggcacgtctt cgccgcgcgc gggcaggggc tggtgctggc tccggagagc gcttgcgtgc 9480
gcgacgacgc gacggttggt gtcctgtatc tggcgcctct gagtgaagac cacgggtccc 9540
gtgaccttga acctgaaaga gagttcgaca gaatcaatct cggcatcgtt gacagcggcc 9600
tggcgcagga tctcctgcac gtcgcccgag ttgtcctggt aggcgatctc tgccatgaac 9660
tgctcgatct cttcctcctg gagatctcct cgtccggcgc gctccacggt ggccgccagg 9720
tcgttggaga tgcgacccat gagctgcgag aaggcgttga ggccgccctc gttccagacc 9780
cggctgtaga ccacgccccc ctcggcgtcg cgggcgcgca tgaccacctg ggccaggttg 9840
agctccacgt gtcgcgtgaa gacggcgtag ttgcgcaggc gctggaaaag gtagttcagg 9900
gtggtggcgg tgtgttcggc gacgaagaag tacatgaccc agcgccgcaa cgtggattca 9960
ttgatgtccc ccaaggcctc caggcgctcc atggcctcgt agaagtccac ggcgaagttg 10020
aaaaactggg agttgcgagc ggacacggtc aactcctcct ccagaagacg gatgagctcg 10080
gcgacagtgt cgcgcacctc gcgctcgaag gccacggggg gcgcttcttc ctcttccacc 10140
tcttcttcca tgattgcttc ttcttcctca gccgggacgg gagggggcgg cggcggggga 10200
ggggcgcggc ggcggcggcg gcgcaccggc aggcggtcga tgaagcgctc gatcatctcc 10260
ccccgcatgc ggcgcatggt ctcggtgacg gcgcggccgt tctcccgggg gcgcagctca 10320
aagacgccgc ctctcatctc gccgcggggc gggcggccgt gaggtagcga gacggcgctg 10380
actatgcatc ttaacaattg ctgtgtaggt acgccgccaa gggacctgat tgagtccaga 10440
tccaccggat ccgaaaacct ttggaggaaa gcgtctatcc agtcgcagtc gcaaggtagg 10500
ctgagcaccg tggcgggcgg gggcgggtcg ggagagttcc tggcggagat gctgctgatg 10560
atgtaattaa agtaggcggt cttgagaagg cggatggtgg acaggagcac catgtctttg 10620

-continued

```
ggtccggcct gttggatgcg gaggcggtcg gccatgcccc aggcctcgtt ctgacaccgg  10680
cgcaggtctt tgtagtagtc ttgcatgagt ctttccaccg gcacctcttc tccttcctct  10740
tctccatctc gccggtggtt tctcgcgccg cccatgcgcg tgaccccaaa gcccctgagc  10800
ggctgcagca gggccaggtc ggcgaccacg cgctcggcca agatggcctg ctgtacctga  10860
gtgagggtcc tctcgaagtc atccatgtcc acgaagcggt ggtaggcgcc cgtgttgatg  10920
gtgtaggtgc agttggccat gacggaccag ttgacggtct ggtgtcccgg ctgcgagagc  10980
tccgtgtacc gcaggcgcga gaaggcgcgg gaatcgaaca cgtagtcgtt gcaagtccgc  11040
accagatact ggtagcccac caggaagtgc ggcggaggtt ggcgatagag gggccagcgc  11100
tgggtggcgg gggcgccggg cgccaggtct tccagcatga ggcggtggta tccgtagatg  11160
tacctggaca tccaggtgat gccggcggcg gtggtggtgg cgcgcgcgta gtcgcggacc  11220
cggttccaga tgtttcgcag ggcgagaag tgttccatgg tcggcacgct ctggccggtg  11280
aggcgcgcgc agtcgttgac gctctataca cacacaaaaa cgaaagcgtt tacagggctt  11340
tcgttctgta gcctggagga aagtaaatgg gttgggttgc ggtgtgcccc ggttcgagac  11400
caagctgagc tcggccggct gaagccgcag ctaacgtggt attggcagtc ccgtctcgac  11460
ccaggccctg tatcctccag gatacggtcg agagcccttt tgctttcttg gccaagcgcc  11520
cgtggcgcga tctgggatag atggtcgcga tgagaggaca aaagcggctc gcttccgtag  11580
tctggagaaa caatcgccag ggttgcgttg cggcgtaccc cggttcgagc cctatggcg  11640
gcttggatcg gccggaaccg cggctaacgt gggctgtggc agccccgtcc tcaggacccc  11700
gccagccgac ttctccagtt acgggagcga gcccctttg tttttattt tttagatgca  11760
tcccgtgctg cggcagatgc gcccctcgcc ccggcccgat cagcagcagc aacagcaggc  11820
atgcagaccc ccctctcctc tacccgcccc ggtcaccacg gccgcggcgg ccgtgtccgg  11880
cgcgggggc gcgctggagt cagatgagcc accgcggcgg cgacctaggc agtatctgga  11940
cttggaagag ggcgagggac tggcgcggct gggggcgagc tctccagagc gccacccgcg  12000
ggtgcagttg aaaagggacg cgcgcgaggc gtacctgccg cggcagaacc tgtttcgcga  12060
ccgcgggggc gaggagcccg aggagatgcg agactgcagg ttccaagcgg ggcgcgagct  12120
gcgccgcggg ttggacagac agcgcctgct gcgcgaggag gactttgagc ccgacacgca  12180
gacgggcatc agccccgcgc gcgcgcacgt ggccgcggcc gacctggtga ccgcctacga  12240
gcagacggtg aaccaggagc gcaacttcca aaaaagcttc aacaaccacg tgcgcacgct  12300
ggtggcgcgc gaggaggtga ccctgggtct catgcatctg tgggacctgg tggaggcgat  12360
cgtgcagaac cccagcagca agcccctgac cgcgcagctg ttcctggtgg tgcagcacag  12420
cagggacaac gaggccttca gggaggcgct gctgaacatc accgagccgg aggggcgctg  12480
gctcctggac ctgataaaca tcctgcagag catagtggtg caggagcgca gcctgagcct  12540
ggccgagaag gtggcggcca ttaactattc tatgctgagc ttgggcaagt tctacgcccg  12600
caagatctac aagacccct acgtgcccat agacaaggag gtgaagatag acagcttcta  12660
catgcgcatg gcgctaaagg tgctgaccct gagcgacgac ctgggagtgt accgcaacga  12720
gcgcatccac aaggccgtga gcgccagccg gcggcgcgag ctgagcgacc gcgagctgat  12780
gcacagtctg cagcgcgcgc tcaccggcgc gggcgagggc gacagggagg tcgagtccta  12840
cttcgacatg gggggctgacc tgcactggca gccgagccgc cgcgccctgg aggcggcggg  12900
ggcgtatggc ggcccccctgg cggccgatga cgaggaagag gaggactatg agctagagga  12960
gggcgagtac ctggaggact gacctggctg gtggtgtttt ggtatagatg caagatccga  13020
```

-continued

```
acgtggcgga cccggcggtc cgggcggcgc tgcagagcca gccgtccggc attaactcct  13080
ctgacgactg ggccgcggcc atgggtcgca tcatggccct gaccgcgcgc aaccccgagg  13140
ccttcaggca gcagcctcag gctaaccggc tggcggccat cttggaagcg gtagtgcccg  13200
cgcgctccaa ccccacccac gagaaggtgc tggccatagt caacgcgctg gcggagagca  13260
gggccatccg ggcggacgag gccggactgg tgtacgatgc gctgctgcag cgggtggcgc  13320
ggtacaacag cggcaacgtg cagaccaacc tggaccgcct ggtgacggac gtgcgcgagg  13380
ccgtggcgca gcgcgagcgc ttgcatcagg acggtaacct gggctcgctg gtggcgctaa  13440
acgccttcct cagcacccag ccggccaacg taccgcgggg gcaggaggac tacaccaact  13500
tcttgagcgc gctgcggctg atggtgaccg aggtccctca gagcgaggtg taccagtcgg  13560
ggcccgacta cttcttccag accagcagac agggcttgca aaccgtgaac ctgagccagg  13620
ctttcaagaa cctgcggggg ctgtggggag tgaaagcgcc caccggcgac cgagctacgg  13680
tgtccagcct gctaaccccc aactcgcgcc tgctgctgct gctgatcgcg cccttcacgg  13740
acagcgggag cgtctcgcgg gagacctatc tgggccacct gctgacgctg taccgcgagg  13800
ccatcgggca ggcgcaggtg gacgagcaca ccttccaaga gatcaccagc gtgagccacg  13860
cgctggggca ggaggacacg ggcagcctgc aggcgaccct gaactacctg ctgaccaaca  13920
ggcggcagaa gattcccacg ctgcacagcc tgacccagga ggaggagcgc atcttgcgct  13980
acgtgcagca gagcgtgagc ctgaacctga tgcgcgacgg cgtgacgccc agcgtggcgc  14040
tggacatgac cgcgcgcaac atggaaccgg gcatgtacgc ttcccagcgg ccgttcatca  14100
accgcctgat ggactacttg catcgggcgg cggccgtgaa ccccgagtac ttcaccaatg  14160
ccattctgaa tccccactgg atgccccctc cgggtttcta caacggagac ttcgaggtgc  14220
ctgaggtcaa tgatgggttc ctctgggatg acatggatga cagtgtgttc tcccccaacc  14280
cgctgcgcgc cgcgtctctg cgattgaagg agggctctga cagggaagga ccgaggagtc  14340
tggcctcctc cctggctctg gggggcggtgg gcgccacggg cgcggcggcg cggggcagca  14400
gccccttccc cagcctggca gactctctga atagcgggcg ggtgagcagg ccccgcttgc  14460
taggcgagga ggagtatctg aacaactccc tgctgcagcc cgtgagggac aaaaacgctc  14520
agcgacagca gtttcccaac aacgggatag agagcctggt ggacaagatg tccagatgga  14580
agacatatgc gcaggagtac aaggagtggg aggaccgcca gccgcggccc ctgccgcccc  14640
ctagacagcg ctggcagcgg cgcgcgtcca accgccgctg gagacaggga cccgaggacg  14700
atgatgactc tgcagatgac agcagcgtgt tggacctggg cgggagcggg aacccctttt  14760
cgcacctgcg cccacgcctg ggcaagatgt tttaaaagag aaaaataaaa ctcaccaagg  14820
ccatggcgac gagcgttggt tttttgttcc cttccttagt atgcggcgcg cggcgatgtt  14880
cgaggagggg cctccccccct cttacgagag cgcgatggga atttctcctg cggcgcccct  14940
gcagcctccc tacgtgcctc ctcggtacct gcaacctaca ggggggagaa atagcatctg  15000
ttactctgag ctgcagcccc tgtacgatac caccagactg tacctggtgg acaacaagtc  15060
cgcggacgtg gcctccctga actaccagaa cgaccacagc gattttttga ccacggtgat  15120
ccaaaacaac gacttcaccc caaccgaggc cagtacccag accataaacc tggacaacag  15180
gtcgaactgg ggcggcgacc tgaagaccat cctgcacacc aacatgccca acgtgaacga  15240
gttcatgttt accaactctt ttaaggcgcg ggttatggtg gcgcgcgagc agggggaggc  15300
gaagtacgag tgggtggact tcacgctgcc cgagggcaac tactcagaga ccatgactat  15360
```

-continued tgacctgatg aacaatgcga tcgtggaaca ctacctgaaa gtgggcaggc agaacggggt 15420
gaaggagagc gatatcgggg tcaagtttga caccagaaac tttcgtctgg gctgggaccc 15480
cgtgaccggg ctggtcatgc cgggggtcta caccaacgag gcctttcatc ccgatatagt 15540
gctcctgccc ggctgtgggg tggactttac ccagagccgg ctgagcaacc tgctgggcgt 15600
tcgcaagcgg caacctttcc aggagggttt caagatcacc tatgaggatc tggagggggg 15660
caacattccc gcgctccttg atctggacgc ctacgaggag agcttgaaac ccgaggagag 15720
cgctggcgac agcggcgaga gtggcgagga gcaagccggc ggcggtggca gcgcgtcggt 15780
agaaaacgaa agtactcccg cagtggcggc agacgctgcg gaggtcgagc cagaggccat 15840
gcagcaggac gcagaggagg gcgcacagga gggcgcgcag gaggacatga acgatgggga 15900
gatcagggga gacactttcg ccacccgggg cgaagaaaaa gaggcagagg cggtggcggc 15960
gacggtggaa gccgaaaccg aggcagaggc agagcccaag accgaagtta tggaagacat 16020
gaatgatgga gaacgtaggg gtgacacgtt tgccacccgg ggcgaagaga aggcggcgga 16080
ggcagaagcc gcggctgagg aggcggctgc ggctgcggcc gaggctgagg ctgcggctga 16140
ggctaaggtc gaagccgatg ttgcggttga ggctcaggct gaggaggagg aggcggcgac 16200
tgaagcagtt aaggaaaagg cccaggcaga gcaggaagag aaaaaacctg tcattcaacc 16260
tctaaaagaa gatagcaaaa agcgcagtta caacgtcatc gagggcagca cctttaccca 16320
gtaccgcagc tggtacctgg cgtacaacta cggcgacccg gtcaaggggg tgcgctcgtg 16380
gaccctgctc tgcacgccgg acgtcacctg cggctccgag cagatgtatt ggtcgctgcc 16440
aaacatgatg caagacccgg tgaccttccg ctccacgcgg caggttagca acttcccggt 16500
ggtgggcgcc gaactgctgc ccgtgcactc caagagtttt tacaacgagc aggccgtcta 16560
ctcccagctg atccgccagg ccacctctct gacccacgtg ttcaatcgct ttcccgagaa 16620
ccagattttg gcgcgcccgc cggcccccac catcaccacc gtcagtgaaa acgttcctgc 16680
cctcacagat cacgggacgc taccgctgcg caacagcatc tcaggagtcc agcgagtgac 16740
cattactgac gccagacgcc ggacctgccc ctacgtttac aaggccttgg gcatagtctc 16800
gccgcgcgtc ctctccagtc gcactttttta aaatacatct accctcacgc ttcaaaatca 16860
tgtccgtact catctcaccc agcaacaaca ccggctgggg gctgcgcgcg cccagcaaga 16920
tgtttggagg ggcgaggaaa cgctccgagc agcacccagt gcgcgtgcgc ggccactacc 16980
gcgcgccctg gggagcgcac aagcgcgggc gcgcagggcg caccactgtg gacgacgcca 17040
ttgactccgt agtggagcag gcgcgccact acacacccgg cgcgccgtcc gcccccgccg 17100
tgtccaccgt ggacgaggcg atcgagagcg tggtacaggg cgcgcggcac tatgccaacc 17160
ttaaaaatcg acgccgtcgc gtggctcgcc gccatcgccg gagaccccgg gccaccgccg 17220
ccgcgcgcct tgctaaggct ctgctcaggc gcgccaggcg aactggccgc cgggccgcca 17280
tgagggccgc acggcgggct gccgccagcg cggccgccgc ggccccacgg gcacgaaggc 17340
gcgcggccgc tgccgccgcc gccgccattt ccagcttggc ctcgacgcgg cgcggtaaca 17400
tatactgggt gcgcgactcg gtaaccggca cgcgggtacc cgtgcgcttt cgcccccccgc 17460 ggaattagca caagacaaca tacacactga gtctcctgct gttgtgtatc ccagcggcga 17520
ccgtcagcag cggcgacatg tccaagcgca aaattaaaga agagatgctc caggtcatcg 17580
cgccggagat ctatgggccc ccgaagaagg aggaggatga ttacaagccc cgcaagctaa 17640
agcgggtcaa aaagaaaaag aaagatgatg acgttgacga ggcggtggag tttgtccgcc 17700
gcatggcgcc caggcgcccc gtgcagtgga agggtcggcg cgtgcagcga gtcctgcgcc 17760

```
ccggcaccgc ggtggtcttt acgcccggcg agcgttccac gcgcactttc aagcgggtgt  17820
acgatgaggt gtacggcgac gaggatctgt tggagcaggc caaccatcgc tttggggagt  17880
ttgcatatgg gaaacggccc cgcgagagcc taaaagagga cctgctggcg ctaccgctgg  17940
acgagggcaa tcccaccccg agtctgaagc cggtaaccct gcaacaggtg ctgcctttga  18000
gcgcgcccag cgagcagaag cgagggttga agcgcgaggg cggggacctg gcacccaccg  18060
tgcagttgat ggtgcccaag cggcagaagc tggaggacgt gctggagaaa atgaaagtag  18120
agcccgggat ccagcccgaa atcaaggtcc gccccatcaa gcaggtggcg cccggcgtgg  18180
gagtccagac cgtggacgtt aggattccca cggaggagat ggaaacccaa accgccactc  18240
cctcttcggc ggctagcgcc accaccggct ccgcttcggt agaggtgcag acggacccct  18300
ggctagccgc cgccgccccg gccgcccccc gttcgcgcgg gcgcaagaga aattatccag  18360
cggccagcgc gctcatgccc cagtacgcac tgcatccatc catcgcgccc acccccggct  18420
accgcgggta ctcgtaccgc ccgcgcagat cagccggcac ccgcggccgc cgccgccgtg  18480
cgaccacaac cagccgccgc cgtcgccgcc gccgccagcc agtgctgacc cccgtgtctg  18540
taaggaaggt ggctcgctcg gggagcacgc tggtggtgcc cagagcgcgc taccacccca  18600
gcattgttta aagccggtct ctgtatggtt cttgcagata tggccctcac ttgtcgcctc  18660
cgcttcccgg tgccgggata ccgaggaaga actcaccgcc gcagaggcat ggcgggcagt  18720
ggtctccgcg gcggccgtcg ccatcgccgg cgcgcaaaga gcaggcgcat gcgcggcggt  18780
gtgctgccct tcctaatccc gctaatcgcc gcggcgatcg gtgccgtgcc cgggatcgcc  18840
tccgtggccc tgcaggcgtc ccagaaacat tgactcttgc aaccttgcaa gcttgcattt  18900
tttggaggaa aaaataaaaa gtctagactc tcacgctcgc ttggtcctgt gactattttg  18960
tagaaaaaag atggaagaca tcaactttgc gtcgctggcc ccgcgtcacg gctcgcgccc  19020
gttcatggga gactggacag atatcggcac cagcaatatg agcggtggcg ccttcagctg  19080
gggcagtctg tggagtggcc ttaaaaattt tggttccacc attaagaact atggcaacaa  19140
agcgtggaac agcagcacgg gtcagatgct gagagacaag ttgaaagagc agaacttcca  19200
ggagaaggtg gcacagggcc tggcctctgg catcagcggg gtggtggaca tagctaacca  19260
ggccgtgcag aaaaagataa acagtcatct ggacccccgc cctcaggtgg aggaaacgcc  19320
tccagccatg gagacggtgt ctcccgaggg caaaggcgaa aagcgcccgc ggcccgacag  19380
ggaagagacc ctggtgtcac acaccgagga gccgccctct tacgaggagg cagtcaaggc  19440
cggcctgccc accactcgcc ccatagctcc catggccacc ggtgtggtgg gtcacaggca  19500
acacaccccc gcgacactag atctgccccc gccgtccgag ccgactcgcc agccaaaggc  19560
ggtgacggtg cccgctccct ccacttccgc cgccaacaga gtgcctctgc gccgcgctgc  19620
gagcggcccc cgggcctcgc gagtcagcgg caactggcag agcacactga acagcatcgt  19680
gggcctggga gtgaggagtg tgaagcgccg ccgttgctac tgaatgagca agctagctaa  19740
cgtgttgtat gtgtgtatgc gtcctatgtc gccgccagag gagctgttga gccgccggcg  19800
ccgtctgcac tccagcgaat ttcaagatgg cgaccccatc gatgatgcct cagtggtcgt  19860
acatgcacat ctcgggccag gacgcttcgg agtacctgag ccccgggctg gtgcagttcg  19920
cccgcgccac agacacctac ttcaacatga gtaacaagtt caggaacccc actgtggcgc  19980
ccacccacga tgtgaccacg gaccggtcgc agcgcctgac gctgcggttc atccccgtgg  20040
atcgggagga caccgcttac tcttacaagg cgcggttcac gctggccgtg ggcgacaacc  20100
```

-continued gcgtgctgga catggcctcc acttactttg acatccgggg ggtgctggac aggggcccca 20160
ctttcaagcc ctactcgggc actgcctaca actccctggc ccccaagggc gctcccaatt 20220
cttgcgagtg ggaggaggaa acacaaaatg aggtacaagc caatgaagaa caactagcag 20280
aagaagagga tgaagaaatg gctcaagagg atcagcagcc tactaaaaaa acccatgtat 20340
atgctcaggc acctctttct ggcgaacaga ttaccaaaga tggcttgcaa ataggagctg 20400
aagttacagg agaaacatca aagcccattt ttgcagacaa gacattccaa ccagaacctc 20460
agataggaga gtctcaatgg aatgaggccg atgctacagt agcaggaggt agggttttga 20520
aaaagactac ccctatgaaa ccttgctatg gatcctatgc cagacctacc aatgccaatg 20580
gagggcaggg gatacttgag gcaaatgcta aaggggaact cgaatctaaa gttgagatgc 20640
agtttttctc taacaccaca actcttaatg taagagacgg tgaaaatggc cttaaaccaa 20700
aagtagtgct gtatagcgaa gatgtcaacc tggaatcccc tgacactcat ctgtcttaca 20760
agcccaaaaa agatgatgtt aatgccaaaa tcatgttggg tcagcaagcc atgcccaaca 20820
gacccaacct cattggattt agagataatt tcattgggct catgtattac aacagcactg 20880
gaaacatggg agtgctggcg ggtcaggcct ctcagttgaa tgctgtggtg gacttgcagg 20940
atagaaacac ggaactgtca tatcagctta tgcttgattc cattggagat agaaccagat 21000
acttttccat gtggaaccag gcagtggata gctatgaccc agatgttaga atcattgaaa 21060
accatggggt ggaggatgag ctgcccaact actgttttcc cttgggcggt ataggaatta 21120
cagatacata ccaggccata aaagcagcca atggtggaga tgctactacg tggtctgctg 21180
ataacacatt tgcagaccgc aacgaaatag gggtgggaaa caacttcgcc atggagatca 21240
acatccaggc caacctctgg agaaacttcc tctatgcgaa cgtgggactc tacctgccag 21300
acaagctcaa gtacaacccc accaacgtgg acatctctga caaccccaac acctatgact 21360
acatgaacaa gcgggtggtg gcccccggcc tggtggactg ctttgtcaat gtgggagcca 21420
ggtggtccct ggactacatg gacaacgtca accccttcaa ccaccaccgc aatgcgggtc 21480
tgcgctaccg ctccatgatc ctgggcaacg ggcgctatgt gcccttccac atccaggtac 21540
cccagaagtt ctttgccatc aagaacctcc tgctcctgcc cggctcctac acctacgagt 21600
ggaacttcag gaaggatgta aacatggtcc tacagagctc tctgggcaat gaccttaggg 21660
tagatggggc cagcatcaag tttgacagca tcaccctcta tgctacattt ttccccatgg 21720
cccacaacac cgcctccacg cttgaggcca tgctgagaaa cgacaccaac gaccagtcct 21780
tcaatgacta cctctctggg gccaacatgc tctacccaat cccagccaag gccaccaacg 21840
tgcccatctc catcccctct cgcaactggg ccgcctttag aggctgggcc tttacccgcc 21900
ttaagaccaa ggagaccccc tccctgggct cgggttttga tccctacttt gtttactcgg 21960
gatccatccc ctacctggat ggcaccttct acctcaacca cactttcaag aagatatcca 22020
tcatgtatga ctcctccgtc agctggccgg gcaacgaccg cttgctcacc cccaatgagt 22080
tcgaggtcaa gcgcgccgtg gacggcgagg gctacaacgt ggcccagtgc aacatgacca 22140
aggactggtt cctggtgcag atgctggcca actacaacat aggctaccag ggcttctaca 22200
tcccagagag ctacaaggac aggatgtatt ccttcttcag aaatttccaa cccatgagcc 22260
gacaggtggt ggacgagacc aattacaagg actatcaggc cattggcatc acccaccagc 22320
acaacaactc gggtttcgtg ggctacctgg cgcccaccat gcgcgaggga caggcctacc 22380
ccgccaactt cccctacccc ctgataggca agaccgcggt cgacagcgtc acccagaaaa 22440
agttcctctg cgaccgcacc ctctggcgca tccccttctc tagcaacttt atgtccatgg 22500
gtgcgctcac ggacctgggc caaaacctgc tttatgccaa ctctgcccat gcgctggaca 22560
tgacttttga ggtggacccc atggacgagc ccacccttct ctatattgtg tttgaagtgt 22620
tcgacgtggt cagagtgcac cagccgcacc gcggtgtcat cgagaccgtg tacctgcgta 22680
cgcccttctc agccggcaac gccaccacct aaggagacag cgccgccgcc tgcatgactg 22740
gttccaccga gcaagagctc agggccatcg ccagagacct gggatgcgga ccctattttt 22800
tgggcaccta tgacaaacgc ttcccgggtt ttatctcccg agacaagctc gcctgcgcca 22860
tcgtcaacac ggccgcgcgc gagaccgggg gcgtgcactg gctggccttt ggctgggacc 22920
cgcgctctaa aacttgctac ctctttgacc cctttggctt ctccgatcag cgcctcaggc 22980
agatttatga gtttgagtac gaggggctgt tgcgccgcag cgcgcttgcc tcctcgcccg 23040
accgctgcat cacccttgag aagtccaccg agaccgtgca ggggccccac tcggccgcct 23100
gcggtctctt ctgttgcatg tttttgcacg cctttgtgca ctggcctcag agtcccatgg 23160
atcgcaaccc caccatgaac ttgctaaagg gagtgcccaa cgccatgctc cagagccccc 23220
aggtcctgcc caccctgcgc cgcaaccagg aacagctcta ccgcttcctg gagcgccact 23280
ccccctactt ccgcagccac agcgcgcgca tccgggggc cacctctttt tgccacttgc 23340
aagaaaacat gcaagacgga aaatgatgta cagcatgctt ttaataaatg taaagactgt 23400
gcactttatt tatacacggg ctctttctgg ttatttattc aacaccgccg tcgccatcta 23460
gaaatcgaaa gggttctgcc gcgcgtcgcc gtgcgccacg ggcagagaca cgttgcgata 23520
ctggaagcgg ctcgcccact tgaactcggg caccaccatg cggggcagtg gttcctcggg 23580
gaaattctcg ctccacaggg tgcgggtcag ctgcagcgcg ctcaggaggt cgggagccga 23640
gatcttgaag tcgcagttgg ggccggaacc ctgcgcgcgc gagttgcggt acacggggtt 23700
gcagcactgg aacaccagca gggccggatt attcacgctg gccagcaggc tctcgtcgct 23760
aatcatgtcg ctgtccagat cctccgcgtt gctcagggcg aatggggtca tcttgcagac 23820
ctgcctgccc aggaaaggcg ggagcccagg cttgccgtta cagtcgcagc gcaggggcat 23880
tagcaggtgc ccacggcccg actgcgcctg cgggtacaac gcgcgcatga aggcttcgat 23940
ctgcctaaaa gccacctggg tcttggctcc ctccgaaaag aacatcccac aggacttgct 24000
ggagaactgg ttcgcgggac agctggcatc gtgcaggcag cagcgcgcgt cagtgttggc 24060
gatctgcacc acgttgcgac cccaccggtt tttcactatc ttggccttgg aagcctgctc 24120
ctttagcgcg cgctggccgt tctcgctggt cacatccatc tctatcacct gttccttgtt 24180
gatcatgttt gtcccgtgca gacactttag gtcgccctcc gtctgggtgc agcggtgctc 24240
ccacagcgcg caaccggtgg gctcccaatt tttgtgggtc acccccgcgt aggcctgcag 24300
gtaggcctgc aggaagcgcc ccatcatggt cataaaggtc ttctggctcg taaaggtcag 24360
ctgcaggccg cgatgctctt cgttcagcca ggtcttgcag atggcggcca gcgcctcggt 24420
ctgctcgggc agcatcttaa aatttgtctt caggtcgtta tccacgtggt acttgtccat 24480
catggcacgc gccgcctcca tgcccttctc ccaggcggac accatgggca ggcttagggg 24540
gtttatcact tccagcggcg aggacaccgt actttcgatt tcttcttcct ccccctcttc 24600
ccggcgcgcg cccccgctgt tgcgcgctct taccgcctgc accaaggggt cgtcttcagg 24660
caagcgccgc accgagcgct tgccgccctt gacctgcttg atcagtaccg gcgggttgct 24720
gaagcccacc atggtcagcg ccgcctgctc ttcttcgtct tcgctgtcta ccactatttc 24780
tggggagggg cttctccgct ctgcggcaaa ggcggcggat cgcttctttt ttttcttggg 24840

-continued

```
agccgccgcg atggagtccg ccacggcgac cgaggtcgag ggcgtggggc tgggggtgcg  24900
cggcaccagg gcctcgtcgc cctcggactc ttcctctgac tccaggcggc ggcggagtcg  24960
cttctttggg ggcgcgcgcg ttagcggcgg cggagacggg gacggggacg gggacgggac  25020
gccctccaca gggggcggtc ttcgcgcaga cccgcggccg cgctcggggg tcttctcgcg  25080
ctggtcttgg tcccgactgg ccattgtatc ctcctcctcc taggcagaga gacataagga  25140
gtctatcatg caagtcgaga aggaggagag cttaaccacc ccctctgaga ccgccgtcgc  25200
cgtcgccccc gctaccgccg acgcgcccgc cacaccgagc gacacccccg cggaccccca  25260
cgccgacgca cccctgttcg aggaagcggc cgtggagcag gacccgggct ttgtctcggc  25320
agaggaggat ttgcaagagg aggaggataa ggaggagaag ccctcagtgc caaaagatca  25380
taaagagcaa gacgagcacg acgcagacgc acaccagggt gaagtcgggc ggggggacgg  25440
agggcatggc ggcgccgact acctagacga aggaaacgac gtgctcttga agcacctgca  25500
tcgtcagtgc gccattgtct gcgacgctct gcaggagcgc agcgaggtgc ccctcagcgt  25560
ggcggaggtc agccgcgcct acgagctcag cctcttttcc ccccgggtgc ccccccgccg  25620
ccgcgaaaac ggcacatgcg agcccaaccc gcgcctcaac ttctaccccg cctttgtggt  25680
gcccgaggtc ctggccacct atcacatctt ctttcaaaat tgcaagatcc ccatctcgtg  25740
ccgcgccaac cgtagccgcg ccgataagat gctggccctg cgccagggcg accacatacc  25800
tgatatcgcc gctttggaag atgtgccaaa gatcttcgag ggtctgggtc gcaacgagaa  25860
gcgggcagca aactctctgc aacaggaaaa cagcgaaaat gagagtcaca ctggagcgct  25920
ggtggagctg gagggcgaca acgcccgcct ggcggtgctc aagcgcagca tcgaggtcac  25980
ccactttgcc taccccgcgc tcaacctgcc ccccaaagtc atgaacgcgg tcatggacgg  26040
gctaatcatg cgccgcggcc ggccccttgc tccagatgca aacttgcatg aggagaccga  26100
ggacggtcag cccgtggtca gcgacgagca gctgacgcgc tggctggaaa ccgcggaccc  26160
cgccgaactg gaggagcggc gcaagatgat gatggccgcg gtgctggtca ccgtagagct  26220
ggagtgtctg cagcgcttct tcggcgaccc cgagatgcag agaaaggtcg aggagaccct  26280
acactacacc ttccgccagg gctacgtgcg ccaggcttgc aagatctcca acgtggagct  26340
cagcaacctg gtgtcctacc tgggcatctt gcatgaaaac cgccttgggc agagcgtgct  26400
acactccacc ctgcgcgggg aggcgcgccg cgactacgtg cgcgactgcg tttacctctt  26460
cctctgctac acctggcaga cggccatggg ggtctggcag cagtgcctgg aggagcgcaa  26520
cctcaaggag ctggagaagc tcctgcagcg cgcgctcaaa gacctctgga cgggctacaa  26580
cgagcgctcg gtggccgccg cgctggccga cctcatcttc cccgagcgcc tgctcaaaac  26640
tctccagcag ggcctgcccg acttcaccag ccaaagcatg ttgcaaaatt ttaggaactt  26700
tatcctggag cgttctggca tcctacccgc cacctgctgc gccctgccca gcgactttgt  26760
ccccctcgtg taccgcgagt gccccccgcc gctgtggggc cactgctacc tgttccaact  26820
ggccaactac ctgtcctacc acgcggacct catggaagac tccagcggcg aggggctcat  26880
ggagtgccac tgccgctgca acctctgcac gccccaccgc tccctggtct gcaacaccca  26940
actgctcagc gagagtcaga ttatcggtac cttcgagcta cagggtccgt cctcctcaga  27000
cgagaagtcc gcggctccgg ggctaaaact cactccgggg ctgtggactt ccgcctacct  27060
gcgcaaattt gtacctgaag actaccacgc ccacgagatc aggttttacg aggaccaatc  27120
ccgcccgccc aaggcggagc tgaccgcctg cgtcatcacc cagggcgaga tcctaggcca  27180
attgcaagcc atccaaaaag cccgccaaga gtttttgctg agaaagggtc ggggggtgta  27240
```

tctggacccc cagtcgggtg aggagctcaa cccggttccc ccgctgccgc cgccgcggga 27300
ccttgcttcc caggataagc atcgccatgg ctcccagaaa gaagcagcag cggccgccac 27360
tgccgccacc ccacacgctg gaggaagagg aggaatactg ggacagtcag gcagaggagg 27420
tttcggacga ggaggagccg gagacggaga tggaagagtg ggaggaggac agcttagacg 27480
aggaggcttc cgaagccgaa gaggcaggcg caacaccgtc accctcggcc gcagccccct 27540
cgcaggcgcc cccgaagtcc gctcccagca tcagcagcaa cagcagcgct ataacctccg 27600
ctcctccacc gccgcgaccc acggccgacc gcagacccaa ccgtagatgg gacaccaccg 27660
gaaccggggc cggtaagtcc tccgggaaag gcaagcaagc gcagcgccaa ggctaccgct 27720
cgtggcgcgc tcacaagaac gccatagtcg cttgcttgca agactgcggg gggaacatct 27780
ccttcgcccg ccgcttcctg ctcttccacc acggtgtggc cttcccccgt aacgtcctgc 27840
attactaccg tcatctctac agcccctact gcggcggcag tgagccagag gcggccggcg 27900
gcagcggcgc ccgtttcggt gcctaggaag acccagggca agacttcagc caagaaactc 27960
gcggcggccg cggcgaacgc ggtcgcgggg gccctgcgcc tgacggtgaa cgaacccctg 28020
tcgacccgcg aactgaggaa ccgaatcttc cccactctct atgccatctt ccagcagagc 28080
agagggcagg atcaggaact gaaagtaaaa aacaggtctc tgcgctccct cacccgcagc 28140
tgtctgtatc acaagagcga agaccagctt cggcgcacgc tggaggacgc tgaggcactc 28200
ttcagcaaat actgcgcgct cactcttaag gactagctcc gcgcccttct cgaatttagg 28260
cgggaacgcc tacgtcatcg cagcgccgcc gtcatgagca aggacattcc cacgccatac 28320
atgtggagct atcagccgca gatgggactc gcggcgggcg cctcccagga ttactccacc 28380
cgcatgaact ggctcagtgc cggcccacac atgatctcac aggttaatga catccgcacc 28440
catcgaaacc aaatattggt ggagcaggcg gcaattacca ccacgccccg caataatccc 28500
aaccccaggg agtggcccgc gtccctggtg tatcaggaaa ttcccggccc caccaccgta 28560
ctacttccgc gtgattccca ggccgaagtc caaatgacta actcaggggc acagctcgcg 28620
ggcggctgtc gtcacagggt gcggcctcct cgccagggta taactcacct gaagatccga 28680
ggcagaggta ttcagctcaa cgacgagtcg gtgagctcct cgctcggtct cagacctgac 28740
gggaccttcc agatagccgg agccggccga tcttccttca cgccccgcca ggcgtacctg 28800
actctgcaga gctcgtcctc ggcgccgcgc tcgggcggca tcgggactct ccagttcgtg 28860
caggagtttg tgccctcggt ctacttcaac cccttctcgg gctctcccgg tcgctacccg 28920
gaccagttca tcccgaactt tgacgccgcg agggactcgg tggacggcta cgactgaatg 28980
tcgggtggac ccggtgcaga gcaacttcgc ctgaagcacc ttgaccactg ccgccgccct 29040
cagtgctttg cccgctgtca gaccggtgag ttccagtact ttccctgcc cgactcgcac 29100 ccggacggcc cggcgcacgg ggtgcgcttt ttcatcccga gtcaggtccg ctctacccta 29160
atcagggagt tcaccgcccg tcccctactg gcggagttgg aaaaggggcc ttctatccta 29220
accattgcct gcatctgctc taaccctgga ttacaccaag atctttgctg tcatttgtgt 29280
gctgagtata ataaaggctg agatcagaat ctactcgggc tcctgtcgcc atcctgtcaa 29340
cgccaccgtc caagcccggc ccgatcagcc cgaggtgaac ctcacctgcg gtctgcaccg 29400
gcgcctgagg aaatacctag cttggtacta caacagcact ccctttgtgg tttacaacag 29460
ctttgaccag gacggggtct cactgaggga taacctctcg aacctgagct actccatcag 29520
gaagaacaac accctcgagc tacttcctcc ttacctgccc gggacttacc agtgtgtcac 29580

-continued

```
cggtccctgc acccacaccc acctgttgat cgtaaacgac tctcttccga gaacagacct  29640
caataactcc tctccgcagt tccccagaac aggaggtgag ctcaggaaac cccgggtaaa  29700
gaagggtgga caagagttaa cacttgtggg gtttctggtg tatgtgacgc tggtggtggc  29760
tcttttgatt aaggcttttc cttccatgtc tgaactatcc ctcttctttt atgaacaact  29820
cgactagtgc taacgggacc ctacccaacg aatcgggatt gaatatcggt aaccaggttg  29880
cagtttcact tttgattacc ttcatagtcc tcttcctgct agtgctgtcg cttctgtgcc  29940
tgcggatcgg gggctgctgc atccacgttt atatctggtg ctggctgttt agaaggttcg  30000
gagaccaccg caggtagaat aaacaaacct agacctagaa atggacggtc tctgcagcga  30060
gcaacgcata ctagagaggc gccggcaaaa agcagagctc gagcgtctta aacaagagct  30120
ccaagacgcc gtggccatac accagtgcaa aaaagggctc ttctgtctgg taaaacaggc  30180
cacgctcacc tatgaaaaaa caggtgacac ccaccgccta ggatacaagc tgcccacaca  30240
gcgccaaaag tttgccctta tgataggtga acaacccatc accgtgaccc agcactccgt  30300
ggagacagaa ggctgcattc atgctccctg caggggcgct gactgcctct acaccttgat  30360
caaaaccctt tgcggtctca gagaccttat ccctttcaat tgatcataac tgtaatcaat  30420
aaaaaatcac ttacttgaaa tctgatagca agcctctgtc caatttttttc agcaacactt  30480
ccttcccctc ttcccaactc tggtactcta ggcgcctcct agctgcaaac ttcctccaca  30540
gtctgaaggg aatgtcagat tcctcctcct cctgtccctc cgcacccacg atcttcatgt  30600
tgttgcagat gaagcgcacc aaaacgtctg acgagagctt caaccccgtg tacccctatg  30660
acacggaaaa cggtcctccc tccgtccctt tcctcacccc tcccttcgtg tctcccgatg  30720
gattccaaga gagcccccccc ggggtcctgt ctctgaacct ggccgagccc ctggtcactt  30780
cccacggcat gctcgccctg aaaatgggaa gtggcctctc cctggacgac gccggcaacc  30840
tcacctctca agatgtcacc accactaccc ctcccctgaa aaaaaccaag accaacctca  30900
gcctagaaac ctcagccccc ctgactgtga gcacctcagg cgccctcacc ctagcagccg  30960
ccgttcccct ggcggtggcc ggcacctccc tcaccatgca atcagaggcc cccctgacag  31020
tccaagatgc aaaactcacc ctggccacca agggcccccct gaccgtgtct gaaggcaaac  31080
tggccttgca gacctcggcc ccgctgacgg ccgctgacag cagcgccctc accgttagcg  31140
ccacaccacc catcagtgta agcagtggaa gtttgggctt agacatggaa gaccccatgt  31200
atactcatga tggaaaactg ggaataagaa ttggaggccc actgagagta gtagacagcc  31260
tgcacacact gactgtagtt accggaaatg gaatagctgt agataacaat gccctccaaa  31320
ctagagttac gggcgccctg ggttatgaca catcaggaaa cctacaactg agagccgcgg  31380
ggggtatgcg aattgatgca aatggccaac ttatccttga tgtggcatac ccatttgatg  31440
ctcaaaacaa tctcagcctt agacttggtc agggacccct gtatgtaaac acagaccaca  31500
acctagattt gaattgcaac agaggtctga ccacaactac caccaacaac acaaaaaaac  31560
ttgaaactaa aattggctca ggcttagact atgataccaa tggtgctgtc attattaaac  31620
ttggtactgg tgtaagcttt gacagcacag gcgccctaac tgtgggaaac actggcgatg  31680
ataaactgac tctgtggaca accccagacc catctccaaa ttgcagaatt cacgcagaca  31740
aagactgcaa gtttactcta gtcctaacta agtgtggaag tcaaatcctg gcttctgtcg  31800
ccgccctagc ggtgtcagga aatctggctt caataacagg caccgttgcc agcgttacca  31860
tctttctcag atttgatcag aatggagtgc ttatggaaaa ctcctcccta gacaagcagt  31920
actggaactt cagaaatggt aactcaacca atgccacccc ctacaccaat gcagttgggt  31980
```

tcatgccaaa cctcgcagca taccccaaga cacagagcca gactgctaaa aacaacattg 32040
taagtcaggt ttacttgaat ggggacaaat ccaaacccat gacccttacc attaccctca 32100
atggaactaa tgaatccagt gaaactagcc aggtgagtca ctactccatg tcatttacat 32160
gggcttggga gagtgggcaa tatgccaccg aaacctttgc caccaattcc tttaccttct 32220
cttacattgc tgaacaataa agaaagcaca gagatgcttg tttttgattt caaaattgtg 32280
tgcttttatt tattttcaag cttacagtat ttccagtagt cattcgaata gagcttaatg 32340
aaactgcatg agaacccttc cacatagctt aaattatcac cagtgcaaat ggagaaaaat 32400
caacatacct ttttatccag atatcacaga accctagtat tcaacctgcc acctccctcc 32460
caacacacag agtacacagt cctttctccc cggctggcct taaaaagcat catatcatgg 32520
gtaacagaca tattcttagg tgttatattc cacacggttt cctgtcgagc caaacgctca 32580
tcagtgatat taataaactc cccgggcagc tcacttaagt tcatgtcgct gtccagctgc 32640
tgagccacag gctgctgtcc aacttgcggt tgcttaacgg gcggcgaagg agaagtccac 32700
gcctacatgg gggtagagtc ataatcgtgc atcaggatag ggcggtggtg ctgcagcagc 32760
gcgcgaataa actgctgccg ccgccgctcc gtcctgcagg aatacaacat ggcagtggtc 32820
tcctcagcga tgattcgcac cgcccgcagc ataaggcgcc ttgtcctccg ggcacagcag 32880
cgcaccctga tctcacttaa atcagcacag taactgcagc acagcaccac aatattgttc 32940
aaaatcccac agtgcaaggc gctgtatcca aagctcatgg cggggaccac agaacccacg 33000
tggccatcat accacaagcg caggtagatt aagtggcgac ccctcataaa cacgctggac 33060
ataaacatta cctcttttgg catgttgtaa ttcaccacct cccggtacca tataaacctc 33120
tgattaaaca tggcgccatc caccaccatc ctaaaccagc tggccaaaac ctgcccgccg 33180
gctatacact gcagggaacc gggactggaa caatgacagt ggagagccca ggactcgtaa 33240
ccatggatca tcatgctcgt catgatatca atgttggcac aacacaggca cacgtgcata 33300
cacttcctca ggattacaag ctcctcccgc gttagaacca tatcccaggg aacaacccat 33360
tcctgaatca gcgtaaatcc cacactgcag ggaagacctc gcacgtaact cacgttgtgc 33420
attgtcaaag tgttacattc gggcagcagc ggatgatcct ccagtatggt agcgcgggtt 33480
tctgtctcaa aaggaggtag acgatcccta ctgtacggag tgcgccgaga caaccgagat 33540
cgtgttggtc gtagtgtcat gccaaatgga acgccggacg tagtcatatt tcctccagca 33600
gaaccaagtg cgcgcgtggc agctatcctt gcgtcttctg tctcgccgcc tgccccgctc 33660
ggtgtagtag ttgtaataca gccactccct cagaccgtca aggcgctccc tggcgtccgg 33720
atctataaca acaccatcct gcagcgccgc cctgatgaca tccaccaccg tagagtatgc 33780
caagcccagc caggaaatgc actcactttg acagcgagag ataggaggag cgggaagaga 33840
tggaagaacc atgatagtaa aagaactttt attccaatcg atcctctaca atgtcaaagt 33900
gtagatctat cagatggcac tggtctcctc cgctgagtcg atcaaaaata acagctaaac 33960
cacaaacaac acgattggtc aaatgctgca caagggcttg cagcataaaa tcgcctcgaa 34020
agtccaccgc aagcataaca tcaaagccac cgcccctatc atgatctatg ataaaaaccc 34080
cacagctatc caccagaccc atatagtttt catctctcca tcgtgaaaaa atatttacaa 34140
gctcctcctt taaatcacct ccaaccaatt caaaaagttg agccagaccg ccctccacct 34200
tcattttcag catgcgcatc atgattgcaa aaattcaggc tcctcagaca cctgtataag 34260
attgagaagc ggaacattaa catcaatgtt tcgctcgcga agatcgcgcc tcagtgcaag 34320

-continued

```
catgatataa tcccacaggt cggagcggat cagcgaggac atctccccgc caggaaccaa  34380

ctcaacggag cctatgctga ttataatacg catattcggg gctatgctaa ccagcacggc  34440

ccccaaatag gcgtactgca taggcggcga caaaaagtga acagtttggg ttaaaaaatc  34500

aggcaaacac tcgcgcaaaa aagcaagaac atcataacca tgctcatgca aatagatgca  34560

agtaagctca ggaacgacca cagaaaaatg cacaattttt ctctcaaaca tgactgcgag  34620

ccctgcaaaa aataaaaaag aaacattaca caagagtagc ctgtcttaca atgggataga  34680

ctactctaac caacataaga cgggccacga catcgcccgc gtggccataa aaaaaattat  34740

ccgtgtgatt aaaaagaagc acagatagct ggccagtcat atccggagtc atcacgtgcg  34800

aacccgtgta gacccccggg ttggacacat cggccaaaga aagaaagcgg ccaatgtatc  34860

ccggaggaat gataacacta agacgaagat acaacagaat aaccccatgg gggggaataa  34920

caaagttagt aggtgaataa aaacgataaa cacccgaaac tccctcctgc gtaggcaaaa  34980

tagcgccctc cccttccaaa acaacataca gcgcttccac agcagccatg acaaaagact  35040

caaaacactc aaaagactca gtcttaccag gaaaataaaa gcactctcac agcaccagca  35100

ctaatcagag tgtgaagagg gccaagtgcc gaacgagtat atataggaat taaaaatgac  35160

gtaaatgtgt aaaggtcaaa aaacgcccag aaaaatacac agaccaacgc ccgaaacgaa  35220

aacccgcgaa aaaataccca gaagttcctc aacaaccgcc acttccgctt tcccacgata  35280

cgtcacttcc tcgaaaatag caaactacat ttcccacatg tacaaaaccg aaaccactcc  35340

ccttgtcacc gcccacaact tacatcttaa ttaacaaacg tcaaagccta cgtcagccgc  35400

cccgcctcgc cccgcccacc tcattatcat attggccaca atccaaaata aggtatatta  35460

ttgatgatg                                                          35469
```

<210> SEQ ID NO 19
<211> LENGTH: 183
<212> TYPE: PRT
<213> ORGANISM: Artificial Sequence
<220> FEATURE:
<223> OTHER INFORMATION: BZ28 fiber knob

<400> SEQUENCE: 19

```
Thr Leu Trp Thr Thr Pro Asp Pro Ser Pro Asn Cys Arg Ile His Ala
1               5                   10                  15

Asp Lys Asp Cys Lys Phe Thr Leu Val Leu Thr Lys Cys Gly Ser Gln
            20                  25                  30

Ile Leu Ala Ser Val Ala Ala Leu Ala Val Ser Gly Asn Leu Ala Ser
        35                  40                  45

Ile Thr Gly Thr Val Ala Ser Val Thr Ile Phe Leu Arg Phe Asp Gln
    50                  55                  60

Asn Gly Val Leu Met Glu Asn Ser Ser Leu Asp Lys Gln Tyr Trp Asn
65                  70                  75                  80

Phe Arg Asn Gly Asn Ser Thr Asn Ala Thr Pro Tyr Thr Asn Ala Val
                85                  90                  95

Gly Phe Met Pro Asn Leu Ala Ala Tyr Pro Lys Thr Gln Ser Gln Thr
            100                 105                 110

Ala Lys Asn Asn Ile Val Ser Gln Val Tyr Leu Asn Gly Asp Lys Ser
        115                 120                 125

Lys Pro Met Thr Leu Thr Ile Thr Leu Asn Gly Thr Asn Glu Ser Ser
    130                 135                 140

Glu Thr Ser Gln Val Ser His Tyr Ser Met Ser Phe Thr Trp Ala Trp
145                 150                 155                 160
```

-continued

```
Glu Ser Gly Gln Tyr Ala Thr Glu Thr Phe Ala Thr Asn Ser Phe Thr
                165                 170                 175

Phe Ser Tyr Ile Ala Glu Gln
            180
```